US012758177B2

(12) United States Patent
Steines et al.

(10) Patent No.: US 12,758,177 B2
(45) Date of Patent: Oct. 13, 2026

(54) AUGMENTED REALITY MAN-MACHINE INTERFACE FOR ROBOTIC SURGERY

(71) Applicant: OnPoint Medical, Inc., Franconia, NH (US)

(72) Inventors: Daniel Steines, Lexington, MA (US); Philipp K. Lang, Franconia, NH (US)

(73) Assignee: OnPoint Medical, Inc., Franconia, NH (US)

(*) Notice: Subject to any disclaimer, the term of this patent is extended or adjusted under 35 U.S.C. 154(b) by 223 days.

(21) Appl. No.: 18/465,388

(22) Filed: Sep. 12, 2023

(65) Prior Publication Data

US 2024/0081773 A1 Mar. 14, 2024

Related U.S. Application Data

(63) Continuation of application No. 17/691,923, filed on Mar. 10, 2022, now Pat. No. 11,786,206.

(Continued)

(51) Int. Cl.

*G06T 19/00* (2011.01)
*A61B 6/00* (2024.01)

(Continued)

(52) U.S. Cl.

CPC .............. *A61B 6/548* (2013.01); *A61B 6/469* (2013.01); *A61B 6/5294* (2013.01); *A61B 90/37* (2016.02); *G02B 27/0172* (2013.01); *G06F 3/04815* (2013.01); *G06T 19/006* (2013.01); *A61B 2090/365* (2016.02);

(Continued)

(58) Field of Classification Search

CPC ....... A61B 6/548; A61B 6/469; A61B 6/5294; A61B 90/37; A61B 2090/365; G02B 27/0172; G02B 2027/0134; G02B 2027/0138; G02B 2027/014; G02B 2027/0141; G06F 3/04815; G06F 3/013; G06F 3/017; G06T 19/006

See application file for complete search history.

(56) References Cited

U.S. PATENT DOCUMENTS 5,526,812 A 6/1996 Dumoulin et al.
5,676,673 A 10/1997 Ferre et al.

(Continued)

FOREIGN PATENT DOCUMENTS

EP 1028659 2/2004
GB 2498833 12/2016

(Continued)

OTHER PUBLICATIONS

1 Supplementary European Search Report in European Application No. EP 22 76 8019 mailed Mar. 10, 2025.

(Continued)

*Primary Examiner* — Grace Q Li

(74) *Attorney, Agent, or Firm* — Greenberg Traurig, LLP; Natalie Salem

(57) ABSTRACT

Systems, devices and methods for augmented reality guidance of surgical procedures using multiple head mounted displays or other augmented reality display devices are described. In addition, systems, devices and methods using head mounted displays or other augmented reality display systems for operating surgical robots and/or imaging systems are described.

20 Claims, 45 Drawing Sheets

Related U.S. Application Data

(60) Provisional application No. 63/232,376, filed on Aug. 12, 2021, provisional application No. 63/173,565, filed on Apr. 12, 2021, provisional application No. 63/163,156, filed on Mar. 19, 2021, provisional application No. 63/158,941, filed on Mar. 10, 2021.

(51) Int. Cl.

| | |
|---|---|
| *A61B 6/46* | (2024.01) |
| *A61B 90/00* | (2016.01) |
| *G02B 27/01* | (2006.01) |
| *G06F 3/01* | (2006.01) |
| *G06F 3/04815* | (2022.01) |

(52) U.S. Cl.

CPC ................ *G02B 2027/0134* (2013.01); *G02B 2027/0138* (2013.01); *G02B 2027/014* (2013.01); *G02B 2027/0141* (2013.01); *G06F 3/013* (2013.01); *G06F 3/017* (2013.01)

(56) References Cited

U.S. PATENT DOCUMENTS

| | | | |
|---|---|---|---|
| 5,800,352 | A | 9/1998 | Ferre et al. |
| 5,803,089 | A | 9/1998 | Ferre et al. |
| 5,829,444 | A | 11/1998 | Ferre et al. |
| 5,873,822 | A | 2/1999 | Ferre et al. |
| D415,146 | S | 10/1999 | Hori |
| 5,967,980 | A | 10/1999 | Ferre et al. |
| 6,175,756 | B1 | 1/2001 | Ferre et al. |
| 6,341,231 | B1 | 1/2002 | Ferre et al. |
| 6,396,497 | B1 | 5/2002 | Reichlen |
| 6,445,943 | B1 | 9/2002 | Ferre et al. |
| 6,599,247 | B1 | 7/2003 | Stetten |
| 6,714,810 | B2 | 3/2004 | Grzeszczuk et al. |
| 7,130,676 | B2 | 10/2006 | Barrick |
| 7,774,044 | B2 | 8/2010 | Sauer et al. |
| 7,812,815 | B2 | 10/2010 | Banerjee et al. |
| 8,320,612 | B2 | 11/2012 | Knobel et al. |
| 8,730,266 | B2 | 5/2014 | Brown et al. |
| 8,989,843 | B2 | 3/2015 | Chien |
| 9,068,820 | B2 | 6/2015 | Kosmecki et al. |
| 9,068,824 | B2 | 6/2015 | Findeisen et al. |
| 9,123,155 | B2 | 9/2015 | Cunningham et al. |
| 9,183,560 | B2 | 11/2015 | Abelow |
| 9,215,293 | B2 | 12/2015 | Miller |
| 9,299,138 | B2 | 3/2016 | Zellner et al. |
| 9,310,559 | B2 | 4/2016 | Macnamara |
| 9,311,284 | B2 | 4/2016 | Warila et al. |
| 9,389,424 | B1 | 7/2016 | Schowengerdt |
| 9,417,452 | B2 | 8/2016 | Schowengerdt et al. |
| 9,429,752 | B2 | 8/2016 | Schowengerdt et al. |
| 9,503,681 | B1 | 11/2016 | Popescu et al. |
| 9,547,940 | B1 | 1/2017 | Sun et al. |
| 9,582,717 | B2 | 2/2017 | Lee et al. |
| 9,792,721 | B2 | 10/2017 | Kosmecki et al. |
| 9,861,446 | B2 | 1/2018 | Lang |
| 9,980,780 | B2 | 5/2018 | Lang |
| 10,078,221 | B2 | 9/2018 | Pilkinton et al. |
| 10,136,952 | B2 | 11/2018 | Couture et al. |
| 10,154,239 | B2 | 12/2018 | Casas |
| 10,159,530 | B2 | 12/2018 | Lang |
| 10,278,777 | B1 | 5/2019 | Lang |
| 10,292,768 | B2 | 5/2019 | Lang |
| 10,368,947 | B2 | 8/2019 | Lang |
| 10,405,927 | B1 | 9/2019 | Lang |
| 10,603,113 | B2 | 3/2020 | Lang |
| 10,743,939 | B1 | 8/2020 | Lang |
| 10,799,296 | B2 | 10/2020 | Lang |
| 10,849,693 | B2 | 12/2020 | Lang |
| 11,013,560 | B2 | 5/2021 | Lang |
| 11,172,990 | B2 | 11/2021 | Lang |
| 11,786,206 | B2 | 10/2023 | Steines et al. |
| 2001/0041838 | A1 | 11/2001 | Holupka et al. |
| 2002/0016349 | A1 | 2/2002 | Heywang et al. |
| 2002/0075201 | A1 | 6/2002 | Sauer et al. |
| 2002/0082498 | A1 | 6/2002 | Wendt et al. |
| 2005/0028146 | A1 | 2/2005 | Quick |
| 2005/0113846 | A1 | 5/2005 | Carson |
| 2005/0215879 | A1 | 9/2005 | Chuanggui |
| 2005/0267353 | A1 | 12/2005 | Marquart et al. |
| 2005/0281465 | A1 | 12/2005 | Marquart et al. |
| 2006/0142739 | A1 | 6/2006 | Disilestro et al. |
| 2007/0015999 | A1 | 1/2007 | Heldreth et al. |
| 2007/0035511 | A1 | 2/2007 | Banerjee et al. |
| 2007/0038944 | A1 | 2/2007 | Carignano et al. |
| 2007/0236514 | A1 | 10/2007 | Agusanto et al. |
| 2007/0276234 | A1 | 11/2007 | Shahidi |
| 2009/0068620 | A1 | 3/2009 | Knobel et al. |
| 2009/0089081 | A1 | 4/2009 | Haddad |
| 2009/0138019 | A1 | 5/2009 | Wasielewski |
| 2009/0267805 | A1 | 10/2009 | Jin et al. |
| 2011/0105895 | A1 | 5/2011 | Kornblau et al. |
| 2011/0190637 | A1 | 8/2011 | Knobel et al. |
| 2013/0093829 | A1 | 4/2013 | Rosenblatt et al. |
| 2013/0096373 | A1 | 4/2013 | Chabanas et al. |
| 2013/0116574 | A1 | 5/2013 | Knobel et al. |
| 2013/0169683 | A1 | 7/2013 | Perez et al. |
| 2013/0261503 | A1 | 10/2013 | Sherman et al. |
| 2013/0261504 | A1 | 10/2013 | Claypool et al. |
| 2013/0261633 | A1 | 10/2013 | Thornberry |
| 2013/0296682 | A1 | 11/2013 | Clavin et al. |
| 2013/0326364 | A1 | 12/2013 | Latta et al. |
| 2014/0081659 | A1 | 3/2014 | Nawana et al. |
| 2014/0085203 | A1 | 3/2014 | Kobayashi |
| 2014/0088941 | A1 | 3/2014 | Banerjee et al. |
| 2014/0118335 | A1 | 5/2014 | Gurman |
| 2014/0135746 | A1 | 5/2014 | Schoepp |
| 2014/0198190 | A1 | 7/2014 | Okumu |
| 2014/0218366 | A1 | 8/2014 | Kosmecki et al. |
| 2014/0275760 | A1 | 9/2014 | Lee et al. |
| 2014/0303491 | A1 | 10/2014 | Shekhar et al. |
| 2014/0334670 | A1 | 11/2014 | Guigues et al. |
| 2015/0100067 | A1 | 4/2015 | Cavanagh et al. |
| 2015/0206218 | A1 | 7/2015 | Banerjee et al. |
| 2015/0366628 | A1 | 12/2015 | Ingmanson |
| 2016/0163105 | A1 | 6/2016 | Hong et al. |
| 2016/0182877 | A1 | 6/2016 | DeLuca |
| 2016/0191887 | A1 | 6/2016 | Casas |
| 2016/0206379 | A1 | 7/2016 | Flett et al. |
| 2016/0220105 | A1 | 8/2016 | Duret |
| 2016/0225189 | A1 | 8/2016 | Nishizawa |
| 2016/0225192 | A1 | 8/2016 | Jones et al. |
| 2016/0228193 | A1 | 8/2016 | Moctezuma de la Barrera et al. |
| 2016/0287337 | A1 | 10/2016 | Aram et al. |
| 2016/0323569 | A1* | 11/2016 | Wang .................. H04N 13/344 |
| 2016/0324580 | A1 | 11/2016 | Esterberg |
| 2016/0381256 | A1 | 12/2016 | Aguirre-Valencia |
| 2017/0027651 | A1 | 2/2017 | Esterberg |
| 2017/0035517 | A1 | 2/2017 | Geri et al. |
| 2017/0071673 | A1 | 3/2017 | Ferro et al. |
| 2017/0108930 | A1 | 4/2017 | Banerjee et al. |
| 2017/0160549 | A1 | 6/2017 | Badiali et al. |
| 2017/0178375 | A1 | 6/2017 | Benishti et al. |
| 2017/0202633 | A1 | 7/2017 | Liu |
| 2017/0220119 | A1* | 8/2017 | Potts ...................... G06F 3/017 |
| 2017/0231714 | A1 | 8/2017 | Kosmecki et al. |
| 2017/0258526 | A1 | 9/2017 | Lang |
| 2017/0312032 | A1 | 11/2017 | Amanatullah et al. |
| 2018/0018827 | A1 | 1/2018 | Stafford et al. |
| 2018/0049622 | A1 | 2/2018 | Ryan et al. |
| 2018/0116728 | A1 | 5/2018 | Lang |
| 2018/0125584 | A1 | 5/2018 | Lang |
| 2018/0256256 | A1 | 9/2018 | May et al. |
| 2018/0263704 | A1 | 9/2018 | Lang |
| 2018/0344286 | A1 | 12/2018 | Mienkina et al. |
| 2019/0000564 | A1 | 1/2019 | Navab et al. |
| 2019/0005848 | A1 | 1/2019 | Kilroy et al. |
| 2019/0038362 | A1* | 2/2019 | Nash ...................... A61B 90/36 |
| 2019/0094989 | A1* | 3/2019 | Chen ...................... G06F 3/012 |
| 2019/0110842 | A1 | 4/2019 | Lang |
| 2019/0192226 | A1 | 6/2019 | Lang |
| 2019/0216452 | A1 | 7/2019 | Nawana et al. |

(56) References Cited

U.S. PATENT DOCUMENTS

| | | | | |
|---|---|---|---|---|
| 2019/0262078 | A1 | 8/2019 | Lang | |
| 2019/0380784 | A1 | 12/2019 | Lang | |
| 2020/0060767 | A1 | 2/2020 | Lang | |
| 2020/0138518 | A1 | 5/2020 | Lang | |
| 2020/0159313 | A1 | 5/2020 | Gibby et al. | |
| 2020/0246074 | A1 | 8/2020 | Lang | |
| 2020/0246081 | A1 | 8/2020 | Johnson et al. | |
| 2020/0305980 | A1 | 10/2020 | Lang | |
| 2021/0022808 | A1 | 1/2021 | Lang | |
| 2021/0038181 | A1* | 2/2021 | Schweizer | A61B 6/466 |
| 2021/0106386 | A1 | 4/2021 | Lang | |
| 2021/0121238 | A1* | 4/2021 | Palushi | A61B 90/37 |
| 2021/0142509 | A1* | 5/2021 | Zhang | A61B 5/064 |
| 2021/0267691 | A1 | 9/2021 | Lang | |
| 2022/0117662 | A1 | 4/2022 | Babb et al. | |
| 2022/0301265 | A1* | 9/2022 | Mitchell | G06F 3/011 |

FOREIGN PATENT DOCUMENTS

| | | |
|---|---|---|
| WO | WO1993025157 | 12/1993 |
| WO | WO 2005088539 | 9/2005 |
| WO | WO 2010034117 | 4/2010 |
| WO | WO 2014057352 | 4/2014 |
| WO | WO 2015110859 | 7/2015 |
| WO | WO 2015145395 | 10/2015 |
| WO | WO 2016028828 | 2/2016 |
| WO | WO 2016162789 | 10/2016 |
| WO | WO 2016195401 | 12/2016 |
| WO | WO 2016207628 | 12/2016 |
| WO | WO 2017160651 | 9/2017 |
| WO | WO 2018085417 | 5/2018 |
| WO | WO 2018085691 | 5/2018 |
| WO | WO 2018052966 | 10/2018 |

OTHER PUBLICATIONS

3D Optical Microscopy for Orthopedic Implants; Bruker Nano Surfaces, Jun. 17, 2016.

A Look into the Body—Augmented Reality in Computer Aided Surgery, Department of Informatics, Research-Highlights; Technische Universitat Munchen.

Abe et al., "A Novel 3D Guidance System Using Augmented Reality for Percutaneous Vertebroplasty", Journal of Neurological Spine, vol. 19, pp. 492-501, Oct. 2013.

Aguerreche L. et al., "Reconfigurable Tangible Devices for 3D Virtual Object Manipulation by Single or Multiple Users." VRST 2010, Nov. 2010, Hong Kong, Hong Kong SAR China. inria-00534095.

Aichert et al., "Image-Based Tracking of the Teeth for Orthodontic Augmented Reality", Medical Image Computing and Computer-Assisted Intervention, Lecture Notes in Computer Science, vol. 7511, Springer, pp. 601-608, 2012.

Anderson et al., "Virtual annotations of the surgical field through an augmented reality transparent display", The Visual Computer, vol. 32, Issue 11, pp. 1481-1498, Nov. 2016.

Armstrong et al., "A Heads-Up Display for Diabetic Limb Salvage Surgery: A View Through the Google Looking Glass"; Journal of Diabetes Science and Technology 2014, vol. 8(5) 951-956.

Azura, R., "A survey of augmented reality." Teleoperators and Virtual Environments, vol. 6, Issue 4, Aug. 1997, pp. 355-385.

Bajura, M., et al., "Merging Virtual Objects with the Real World: Seeing Ultrasound Imagery Within the Patient.", In Proceedings of SIGGRAPH '92, 1992, New York: ACM Press, pp. 203-210.

Baker et al., "The Emergence of Augmented Reality in Orthopaedic Surgery and Education", The Orthopaedic Journal at Harvard Medical School, vol. 16, pp. 8-16, Jun. 2015.

Bauer et al., "Joint ToF Image Denoising and Registration with a CT Surface in Radiation Therapy", Scale Space and Variational Methods in Computer Vision, Lecture Notes in Computer Science, Springer, vol. 6667, pp. 98-109.

Bauer et al., "Multi-Modal Surface Registration for Markerless Initial Patient Setup in Radiation Therapy Using Microsoft's Kinect Sensor", 2011 IEEE International Conference on Computer Vision Workshops (ICCV Workshops), Barcelona, Nov. 2011, pp. 1175-1181, Jan. 16, 2012.

Bauer et al., "Real-Time Range Imaging in Health Care: A Survey", Time-of-Flight and Depth Imaging, Sensors, Algorithms, and Applications. Lecture Notes in Computer Science, vol. 8200, pp. 228-254, 2017.

Bauer, Sebastian, Doctoral Thesis, "Rigid and Non-Rigid Surface Registration for Range Imaging Applications in Medicine", urn:nbn:de:bvb:29-opus4-54665, Nov. 27, 2014.

Benford, S. et al., "User embodiment in collaborative virtual environments", Proceedings of the SIGCHI conference on Human factors in computing systems, CHI '95, pp. 242-249, 1995.

Besl PJ, McKay ND. 2, 1992. A method for registration of 3-D shapes. IEEE Trans PAMI, vol. 14, pp. 239-256.

Bichlmeier C., et al. "Contextual Anatomic Mimesis Hybrid In-Situ Visualization Method for Improving Multi-Sensory Depth Perception in Medical Augmented Reality.", IEEE 2007, 2007 6th IEEE and ACM International Symposium on Mixed and Augmented Reality.

Bichlmeier et al., "Virtually Extended Surgical Drilling Device: Virtual Mirror for Navigated Spine Surgery"; MICCAI 2007, Part I, Lncs 4791, pp. 434-441.

Billinghurst, et al., "The MagicBook: A Transitional AR Interface.", Computers and Graphics, Nov. 2001, pp. 745-753.

Billinghurst, M., et al., "Collaborative Mixed Reality", First International Symposium on Mixed Reality (ISMR '99). Mixed Reality—Merging Real and Virtual Worlds, pp. 261-284. Berlin: Springer Verlag.

Billinghurst, M., et al., "Collaborative Augmented Reality.", Communications of the ACM 2002, vol. 45 Issue 7, pp. 64-70 (2002).

Billinghurst, M., et al., "Experiments with Face to Face Collaborative AR Interfaces.", Virtual Reality Journal, vol. 4, No. 2, (2002).

Birkfellner et al., "A Head-Mounted Operating Binocular for Augmented Reality Visualization in Medicine—Design and Initial Evaluation", IEEE Transactions on Medical Imaging, vol. 21, No. 8, pp. 991-997, Aug. 2002.

Birkfellner et al., "Computer-enhanced stereoscopic vision in a head-mounted operating binocular", Physics in Medicine & Biology, vol. 48, No. 3, pp. 49-57, Feb. 7, 2003.

Birkfellner et al., "In-Vitro Aassessment of a Registration Protocol for Image Guided Implant Dentistry", Clinical Oral Implants Research, vol. 12, Issue 1, pp. 69-78, Feb. 2001.

Blackwell et al., "An Image Overlay System for Medical Data Visualization", In: Wells W.M., Colchester A., Delp S. (eds) Medical Image Computing and Computer-Assisted Intervention—MICCAI'98. MICCAI 1998. Lecture Notes in Computer Science, vol. 1496. Springer, Berlin, Heidelberg; pp. 232-240.

Blackwell et al., "An Image Overlay System for Medical Data Visualization", Medical Image Analysis vol. 4, pp. 67-72, 2000.

Blackwell et al., "Augmented Reality and Its Future in Orthopaedics", Clinical Orthopaedics & Related Research, vol. 354, pp. 111-122, Sep. 1998.

Castillo et al., "Augmented Reality for Assistance of Total Knee Replacement", Journal of Electrical and Computer Engineering, vol. 2016, Article 9358369, pp. 1-6, 2016.

Catani et al., "Knee Surgery Using Computer Assisted Surgery and Robotics", Springer Heidelberg Publishing, Book, pp. 1-221, 2013.

Chandak, "MEMS Based Wireless Controlled Robot with Voice and Video Camera"; International Journal of Scientific & Engineering Research, vol. 5, Issue 4, Apr. 2014.

Charbonnier et al., "Real Virtuality: Perspectives offered by the combination of Virtual Reality headsets and Motion Capture", Artanim, Real Virtuality White Paper, Aug. 23, 2015.

Chen et al., "Development of a surgical navigation system based on augmented reality using an optical see-through head-mounted display"; Journal of Biomedical Informatics 55 (2015) 124-131.

Cruz-Neira C. et al., "The cave: audio visual experience automatic virtual environment.", Commun. ACM, vol. 35, No. 6, pp. 64-72, Jun. 1992.

(56) References Cited

OTHER PUBLICATIONS

Cui et al., "KinectAvatar: Fully Automatic Body Capture Using a Single Kinect", ACCV'12 Proceedings of the 11th International Conference on Computer Vision - vol. 2, pp. 133-147, Nov. 2012.
Daniel and Ramos, "Augmented Reality for Assistance of Total Knee Replacement", Journal of Electrical and Computer Engineering, vol. 2016, Article ID 9358369, Hindawi Publishing Corporation.
Davies et al., "Computer Assisted Orthopaedic Surgery", 8th Annual Meeting of CAOS-International Proceedings, Apr. 2008.
Delambert et al., "Electromagnetic Tracking for Registration and Navigation in Endovascular Aneurysm Repair: A Phantom Study" European Journal of Vascular and Endovascular Surgery, vol. 43, pp. 684-689, 2012.
Draelos, Mark, "The Kinect Up Close: Modifications for Short-Range Depth Imaging", NC State Theses and Dissertations, pp. 1-88, Mar. 26, 2012.
Elmi-Terander et al., "Surgical Navigation Technology Based on Augmented Reality and Integrated 3D Intraoperative Imaging"; Spine Surgery, vol. 41, No. 21, pp. E1303-1311, 2016.
Ferrari et al., "Video See-Through in the Clinical Practice", 1st International Workshop on Engineering Interactive Computing Systems for Medicine and Health Care, EICS4Med. vol. 727, pp. 19-24, 2011.
Fischer et al., "Medical Augmented Reality Based on Commercial Image Guided Surgery", European Association for Computer Graphics, Proceedings of the 10th Eurographics Symposium on Virtual Environments, pp. 83-86, Jun. 2004.
Fitzmaurice, G., et al., "Bricks: Laying the Foundations for Graspable User Interfaces.", Proceedings of Conference on Human Factors in Computing Systems (CHI '95), Denver, Colorado, ACM Press, 442-449, (1995).
Flusser et al., "Image Fusion: Principles, Methods and Applications", Tutorial EISIPCO 2007 Lecture Notes.
Fritz et al., "Augmented Reality Visualization with Image Overlay for MRI-Guided Intervention: Accuracy for Lumbar Spinal Procedures with a 1.5-T MRI System", Vascular and Interventional Radiology, AJR: 198, Mar. 2012.
Fritz et al., "Augmented Reality Visualization with Use of Image Overlay Technology for MR Imaging—guided Interventions: Assessment of Performance in Cadaceric Shoulder and Hip Arthrography at 1.5T"; Radiology: vol. 265, No. 1, Oct. 2012, pp. 254-259.
Garon, Mathieu; Boulet, Pierre-Olivier; Doiron, Jean-Philippe; Beaulieu, Luc; Lalonde, Jean-François (2016): Real-time High Resolution 3D Data on the HoloLens. In: International Symposium on Mixed and Augmented Reality (ISMAR).
Garrido-Jurado, S.; Muñoz-Salinas, R.; Madrid-Cuevas, F. J.; Marín-Jiménez, M. J. (2014): Automatic generation and detection of highly reliable fiducial markers under occlusion. In: Pattern Recognition 47 (6), S. 2280-2292. DOI: 10.1016/j.patcog.2014.01.005.
Gavaghan et al., "Augmented Reality Image Overlay Projection for Image Guided Open Liver Ablation of Metastatic Liver Cancer"; C.A. Linte et al. (Eds.): AE-CAI 2011, LNCS, pp. 36-46, 2012.
Gee A, et al., "Processing and visualizing three-dimensional ultrasound data.", The British Journal of Radiology, vol. 77, S186-S193, (2004).
George et al., "Low Cost Augmented Reality for Training of MRI-Guided Needle Biopsy of the Spine", Medicine Meets Virtual Reality 16, pp. 138-140, IOS Press, 2008.
Germano et al., Advanced Techniques in Image-Guided Brain and Spine Surgery, Thieme Medical Publishers, Incorporated, 2002.
Gonzalez, Smart Multi-Level Tool for Remote Patient Monitoring Based on a Wireless Sensor Network and Mobile Augmented Reality, Sensors, Sep. 2014; 14(9): 17212-17234.
Gorbert, M. et al., "Triangles: Tangible Interface for Manipulation and Exploration of Digital Information Topography.", Proceedings of CHI '98, Apr. 18-23, 1998, © 1998 ACM.
Gromov et al., "What is the optimal alignment of the tibial and femoral components in knee arthroplasty ?: An overview of the literature"; Acta Orthopaedica 2014; 85(5): 480-487.
Hayashibe et al., "Surgical Navigation Display System Using Volume Rendering of Intraoperatively Scanned CT Images", Computer Aided Surgery, vol. 11, No. 5, pp. 240-246, Sep. 2006.
Hinterstoisser, S. Holzer S.; Cagniart, C.; Ilic, S.; Konolige, K.; Navab, N.; Lepetit, V. (2011b): Multimodal Templates for Real-Time Detection of Texture-less Objects in Heavily Cluttered Scenes.
Hinterstoisser, S.; Cagniart, C.; Ilic, S.; Sturm, P.; Navab, N.; Fua, P.; Lepetit, V. (2012a): Gradient Response Maps for Real-Time Detection of Texture-Less Objects. In: IEEE Transactions on Pattern Analysis and Machine Intelligence.
Hinterstoisser, S.; Lepetit, V.; Benhimane, S.; Fua, P.; Navab, N. (2011a): Learning Real-Time Perspective Patch Rectification. In: International Journal of Computer Vision (IJCV), Springer. DOI: 10.1007/s11263-010-0379-x.
Hinterstoisser, S.; Lepetit, V.; Ilic, S.; Holzer, S.; Bradski, G.; Konolige, K.; Navab, N. (2012b): Model Based Training, Detection and Pose Estimation of Texture-Less 3D Objects in Heavily Cluttered Scenes.
Hoff, "Fusion of Data from Head-Mounted and Fixed Sensors"; First International Workshop on Augmented Reality, 1, 1998, pp. 1-15.
Holographic weapon sight—Wikipedia https://en.wikipedia.org/wiki/Holographic_weapon_sight retrieved on Nov. 22, 2016.
Hu et al., "A Convenient Method of Video See-through Augmented Reality Based on Image-Guided Surgery System", Internet Computing for Engineering and Science, 2013 Seventh International Conference on Internet Computing for Engineering and Science, Shanghai, pp. 100-103, Dec. 12, 2013.
Hua et al., "A 3D Integral Imaging Optical See-Through Head-Mounted Display", Optical Society of America, vol. 22, No. 11, pp. 1-8, Jun. 2, 2014.
Ishii, H., et al., "Iterative Design of Seamless Collaboration Media. ", Communications of the ACM, vol. 37, No. 8, Aug. 1994, pp. 83-97.
Ji et al., "Real-Time Eye, Gaze, and Face Pose Tracking for Monitoring Driver Vigilance"; Real-Time Imaging 8, pp. 357-377, 2002.
Jiang et al., "A Robust Automated Markerless Registration Framework for Neurosurgery Navigation", The International Journal of Medical Robotics and Computer Assisted Surgery, vol. 11, pp. 436-447, Oct. 19, 2014.
Jolesz, Ferenc A., "Intraoperative Imaging and Image-Guided Therapy", Springer Science & Business Media, 893 pages, Jan. 14, 2014.
Kanade et al., "Simulation, Planning, and Execution of Computer-Assisted Surgery", Proceedings of the NSF Grand Challenges Workshop, 1996.
Kato, H.; Billinghurst, M. (1999): Marker tracking and HMD calibration for a video-based augmented reality conferencing system. In: Augmented Reality, 1999. (IWAR '99) Proceedings. 2nd IEEE and ACM International Workshop on, S. 85-94.
Kersten-Oertel et al., "The State of the Art of Visualization in Mixed Reality Image Guided Surgery", Computerized Medical Imaging and Graphics, vol. 37, pp. 98-112, Jan. 2013.
Kim et al., "Registration Accuracy Enhancement of a Surgical Navigation System for Anterior Cruciate Ligament Reconstruction: A Phantom and Cadaveric Study", The Knee, vol. 24, pp. 329-339, 2017.
Kolodzey et al., "Wearable technology in the operating room: a systematic review"; GMJ Innov 2017; 3:55-63.
Kumar et al., "A Portable Wireless Head Movement Controlled Human-Computer Interface for People with Disabilities", International Journal of Advanced Research in Electrical, Electronics and Instrumentation Engineering, vol. 3, Issue 7, Jul. 2014.
Kutter et al., "Real-time Volume Rendering for High Quality Visualization in Augmented Reality", International Workshop on Augmented Environments for Medical Imaging including Augmented Reality in Computer-aided Surgery (AMI-ARCS 2008), New York, MICCAI Society, Sep. 2008.
Lamata et al., "Augmented Reality for Minimally Invasive Surgery: Overview and Some Recent Advances"; Augmented Reality, Jan. 2010.

(56) References Cited

OTHER PUBLICATIONS

Liao et al., "3-D Augmented Reality for MRI-Guided Surgery Using Integral Videography Autostereoscopic Image Overlay", IEEE Transactions on Biomedical Engineering, vol. 57, No. 6, pp. 1476-1486, Jun. 2010.
Liao et al., "Surgical Navigation by Autostereoscopic Image Overlay of Integral Videography", IEEE Transactions on Information Technology in Biomedicine, vol. 8, No. 2, pp. 114-121, Jun. 2004.
Lievin et al., "Stereoscopic Augmented Reality System for Computer-Assisted Surgery", International Congress Series, vol. 1230, pp. 107-111, Jun. 2001.
Lindert et al., "The use of a head-mounted display for visualization in neuroendoscopy", Computer Aided Surgery, 2004; 9(6): 251-256.
Linte et al., "On Mixed Reality Environments for Minimally Invasive Therapy Guidance: Systems Architecture, Successes and Challenges in their Implementation from Laboratory to Clinic", Comput Med Imaging Graph, Mar. 2013; 37(2): 83-97, DOI: 10.1016/j.compmedimag.2012.12.002.
Liu et al., "An Optical See-Through Head Mounted Display with Addressable Focal Planes" IEEE International Symposium on Mixed and Augmented Reality, Cambridge, UK, pp. 33-42, Oct. 3, 2008.
Lorensen WE, Cline HE. [ed.], in M.C. Stone. 1987. Marching cubes: A high resolution 3d surface construction algorithm. Proceedings of SIGGRAPH 87. pp. 163-169.
Maier-Hein et al., "Optical Techniques for 3D Surface Reconstruction in Computer-Assisted Laparoscopic Surgery", Medical Image Analysis, vol. 17, pp. 974-996, May 3, 2013.
Maier-Hein, L et al., "Towards Mobile Augmented Reality for On-Patient Visualization of Medical Images.", Bildverarbeitung für die Medizin 2011: Algorithmen—Systeme—Anwendungen Proceedings des Workshops vom 20.—22. März 2011 in Lübeck (pp. 389-393).
Masamune et al., "An Image Overlay System with Enhanced Reality for Percutaneous Therapy Performed Inside CT Scanner", Medical Image Computing and Computer-Assisted Intervention, Lecture Notes in Computer Science, vol. 2489, pp. 77-84, Oct. 2002.
Maurer et al., "Augmented-Real Visualization of Brain Structures with Stereo and Kinetic Depth Cues: System Description and Initial Evaluation with Head Phantom", Proceedings, vol. 4319, Medical Imaging 2001: Visualization, Display, and Image-Guided Procedures, pp. 445-456, May 28, 2001.
Medeiros D. et al., "Proposal and evaluation of a tablet-based tool for 3D virtual environments.", SBC Journal on 3D Interactive Systems, vol. 4, No. 2, pp. 30-40, (2013).
Melzer, "Head-Mounted Displays", The Avionics Handbook, 2001.
Menozzi et al., "Development of Vision-Aided Navigation for a Wearable Outdoor Augmented Reality System", IEEE Plans, Position Location and Navigation Symposium, Article No. 6851442, pp. 760-772, 2014.
MicroVision 2015 Annual Report and Proxy Statement for 2016 Annual Meeting of Shareholders.
Moore et al., "Image Guidance for Spinal Facet Injections Using Tracked Ultrasound", MICCAI 2009, Part I, LNCS 5761, pp. 516-523 2009.
Muller et al., "Automatic Multi-Modal ToF/CT Organ Surface Registration", Bildverarbeitung für die Medizin, pp. 154-158, Mar. 2011.
Newcombe, R. A.; Izadi, S.; Hilliges, O.; Molyneaux, D.; Kim, D.; Davison, A. J. et al. (2011): KinectFusion. Real-time dense surface mapping and tracking. In: 2011 10th IEEE International Symposium on Mixed and Augmented Reality, S. 127-136.
Nicolau, "Augmented Reality in Laparoscopic Surgical Oncology.", Surgical Oncology, vol. 20, pp. 89-201 (2011).
Nikou et al., "Augmented Reality Imaging Technology for Orthopaedic Surgery", Operative Techniques in Orthopaedics, vol. 10, No. 1 (January), 2000: pp. 82-86.
Noonan et al., "The Design and Initial Calibration of an Optical Tracking System Using the Microsoft Kinect", IEEE Nuclear Science Symposium Conference Record, pp. 3614-3617, Oct. 2011.
Okamura, Allison, "Tracking and Surgical Navigation, Registration", Stanford Lecture 8: ME 328: Medical Robotics, pp. 1-19, Spring 2013.
Ortega et al., "Usefulness of a head mounted monitor device for viewing intraoperative fluoroscopy during orthopaedic procedures", Arch Orthop Trauma Surg (2008) 128:1123-1126.
Paprosky et al., "Intellijoint HIP: a 3D mini-optical navigation tool for improving intraoperative accuracy during total hip arthroplasty"; Med Devices (Auckl). 2016; 9: 401-408.
Pauly et al., "Machine Learning-Based Augmented Reality for Improved Surgical Scene Understanding", Computerized Medical Imaging and Graphics, vol. 1280, pp. 1-6, Jun. 2014.
Peters et al., "Image-Guided Interventions, Technology and Applications", Springer Science and Business Media, 576 pages, 2018.
Ponce et al., "Emerging Technology in Surgical Education: Combining Real-Time Augmented Reality and Wearable Computing Devices", The Cutting Edge, Nov. 2014, vol. 37, No. 11.
Qian, Long; Azimi, Ehsan; Kazanzides, Peter; Navab, Nassir (2017): Comprehensive Tracker Based Display Calibration for Holographic Optical See-Through Head-Mounted Display.
Ren et al., "Marker-Based Surgical Instrument Tracking Using Dual Kinect Sensors", IEEE Transactions on Automation Science and Engineering, vol. 11, No. 3, pp. 921-924, Jul. 2014.
Rhodes, "A brief history of wearable computing", MIT Wearable Computing Project.
Rinaldi et al., "Computer-Guided Applications for Dental Implants, Bone Grafting, and Reconstructive Surgery", Elsevier Inc., 556 pages, 2016.
Robinett et al., "A Computational Model for the Stereoscopic Optics of a Head-Mounted Display", Proceedings vol. 1457, Stereoscopic Displays and Applications II, pp. 140-160, 1991.
Rolland et al., "A Comparison of Optical and Video See-through Head-mounted Displays", Proceedings vol. 2351, Telemanipulator and Telepresence Technologies, pp. 293-307, Dec. 21, 1995.
Rolland et al., "Optical Versus Video See-Through Head-Mounted Displays in Medical Visualization", Presence: Teleoperators and Virtual Environments, vol. 9, Issue 3, pp. 287-309, Jun. 2000.
Rosenthal et al., "Augmented Reality Guidance for Needle Biopsies: A Randomized, Controlled Trial in Phantoms"; MICCAI 2001, LNCS 2208: 240-248.
Rosman et al., "Articulated Motion Segmentation of Point Clouds by Group-Valued Regularization", Eurographics Workshop on 3D Object Retrieval, EG 3DOR, pp. 77-84, May 2012.
Salmi Jamali, S. et al., "Utilising Mobile-Augmented Reality for Learning Human Anatomy.", 7th World Conference on Educational Sciences, (WCES-2015), Feb. 5-7, 2015, Novotel Athens Convention Center, Athens, Greece.
Sanko, "Microvision's Nomad Augmented Vision System: The How and the Why"; SID Pacific Northwest Chapter Meeting, Jun. 11, 2003.
Sauer et al., "An Augmented Reality Navigation System with a Single-Camera Tracker: System Design and Needle Biopsy Phantom Trial", Proceedings of the 5th International Conference on Medical Image Computing and Computer-Assisted Intervention—Part II, pp. 116-124, Sep. 2002.
Sauer et al., "Augmented Workspace: Designing an AR Testbed", Proceedings IEEE and ACM International Symposium on Augmented Reality, pp. 47-53, Munich 2000.
Schramm, Kinect: The Company Behind the Tech Explains How it Works, Jun. 19, 2010, https://www.engadget.com/2010/06/19/kinect-how-it-works-from-the-company-behind-the- tech/?guccounter=1&guce_referrer=aHR0cHM6Ly93d3cuZ29vZ2xlLmNvbS8&guce_referrer_sig=AQAAAKHcnRaFMexHHXiiRrcGjKYjWQ2VJGsMA556eCVncvte7f0VM4aN3GpWj1WqU3RfCnTwHcTbxmibv1Iz_TUFgILvsRhShqXDrSM63OcvvjlSzpUoBvsC2LsOmHqf-zifqdYelctf0D0MDM78YhH-u7w9JUfxuLDGVUxUi9hDQLZo.
Scuderi et al., "Total Knee Arthroplasty with a Novel Navigation System Within the Surgical Field", Orthopedic Clinics, vol. 45, Issue 2, pp. 167-173, Apr. 2014.
Shen et al., "3D Augmented Reality with Integral Imaging Display", Proceedings of SPIE—The International Society for Optical Engineering, vol. 9867, Article No. 9867OY, Apr. 2016.

(56) References Cited

OTHER PUBLICATIONS

Sherstyuk et al., "Dynamic Eye Convergence for Head-Mounted Displays Improves User Performance in Virtual Environments", Proceedings of the ACM SIGGRAPH Symposium on Interactive 3D Graphics and Games, pp. 23-30, Mar. 2012.
State et al., "Stereo Imagery from the UNC Augmented Reality System for Breast Biopsy Guidance", MMVR 2003.
Tan, D. J.; Tombari, F.; Ilic, S.; Navab, N. (2015): A Versatile Learning-Based 3D Temporal Tracker. Scalable, Robust, Online. In: 2015 IEEE International Conference on Computer Vision (ICCV), S. 693-701.
Tong et al., "Scanning 3D Full Human Bodies Using Kinects", IEEE Transactions on Visualization and Computer Graphics, vol. 18, Issue 4, pp. 643-650, Apr. 1, 2012.
Traub, J., Stefan, P., Heining, S.M., Sielhorst, T., Riquarts, C., Eulerz, E., Navab, N. (2006): Hybrid Navigation Interface for Orthopedic and Trauma Surgery. R. Larsen, M. Nielsen, and J. Sporring (Eds.): MICCAI 2006, LNCS 4190, pp. 373-380.
Trevisan et al., "Towards Markerless Augmented Medical Visualization", AMI-ARCS, pp. 57-66, 2004.
Vagvolgyi et al., "Video to CT Registration for Image Overlay on Solid Organs", Procedural Augmented Reality in Medical Imaging and Augmented Reality in Computer-Aided Surgery (AMIARCS) pp. 78-86, 2008.
Vercauteren et al., "Real Time Autonomous Video Image Registration for Endomicroscopy: Fighting the Compromises", Three-Dimensional and Multidimensional Microscopy: Image Acquisition and Processing XV., vol. 6861, pp. 68610C. International Society for Optics and Photonics, Feb. 12, 2008.
Vogt et al., "Reality Augmentation for Medical Procedures: System Architecture, Single Camera Marker Tracking, and System Evaluation", International Journal of Computer Vision, vol. 70, No. 2, pp. 179-190, 2006.
Vogt, Sebastian, "Real-Time Augmented Reality for Image-Guided Interventions", PhD Thesis, Nürnberg: Der Technischen Fakultät der Universität Erlangen, 2009.
Wang et al., "3D Modeling from Wide Baseline Range Scans Using Contour Coherence", Proceedings of the IEEE Conference on Computer Vision and Pattern Recognition, pp. 4018-4025, 2014.
Wang et al., "Augmented Reality 3D Displays with Micro Integral Imaging"; Journal of Display Technology, Oct. 2014.
Wang et al., "Augmented Reality Navigation with Automatic Marker-Free Image Registration Using 3-D Image Overlay for Dental Surgery", IEEE Transactions on Biomedical Engineering, vol. 61, No. 4, pp. 1295-1304, Apr. 2014.
Wang H. et al., "Precision insertion of percutaneous sacroiliac screws using a novel augmented reality-based navigation system: a pilot study"., Intl. Orthop. (SICOT) 2016, 40: 1941-1947.
Watsen, K., et al., "A Handheld Computer as an Interaction Device to a Virtual Environment.", Proceedings of the International Projection Technologies Workshop, Stuttgart, Germany, May 10-11, 1999.
Weiss et al., "Augmented Reality Visualization Using Image-Overlay for MR-Guided Interventions: System Description, Feasibility, and Initial Evaluation in a Spine Phantom", Musculoskeletal Imaging, AJR:196, Mar. 2011, DOI:10.2214/AJR.10.5038.
Wellner, P., "Interacting with Paper on the DigitalDesk.", Communications of the ACM. 36, 7, 87- 96, (1993).
Wilson et al., "Validation of Three-Dimensional Models of the Distal Femur Created from Surgical Navigation Point Cloud Data"; CAOS 2015.
Yamazaki, K. et al., "Gesture Laser and Gesture Laser Car- Development of an Embodied Space to Support Remote Instruction.", In Bodker, S., Kyng, M. and Schmidt, K. (eds.), Proceedings of the Sixth European Conference on Computer Supported Cooperative Work—ECSC W'99, Sep. 12-16, Copenhagen, Denmark. Kluwer Academic Publishers, Dordrecht.
Yang H. et al., "Exploring collaborative navigation.", Proceedings of the 4th international conference on Collaborative virtual environments, CVE, pp. 135-142, (2002).
Ye et al., "Accurate 3D Pose Estimation from a Single Depth Image", IEEE International Conference on Computer Vision (ICCV), pp. 731-738, Nov. 2011.
Yoon et al., "Technical Feasibility and Safety of an Intraoperative Head-Up Display Device During Spine Instrumentation", The International Journal of Medical Robotics and Computer Assisted Surgery, vol. 13, No. 3, pp. 1-9, Sep. 2017.
International Search Report in PCT/US2022/019825 mailed Aug. 15, 2022.

* cited by examiner

AUGMENTED REALITY MAN-MACHINE INTERFACE FOR ROBOTIC SURGERY

RELATED APPLICATIONS

This application is a continuation of U.S. patent application Ser. No. 17/691,923, filed Mar. 10, 2022, which claims the benefit of and the priority to U.S. Provisional Application Ser. No. 63/158,941, filed Mar. 10, 2021, U.S. Provisional Application Ser. No. 63/163,156, filed Mar. 19, 2021, U.S. Provisional Application Ser. No. 63/173,565, filed Apr. 12, 2021, and U.S. Provisional Application Ser. No. 63/232,376, filed Aug. 12, 2021, the entire contents of each of which is hereby incorporated by reference in their entireties.

TECHNICAL FIELD

Aspects of the present disclosure relate to systems, devices and methods for performing a surgical step or surgical procedure with visual guidance using one or more head mounted displays and with display of one or more imaging studies. Aspects of the present disclosure relate to systems, devices and methods for operating one or more head mounted displays with real-time wireless display of tracking information of tools or instruments registered with the patient's anatomy. Aspects of the present disclosure relate to systems, devices and methods for operating an imaging system with augmented reality display of an image acquisition area or volume prior to image acquisition.

BACKGROUND

With computer assisted surgery, e.g. surgical navigation or robotics, pre-operative and/or intra-operative imaging studies of the patient can be used. The imaging studies can be displayed in the operating room on an external computer monitor and the patient's anatomy, e.g. landmarks, can be registered in relationship to the information displayed on the monitor. Since the surgical field is in a different location and has a different view coordinate system for the surgeon's eyes than the external computer monitor, hand-eye coordination can be challenging for the surgeon. Image acquisition for pre-operative and/or intra-operative imaging studies frequently requires the acquisition of imaging data prior to acquiring the definitive imaging studies, for example used for diagnostic purposes or image guidance purposes.

SUMMARY

Aspects of the disclosure relate to a system comprising at least one head mounted display, a robot, wherein the robot comprises an end effector, a first computing system comprising one or more computer processors, and a second computing system comprising one or more computer processors, wherein the first computing system is in communication with the robot, wherein the second computing system is in communication with the at least one head mounted display, wherein the second computing system is configured to display, by the at least one head mounted display, a virtual user interface comprising at least one virtual object, wherein the second computing system is configured to generate a command based at least in part on at least one interaction with the at least one virtual object displayed in the virtual user interface, wherein the second computing system is configured to transmit the command to the first computing system using wireless transmission, wherein the command is configured to cause the first computing system to control the robot for movement, activation, operation, de-activation, or any combination thereof, of a robot component, a robot motor, a robot actuator, a robot drive, a robot controller, a robot hydraulic system, a robot piezoelectric system, a robot switch, the end effector, or any combination thereof.

In some embodiments, the command is configured to control the end effector within a predetermined operating boundary, a predetermined operating range, a predetermined operating zone, or a predetermined operating volume.

In some embodiments, the first computing system is connected to the robot by wire, or wherein the first computing system is connected to the robot by wireless connection.

In some embodiments, the second computing system is connected to the at least one head mounted display by wire, or wherein the second computing system is connected to the at least one head mounted display by wireless connection.

In some embodiments, the second computing system is configured to display, by the at least one head mounted display, a representation of a predetermined operating boundary, a predetermined operating range, a predetermined operating zone, or a predetermined operating volume of the end effector or an expected outcome following the movement, activation, operation, de-activation or a combination thereof of the robot component, robot motor, robot actuator, robot drive, robot controller, robot hydraulic system, robot piezoelectric system, robot switch, the end effector, or any combination thereof.

In some embodiments, the end effector comprises a physical surgical tool or a physical surgical instrument.

In some embodiments, the first computing system is configured to obtain real-time tracking information of a component of the robot, the end effector, a target object, a target anatomic structure of a patient, the at least one head mounted display, a physical tool, a physical instrument, a physical implant, a physical object, or any combination thereof.

In some embodiments, the second computing system is configured to obtain real-time tracking information of a component of the robot, the end effector, a target object, a target anatomic structure of a patient, the at least one head mounted display, a physical tool, a physical instrument, a physical implant, a physical object, or any combination thereof.

In some embodiments, the first computing system is configured to obtain real-time tracking information of a physical tool, a physical instrument, or any combination thereof coupled to the robot.

In some embodiments, the second computing system is configured to obtain real-time tracking information of a physical tool, a physical instrument, or any combination thereof coupled to the robot. In some embodiments, the first computing system is configured to wirelessly transmit the real-time tracking information of the component of the robot, the end effector, a target object, a target anatomic structure of a patient, the at least one head mounted display, a physical tool, a physical instrument, a physical implant, a physical object, or any combination thereof. In some embodiments, the second computing system is configured to wirelessly transmit the real-time tracking information of the component of the robot, the end effector, a target object, a target anatomic structure of a patient, the at least one head mounted display, a physical tool, a physical instrument, a physical implant, a physical object, or any combination thereof.

In some embodiments, the second computing system is configured for displaying, by the at least one head mounted display, a 3D stereoscopic view. In some embodiments, the 3D stereoscopic view is superimposed onto an anatomic structure of a patient. In some embodiments, the 3D stereoscopic view comprises a predetermined trajectory of the end effector, a representation of a predetermined operating boundary of the end effector, a representation of a predetermined operating range of the end effector, a representation of a predetermined operating zone of the end effector, a representation of a predetermined operating volume of the end effector, or a combination thereof. In some embodiments, the 3D stereoscopic view comprises a predetermined trajectory of the end effector, a representation of a predetermined operating boundary of the end effector, a representation of a predetermined operating range of the end effector, a representation of a predetermined operating zone of the end effector, a representation of a predetermined operating volume of the end effector or a combination thereof following the movement, activation, operation, deactivation or combination thereof of the robot component, robot motor, robot actuator, robot drive, robot controller, robot hydraulic system, robot piezoelectric system, robot switch, the end effector or any combination thereof.

In some embodiments, the first computing system, the second computing systems or both are configured to turn on or turn off the display of the virtual user interface. In some embodiments, the 3D stereoscopic view comprises a predetermined trajectory of the end effector, a representation of a predetermined operating boundary of the end effector, a representation of a predetermined operating range of the end effector, a representation of a predetermined operating zone of the end effector, a representation of a predetermined operating volume of the end effector or a combination thereof prior to executing the command.

In some embodiments, the wireless transmission comprises a Bluetooth signal, WiFi signal, LiFi signal, a radiofrequency signal, a microwave signal, an ultrasound signal, an infrared signal, an electromagnetic wave or any combination thereof.

In some embodiments, the system comprises two or more head mounted displays, wherein the wireless transmission is a multicast, broadcast transmission or any combination thereof.

In some embodiments, the at least one virtual object comprises one or more virtual button, virtual field, virtual cursor, virtual pointer, virtual slider, virtual trackball, virtual node, virtual numeric display, virtual touchpad, virtual keyboard, or a combination thereof.

In some embodiments, the interaction is a collision detection between a physical object and the at least one virtual object. In some embodiments, the interaction is a collision detection between a user's finger and the at least one virtual object. In some embodiments, the interaction is a collision detection between a tracked pointer, tracked tool, tracked instrument, or a combination thereof and the at least one virtual object.

In some embodiments, the interaction with the at least one virtual object comprises a gaze tracking.

Aspects of the disclosure relate to a system comprising at least one head mounted display, a robot, wherein the robot comprises an end effector, a first computing system comprising one or more computer processors, wherein the first computing system is in communication with the robot, a second computing system comprising one or more computer processors, wherein the second computing system is in communication with the at least one head mounted display, wherein the second computing system is configured to display, by the at least one head mounted display, a virtual user interface comprising at least one virtual object, wherein the second computing system is configured to generate an event message based at least in part on at least one interaction with the at least one virtual object displayed in the virtual user interface, wherein the second computing system is configured to transmit the event message to the first computing system using wireless transmission, wherein the second computing system is configured to generate a command based on the event message, and wherein the command is configured to cause the first computing system to control the robot for movement, activation, operation, deactivation, or any combination thereof, of a robot component, a robot motor, a robot actuator, a robot drive, a robot controller, a robot hydraulic system, a robot piezoelectric system, a robot switch, the end effector, or any combination thereof.

In some embodiments, the end effector comprises a scalpel, a saw, a cutting tool, a wire, a needle, a pin, a drill, a burr, a mill, a reamer, an impactor, a broach, a laser, a radiofrequency device, a thermocoagulation device, a cryoablation device, a radioactive probe, a radioactivity emitting device, a pulsed energy emitting device, an ultrasonic energy emitting device, a microwave energy emitting device or a combination thereof.

In some embodiments, the command comprises a subcommand, wherein the subcommand is configured to execute an accept or cancel function of the command.

Aspects of the disclosure relate to system, comprising: (a) at least one head mounted display, at least one camera or scanning device, wherein the at least one camera or scanning device is configured to track real-time information of the at least one head mounted display, of at least one anatomic structure of a patient, and of at least one physical surgical tool or physical surgical instrument, (b) a first computing system comprising one or more computer processors, wherein the first computing system is configured to obtain the real-time tracking information of the at least one head mounted display, the at least one anatomic structure of a patient, and the at least one physical surgical tool or physical surgical instrument, wherein the first computing system is configured for wireless transmission of the real-time tracking information of the at least one head mounted display, the at least one anatomic structure of the patient, and the at least one physical surgical tool or physical surgical instrument, (c) a second computing system comprising one or more computer processors, wherein the second computing system is configured for wireless reception of the real-time tracking information of the at least one head mounted display, the at least one anatomic structure of the patient, and the at least one physical surgical tool or physical surgical instrument, wherein the second computing system is configured to generate a 3D stereoscopic view, wherein the stereoscopic view comprises a 3D representation of the at least one tracked physical surgical tool or physical surgical instrument, and wherein the at least one head mounted display is configured to display the 3D stereoscopic view.

In some embodiments, the one or more computer processors of the second computing system generate the 3D stereoscopic view for a view angle of the head mounted display relative to the at least one anatomic structure of the patient using the real-time tracking information of the at least one head mounted display.

In some embodiments, the real-time tracking information comprises tracking information of multiple head mounted displays. In some embodiments, the real-time tracking information comprises a head mounted display specific label or tag for each head mounted display, or wherein the real-time tracking information is labeled for each tracked head mounted display. In some embodiments, the wireless transmission is a multicast or broadcast transmission to the multiple head mounted displays.

In some embodiments, the real-time tracking information comprises tracking information of two or more head mounted displays. In some embodiments, the two or more head mounted displays are located in different locations. In some embodiments, the real-time tracking information comprises a head mounted display label for each head mounted display, wherein each heard mounted display has a different label. In some embodiments, the real-time tracking information is labeled for each tracked head mounted display.

In some embodiments, the one or more computer processors of the second computing system generate the 3D stereoscopic view for an interpupillary distance adjusted for a user wearing the head mounted display.

In some embodiments, the second computing system is communicatively coupled to the at least one head mounted display.

In some embodiments, the second computing system is integrated with the at least one head mounted display.

In some embodiments, the second computing system is separate from the at least one head mounted display and is connected to a display unit of the at least one head mounted display using at least one cable.

In some embodiments, the wireless transmission, the wireless reception, or both comprise a WiFi signal, a LiFi signal, a Bluetooth signal or a combination thereof.

In some embodiments, the camera or scanning device is separate from the at least one head mounted display.

In some embodiments, the camera or scanning device is integrated or attached to the at least one head mounted display.

In some embodiments, the wireless transmission comprises sending data packets comprising the real-time tracking information of the at least one head mounted display, the at least one anatomic structure of a patient, and the at least one physical surgical tool or physical surgical instrument, at a rate of 20 Hz or greater.

In some embodiments, the wireless reception comprises receiving data packets comprising the real-time tracking information of the at least one head mounted display, the at least one anatomic structure of a patient, and the at least one physical surgical tool or physical surgical instrument, at a rate of 20 Hz or greater.

In some embodiments, the system further comprises a third computing system, wherein the third computing system is configured for wireless reception of the real-time tracking information from the first computing system and wherein the third computing system is configured for wireless transmission of the real-time tracking information to the second computing system. In some embodiments, the third computing system comprises a chain of computing systems configured for wireless reception and wireless transmission of the real-time tracking information.

In some embodiments, the system further comprises a third computing system, wherein the third computing system is communicatively coupled to a second head mounted display, wherein the third computing system is configured for wireless reception of the real-time tracking information of the second head mounted display, the at least one anatomic structure of a patient, and the at least one physical surgical tool or physical surgical instrument, wherein the third computing system is configured to generate a 3D stereoscopic view by the second head mounted display using the tracking information of the second head mounted display.

In some embodiments, the tracking information of the second head mounted comprises a label specific to the second head mounted display for identifying the tracking information of the second head mounted display by the third computing system.

In some embodiments, the system further comprises a fourth computing system, wherein the fourth computing system is communicatively coupled to a third head mounted display, wherein the fourth computing system is configured for wireless reception of the real-time tracking information of the third head mounted display, the at least one anatomic structure of a patient, and the at least one physical surgical tool or physical surgical instrument, wherein the fourth computing system is configured to generate a 3D stereoscopic view by the third head mounted display using the tracking information of the third head mounted display.

In some embodiments, the tracking information of the third head mounted comprises a label specific to the third head mounted display for identifying the tracking information of the third head mounted display by the fourth computing system.

In some embodiments, the system further comprises a fifth computing system, wherein the fifth computing system is communicatively coupled to a fourth head mounted display, wherein the fifth computing system is configured for wireless reception of the real-time tracking information of the fourth head mounted display, the at least one anatomic structure of a patient, and the at least one physical surgical tool or physical surgical instrument, wherein the fifth computing system is configured to generate a 3D stereoscopic view by the fourth head mounted display using the tracking information of the fourth head mounted display.

In some embodiments, the tracking information of the fourth head mounted comprises a label specific to the fourth head mounted display for identifying the tracking information of the fourth head mounted display by the fifth computing system.

In some embodiments, the real-time tracking information comprises one or more coordinates. In some embodiments, the one or more coordinates comprise coordinates of the at least one anatomic structure of the patient. In some embodiments, the one or more coordinates comprise coordinates of the at least one physical surgical tool or physical surgical instrument. In some embodiments, the one or more coordinates comprise coordinates of the at least one head mounted display.

In some embodiments, the at least one head mounted display comprises at least one optical see-through head mounted display.

In some embodiments, the at least one head mounted display comprises at least one video see-through head mounted display.

In some embodiments, the at least one camera or scanning device comprises a laser scanner, a time-of-flight 3D laser scanner, a structured-light 3D scanner, a hand-held laser scanner, a LIDAR scanner, a time-of-flight camera, a depth camera, a video system, a stereoscopic camera system, a camera array, or a combination thereof.

In some embodiments, the system comprises at least one inertial measurement unit. In some embodiments, the at least one inertial measurement unit is integrated or attached to the at least one physical surgical tool or physical surgical instrument. In some embodiments, the at least one inertial measurement unit is integrated or attached to the at least one anatomic structure of the patient. In some embodiments, the at least one inertial measurement unit is integrated or attached to the at least one head mounted display. In some embodiments, the real-time tracking information of the at least one head mounted display comprises information from the at least one inertial measurement unit.

Aspects of the disclosure relate to a system, comprising (a) two or more head mounted displays, (b) at least one camera or scanning device, wherein the at least one camera or scanning device is configured to track real-time information of the two or more head mounted displays, of at least one anatomic structure of a patient, and of at least one physical surgical tool or physical surgical instrument, (c) a first computing system comprising one or more computer processors, wherein the first computing system is configured to obtain real-time tracking information of at least one anatomic structure of a patient, of at least one physical surgical tool or physical surgical instrument, and of the two or more head mounted displays, wherein the tracking information of the two or more head mounted displays is labeled for each of the two or more head mounted displays, wherein the first computing system is configured for wireless transmission of the real-time tracking information of the at least one anatomic structure of the patient, the tracking information of the at least one physical surgical tool or physical surgical instrument, and the labeled tracking information of the two or more head mounted displays, (d) a second computing system, wherein the second computing system is configured for wireless reception of the real-time tracking information of the at least one anatomic structure of the patient, the tracking information of the at least one physical surgical tool or physical surgical instrument, and the labeled tracking information of the first of the two or more head mounted displays, wherein the second computing system is configured to generate a first 3D stereoscopic display specific for a first viewing perspective of the first head mounted display using the labeled tracking information of the first head mounted display, wherein the first head mounted display is configured to display the 3D stereoscopic display, (e) a third computing system, wherein the third computing system is configured for wireless reception of the real-time tracking information of the at least one anatomic structure of the patient, the tracking information of the at least one physical surgical tool or physical surgical instrument, and the labeled tracking information of the second of the two or more head mounted displays, wherein the third computing system is configured to generate a second 3D stereoscopic display specific for a second viewing perspective of the second head mounted display using the labeled tracking information of the second head mounted display, wherein the first and second stereoscopic displays comprise a 3D representation of the at least one physical surgical tool or physical surgical instrument.

In some embodiments, the second computing system is communicatively coupled to a first of the two or more head mounted displays, and wherein the third computing system is communicatively coupled to a second of the two or more head mounted displays.

Aspects of the disclosure relate to a system of preparing an imaging data acquisition associated with a patient comprising at least one computer processor, an augmented reality display device, an imaging system, wherein the at least one computer processor is configured to obtain real-time tracking information of one or more components of the imaging system, wherein the at least one computer processor is configured to generate a 3D representation of a surface, a volume or combination thereof, wherein the 3D representation of the surface, volume or combination thereof is at least in part derived from information about a geometry of the one or more components of the imaging system, information about a geometry of the image acquisition, information about one or more image acquisition parameters, or a combination thereof, wherein the at least one computer processor is configured to generate an augmented view, the augmented view comprising the 3D representation of the surface, volume or combination thereof, wherein the at least one computer processor is configured to display, by the augmented reality display device, the augmented view at a defined position and orientation relative to the one or more components of the imaging system, and wherein the position and orientation of the augmented view is updated based on the real time tracking information of the one or more components of the imaging system.

In some embodiments, the 3D representation of the surface, volume or combination thereof does not contain imaging data from a patient.

In some embodiments, the imaging system is configured to acquire 2D, 3D, or 2D and 3D imaging data of the patient within the 3D representation of the surface, volume or combination thereof.

In some embodiments, the at least one computer processor is configured to generate the 3D representation of the surface, volume or combination thereof before acquisition of 2D, 3D, or 2D and 3D imaging data of the patient, or wherein the at least one computer processor is configured to display the 3D representation of the surface, volume or combination thereof before acquisition of 2D, 3D, or 2D and 3D imaging data of the patient.

In some embodiments, the surface, volume or combination thereof comprises information about a limit, an edge, a margin, a boundary, a circumference, a perimeter, an envelope or a combination thereof of a 2D, 3D, or 2D and 3D imaging data acquisition.

In some embodiments, the at least one computer processor is configured to generate the surface, volume or combination thereof at least in part from information about a geometry of the imaging system, information about a geometry of the image acquisition, information about one or more image acquisition parameters, or a combination thereof.

In some embodiments, the system is configured to facilitate determining a desired position and orientation of the augmented view, wherein the desired position and orientation comprises a target anatomic structure of the patient.

In some embodiments, the at least one computer processor is configured to adjust the augmented view responsive to movement of the one or more tracked components of the imaging system, wherein the adjustment is configured to maintain the augmented view at the defined position and orientation relative to the one or more components of the imaging system.

In some embodiments, the information about the geometry of the imaging system, information about the geometry of the image acquisition, information about one or more image acquisition parameter, or a combination thereof comprises information about one or more imaging system components, a geometric relationship between one or more imaging system components, a collimator, a grid, an image intensifier, a detector resolution, an x-ray source, an x-ray tube setting, a kVp setting, an mA setting, an mAs setting, a collimation, a tube—detector distance, a tube—patient distance, patient—detector distance, a patient—image intensifier distance, a table height relative to a tube, a detector, a table position relative to a tube, a detector, or combination thereof, a patient position, a C-arm position, orientation, or combination thereof, a gantry position, orientation or combination thereof, a grid height, a grid width, a grid ratio, a field of view, a center of a field of view, a periphery of a field of view, a matrix, a pixel size, a voxel size, an image size, an image volume, an imaging plane, an image dimension in x, y, z and/or oblique direction, an image location, an image volume location, a scan coverage, a pitch, an in-plane resolution, a slice thickness, an increment, a detector configuration, a detector resolution, a detector density, a tube current, a tube potential, a reconstruction algorithm, a scan range, a scan boundary, a scan limit, a rotational axis of the imaging system, a rotational center of the imaging system, a reconstructed slice thickness, a segmentation algorithm, a window, a level, a brightness, a contrast, a display resolution, or a combination thereof.

In some embodiments, the imaging system comprises an x-ray system, a fluoroscopy system, a C-arm, a 3D C-arm, a digital tomosynthesis imaging system, an angiography system, a bi-planar angiography system, a 3D angiography system, a CT scanner, an MRI scanner, a PET scanner, a SPECT scanner, a nuclear scintigraphy system, a 2D ultrasound imaging system, a 3D ultrasound imaging system, or a combination thereof.

In some embodiments, the at least one computer processor is configured to obtain real-time tracking information of the augmented reality display device, an anatomic structure of the patient, a patient table used with the imaging system, the imaging system, the one or more components of the imaging system, or a combination thereof.

In some embodiments, the system further comprises a camera or scanner configured to acquire the real-time tracking information of the augmented reality display device, the anatomic structure of the patient, the patient table used with the imaging system, the imaging system, the one or more components of the imaging system, or a combination thereof. In some embodiments, the camera or scanner comprises a navigation system, a 3D scanner, a LIDAR system, a depth sensor, an IMU or a combination thereof. In some embodiments, the real-time tracking information comprises coordinate information of the augmented reality display device, the anatomic structure of the patient, the patient table used with the imaging system, the imaging system, the one or more components of the imaging system, or a combination thereof.

In some embodiments, the real-time tracking information comprises location information of the augmented reality display device, the anatomic structure of the patient, the patient table used with the imaging system, the imaging system, one or more components of the imaging system components, or a combination thereof. In some embodiments, the camera or scanner comprises a laser scanner, time-of-flight 3D scanner, structured-light 3D scanner, hand-held laser scanner, a time-of-flight camera or a combination thereof.

In some embodiments, the system is configured to obtain real-time tracking information of the imaging system using intrinsic information from the imaging system, wherein the intrinsic information comprises pose data, sensor data, camera data, 3D scanner data, controller data, drive data, actuator data, end effector data, data from one or more potentiometers, data from one or more video systems, data from one or more LIDAR systems, data from one or more depth sensors, data from one or more inertial measurement units, data from one or more accelerometers, data from one or more magnetometers, data from one or more gyroscopes, data from one or more force sensors, data from one or more pressure sensors, data from one or more position sensors, data from one or more orientation sensors, data from one or more motion sensors, position and/or orientation data from step motors, position and/or orientation data from electric motors, position and/or orientation data from hydraulic motors, position and/or orientation data from electric and/or mechanical actuators, position and/or orientation data from drives, position and/or orientation data from robotic controllers, position and/or orientation data from one or more robotic computer processors, or a combination thereof.

In some embodiments, the imaging system is configured to generate an x-ray beam. In some embodiments, the x-ray beam of the imaging system is cone shaped or cylindrical. In some embodiments, the x-ray beam of the imaging system originates from one or more point sources.

In some embodiments, the x-ray beam of the imaging system is collimated.

In some embodiments, the imaging system is configured to generate an x-ray beam, wherein the 3D representation of the surface, volume or combination thereof comprises information about a limit, an edge, a margin, a boundary, a circumference, a perimeter, an envelope or a combination thereof of the x-ray beam.

In some embodiments, the system further comprising a user interface. In some embodiments, the user interface comprises a virtual user interface, wherein the virtual interface comprises at least one virtual object. In some embodiments, the at least one virtual object comprises one or more virtual button, virtual field, virtual cursor, virtual pointer, virtual slider, virtual trackball, virtual node, virtual numeric display, virtual touchpad, virtual keyboard, or a combination thereof. In some embodiments, the virtual user interface comprises a gesture recognition, gaze recognition, gaze lock, eye tracking, hand tracking, pointer tracking, instrument tracking, tool tracking, or a combination thereof. In some embodiments, the at least one computer processor is configured to generate a command based at least in part on at least one interaction of a user with the at least one virtual object displayed in the virtual user interface. In some embodiments, the command is configured to move, tilt, or rotate one or more components of the imaging system, one or more components of a patient table or a combination thereof. In some embodiments, the command is configured to activate, operate, de-activate or a combination thereof a motor, an actuator, a drive, a controller, a hydraulic system, a switch, an electronic circuit, a computer chip, an x-ray tube, an image intensifier, a functional unit of an imaging system, or a combination thereof. In some embodiments, the command is configured to move or modify a geometry of the imaging system, a patient table, a geometric relationship between one or more imaging system components, a collimator, a grid, an image intensifier, a detector resolution, a setting of the imaging system, a parameter of the imaging system, a parameter of the imaging data acquisition, a display parameter, an x-ray source setting, an x-ray tube setting, a kVp setting, an mA setting, an mAs setting, a collimation, a tube—detector distance, a tube—patient distance, patient—detector distance, a patient—image intensifier distance, a table height relative to a tube, a detector, a table position relative to a tube, a detector, a patient position, a C-arm position, orientation, or combination thereof, a gantry position, orientation or combination thereof, a grid height, a grid width, a grid ratio, a field of view, a matrix, a pixel size, a voxel size, an image size, an image volume, an imaging plane, an image dimension in x, y, z and/or oblique direction, an image location, an image volume location, a scan coverage, a pitch, an in-plane resolution, a slice thickness, an increment, a detector configuration, a detector resolution, a detector density, a tube current, a tube potential, a reconstruction algorithm, a scan range, a scan boundary, a scan limit, a reconstructed slice thickness, a segmentation algorithm, a window, a level, a brightness, a contrast, a display resolution, or a combination thereof. In some embodiments, the command is configured to set and/or modify one or more image acquisition parameters of the imaging system. In some embodiments, the command is configured to set, move, and/or modify a position, orientation, size, area, volume, or combination thereof of a 2D, 3D or 2D and 3D imaging data acquisition. In some embodiments, the command is configured to set, move, and/or modify one or more coordinates of the 3D representation. In some embodiments, the command is configured to set, move and/or modify a dimension, a size, an area, a volume or a combination thereof of the 3D representation. In some embodiments, the setting, moving, and/or modifying of the dimension, size, area, volume or a combination thereof of the 3D representation is configured to set, move and/or modify a 2D, 3D or 2D and 3D imaging data acquisition to remain at the location of the 3D representation. In some embodiments, the command is configured to activate, operate, de-activate or a combination thereof a sensor, a camera, a video system, a 3D scanner, a Lidar system, a navigation system, a potentiometer, a piezoelectric system, a piezoelectric mechanism, a piezoelectric lock or release system, a controller, a drive, a motor, a hydraulic system, an actuator, or a combination thereof of the imaging system, an imaging system component, a patient table or a combination thereof. In some embodiments, the sensor comprises a depth sensor, inertial measurement unit, accelerometer, magnetometer, gyroscope, force sensor, pressure sensor, position sensor, orientation sensor, motion sensor, or a combination thereof.

In some embodiments, one or more components of the imaging system are attached to or integrated into a robot. In some embodiments, the robot is configured to move one or more components of the imaging system.

In some embodiments, the virtual user interface is configured to generate an event message triggered by a collision detection. In some embodiments, the system further comprises an event handler configured to process the event message. In some embodiments, the event handler is configured to generate a command.

In some embodiments, the computing system is configured to generate a command, wherein the command is triggered by the virtual user interface.

In some embodiments, the system is configured to determine a desired location of the augmented view associated with the imaging system to acquire 2D, 3D, or 2D and 3D imaging data at the desired location.

In some embodiments, the augmented reality display device is a head mounted display, and the augmented view comprises a 3D stereoscopic view.

In some embodiments, the at least one computer processor is configured to project the 3D stereoscopic view at the coordinates of intended 2D, 3D or 2D and 3D imaging data acquisition of the patient. In some embodiments, the location of the 2D, 3D, or 2D and 3D imaging data acquisition comprises one or more target anatomic structures of the patient.

Aspects of the disclosure relate to a method of preparing an image acquisition by an imaging system in a patient comprising: tracking one or more components of the imaging system in real time; obtaining, by the at least one computer processor, information about a geometry of one or more components of the imaging system, information about a geometry of the image acquisition, information about one or more image acquisition parameters, or a combination thereof; generating, by the at least one computer processor, a 3D representation of a surface, a volume or combination thereof, wherein the 3D representation of the surface, the volume or combination thereof is at least in part derived from the information about the geometry of the one or more components of the imaging system, information about the geometry of the image acquisition, information about the one or more image acquisition parameters, or combination thereof; generating, by the at least one computer processor, an augmented view, the augmented view comprising the 3D representation of the surface, volume or combination thereof; and displaying, by an augmented reality display device, the augmented view, wherein the position and orientation of the augmented view is defined relative to the one or more components of the imaging system and is updated based on real time tracking information of the one or more components of the imaging system.

In some embodiments, the 3D representation of the surface, volume or combination thereof does not contain imaging data from the patient.

In some embodiments, the imaging system is configured to acquire 2D, 3D, or 2D and 3D imaging data of the patient, and wherein the 2D, 3D, or 2D and 3D imaging data of the patient are acquired within the 3D representation of the surface, volume or combination thereof.

In some embodiments, the augmented view at the defined position relative to the one or more components of the imaging system moves in relation with the tracked one or more components of the imaging system, wherein the moving facilitates superimposing or aligning the 3D representation with a target anatomic structure of the patient.

In some embodiments, the position, orientation, position and orientation of the augmented view is adjusted in response to movement of the tracked one or more components of the imaging system.

In some embodiments, the step of generating the augmented view is before the step of acquiring 2D, 3D, or 2D and 3D imaging data of the patient, or wherein the step of displaying the augmented view is before the step of acquiring 2D, 3D, or 2D and 3D imaging data of the patient.

In some embodiments, the augmented reality display device is a head mounted display, and wherein the augmented view comprises a 3D stereoscopic view.

BRIEF DESCRIPTION OF THE DRAWINGS

Illustrative, non-limiting example embodiments will be more clearly understood from the following detailed description taken in conjunction with the accompanying drawings.

DETAILED DESCRIPTION

Figure 1:
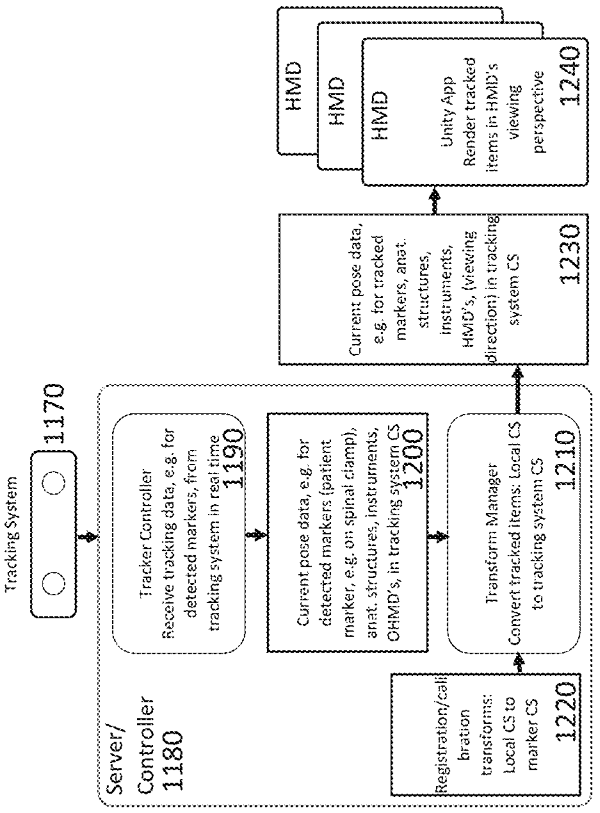
FIG. 1 shows a non-limiting example of a system configuration for tracking of, for example, anatomic structures, instruments, implants, robots, imaging systems, or any combination thereof and display by one or more including multiple head mounted displays, e.g. with rendering for the viewing direction of each head mounted display.

The following description provides exemplary embodiments only, and is not intended to limit the scope, applicability, or configuration of the disclosure. Rather, the following description of the exemplary embodiments will provide those skilled in the art with an enabling description for implementing one or more exemplary embodiments. It will be understood that various changes may be made in the function and arrangement of elements without departing from the spirit and scope of the presently disclosed embodiments.

Aspects of the present disclosure provide, among other things, systems, devices and methods for a simultaneous visualization of live data of the patient and digital representations of virtual data such as virtual operating ranges, virtual operating areas, virtual operating volumes, e.g. for robots and/or imaging system, virtual image acquisition ranges, virtual image acquisition areas, virtual image acquisition volumes, e.g. for imaging systems, virtual cuts and/or virtual surgical guides including cut blocks, drilling guides, one or more virtual axes, one or more virtual planes or a combination thereof through a head mounted display (HMD) or other augmented reality display system. In some embodiments, the system can include one or more HMDs or other augmented reality display systems, one or more processors and one or more user interfaces. In some embodiments, the surgical site including live data of the patient, the HMD, and the virtual data are registered in a common coordinate system. In some embodiments, the virtual data are superimposed onto and aligned with the live data of the patient. In some embodiments, the head mounted display is a see-through HMD, e.g. a video see-through HMD or an optical see-through HMD. Unlike virtual reality head systems that blend out live data, the HMD can allow the surgeon to see the live data of the patient through the HMD, e.g. the surgical field, while at the same time observing virtual data of the patient and/or virtual surgical instruments or implants with a predetermined position and/or orientation using the display of the HMD unit.

In any of the embodiments of the disclosure, a video see-through HMD or an optical see-through HMD can be used. In any of the embodiments of the disclosure, other augmented reality display devices can be used, e.g. in conjunction with an HMD or instead of an HMD, for example a tablet, e.g. an iPad (Apple, Cupertino, CA) or Surface (Microsoft, Redmond, WI), or a smart phone, e.g. an iPhone (Apple Cupertino, CA). When other augmented reality display devices are used, they can comprise an optional video camera or scanner, e.g. 3D scanner, including, for example, a LIDAR system, for scanning physical objects, such as an imaging system, a surgical robot (also referred herein as robotic system or surgical robotic system), an OR table, a patient on the OR table, an imaging system table, a patient on the imaging system table, a physical tool, a physical instrument, an end effector etc. The augmented reality display can comprise a composite or mixed reality or augmented reality display of the video feed and virtual devices or virtual objects, e.g. a virtual end effector or a 3D representation of an x-ray beam or intended image acquisition. Any virtual devices, virtual surgical guide, virtual tool or instrument, or virtual object known in the art or described in the specification can be co-displayed with the video feed or video images. The virtual devices, virtual surgical guide, virtual tool or instrument, or virtual object known in the art or described in the specification can be displayed in conjunction with the video feed and can optionally be registered with the physical objects, devices (e.g. an imaging system or a surgical robot) or a physical patient or target anatomic structure included in the video feed or video images. Any of the registration techniques described in the specification or known in the art can be used. The terms mixed reality and augmented reality as used throughout the disclosure can be used interchangeably. In any of the illustrations, the term HMD (i.e. head mounted display) can be used interchangeably with an augmented reality display device, mixed reality display device, e.g. a tablet or smart phone. In some embodiments, the terms head mounted display, HMD, augmented reality display device, mixed reality display device can be used interchangeably.

In some embodiments, an operator such as a surgeon can look through an HMD observing physical data or information on a patient, e.g. a surgical site or changes induced on a surgical site, while pre-existing data of the patient are superimposed onto the physical visual representation of the live patient. Systems, methods and techniques to improve the accuracy of the display of the virtual data superimposed onto the live data of the patient are described in International Patent Application No. PCT/US2018/012459, which is incorporated herein by reference in its entirety.

Methods and systems of registration and cross-referencing including registration and cross-referencing surgical sites and one or more HMDs or other augmented reality display systems (e.g. using inside-out tracking techniques, outside-in tracking techniques, and combinations thereof) such as the ones described in PCT International Application Serial Nos. PCT/US2017/021859, PCT/US2018/013774 and PCT/US2019/015522 can be used. Methods, techniques, and systems of displaying virtual data in various surgical, medical or dental applications using one or more HMDs or other augmented reality display systems such as the ones described in PCT International Application Serial Nos. PCT/US2017/021859, PCT/US2018/013774, PCT/US2019/61698, PCT/US2019/015522, and U.S. Pat. No. 9,861,446 can be used. These applications are hereby incorporated by reference in their entireties.

Aspects of the present disclosure relate to systems, devices and methods for performing a surgical step or surgical procedure with visual guidance using a head mounted display. In some embodiments, the head mounted display can be a see-through head mounted display, e.g. an optical see-through head mounted display, for example for augmented reality applications. In some embodiments, the head mounted display can be a non-see through head mounted display, e.g. video-see through type, for virtual reality applications, optionally with video display including video streaming of live data from the patient, e.g. video feed from a camera integrated into, attached to, or separate from the head mounted display. The head mounted display can provide surgical guidance in a mixed reality environment.

Some aspects of the disclosure relate to a system for performing a surgical procedure, the system comprising: a processor; a see-through head mounted display or other augmented reality display device; and a marker attached to a patient, wherein, the system is configured to generate a 3D stereoscopic view or augmented view of a virtual surgical guide, wherein the virtual surgical guide is a placement indicator at one or more predetermined coordinates indicating a predetermined position, predetermined orientation or combination thereof for aligning a physical surgical tool or a physical surgical instrument, wherein the system is configured to display the 3D stereoscopic view by the see through head mounted display onto the patient, e.g. a patient's spine, a patient's joint, a patient's tooth, gum, dental structure or combination thereof. The processor can be configured to determine a distance between one or more predetermined coordinates of the virtual surgical guide and the see through head mounted display, wherein the one or more predetermined coordinates of the virtual surgical guide can be referenced to or based on the marker. In some embodiments, the processor can be configured to adjust at least one focal plane, focal point, convergence or combination thereof of the display of the 3D stereoscopic view based on a determined distance, e.g. using inside-out or outside-in tracking or a combination thereof.

In some embodiments, the system can be configured to track, e.g. in real-time, a robot component, an end effector, an imaging system component, or a combination thereof. Inside-out tracking can comprise tracking, for example, a head mounted display, an augmented reality display device, an anatomic structure of the patient, a patient table used with the imaging system, an imaging system, one or more components of the imaging system, a surgical instrument, a surgical tool, an implant, a surgical robot, a robot integrated with or part of the imaging system, a physical object or any combination thereof using at least one camera, scanner (including navigation systems, LIDAR systems etc.) or combination thereof integrated into a head mounted display or augmented reality display device. Outside-in tracking can comprise tracking, for example, a head mounted display, an augmented reality display device, an anatomic structure of the patient, a patient table used with the imaging system, an imaging system, one or more components of the imaging system, a surgical instrument, a surgical tool, an implant, a surgical robot, a robot integrated with or part of the imaging system, a physical object or any combination thereof using at least one camera, scanner (including navigation systems, LIDAR systems etc.) or combination thereof separate from a head mounted display or augmented reality display device.

In some embodiments, the system comprises one or more markers. In some embodiments, the marker can be configured to reflect or emit light with a wavelength between 380 nm and 700 nm.

In some embodiments, the marker can be configured to reflect or emit light with a wavelength greater than 700 nm. In some embodiments, the marker can be a radiofrequency marker, or the marker can be an optical marker, wherein the optical marker can include a geometric pattern.

In some embodiments, the one or more markers can comprise at least one marker attached to the patient, at least one marker attached to a see through head mounted display, at least one marker attached to a structure in the operating room or any combination thereof.

In some embodiments, the system can be configured to determine one or more coordinates using one or more cameras.

In some embodiments, the one or more cameras detect light with a wavelength between 380 nm and 700 nm. In some embodiments, the one or more cameras detect light with a wavelength above 700 nm. In some embodiments, the one or more cameras detect light with a wavelength between 380 nm and 700 nm, above 700 nm or a combination thereof.

In some embodiments, the system comprises at least one camera, scanner, 3D scanner, LIDAR system, depth sensor, inertial measurement unit (IMU), oscilloscope, gyroscope, or a combination thereof integrated into or attached to the head mounted display. In some embodiments, at least one camera, scanner, 3D scanner, LIDAR system, depth sensor, IMU, oscilloscope, gyroscope or a combination thereof is separate from the head mounted display. In some embodiments, the one or more camera, scanner, 3D scanner, LIDAR system, depth sensor, IMU, oscilloscope, gyroscope or a combination thereof are configured to determine the position, orientation, or position and orientation of the marker. In some embodiments, the one or more camera, scanner, 3D scanner, LIDAR system, depth sensor, IMU, oscilloscope, gyroscope or a combination thereof are configured to determine one or more coordinates of the marker. In some embodiments, the one or more camera, scanner, 3D scanner, LIDAR system, depth sensor, IMU, oscilloscope, gyroscope or a combination thereof are configured to track the one or more coordinates of the marker during movement of the marker. In some embodiments, the one or more camera, scanner, 3D scanner, LIDAR system, depth sensor, IMU, oscilloscope, gyroscope or a combination thereof are configured to determine one or more coordinates of the patient directly (e.g. markerless), e.g. by detecting select anatomic landmarks and/or structures and/or surfaces, e.g. a spinal structure and/or surface, articular structure and/or surface, tooth and/or surface, gum and/or surface, dental structure and/or surface, other structure and/or surface or body tissues. In some embodiments, the one or more camera, scanner, 3D scanner, LIDAR system, depth sensor, IMU or a combination thereof are configured to determine one or more coordinates of the see through head mounted display.

In some embodiments, the system is configured to track the one or more coordinates of the see through head mounted display during movement of the patient, the see through head mounted display, or the patient and the see through head mounted display. The movement of the patient can be, for example, the movement of a spine, one or more spinal elements, a head, a joint, one or more articular surfaces, a mandible, a maxilla, a tooth.

In some embodiments, the system comprises one or more processors. In some embodiments, the one or more processors are configured to generate the 3D stereoscopic view of the virtual surgical guide, virtual display, e.g. virtual axis, virtual plane, virtual operating range, area or volume (e.g. of a robot and/or imaging system), virtual image acquisition range, area or volume (e.g. of an imaging system). In some embodiments, the one or more processors are configured to determine the distance between the one or more predetermined coordinates of the virtual surgical guide, virtual display, e.g. virtual axis, virtual plane, virtual operating range, area or volume (e.g. of a robot and/or imaging system), virtual image acquisition range, area or volume (e.g. of an imaging system) and the see through head mounted display. In some embodiments, the one or more processors are configured to track one or more coordinates of at least one or more markers, one or more anatomic structures, one or more see through head mounted displays, or combinations thereof during movement of the patient, the see through head mounted display or the patient and the see through head mounted display. In some embodiments, the one or more processors are configured to determine the distance between the one or more predetermined coordinates of the virtual surgical guide, virtual display, e.g. virtual axis, virtual plane, virtual operating boundary, virtual operating range, area or volume (e.g. of a robot and/or imaging system), virtual image acquisition range, area or volume (e.g. of an imaging system) and the see through head mounted display during movement of the marker and/or the anatomic structure, movement of the see through head mounted display, or movement of the marker and/or the anatomic structure and the see through head mounted display. In some embodiments, one or more processors are configured to adjust at least one focal plane, focal point, convergence or combination thereof based on a change in a determined distance, e.g. from an HMD to a surgical site and/or anatomic structure. In some embodiments, one or more computer processors and/or computing systems, e.g. a first, second, third, fourth, etc. computer processor and/or computing systems are configured to display, e.g. by a computer monitor and/or one or more head mounted displays, a virtual surgical guide, e.g. a virtual axis, virtual plane, a virtual operating range, virtual operating area or virtual operating volume (e.g. of a robot and/or imaging system), a virtual image acquisition range, virtual image acquisition area or virtual image acquisition volume (e.g. of an imaging system). A first computer processor and/or computing system can be configured to communicate (e.g. via direct cable connection or wireless connection) to a robot and/or an imaging system or to be communicatively coupled to the robot and/or imaging system. A second computer processor and/or computing system can be configured to communicate (e.g. via direct cable connection or wireless connection) to one or more head mounted displays or to be communicatively coupled to the head mounted display(s).

In some embodiments, the physical surgical tool or physical surgical instrument can be configured to effect a tissue removal in the patient. A tissue removal can be, for example, an osteotomy of a bone (e.g. using an osteotome, as used in spinal deformity operations or in articular procedures), a pinning, drilling, milling, reaming, broaching, impacting and/or cutting of a bone using, for example, a pin, drill, mill, reamer, broach, impactor, and/or saw or sawblade, optionally attached to or integrated into a robot (e.g. hand-held or attached to an OR table) or a robotic arm. In some embodiments, a robotic end effector can be configured to effect a tissue removal or tissue alteration in the patient. The tissue removal or tissue alteration can be a removal of bone or a removal of cartilage or a removal of bone and cartilage, or a removal of a tooth and/or dental tissue, a tissue ablation, a tissue coagulation, a cell transfer, an implantation etc. Examples include a thermocoagulation, a cryoablation, a cutting with a scalpel or other cutting device. A tissue removal or alteration can be a removal or addition/supplementation of bone, bone tissue, cartilage, dental tissue, gum, gum tissue, brain, brain tissue, organ (e.g. liver, spleen, kidneys, bowel, stomach, heart, lung, thyroid, parathyroid tissue), skin, dermal tissue, subcutaneous tissue, or any combination thereof.

Aspects of the present disclosure relate to devices and methods for performing a surgical step or surgical procedure with visual guidance using one or more head mounted displays and with display of one or more imaging studies, e.g. x-rays, Panorex views, CT scan (for example, spiral CT, cone beam CT), MRI scan, ultrasound scan, PET scan, SPECT scan or a combination thereof.

Bluetooth

In some embodiments, the device can comprise a Bluetooth transmitter and/or receiver.

Bluetooth can be a packet-based protocol with a master/slave architecture. One master can communicate with multiple slaves in a piconet. A master Bluetooth device can communicate with multiple devices in a piconet. The devices can switch roles, by agreement, and the slave can become the master (for example, a headset initiating a connection to a phone can begin as master—as an initiator of the connection—but may subsequently operate as the slave).

Bluetooth can be a layer protocol architecture comprising core protocols, cable replacement protocols, telephony control protocols, and adopted protocols. The device can, in some embodiments, employ high-speed Bluetooth protocols. The device can comprise an interface between a server and the device using a Bluetooth device. The interface can be HCI (Host Controller Interface).

The Host Controller Interface can provide a command interface for the controller and for the link manager, which can allow access to the hardware status and control certain registers. This interface can provide an access layer for all Bluetooth devices. The HCI layer of the machine can exchange commands and data with the HCI firmware present in the Bluetooth device. The HCI can, in some embodiments, automatically discover other Bluetooth devices that are within the coverage radius.

The hardware that constitutes a Bluetooth device, including the Bluetooth device that can optionally be within the device, can include two parts: a radio device, responsible for modulating and transmitting the signal and a digital controller. These specific parts can, in some embodiments be physically separate and can in other embodiments be physically together.

The digital controller can, in some embodiments, be a computer processor or a central processing unit (CPU). In some embodiments, the computer processor CPU can run a Link Controller; and interfaces with the host device, such as the Host Controller Interface. The Link Controller can be responsible for the processing of the baseband and the management of ARQ and physical layer FEC protocols. The computer processor or the CPU can, in some embodiments, handle the transfer functions (both asynchronous and synchronous), audio coding, and data encryption. The computer processor or CPU of the device can, in some embodiments, be responsible for performing the instructions related to the Bluetooth of the host device, in order to simplify its operation. For the performance of specific instructions related to the Bluetooth of the host device, the computer processor or the CPU can run software called Link Manager that has the function of communicating with other devices through the LMP protocol.

The Link Manager can, in some embodiments, establish the connection between devices. For example, the Link Manager can establish the connection between the devices. The Link Manager can be responsible for the establishment, authentication and configuration of the link. The Link Manager can furthermore find other managers and communicates with them due to the management protocol of the LMP link.

The Link Manager Protocol can comprise a number of PDUs (Protocol Data Units) that can be sent from one device to another. The following is a list of supported services:

1) Transmission and reception of data
2) Name request
3) Request of the link addresses
4) Establishment of the connection
5) Authentication
6) Negotiation of link mode and connection establishment The system, when in discoverable mode, can transmit the following information on demand:

1) Device name
2) Device class
3) List of services
4) Technical information (for example: device features, manufacturer, Bluetooth specification used, clock offset)

The system can have a unique 48-bit address. The system can have a friendly Bluetooth name, which can be set by the user. This name can appear when another user scans for devices and in lists of paired devices.

During pairing between the server and the system the two can establish a relationship by creating a shared secret or a link key. If both devices store the same link key, they can be paired or bonded.

The following are pairing mechanisms that can be used in some embodiments of the disclosure:

1) Legacy pairing, wherein each device must enter a PIN code; pairing is only successful if both devices enter the same PIN code. Legacy has the following authentication mechanisms:
   a. Limited input devices, wherein the devices have a fixed PIN, for example "1111" or "2222", that are hard-coded into the device
   b. Numeric input devices, wherein the user can enter a numeric value up to 16 digits in length
   c. Alpha-numeric input devices wherein the user can enter full UTF-8 text as a PIN code
2) Secure Simple Pairing (SSP), using a public key cryptography, and certain modifications can help protect against man in the middle, or MITM attacks. SSP has the following authentication mechanisms:
   a. Just works: This method functions with no user interaction. However, the device may prompt the user to confirm the pairing process.
   b. Numeric comparison: The devices being paired display a 6-digit numeric code. The user can compare the numbers to ensure they are the exact same. If the comparison succeeds, the user(s) can confirm pairing on the device(s) that can accept an input. This method provides MITM protection, assuming the user confirms on both devices and actually performs the comparison properly.
   c. Passkey Entry: This mechanism can be used between a device with a display and a device with numeric keypad entry (such as a keyboard), or two devices with numeric keypad entry. In the first case, the display presents a 6-digit numeric code to the user, who then enters the code on the keypad. In the second case, the user of each device enters the same 6-digit number.
   d. Out of band (OOB): This method uses an external means of communication, such as near-field communication (NFC) to exchange information used in the pairing process. Pairing is completed using the Bluetooth radio, but requires information from the OOB mechanism.

In some embodiments, the device comprises a Bluetooth transmitter and/or receiver wherein the Bluetooth transmitter and/or receiver is configured to work in conjunction with an augmented reality surgical guidance system, a surgical navigation system, a robot, a robotic system, and/or a handheld robot.

In some embodiments, the Bluetooth transmitter and/or receiver and the established connection between the Bluetooth transmitter and/or receiver and the augmented reality surgical guidance system, surgical navigation system, robot, robotic system, and/or handheld robot can work in conjunction with one or more on/off switches and/or one or more potentiometers, e.g. digital potentiometers, and/or one or more rheostats and/or one or more actuators to regulate the speed of the movement of the saw blade or movement of the drill bit or to provide haptic feedback.

For example, in cases where the augmented reality surgical guidance system, surgical navigation system, robot, robotic system, and/or handheld robot detects a movement of a surgical instrument or tool deviating from an intended surgical axis, target, target area, target volume, tissue resection target, area, volume (e.g. bone or tissue removal or resection, e.g. with a bone drill or bone saw) by a specific distance in any direction in one or more dimensions, the augmented reality surgical guidance system, surgical navigation system, robot, robotic system, and/or handheld robot can transmit information to the Bluetooth receiver which can regulate the Bluetooth switch, including both a transmitter and receiver, to activate an on/off switch and/or a potentiometer, e.g. digital, and/or a rheostat and/or a specific actuator for haptic feedback. In cases where the augmented reality surgical guidance system, surgical navigation system, robot, robotic system, and/or handheld robot detects a movement of a drill or saw or other power tool that approaches, for example, a specific anatomical structure or safe zone, the augmented reality surgical guidance system, surgical navigation system, robot, robotic system, and/or handheld robot can similarly work in conjunction with the Bluetooth switch within the device attached to the drill or saw to adjust, control, and/or regulate an on/off switch and/or a potentiometer and/or a rheostat and/or a specific actuator for haptic feedback. The same concept can similarly work for turning on or increasing the speed of the movement of the saw blade or the drill bit or other power tool or instrument when approaching certain anatomic structures.

The Bluetooth switch, Bluetooth receiver, and/or Bluetooth transmitter can, in some embodiments, employ low latency Bluetooth in order to provide instant saw or drill speed regulation or instant haptic feedback.

WiFi

In some embodiments, the device comprises a WiFi transmitter and/or receiver. In some embodiments, the device can comprise WiFi capability. Different versions of WiFi can be used including but not limited to: 802.11a, 802.11b, 802.11g, 802.11n (Wi-Fi 4[40]), 802.11h, 802.11i, 802.11-2007, 802.11-2012, 802.11ac (Wi-Fi 5[40]), 802.11ad, 802.11af, 802.11-2016, 802.11ah, 802.11ai, 802.11aj, 802.11aq, 802.11ax (Wi-Fi 6[40]), and 802.11ay. In some embodiments, the device comprises a WiFi transmitter and/or receiver wherein the WiFi transmitter and/or receiver is configured to work in conjunction with a surgical guidance system. In some embodiments, the system can include routers that can be configured for intranet and internet connections.

In some embodiments, the system can utilize several distinct radio frequency ranges. For example, the system utilizes the 802.11 standard, it can include distinct radio frequencies ranges for use in Wi-FI communications such as: 900 MHz, 2.4 GHz, 5 GHz, 5.9 GHz, and 60 GHz bands. Each frequency or range can have a multitude of channels.

In some embodiments, the system and/or device's Wi-Fi can be part of the IEEE 802 protocol family. In some embodiments, the system and/or device can comprise one or more transmitters. WiFi transmitters are low power devices.

In some embodiments, the system and/or device can comprise one or more antennas.

The system and/or device can comprise an access point compliant with 802.11b and/or 802.11g.

Using the stock omnidirectional antenna can have a range of 100 m (0.062 mi). The identical radio with an external semi parabolic antenna (15 dB gain) with a similarly equipped receiver at the far end can have a range over 20 miles.

In some embodiments, the system and/or device can comprise multiple-input and multiple-output. The system and/or device including but not limited to standards such as IEEE 802.11n and IEEE 802.11ac, can comprise multiple antennas for extended range and higher speeds.

In some embodiments, the WiFi can comprise Local Area Networks (LAN). In some embodiments, the device can include one or more access points. A wireless access point can connect a group of wireless devices to an adjacent wired LAN. In some embodiments, the device can include one or more wireless adapters. Wireless adapters can allow devices to connect to a wireless network In some embodiments, the device can include one or more routers. Wireless routers can integrate a Wireless Access Point, Ethernet switch, and internal router firmware application that provides IP routing, NAT, and DNS forwarding through an integrated WAN-interface.

In some embodiments, the device can include one or more wireless network bridges.

Wireless network bridges can act to connect two networks to form a single network at the data-link layer over Wi-Fi. The main standard is the wireless distribution system (WDS).

Wireless bridging can connect a wired network to a wireless network.

In some embodiments, the device can include one or more security features. Security features can be any security standard known in the art.

In some embodiments, the WiFi transmitter and/or receiver and the established connection between the WiFi transmitter and/or receiver and the augmented reality surgical guidance system can work in conjunction with one or more on/off switches and/or one or more potentiometers and/or one or more rheostats and/or one or more actuators to regulate the oscillation of a saw blade or movement of a drill bit or to provide haptic feedback.

For example, in cases where the augmented reality surgical guidance system detects a movement of a drill or saw or other power tool or instrument deviating from the intended cut/drill surgical axis, the surgical guidance system can regulate a WiFi switch, including both a transmitter and receiver, to activate an on/off switch and/or a potentiometer, e.g. digital, and/or a rheostat and/or a specific actuator for haptic feedback. In cases where the surgical guidance system detects a movement of a drill or saw or other power tool or instrument that approaches, for example, a specific anatomical structure or safe zone, the surgical guidance system can similarly work in conjunction with a WiFi switch within the device attached to a drill or saw or other power tool or instrument to activate an on/off switch and/or a potentiometer and/or a rheostat and/or a specific actuator for haptic feedback. The same concept can similarly work for turning on or increasing the speed of the movement of a saw blade or a drill bit or other power tool or instrument when approaching certain anatomic structures.

LiFi

In some embodiments, the device can comprise a LiFi transmitter and/or receiver. In some embodiments, the device can comprise LiFi capability. LiFi can use light from light-emitting diodes (LEDs) as a medium to deliver networked, mobile, high-speed communication.

In some embodiments, the system can comprise visible light communications (VLC). VLC works by switching the current to the LEDs off and on at very high speeds.

In some embodiments, the system can comprise Bg-Fi. Bg-Fi can be a Li-Fi system consisting of an application for a mobile device, and a simple consumer product device, with color sensor, microcontroller, and embedded software. Light from the mobile device display communicates to the color sensor on the consumer product, which converts the light into digital information. Light emitting diodes enable the consumer product to communicate synchronously with the mobile device.

In some embodiments, the Li-Fi system can be wireless and can use 802.11 protocols. In some embodiments, the LiFi system can use ultraviolet, infrared and visible light communication.

One part of the visible light communication can be designed from communication protocols established by the IEEE 802 workgroup. The IEEE 802.15.7 standard can, in some embodiments, define the physical layer (PHY) and media access control (MAC) layer.

The modulation formats recognized for PHY I and PHY II are on-off keying (OOK) and variable pulse position modulation (VPPM). The Manchester coding used for the PHY I and PHY II layers can include the clock inside the transmitted data by representing a logic 0 with an OOK symbol "01" and a logic 1 with an OOK symbol "10", all with a DC component. The DC component avoids light extinction in case of an extended run of logic 0's.

The use of LiFi provides additional benefits as the light waves are unlikely to affect or hinder the efficiency of a medical procedure or medical devices.

In some embodiments, the device can comprise a LiFi transmitter and/or receiver wherein the LiFi transmitter and/or receiver is configured to work in conjunction with a surgical guidance system. In some embodiments, the LiFi transmitter and/or receiver and the established connection between the LiFi transmitter and/or receiver and the augmented reality surgical guidance system can work in conjunction with one or more on/off switches and/or one or more potentiometers and/or one or more rheostats and/or one or more actuators to regulate the oscillation of a saw blade or movement of a drill bit or to provide haptic feedback.

For example, in cases where an augmented reality surgical guidance system detects a movement of a drill or saw deviating from the intended cut/drill surgical axis, the surgical guidance system can regulate the LiFi switch, including both a transmitter and receiver, to activate an on/off switch and/or a potentiometer and/or a rheostat and/or a specific actuator for haptic feedback. In cases where the surgical guidance system detects a movement of a drill or saw that approaches, for example, a specific anatomical structure or safe zone, the surgical guidance system can similarly work in conjunction with the LiFi switch within a device attached to or integrated into a drill or saw to activate an on/off switch and/or a potentiometer and/or a rheostat and/or a specific actuator for haptic feedback. The same concept can similarly work for turning on or increasing the speed of the movement of a saw blade or a drill bit when approaching certain anatomic structures.

In some embodiments, other forms of wireless data transmission known in the art can be used, not only Bluetooth, Wifi, Lifi, but also, but not limited to, a radiofrequency signal, a microwave signal, an ultrasound signal, an infrared signal, an electromagnetic wave or a combination thereof. Any form of wireless data transmission known in the art can be used in any of the embodiments.

In some embodiments, the system comprises at least one camera, video system and/or scanner (e.g. a 3D scanner, a laser scanner, a LIDAR system or LIDAR scanner), a depth sensor, an IMU or a combination thereof integrated into or attached to the see through head mounted display. In some embodiments, at least one camera, video system and/or scanner (e.g. a 3D scanner, a laser scanner, a LIDAR system or LIDAR scanner), a depth sensor, an IMU or a combination thereof is/are separate from the head mounted display. In some embodiments, one or more camera, video system, scanner, 3D scanner, LIDAR system, depth sensor, IMU or a combination thereof are configured to determine the position, orientation, or position and orientation of a marker, a surface, and/or a tissue. In some embodiments, one or more camera, video system, scanner, 3D scanner, LIDAR system, depth sensor, IMU or a combination thereof are configured to determine one or more coordinates of a marker, a surface, and/or a tissue. In some embodiments, one or more camera, video system, scanner, 3D scanner, LIDAR system, depth sensor, IMU, oscilloscope, gyroscope or a combination thereof are configured to track one or more coordinates of a marker, a surface, and/or a tissue during movement of the marker, the surface, and/or the tissue. In some embodiments, one or more camera, video system, scanner, 3D scanner, LIDAR system, depth sensor, IMU, oscilloscope, gyroscope or a combination thereof are configured to determine one or more coordinates of a see through head mounted display. In some embodiments, one or more markers can be attached to or integrated into a physical instrument, a physical tool, a physical trial implant, a physical implant, a physical device, one or more HMDs or other augmented reality display systems, a robot, a robotic arm, a handheld robot, an end effector, an imaging system, one or more components of an imaging system or a combination thereof.

Imaging Systems

The term imaging system as used throughout the specification can comprise any imaging system using ionizing or non-ionizing radiation. The term imaging system as used throughout the specification can comprise any imaging system utilizing x-rays, e.g. a radiography system, a projection radiography system, a fluoroscopy system, a 2D fluoroscopy system, a 3D fluoroscopy system (e.g. using a 3D C-arm system), a cone beam CT system, a spiral CT system, CT imaging systems using pencil beam geometry, fan beam geometry, open beam geometry, a CT imaging system using a single detector array, a CT imaging system using multiple detector arrays, an electron beam CT imaging system, a conventional radiography system, a digital radiography system, a digital tomosynthesis system, a dual energy imaging system, a dual energy subtraction imaging system, a subtraction imaging system, an angiography imaging system, a uni-planar angiography system, a bi-planar angiography system, a 3D angiography system; the term imaging system as used throughout the specification can comprise a magnetic resonance imaging (MRI) system, an ultrasound imaging system; the term imaging system as used throughout the specification can comprise a radionuclide imaging system, a scintillation detector imaging system for radionuclide imaging, a semiconductor detector imaging system for radionuclide imaging, a pulse height spectroscopy imaging system for radionuclide imaging, a planar nuclear imaging system, a cardiac radionuclide imaging system, a single photon emission computed tomography (SPECT) imaging system, a positron emission tomography (PET) imaging system. The term imaging system as used throughout the specification can comprise or any combination of the foregoing imaging systems, e.g. a combined x-ray—ultrasound imaging system, a SPECT MRI imaging system, a PET MRI imaging system, a 2D radiography/fluoroscopy—3D cone beam CT imaging system etc.

In any of the embodiments, the term imaging parameter can be used interchangeably with the terms image acquisition parameter, acquisition parameter, acquisition setting, image acquisition setting.

TABLE 1

| Non-limiting examples of imaging parameters, settings, geometries (partial list) of one or more components of an imaging system, available for setting, adjustment, modification for different imaging systems, e.g. using a virtual user interface displayed by one or more head mounted displays or other augmented reality display systems: |
|---|
| X-ray, fluoroscopy, C-arm (2D, 3D imaging, e.g. including cone beam CT), CT (e.g. for different scanners, geometries, CT technologies (for example spiral CT, etc.) described in specification or known in the art): |
| x-ray tube setting |
| kVp |
| mAs |
| collimation |
| tube - detector distance |
| tube - patient distance |
| patient - detector distance |
| patient - image intensifier distance |

TABLE 1-continued

| Non-limiting examples of imaging parameters, settings, geometries (partial list) of one or more components of an imaging system, available for setting, adjustment, modification for different imaging systems, e.g. using a virtual user interface displayed by one or more head mounted displays or other augmented reality display systems: |
|---|
| table height (e.g. relative to tube, detector, or combination thereof) |
| table position (e.g. relative to tube, detector, or combination thereof) |
| patient position |
| C-arm position, orientation, location |
| gantry position, orientation, location |
| collimation |
| grid height |
| grid width |
| grid ratio |
| field of view |
| center of a field of view |
| margins, perimeter, limits of a field of view |
| matrix |
| pixel size |
| voxel size |
| image size |
| image volume |
| imaging plane |
| image dimensions in x, y, z and/or oblique directions, e.g. scan coverage |
| image location |
| image volume location |
| pitch |
| in plane resolution |
| slice thickness |
| increment |
| detector configuration |
| detector resolution |
| detector density |
| tube current |
| tube potential |
| reconstruction algorithm, e.g. brain, soft-tissue, abdomen, bone |
| scan range, |
| scan boundary |
| scan limit |
| scan range |
| rotational center (e.g. of a spiral acquisition, a detector movement, a tube movement, a C-arm movement) |
| rotational axis (e.g. of a spiral acquisition, a detector movement, a tube movement, a C-arm movement) |
| reconstructed slice thickness |
| segmentation algorithm |
| window and/or level |
| brightness |
| contrast |
| display resolution |
| Ultrasound: |
| wavelength |
| frequency |
| speed |
| speed of sound |
| depth |
| gain |
| frame rate |
| width |
| line density |
| persistence |
| sensitivity |
| dynamic range |
| relative intensity (e.g. in dB) |
| relative pressure (e.g. in dB) |
| amplitude |
| pressure amplitude ratio |
| intensity ratio |
| power |
| transducer geometry |
| linear/phased transducer activation |
| near field geometry |
| far field geometry |
| beam geometry |
| beam divergence |
| transmit focusing |

TABLE 1-continued

| Non-limiting examples of imaging parameters, settings, geometries (partial list) of one or more components of an imaging system, available for setting, adjustment, modification for different imaging systems, e.g. using a virtual user interface displayed by one or more head mounted displays or other augmented reality display systems: |
|---|
| receive focusing |
| acoustic lens geometry (e.g. deformable) |
| pre-amplification settings |
| beam steering settings |
| dynamic focusing settings |
| signal summation settings |
| time gain compensation settings |
| logarithmic compression settings |
| demodulation, envelope detection settings |
| A-mode settings |
| B-mode settings |
| M-mode settings |
| Doppler settings |
| Doppler wave settings |
| Doppler angle |
| Doppler shift |
| Doppler shift settings |
| Respiratory gating |
| Cardiac gating |
| Respiratory gating settings |
| Cardiac gating settings |
| Harmonic imaging settings |
| Harmonic wave settings |
| Aliasing, anti-aliasing settings |
| patient position |
| transducer position/orientation |
| patient scan region position/orientation |
| field of view |
| matrix |
| pixel size |
| voxel size |
| image size |
| image volume |
| imaging plane |
| in plane resolution |
| slice thickness |
| scan range |
| reconstructed slice thickness |
| segmentation algorithm |
| window and/or level |
| brightness |
| contrast |
| display resolution |
| MRI: |
| repetition time |
| echo time |
| inversion time |
| flip angle |
| echo train length |
| number of excitations |
| pulse sequence, e.g. spin echo, gradient echo, fast field echo, turbo spin echo, |
| table height |
| table position |
| patient position |
| field of view |
| matrix |
| pixel size |
| voxel size |
| image size |
| image volume |
| imaging plane |
| image dimensions in x, y, z and/or oblique directions, e.g. scan coverage |
| in plane resolution |
| slice thickness |
| 2D Fourier Transform acquisition parameters |
| 3D Fourier Transform acquisition parameters |
| magnetization transfer contrast parameters |
| k-space sampling parameters |
| coil |
| coil parameters |
| coil geometry |
| phased array coil system |
| transmit and/or receive coil |

TABLE 1-continued

| Non-limiting examples of imaging parameters, settings, geometries (partial list) of one or more components of an imaging system, available for setting, adjustment, modification for different imaging systems, e.g. using a virtual user interface displayed by one or more head mounted displays or other augmented reality display systems: |
|---|
| coil sensitivity |
| coil sensitivity profile |
| gradient coil settings |
| gradient rise time |
| gradient strength |
| reconstruction algorithm |
| scan range |
| reconstructed slice thickness |
| segmentation algorithm |
| window and/or level |
| brightness |
| contrast |
| display resolution |
| Radionuclide based imaging, e.g. nuclear scintigraphy, SPECT, PET etc.: |
| table height |
| table position |
| patient position |
| gantry position, orientation, location |
| detector dimensions |
| detector resolution |
| image resolution |
| scatter |
| collimation |
| collimator settings |
| position of septal collimators, collimator rings |
| single energy acquisition settings |
| multi energy acquisition settings |
| 2D acquisition settings |
| 3D acquisition settings |
| field of view |
| matrix |
| pixel size |
| voxel size |
| image size |
| image volume |
| imaging plane |
| image dimensions in x, y, z and/or oblique directions, e.g. scan coverage |
| in plane resolution |
| slice thickness |
| reconstruction algorithm |
| filter parameters |
| filter kernel |
| radionuclide decay |
| scan range |
| reconstructed slice thickness |
| segmentation algorithm |
| window and/or level |
| brightness |
| contrast |
| display resolution |

The term imaging parameter or imaging parameters as used throughout the specification can comprise one or more of the above parameters and/or other parameters known in the art. Any of the foregoing parameters can be set, defined, determined, adjusted, modified using a user interface, including a graphical user interface. The graphical user interface can comprise virtual user interface, e.g. using a head mounted display or other augmented reality display device. The virtual interface can, for example, use a collision detection, e.g. for generating and/or enabling one or more commands. Any of the above imaging parameters and/or other imaging parameters known in the art can be set, defined, determined, adjusted, modified using a virtual user interface, using any of the embodiments described in the specification, and/or any combination of embodiments described in the specification.

The term virtual interface can be used interchangeably with the term virtual user interface. A virtual user interface can be a graphical user interface. A virtual user interface can be displayed by one or more head mounted displays or other augmented reality display devices. The virtual user interface displayed by a first, second, third, fourth etc. head mounted display can be the same or different. A virtual user interface can comprise at least one virtual object. A virtual user interface or the at least one virtual object can comprise one or more virtual button, virtual field, virtual cursor, virtual pointer, virtual slider, virtual trackball, virtual node, virtual numeric display, virtual touchpad, virtual keyboard, or a combination thereof. One or more commands can be generated by an interaction, e.g. of a user, with a virtual user interface. The interaction can be, for example, a collision detection, e.g. between a user's finger and a virtual object, e.g. a virtual button, or between a tracked pointer or tool or surgical instrument and a virtual object.

In one embodiment, as shown in non-limiting, strictly exemplary fashion in FIG. 1, the system can comprise, for example, a tracking camera or tracking system 1170 (e.g. an optical tracking system, an electromagnetic tracking system, one or more visible light and/or infrared cameras, video systems, scanners, e.g. 3D scanners, laser scanners, LIDAR systems, depth sensors); a server/controller/computing unit 1180; a tracker controller 1190 to receive tracking data, e.g. for markers detected by camera 1170, optionally in real-time. The server/controller/computer unit can process and/or comprise current pose data, for example for detected markers, e.g. on a patient, e.g. a spinal clamp, one or more tools or instruments, and/or optionally one or more HMDs 1200. A transform manager can convert tracked items, for example from a local coordinate system (CS) to a camera coordinate system (CS) 1210. A registration and/or calibration 1220 can transform a local coordinate system to a marker coordinate system, optionally. Steps, processes, commands and/or functions 1190, 1200, 1210, 1220 can be processed or operated by the server/controller/computing unit 1180. The current pose data 1230 for tracked items, e.g. a patient, an anatomic structure, a marker (for example on a spinal clamp, and/or any marker attached to a patient, and/or any marker on any tool or instrument, and/or any marker on one or more HMDs or other augmented reality display devices), a physical tool or instrument, and/or one or more HMDs or other augmented reality display devices including information about the viewing direction of the one or more HMDs or other augmented reality display devices, can be located in the camera coordinate system and can be transferred to one or more HMDs or other augmented reality display devices, e.g. a first, second, third, fourth etc. HMD 1240 or other augmented reality display devices. The one or more HMDs 1240 or other augmented reality display devices can, for example, run a Unity app and render the one or more tracked items in the viewing perspective of the respective one or more HMDs or other augmented reality display devices.

In some embodiments, a first computing system comprising one or more processor can be configured to transmit data to a second computing system configured to generate a display by a head mounted display or other augmented reality display device based on the transmitted data.

In some embodiments, a first computing system comprising one or more processor can be configured to transmit data to a second computing system configured to generate a display by a head mounted display or other augmented reality display device. In some embodiments, a second computing system configured to generate a display by a head mounted display or other augmented reality display device can be configured to transmit data to a first computing system separate from the head mounted display or other augmented reality display device. In some embodiments, the first computing system and the second computing system can be configured to transmit and/or receive data from each other, e.g. for updating a display by a head mounted display or other augmented reality display device.

The data or data packets that can be received and/or transmitted can comprise, for example, any of the data listed in Table 2:

TABLE 2

| Data or data packets for wireless transmission and/or reception between two or more computing systems, including computing systems communicably connected to one, two or more mobile HMD units and/or other augmented reality display devices and/or computing systems communicably connected to a surgical robot and/or an imaging system. |
|---|
| 2D imaging data (including data derived from 2D imaging studies) of a patient, e.g. of an anatomic structre, at least a portion of a spine, spinal structure, joint, tooth, dental structure, vascular structure, or other body part of the patient, e.g. |
| Pre-operative imaging data (CT, MRI, ultrasound etc.) |
| Intra-operative imaging data, for example received from an intra-operative imaging system, such as a 2D, 3D C-arm, cone beam CT, CT etc. |
| 3D imaging data (including data derived from 2D and/or 3D imaging studies) of at least a patient, e.g. of an anatomic structure, a portion of a spine, spinal structure, joint, tooth, dental structure, vascular structure, or other body part of the patient |
| Pre-operative imaging data (CT, MRI, ultrasound etc.) |
| Intra-operative imaging data, for example received from an intra-operative imaging system, such as a 2D, 3D C-arm, cone beam CT, CT etc. |
| Coordinate data or information of a patient, e.g. of an anatomic structure, a spine, spinal structure, joint, tooth, dental structure, vascular structure, or other body part of the patient |
| Real-time or near real-time tracking data or information of a patient, e.g. of an anatomic structure, a spine, spinal structure, joint, tooth, dental structure, vascular structure, or other body part of the patient |
| Coordinate data or information of one or more physical pointer |
| Real-time or near real-time tracking data or information of one or more physical pointer |
| Coordinate data or information of one or more physical tools or instruments |
| Real-time or near real-time tracking data or information of one or more physical tools or instruments |
| Coordinate information of one or more physical implants, physical implant components, or physical trial implants |
| Real-time or near real-time tracking data or information of one or more physical implants, physical implant components, or physical trial implants |
| Coordinate data or information of one or more end effectors, physical tools or instruments integrated or attached to or part of a robot, e.g. a robotic arm, handheld robot or a combination thereof, and/or coordinate data or information of one or more components of the robot, for example with at least a portion of the coordinate data or information generated with use of pose data, sensor data, camera data, 3D scanner data, controller data, drive data, actuator data, end effector data or a combination thereof of the robot (e.g. intrinsic data) (for example obtained using internal or integrated sensors, potentiometers, cameras, video systems, 3D scanners, LIDAR systems, depth sensors, inertial measurement units, accelerometers, magnetometers, gyroscopes, force sensors, pressure sensors, position sensors, orientation sensors, motion sensors, position and/or orientation feedback from step motors, position and/or orientation feedback from |

TABLE 2-continued

| Data or data packets for wireless transmission and/or reception between two or more computing systems, including computing systems communicably connected to one, two or more mobile HMD units and/or other augmented reality display devices and/or computing systems communicably connected to a surgical robot and/or an imaging system. |
|---|
| electric motors, position and/or orientation feedback from hydraulic motors, position and/or orientation feedback from electric and/or mechanical actuators, position and/or orientation feedback from drives, position and/or orientation feedback from robotic controllers, position and/or orientation feedback from one or more robotic computer processors, or a combination thereof) |
| Real-time or near real-time tracking data or information of one or more end effectors, physical tools or instruments integrated or attached to or part of a robot, e.g. a robotic arm, handheld robot or a combination thereof, and/or real-time or near real-time tracking data or information of one or more components of the robot, for example with at least a portion of the tracking data or information generated with use of pose data, sensor data, camera data, 3D scanner data, controller data, drive data, actuator data, end effector data or a combination thereof of the robot (e.g. intrinsic data) (for example obtained using internal or integrated sensors, potentiometers, cameras, video systems, 3D scanners, LIDAR systems, depth sensors, inertial measurement units, accelerometers, magnetometers, gyroscopes, force sensors, pressure sensors, position sensors, orientation sensors, motion sensors, position and/or orientation feedback from step motors, position and/or orientation feedback from electric motors, position and/or orientation feedback from hydraulic motors, position and/or orientation feedback from electric and/or mechanical actuators, position and/or orientation feedback from drives, position and/or orientation feedback from robotic controllers, position and/or orientation feedback from one or more robotic computer processors, or a combination thereof) |
| Coordinate information of one or more physical implants, physical implant components, or physical trial implants attached to a robot, e.g. a robotic arm, handheld robot or a combination thereof, for example with at least a portion of the coordinate data or information generated with use of pose data, sensor data, camera data, 3D scanner data, controller data, drive data, actuator data, end effector data or a combination thereof of the robot (e.g. intrinsic data) (for example obtained using internal or integrated sensors, potentiometers, cameras, video systems, 3D scanners, LIDAR systems, depth sensors, inertial measurement units, accelerometers, magnetometers, gyroscopes, force sensors, pressure sensors, position sensors, orientation sensors, motion sensors, position and/or orientation feedback from step motors, position and/or orientation feedback from electric motors, position and/or orientation feedback from hydraulic motors, position and/or orientation feedback from electric and/or mechanical actuators, position and/or orientation feedback from drives, position and/or orientation feedback from robotic controllers, position and/or orientation feedback from one or more robotic computer processors, or a combination thereof) |
| Real-time or near real-time tracking data or information of one or more physical implants, physical implant components, or physical trial implants attached to a robot, e.g. a robotic arm, handheld robot or a combination thereof, for example with at least a portion of the tracking data or information generated with use of pose data, sensor data, camera data, 3D scanner data, controller data, drive data, actuator data, end effector data or a combination thereof of the robot (e.g. intrinsic data) (for example obtained using internal or integrated sensors, potentiometers, cameras, video systems, 3D scanners, LIDAR systems, depth sensors, inertial measurement units, accelerometers, magnetometers, gyroscopes, force sensors, pressure sensors, position sensors, orientation sensors, motion sensors, position and/or orientation feedback from step motors, position and/or orientation feedback from electric motors, position and/or orientation feedback from hydraulic motors, position and/or orientation feedback from electric and/or mechanical actuators, position and/or orientation feedback from drives, position and/or orientation feedback from robotic controllers, position and/or orientation feedback from one or more robotic computer processors, or a combination thereof) |
| Coordinate data or information of one or more components of an imaging system, for example with at least a portion of the coordinate data or information generated with use of pose data, sensor data, camera data, 3D scanner data, controller data, drive data, actuator data, or a combination thereof of the one or more components of the imaging system (e.g. intrinsic data) (for example obtained using internal or integrated sensors, potentiometers, cameras, video systems, 3D scanners, LIDAR systems, depth sensors, inertial measurement units, accelerometers, magnetometers, gyroscopes, force sensors, pressure sensors, position sensors, orientation sensors, motion sensors, position and/or orientation feedback from step motors, position and/or orientation feedback from electric motors, position and/or orientation feedback from hydraulic motors, position and/or orientation feedback from electric and/or mechanical actuators, position and/or orientation feedback from drives, position and/or orientation feedback from one or more controllers, position and/or orientation feedback from one or more computer processors, or a combination thereof) |
| Real-time or near real-time tracking data or information of one or more components of an imaging system, for example with at least a portion of the tracking data or information generated with use of pose data, sensor data, camera data, 3D scanner data, controller data, drive data, actuator data, or a combination thereof of the one or more components of an imaging system (e.g. intrinsic data) (for example obtained using internal or integrated sensors, potentiometers, cameras, video systems, 3D scanners, LIDAR systems, depth sensors, inertial measurement units, accelerometers, magnetometers, gyroscopes, force sensors, pressure sensors, position sensors, orientation sensors, motion sensors, position and/or orientation feedback from step motors, position and/or orientation |

TABLE 2-continued

| Data or data packets for wireless transmission and/or reception between two or more computing systems, including computing systems communicably connected to one, two or more mobile HMD units and/or other augmented reality display devices and/or computing systems communicably connected to a surgical robot and/or an imaging system. |
|---|
| feedback from electric motors, position and/or orientation feedback from hydraulic motors, position and/or orientation feedback from electric and/or mechanical actuators, position and/or orientation feedback from drives, position and/or orientation feedback from one or more controllers, position and/or orientation feedback from one or more computer processors, or a combination thereof) |
| Coordinate data or information of one or more end effectors, physical tools or instruments integrated or attached to or part of a robot, e.g. a robotic arm, handheld robot or a combination thereof, and/or coordinate data or information of one or more components of the robot, for example with at least a portion of the coordinate data or information generated with use of one or more cameras, video systems, 3D scanners, LIDAR systems, depth sensors, or combination thereof, integrated or attached to one or more HMDs or other augmented reality display systems, separate from one or more HMDs or other augmented reality display systems (e.g. on a stand, tripod, attached to or integrated into OR lighting, OR fixtures, an imaging system (e.g. x-ray, cone beam CT, CT)), or a combination thereof, with one or more computer processors configured, using the one or more cameras, video systems, 3D scanners, LIDAR systems, depth sensors, or combination thereof, to determine, for example, the position, orientation, direction of movement, one or more coordinates, or combination thereof of the one or more end effectors, physical tools or instruments integrated or attached to or part of a robot, and/or one or more markers, e.g. active markers (e.g. RF markers), passive markers (e.g. infrared markers), optical markers (e.g. with geometric patterns, QR codes, bar codes, defined shapes, e.g. triangles, squares, rectangles etc.), LEDs or a combination thereof integrated or attached to the one or more physical tools or instruments, integrated or attached to at least portions of the robot (e.g. the robotic arm, handheld robot or the combination thereof), or integrated or attached to the one or more physical tools or instruments and integrated or attached to at least portions of the robot |
| Real-time or near real-time tracking data or information of one or more end effectors, physical tools or instruments integrated or attached to a robot, e.g. a robotic arm, handheld robot or a combination thereof, and/or real-time or near real-time tracking data or information of one or more components of the robot, for example with at least a portion of the tracking data or information generated with use of one or more cameras, video systems, 3D scanners, LIDAR systems, depth sensors, or combination thereof, integrated or attached to one or more HMDs or other augmented reality display systems, separate from one or more HMDs or other augmented reality display systems (e.g. on a stand, tripod, attached to or integrated into OR lighting, OR fixtures, an imaging system (e.g. x-ray, cone beam CT, CT)), or a combination thereof, with one or more computer processors configured, using the one or more cameras, video systems, 3D scanners, LIDAR systems, depth sensors, or combination thereof, to determine, for example, the position, orientation, direction of movement, one or more coordinates, or combination thereof of the one or more end effectors, physical tools or instruments integrated or attached to or part of a robot, and/or one or more markers, e.g. active markers (e.g. RF markers), passive markers (e.g. infrared markers), optical markers (e.g. with geometric patterns, QR codes, bar codes, defined shapes, e.g. triangles, squares, rectangles etc.), LEDs or a combination thereof integrated or attached to the one or more physical tools or instruments, integrated or attached to at least portions of the robot (e.g. the robotic arm, handheld robot or the combination thereof), or integrated or attached to the one or more physical tools or instruments and integrated or attached to at least portions of the robot |
| Coordinate information of one or more physical implants, physical implant components, or physical trial implants attached to a robot, e.g. a robotic arm, handheld robot or a combination thereof, for example with at least a portion of the coordinate data or information generated with use of one or more cameras, video systems, 3D scanners, LIDAR systems, depth sensors, or combination thereof, integrated or attached to one or more HMDs or other augmented reality display systems, separate from one or more HMDs or other augmented reality display systems (e.g. on a stand, tripod, attached to or integrated into OR lighting, OR fixtures, an imaging system (e.g. x-ray, cone beam CT, CT)), or a combination thereof, with one or more computer processors configured, using the one or more cameras, video systems, 3D scanners, LIDAR systems, depth sensors, or combination thereof, to determine, for example, the position, orientation, direction of movement, one or more coordinates, or combination thereof of the one or more physical implants, physical implant components, or physical trial implants attached to a robot, and/or one or more markers, e.g. active markers (e.g. RF markers), passive markers (e.g. infrared markers), optical markers (e.g. with geometric patterns, QR codes, bar codes, defined shapes, e.g. triangles, squares, rectangles etc.), LEDs or a combination thereof integrated or attached to the one or more physical tools or instruments, integrated or attached to at least portions of the robot (e.g. the robotic arm, handheld robot or the combination thereof), or integrated or attached to the one or more physical tools or instruments and integrated or attached to at least portions of the robot |
| Real-time or near real-time tracking data or information of one or more physical implants, physical implant components, or physical trial implants attached to a robot, e.g. a robotic arm, handheld robot or a combination thereof, for example with at least a portion of the tracking data or information generated with use of one or more cameras, video systems, 3D scanners, LIDAR systems, depth sensors, or combination thereof, integrated or attached to one or more HMDs or other augmented reality display systems, separate from one or more HMDs or other augmented reality display systems (e.g. on a stand, tripod, attached to or integrated into OR lighting, OR fixtures, an imaging system (e.g. x-ray, cone |

TABLE 2-continued

| Data or data packets for wireless transmission and/or reception between two or more computing systems, including computing systems communicably connected to one, two or more mobile HMD units and/or other augmented reality display devices and/or computing systems communicably connected to a surgical robot and/or an imaging system. |
| --- |
| beam CT, CT)), or a combination thereof, with one or more computer processors configured, using the one or more cameras, video systems, 3D scanners, LIDAR systems, depth sensors, or combination thereof, to determine, for example, the position, orientation, direction of movement, one or more coordinates, or combination thereof of the one or more physical implants, physical implant components, or physical trial implants attached to a robot, and/or one or more markers, e.g. active markers (e.g. RF markers), passive markers (e.g. infrared markers), optical markers (e.g. with geometric patterns, QR codes, bar codes, defined shapes, e.g. triangles, squares, rectangles etc.), LEDs or a combination thereof integrated or attached to the one or more physical tools or instruments, integrated or attached to at least portions of the robot (e.g. the robotic arm, handheld robot or the combination thereof), or integrated or attached to the one or more physical tools or instruments and integrated or attached to at least portions of the robot |
| Coordinate data or information of one or more components of an imaging system, for example with at least a portion of the coordinate data or information generated with use of one or more cameras, video systems, 3D scanners, LIDAR systems, depth sensors, or combination thereof, integrated or attached to one or more HMDs or other augmented reality display systems, separate from one or more HMDs or other augmented reality display systems (e.g. on a stand, tripod, attached to or integrated into OR lighting, OR fixtures, the imaging system (e.g. x-ray, cone beam CT, CT)), or a combination thereof, with one or more computer processors configured, using the one or more cameras, video systems, 3D scanners, LIDAR systems, depth sensors, or combination thereof, to determine, for example, the position, orientation, direction of movement, one or more coordinates, or combination thereof of the one or more components of the imaging system, and/or one or more markers, e.g. active markers (e.g. RF markers), passive markers (e.g. infrared markers), optical markers (e.g. with geometric patterns, QR codes, bar codes, defined shapes, e.g. triangles, squares, rectangles etc.), LEDs or a combination thereof integrated or attached to the one or more components of the imaging system |
| Real-time or near real-time tracking data or information of one or more components of an imaging system, for example with at least a portion of the tracking data or information generated with use of one or more cameras, video systems, 3D scanners, LIDAR systems, depth sensors, or combination thereof, integrated or attached to one or more HMDs or other augmented reality display systems, separate from one or more HMDs or other augmented reality display systems (e.g. on a stand, tripod, attached to or integrated into OR lighting, OR fixtures, the imaging system (e.g. x-ray, cone beam CT, CT)), or a combination thereof, with one or more computer processors configured, using the one or more cameras, video systems, 3D scanners, LIDAR systems, depth sensors, or combination thereof, to determine, for example, the position, orientation, direction of movement, one or more coordinates, or combination thereof of the one or more components of the imaging system |
| Coordinate data or information of one or more HMDs or other augmented reality display systems (including, for example, but not limited to, HMD housing, HMD visor, HMD display [e.g. a mirror, combiner, optical waveguide, optics, display unit]), comprising, for example, information about HMD or other augmented reality display system position, orientation, pitch or tilt, direction of movement, optionally labeled or coded for each specific HMD or other augmented reality display system (e.g. by a computer processor integrated into, attached to, or connected to a camera or scanner, a computer processor integrated into, attached to, or connected to a first computing unit (e.g. in a server), and/or a computer processor integrated into, attached to, or connected to a second computing unit (e.g. in a client, for example integrated into an HMD or other augmented reality display system or connected to an HMD or other augmented reality display system) |
| Real-time or near real-time tracking data of one or more HMDs or other augmented reality display systems (including, for example, but not limited to, HMD housing, HMD visor, HMD display [e.g. a mirror, combiner, optical waveguide, optics, display unit]), comprising, for example, information about HMD or other augmented reality display system position, orientation, pitch or tilt, direction of movement, optionally labeled or coded for each specific HMD or other augmented reality display system (e.g. by a computer processor integrated into, attached to, or connected to a camera or scanner, a computer processor integrated into, attached to, or connected to a first computing unit (e.g. in a server), and/or a computer processor integrated into, attached to, or connected to a second computing unit (e.g. in a client, for example integrated into an HMD or other augmented reality display system or connected to an HMD or other augmented reality display system) |
| Real-time or near real-time data about the position, orientation, position and orientation, pitch or tilt, direction of movement of one or more HMDs or other augmented reality display system (including, for example, but not limited to, HMD housing, HMD visor, HMD display [e.g. a mirror, combiner, optical waveguide, optics, display unit]), optionally labeled or coded for each specific HMD or other augmented reality display system (e.g. by a computer processor integrated into, attached to, or connected to a camera or scanner, a computer processor integrated into, attached to, or connected to a first computing unit (e.g. in a server), and/or a computer processor integrated into, attached to, or connected to a second computing unit (e.g. in a client, for example integrated into an HMD or other augmented reality display system or connected to an HMD or other augmented reality display system) |

TABLE 2-continued

| Data or data packets for wireless transmission and/or reception between two or more computing systems, including computing systems communicably connected to one, two or more mobile HMD units and/or other augmented reality display devices and/or computing systems communicably connected to a surgical robot and/or an imaging system. |
| --- |
| User specific settings and/or parameters |
| User specific display settings (e.g. color preferences, location of alphanumeric data, scan data, image data, 3D displays within the field of view of an HMD) |
| Interpupillary distance, e.g. determined via physical measurement and/or electronic measurement (for example by moving/aligning virtual objects displayed by an HMD); optionally stored on a first computing system, e.g. communicably coupled to a server, for example connected to a navigation system, robot, and/or imaging system, and transmitted to/received by a second computing system communicably coupled to the HMD; or optionally stored on a second computing system communicably coupled to the HMD and transmitted to/received by a first computing system, e.g. communicably coupled to a server, for example connected to a navigation system, robot, and/or imaging system |
| Coordinate data or information of one or more virtual display (including, for example, a virtual retinal display) (e.g. a virtual interface) by one or more HMDs or other augmented reality display systems, comprising, for example, information about virtual display position, orientation, pitch or tilt, direction of movement, optionally labeled or coded for each specific virtual display and/or HMD or other augmented reality display system (e.g. by a computer processor integrated into, attached to, or connected to a camera or scanner, a computer processor integrated into, attached to, or connected to a first computing unit (e.g. in a server), and/or a computer processor integrated into, attached to, or connected to a second computing unit (e.g. in a client, for example integrated into an HMD or other augmented reality display system or connected to an HMD or other augmented reality display system) |
| Real-time or near real-time tracking data of one or more virtual display (including, for example, a virtual retinal display) (e.g. a virtual interface) by one or more HMDs or other augmented reality display systems, comprising, for example, information about virtual display position, orientation, pitch or tilt, direction of movement, optionally labeled or coded for each specific virtual display and/or HMD or other augmented reality display system (e.g. by a computer processor integrated into, attached to, or connected to a camera or scanner, a computer processor integrated into, attached to, or connected to a first computing unit (e.g. in a server), and/or a computer processor integrated into, attached to, or connected to a second computing unit (e.g. in a client, for example integrated into an HMD or other augmented reality display system or connected to an HMD or other augmented reality display system) |
| Real-time or near real-time data about the position, orientation, position and orientation, pitch or tilt, direction of movement of one or more virtual display (including, for example, a virtual retinal display) (e.g. a virtual interface) by one or more HMDs or other augmented reality display system, optionally labeled or coded for each specific virtual display and/or HMD or other augmented reality display system (e.g. by a computer processor integrated into, attached to, or connected to a camera or scanner, a computer processor integrated into, attached to, or connected to a first computing unit (e.g. in a server), and/or a computer processor integrated into, attached to, or connected to a second computing unit (e.g. in a client, for example integrated into an HMD or other augmented reality display system or connected to an HMD or other augmented reality display system) 3D volume information of one or more physical tools or instruments |
| Real-time or near real-time data about one or more interactions, e.g. one or more collisions, of a tracked physical tool or instrument, e.g. a tracked pointer, a tracked stylus, a tracked tool, a tracked instrument or a combination thereof, with one or more virtual displays (e.g. a virtual interface) (including, for example, a virtual retinal display) |
| Real-time or near real-time changes, modifications, or alterations of one or more virtual displays (e.g. a virtual interface) (including, for example, a virtual retinal display) as a result of or triggered by one or more interactions, e.g. one or more collisions, with a tracked physical tool or instrument, e.g. a tracked pointer, a tracked stylus, a tracked tool, a tracked instrument or a combination thereof |
| 3D volume information of one or more physical implants, physical implant components, or physical trial implants |
| 3D volume information of one or more physical tools or instruments |
| 3D surface information of one or more physical tools or instruments |
| 3D surface information of one or more physical implants, physical implant components, or physical trial implants |
| 2D or 3D representations (for example 2D or 3D anatomic models, models derived from imaging data, e.g. of a patient) (including, for example, 3D volume or 3D surface data) of at least a portion of one or more structures or body parts of a patient e.g. of at least a portion of a spine, spinal structure, joint, tooth, dental structure, vascular structure, or other body part |
| 2D or 3D representations (including, for example, 3D volume or 3D surface data) of at least a portion of one or more virtual tools or instruments (e.g. corresponding to at least a portion of one or more physical tools or instruments, e.g. a tool or instrument axis) |
| 2D or 3D representations (including, for example, 3D volume or 3D surface data) of at least a portion of one or more virtual implants, virtual implant components, or virtual trial implants (e.g. corresponding to at least a portion of one or more physical implants, physical implant components, or physical trial implants, e.g. an implant axis and/or an implant outline) |

TABLE 2-continued

| Data or data packets for wireless transmission and/or reception between two or more computing systems, including computing systems communicably connected to one, two or more mobile HMD units and/or other augmented reality display devices and/or computing systems communicably connected to a surgical robot and/or an imaging system. |
|---|
| 2D or 3D representations (including, for example, 3D volume or 3D surface data) of virtual surgical guides, e.g. one or more virtual lines, virtual trajectories, virtual axes, virtual planes, virtual cut planes, virtual saw blades, virtual cut blocks, virtual inserts etc. |
| Target data, targeting data, e.g. in 2D or 3D |
| Stereoscopic view of any of the foregoing, e.g. generated for one or more HMDs (for example accounting for user specification and/or characteristics, such as interpupillary distance |
| Any combination of one or more of the foregoing |

The data or data packets can comprise stereoscopic and/or non-stereoscopic views or data prepared for stereoscopic and/or non-stereoscopic views or displays by one or more HMDs or other augmented reality display systems. Stereoscopic and/or non-stereoscopic views or data prepared for stereoscopic and/or non-stereoscopic views or displays by one or more HMDs or other augmented reality display systems can be updated in near real-time or real-time, e.g. with a rate of 10 Hz, 15 Hz, 20 Hz, 25 Hz, 30 Hz, 35 Hz, 40 Hz, 45 Hz, 50 Hz, 55 Hz, 60 Hz, 65 Hz, 70 Hz, 80 Hz, 90 Hz, 100 Hz, or any other rate or frequency including higher rates or frequencies.

Position, orientation, position and orientation, direction of movement and/or tracking data for one or more HMDs or other augmented reality display systems can be obtained, measured and/or generated using, for example, one or more cameras or scanners (e.g. video systems, 3D scanners, LIDAR systems, depth sensors; using visible light and/or infrared and/or any other wavelength) integrated into or attached to the one or more HMDs or other augmented reality display systems, one or more cameras and/or scanners (e.g. video systems, 3D scanners, LIDAR systems, depth sensors; using visible light and/or infrared and/or any other wavelength) separate from the one or more HMDs or other augmented reality display systems, one or more lasers, e.g. integrated or attached to the one or more HMDs or other augmented reality display systems and/or separate from the one or more HMDs or other augmented reality display systems, one or more inertial measurement units integrated or attached to the one or more HMDs or other augmented reality display systems or a surgeon's head, one or more markers, e.g. active markers (e.g. RF markers), passive markers (e.g. infrared markers), optical markers (e.g. with geometric patterns, QR codes, bar codes, defined shapes, e.g. triangles, squares, rectangles etc.) integrated or attached to the one or more HMDs or other augmented reality display systems, any combination thereof optionally visible to the camera(s) and/or scanner(s), or any combination thereof.

Position, orientation, position and orientation, direction of movement and/or tracking data for one or more HMDs or other augmented reality display systems can be generated, transmitted and/or received in near real time or in real time, e.g. with a rate of 10 Hz, 15 Hz, 20 Hz, 25 Hz, 30 Hz, 35 Hz, 40 Hz, 45 Hz, 50 Hz, 55 Hz, 60 Hz, 65 Hz, 70 Hz, 80 Hz, 90 Hz, 100 Hz, or any other rate or frequency including higher rates or frequencies.

Position, orientation, position and orientation, direction of movement and/or tracking data for one or more HMDs or other augmented reality display systems can be transmitted by one or more computer processors integrated into or connected to the one or more HMDs or other augmented reality display systems via a wireless access point or router wirelessly to a separate computing system with one or more computer processors. The separate computing system can process the data about the position, orientation, position and orientation, direction of movement and/or tracking data of the one or more HMDs or other augmented reality display systems received and package them with other data for corresponding time points or time intervals, e.g. patient tracking data and/or instrument tracking data, for transmission, optionally back to the one or more HMDs or other augmented reality display systems.

Position, orientation, position and orientation, direction of movement and/or tracking data for one or more HMDs or other augmented reality display systems can be obtained, acquired and/or generated by one or more cameras or scanners separate from the one or more HMDs or other augmented reality display systems and can be processed by one or more computer processors connected to or integrated into the camera and/or scanner and/or connected to or integrated into a separate computing system, e.g. a server, optionally connected directly or wirelessly to the camera or scanner. The separate computing system can process the data about the position, orientation, position and orientation, direction of movement and/or tracking data of the one or more HMDs or other augmented reality display systems received and package them with other data for corresponding time points or time intervals, e.g. patient tracking data and/or instrument tracking data, for transmission (and/or reception), for example back to the one or more HMDs or other augmented reality display systems.

Any of the data listed in Table 2 and any additional data can be transmitted and/or received in real-time, or near real-time, with transmitting and/or receiving rates of 10 Hz, 15 Hz, 20 Hz, 25 Hz, 30 Hz, 35 Hz, 40 Hz, 45 Hz, 50 Hz, 55 Hz, 60 Hz, 65 Hz, 70 Hz, 80 Hz, 90 Hz, 100 Hz, or any other rate or frequency including higher rates or frequencies.

When multiple data sets, e.g. different types of data such as instrument tracking data and/or HMD or other augmented reality display system tracking data and/or patient or surgical site (e.g. a spine, joint, tooth or vascular structure) tracking data and/or virtual user interface and/or interaction with virtual user interface data (e.g. with a tracked physical tool or instrument) are transmitted and/or received, they can be transmitted and/or received simultaneously or non-simultaneously. Data sets including any of the data listed in Table 2 can optionally be labelled, e.g. with a time stamp, time point, time interval (e.g. within 1 transmission or data reception, for example, for a rate of 60 Hz, within 16.66 ms or less or, for example, any other value within the time allocated for transmission and reception), a time label, a time tag or any combination thereof.

In some embodiments, coordinate information, registration data, tracking data or a combination thereof of one or more HMDs or other augmented reality display systems can optionally be labeled or coded for each specific HMD or other augmented reality display system, e.g. by a computer processor integrated into, attached to, or connected to a camera or scanner (optionally part of a first or second computing unit), a computer processor integrated into, attached to, or connected to a first computing unit (e.g. in a server), and/or a computer processor integrated into, attached to, or connected to a second computing unit (e.g. in a client, for example integrated into an HMD or other augmented reality display system or connected to an HMD or other augmented reality display system).

In some embodiments, data packets (for example, as listed in Table 2) can comprise multiple types of data, e.g. data comprising instrument tracking data, data comprising HMD or other augmented reality display system tracking data and/or a data comprising patient or surgical site (e.g. a spine, joint, dental, vascular, organ or neural structure) tracking data and/or virtual user interface data and/or interaction with virtual user interface data (e.g. with a tracked physical tool or instrument), all packaged within the same data packet. As the data packet(s) is/are transmitted or received, e.g. data comprising instrument tracking data and/or data comprising HMD or other augmented reality display system tracking data and/or a data comprising patient or surgical site (e.g. a spine, joint, dental, vascular, organ or neural structure) tracking data and/or virtual user interface data and/or interaction with virtual user interface data (e.g. with a tracked physical tool or instrument) can be transmitted or received together, e.g. simultaneously.

In some embodiments, transmission and/or reception can be processed by one or more computer processors, e.g. in a first and/or a second computing system, and/or integrated or attached to a camera or scanner (e.g. integrated or attached to an HMD or other augmented reality display system, integrated or attached to a robot, separate from an HMD or other augmented reality display system or robot etc.), so that data, for example, instrument tracking data and/or HMD or other augmented reality display system tracking data and/or patient or surgical site (e.g. a spine or joint) tracking data, acquired with the same time stamp, time point, time label, time tag, or within the same time interval or any combination thereof are transmitted and/or received in the same data packet.

In some embodiments, transmission and/or reception can be processed by one or more computer processors so that data, for example, instrument tracking data and/or HMD or other augmented reality display system tracking data and/or patient or surgical site (e.g. a spine or joint) tracking data and/or virtual user interface data and/or interaction with virtual user interface data (e.g. with a tracked physical tool or instrument), acquired within the same time interval (and optionally labelled with the same time interval) are transmitted and/or received by one or more computer processors, e.g. in a first and/or a second computing system, within a defined time period in multiple data packets; the defined time period can be corresponding to, matching, or overlapping with the time interval. Optionally the defined time period for transmitting and/or receiving data packets can be a time period bounded or defined by or derived from the transmission and/or reception rate, e.g. <0.16666666 sec for a transmission and/or reception rate of 60 Hz, or <0.0333333 sec for a transmission and/or reception rate of 30 Hz, <0.04 sec for a transmission and/or reception rate of 25 Hz, or any other value.

Data packets (for example, as listed in Table 2), e.g. a first data packet comprising instrument tracking data, a second data packet comprising HMD or other augmented reality display system tracking data and/or a third data packet comprising patient or surgical site (e.g. a spine, joint, dental, vascular, organ or neural structure) tracking data and/or a fourth data packet comprising virtual user interface data and/or interaction with virtual user interface data (e.g. with a tracked physical tool or instrument) can be transmitted and/or received simultaneously, for example using different frequencies. Data packets, e.g. a first data packet comprising instrument tracking data, a second data packet comprising HMD or other augmented reality display system tracking data and/or a third data packet comprising patient or surgical site (e.g. a spine or joint) tracking data and/or a fourth data packet comprising virtual user interface data and/or interaction with virtual user interface data (e.g. with a tracked physical tool or instrument) can be transmitted and/or received sequentially (e.g. using the same or different frequencies). Data packets, e.g. a first data packet comprising instrument tracking data, a second data packet comprising HMD or other augmented reality display system tracking data and/or a third data packet comprising patient or surgical site (e.g. a spine or joint) tracking data and/or a fourth data packet comprising virtual user interface data and/or interaction with virtual user interface data (e.g. with a tracked physical tool or instrument) can be transmitted and/or received in an offset manner, e.g. with a pause or lag interval spaced in between. Data packets, e.g. a first data packet comprising instrument tracking data, a second data packet comprising HMD or other augmented reality display system tracking data and/or a third data packet comprising patient or surgical site (e.g. a spine or joint) tracking data and/or a fourth data packet comprising virtual user interface data and/or interaction with virtual user interface data (e.g. with a tracked physical tool or instrument) can be transmitted and/or received in an interleaved manner. Data packets, e.g. a first data packet comprising instrument tracking data, a second data packet comprising HMD or other augmented reality display system tracking data and/or a third data packet comprising patient or surgical site (e.g. a spine or joint) tracking data and/or a fourth data packet comprising virtual user interface data and/or interaction with virtual user interface data (e.g. with a tracked physical tool or instrument) can be transmitted and/or received in a non-overlapping manner during the transmission and/or the reception. Data packets, e.g. a first data packet comprising instrument tracking data, a second data packet comprising HMD or other augmented reality display system tracking data and/or a third data packet comprising patient or surgical site (e.g. a spine or joint) tracking data and/or a fourth data packet comprising virtual user interface data and/or interaction with virtual user interface data (e.g. with a tracked physical tool or instrument) can be transmitted and/or received in an overlapping manner during the transmission and/or the reception.

Thus, data packets, e.g. comprising one or more of data comprising instrument tracking data, data comprising HMD or other augmented reality display system tracking data, or data comprising patient or surgical site data can be transmitted or received in a simultaneous, synchronous fashion and/or alternatively in an non-synchronous or asynchronous fashion.

The data can be transmitted in near real time or in real time, e.g. with a rate of 10 Hz, 15 Hz, 20 Hz, 25 Hz, 30 Hz, 35 Hz, 40 Hz, 45 Hz, 50 Hz, 55 Hz, 60 Hz, 65 Hz, 70 Hz, 80 Hz, 90 Hz, 100 Hz, or any other rate or frequency including higher rates or frequencies.

Data transmission can be performed using wireless data transmission protocols known in the art, e.g. Bluetooth, Wifi, LiFi, etc. and, as described, for example in PCT International Application Serial Nos. PCT/US2017/021859, PCT/US2018/013774, PCT/US2019/061698 and PCT/US2019/015522, which are hereby incorporated by reference in their entirety.

In some embodiments, the system can comprise a tracking system or sensor, e.g. optical tracking systems, for example using infrared and/or visible light cameras, video systems, 3D scanners, LIDAR systems, depth sensors, radiofrequency tracking systems, or combinations thereof, e.g. for outside-in or inside-out tracking. Multiple tracking systems can be used at the same time or, optionally combined, e.g. inside-out and outside-in tracking. Any tracking, sensor, or registration system known in the art (e.g. optical tracking systems, for example using infrared and/or visible light cameras, video systems, 3D scanners, LIDAR systems, depth sensors, radiofrequency tracking systems, or combinations thereof), can be used, for example as described in a non-limiting fashion in PCT International Application Serial Nos. PCT/US2017/021859, PCT/US2018/013774, PCT/US2019/061698 and PCT/US2019/015522, which are hereby incorporated by reference in their entirety.

A first computing system can comprise one or more computer processors. The second computing system can comprise one or more computer processors. The second computing system can be part of one or more mobile, wireless HMD or other augmented reality display system units. The second computing system can be part of a first mobile, wireless HMD or other augmented reality display system unit. A third computing system can be part of a second mobile wireless HMD or other augmented reality display system unit. A fourth computing system can be part of a third mobile wireless HMD or other augmented reality display system unit. A fifth computing system can be part of a third mobile wireless HMD or other augmented reality display system unit, etc.

A first computing system can comprise one or more computer processors. A first computing system can, for example, be a server or controller or computing unit as shown in FIG. 1, 1180.

Figure 2:
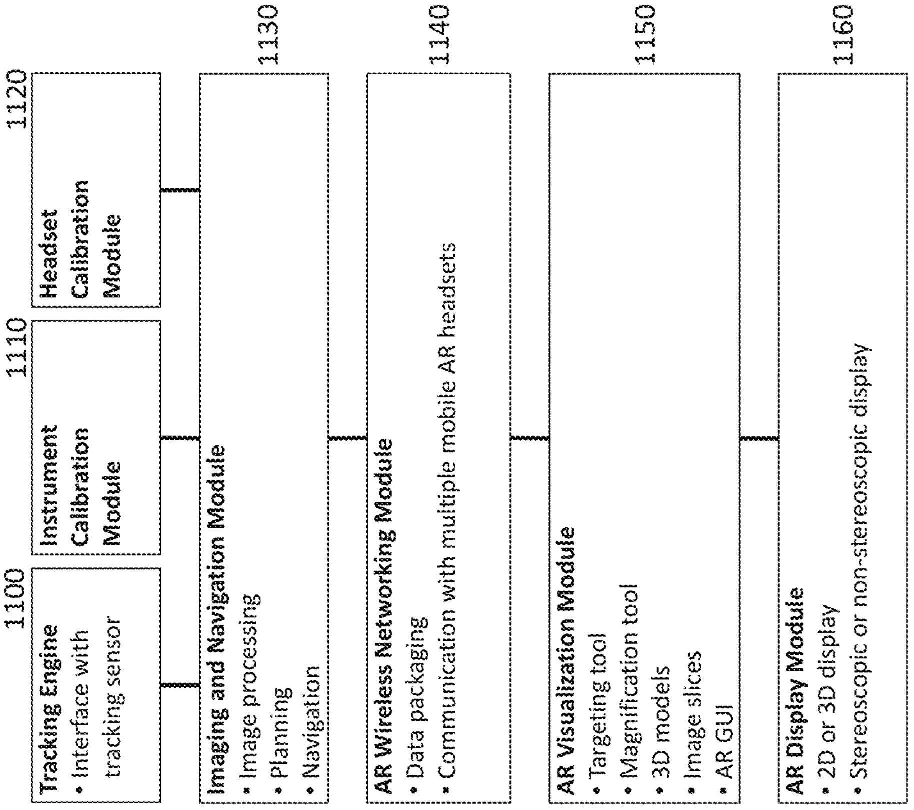
FIG. 2 shows a non-limiting example of a system with modular system configuration, comprising, for example, a tracking module, an instrument calibration module, a headset calibration module, an imaging and navigation module, an augmented reality (AR) wireless networking module, an AR visualization module, and an AR display module.

The one or more computer processors can be configured to run different operating modules as shown, for example, in FIG. 2, e.g.

- A tracking module or tracking engine 1100. The tracking module or tracking engine can comprise a tracking system or sensor, e.g. a video camera, infrared camera, 3D scanner, laser scanner, LIDAR, imaging system etc., e.g. for outside-in or inside-out tracking. The one or more computer processors and software running on the one or more computer processor can comprise an interface, e.g. a graphical user interface, for operating the tracking system or tracking sensor. An interface can be configured for communication with other operating modules, e.g. integrated with the first computing system or the second computing system. The tracking module or tracking engine 1100 can, for example, obtain tracking information or data and/or track one or more physical instruments and/or tools, one or more anatomic structures, landmarks, and/or surfaces of a patient (e.g. in a surgical site) and/or one or more HMDs or other augmented reality display systems. The tracking module or engine 1100 can, optionally, label or code the tracking data and/or information for each specific HMD or other augmented reality display system, e.g. by a computer processor integrated into, attached to, or connected to a camera or scanner (optionally part of a first or second computing unit), a computer processor integrated into, attached to, or connected to a first computing unit (e.g. in a server), and/or a computer processor integrated into, attached to, or connected to a second computing unit (e.g. in a client, for example integrated into an HMD or other augmented reality display system or connected to an HMD or other augmented reality display system). The tracking module or engine 1100 can, for example, apply a label or code specific for each HMD or other augmented reality display system based on tracking data and/or information received for and/or from each individual HMD or other augmented reality display system. The tracking data and/or information can, for example, be data or information from a camera or scanner integrated into or attached to an HMD or other augmented reality display system. The tracking data and/or information can, for example, be from a camera or scanner separate from an HMD or other augmented reality display system. The tracking data and/or information can, for example, be from one or more cameras or scanners integrated into an HMD or other augmented reality display system or attached or connected to an HMD or other augmented reality display system and from one or more cameras or scanners separate from an HMD or other augmented reality display system (e.g. attached to an OR light, OR fixture, OR wall, a robot etc.). The tracking data and/or information can, for example, comprise data of one or more markers, e.g. attached to one or more HMDs or other augmented reality display systems, a patient (e.g. an anatomic structure, landmark or surface of the patient), a physical surgical tool or instrument, a physical implant or a combination thereof. In some embodiments, one or more markers can be configured specific for each HMD or other augmented reality display system, e.g. using a unique bar code, QR code, fiducial marker configuration, RF signal etc., which can, for example, be recognized by one or more computer processors.
- An instrument calibration module 1110. The one or more computer processors can be configured to run an instrument calibration module. The instrument calibration module can comprise an interface. The instrument calibration module can be configured for determining an instrument or tool tip, an instrument or tool axis, an instrument or tool length, an instrument or tool rotational wobble etc. The tracking module or tracking engine and/or an interface can be configured for communication with other operating modules, e.g. integrated with the first computing system or the second computing system.
- A headset calibration module 1120. The one or more computer processors can be configured to run a headset calibration module. The headset calibration module can comprise an interface. The headset calibration module, including its interface, can, for example, be configured for determining an interpupillary distance, a distance from the eye (e.g. pupil, iris, retina) to the display (e.g. a waveguide, mirror etc.), and/or for setting or adjusting an interpupillary distance in the headset, for setting or adjusting a field of view, for setting or adjusting a distance from the eye to the display for a given user, for setting or adjusting user display preferences (e.g. color, targeting tools, magnification, alphanumeric display, display window location, alphanumeric data location etc. The headset calibration module and/or an interface can be configured for communication with other operating modules, e.g. integrated with the first computing system or the second computing system.

An imaging and navigation module 1130. The one or more computer processors can be configured to run an imaging and navigation module. The imaging and navigation module can, for example, comprise a PACS interface, an interface to an imaging system, e.g. x-ray, C-arm, 3D C-arm, cone-beam CT, CT, MRI etc., a DICOM reader, an image processing and display unit, e.g. for multi-planar reconstruction and/or display, 3D reconstruction and/or display, a planning module, e.g. with an interface for a user, surgeon (e.g. for screw or implant selection and placement), a navigation module, e.g. with coordinate output from a planning module. The imaging and navigation module and/or an interface can be configured for communication with other operating modules, e.g. integrated with the first computing system or the second computing system.

An AR or VR wireless networking module 1140. In the AR or VR wireless networking module, one or more computer processors can be configured for packaging of data, e.g. data listed in Table 2. Packing of data can, optionally, comprise data compression.

Packaging of data can, optionally, comprise segmentation or separation into different time segments. Data packets for different time segments can, for example, be generated at a rate of 10 Hz, 15 Hz, 20 Hz, 25 Hz, 30 Hz, 35 Hz, 40 Hz, 45 Hz, 50 Hz, 55 Hz, 60 Hz, 65 Hz, 70 Hz, 80 Hz, 90 Hz, 100 Hz, or any other rate or frequency including higher rates or frequencies. One or more computer processors can be configured to transmit data packets using a wireless access point to a second, third, fourth or more computing system.

One or more computer processors can be configured to receive data packets using the wireless access point from a second, third, fourth or more computing system. In some embodiments, multiple wireless access points can be used. Any wireless communication protocol known in the art, e.g. Bluetooth, WiFi, LiFi, can be used.

An AR or VR visualization module 1150. One or more computer processors can be configured for generating display data for display by one or more HMDs or other augmented reality display systems. The display data can comprise targeting displays, e.g. target disk like, magnified displays, color labeled displays (e.g. red, yellow, green indicating position or alignment accuracy or thresholds), 3D models of the patient, image slices, 3D models or 3D or 2D graphical representations of tools or instruments (e.g. tracked physical tools or instruments) alphanumeric displays, and/or an AR or VR enabled graphical user interface (e.g. gesture recognition, using gesture recognition, virtual pointers, a virtual mouse, a virtual keyboard, virtual buttons, gaze recognition, gaze lock or a combination thereof). An AR or VR visualization module can comprise a display of a virtual user interface and/or a display of one or more virtual interactions, e.g. collisions, with a virtual user interface (e.g. with a tracked physical tool or instrument). The AR or VR visualization and/or display module and/or an interface can be configured for communication with other operating modules, e.g. integrated with the first computing system or the second computing system.

An AR or VR display module 1160. One or more computer processors can be configured for generating one or more 3D stereoscopic views, for example at a rate similar to the data transmission or reception and/or at a different rate. The 3D stereoscopic view can, for example, be adjusted for user specific characteristics (e.g. interpupillary distance, distance from pupil to mirror etc.). The 3D stereoscopic view can, for example, be adjusted for the distance from the pupil or the display to the patient, e.g. a surgical site, for example, in a spine, knee, hip, organ, vessel etc.; adjustments can comprise adjustments of focal plane or point, adjustments of scale or magnification of virtual displays and display items, adjustments of convergence. Adjustments can be in real-time or near real-time. Adjustments can be at less than real-time. An AR or VR display module can comprise a display of a virtual user interface and/or a display of one or more virtual interactions, e.g. collisions, with a virtual user interface (e.g. with a tracked physical tool or instrument).

One or more of the modules 1100-1160 can be integrated or combined. For example, the AR visualization module 1150 can be integrated or combined with the AR display module 1160.

One or more of the modules 1100-1160 can be run by the same computer processor or the same group of computer processors. One or more of the modules 1100-1160 can be run by different computer processors.

One or more of the computer processors operating a tracking engine or tracking module 1100, one or more computer processors operating an instrument calibration module 1110, one or more of the computer processors operating a headset calibration module 1120, one or more of the computer processors operating an imaging and navigation module 1130, one or more of the computer processors operating an AR wireless networking module 1140, one or more of the computer processors operating an AR visualization module 1150, and/or one or more of the computer processors operating an AR display module 1160 can be the same.

One or more of the computer processors operating a tracking engine or tracking module 1100, one or more computer processors operating an instrument calibration module 1110, one or more of the computer processors operating a headset calibration module 1120, one or more of the computer processors operating an imaging and navigation module 1130, one or more of the computer processors operating an AR wireless networking module 1140, one or more of the computer processors operating an AR visualization module 1150, and/or one or more of the computer processors operating an AR display module 1160 can be different.

The first computing system can, for example, be stationary, e.g. on a cart or stand. In some embodiments, the first computing system can also be mobile, e.g. part of a mobile, wireless HMD system or other augmented reality display system.

A second, third, fourth, fifth or more computing systems can comprise one or more computer processors. The one or more computer processors can be configured to run different operating modules as shown, for example, in FIG. 2, e.g.

A tracking module or tracking engine 1100. The tracking module or tracking engine can comprise a tracking system or sensor, e.g. a video camera, infrared camera, 3D scanner, laser scanner, LIDAR, imaging system etc., e.g. for outside-in or inside-out tracking. The one or more computer processors and software running on the one or more computer processor can comprise an interface, e.g. a graphical user interface, for operating the tracking system or tracking sensor. An interface can be configured for communication with other operating modules, e.g. integrated with the first computing system or the second computing system. The tracking module or tracking engine 1100 can, for example, obtain tracking information or data and/or track one or more physical instruments and/or tools, one or more anatomic structures, landmarks, and/or surfaces of a patient (e.g. in a surgical site) and/or one or more HMDs or other augmented reality display systems. The tracking module or engine 1100 can, optionally, label or code the tracking data and/or information for each specific HMD or other augmented reality display system, e.g. by a computer processor integrated into, attached to, or connected to a camera or scanner (optionally part of a first or second computing unit), a computer processor integrated into, attached to, or connected to a first computing unit (e.g. in a server), and/or a computer processor integrated into, attached to, or connected to a second computing unit (e.g. in a client, for example integrated into an HMD or other augmented reality display system or connected to an HMD or other augmented reality display system). The tracking module or engine 1100 can, for example, apply a label or code specific for each HMD or other augmented reality display system based on tracking data and/or information received for and/or from each individual HMD or other augmented reality display system. The tracking data and/or information can, for example, be data or information from a camera or scanner integrated into or attached to an HMD or other augmented reality display system. The tracking data and/or information can, for example, be from a camera or scanner separate from an HMD or other augmented reality display system. The tracking data and/or information can, for example, be from one or more cameras or scanners integrated into an HMD or other augmented reality display system or attached or connected to an HMD or other augmented reality display system and from one or more cameras or scanners separate from an HMD or other augmented reality display system (e.g. attached to an OR light, OR fixture, OR wall, a robot etc.). The tracking data and/or information can, for example, comprise data of one or more markers, e.g. attached to one or more HMDs or other augmented reality display systems, a patient (e.g. an anatomic structure, landmark or surface of the patient), a physical surgical tool or instrument, a physical implant or a combination thereof. In some embodiments, one or more markers can be configured specific for each HMD or other augmented reality display system, e.g. using a unique bar code, QR code, fiducial marker configuration, RF signal etc., which can, for example, be recognized by one or more computer processors.

An instrument calibration module 1110. The one or more computer processors can be configured to run an instrument calibration module. The instrument calibration module can comprise an interface. The instrument calibration module can be configured for determining an instrument or tool tip, an instrument or tool axis, an instrument or tool length, an instrument or tool rotational wobble etc. The tracking module or tracking engine and/or an interface can be configured for communication with other operating modules, e.g. integrated with the first computing system or the second computing system.

A headset calibration module 1120. The one or more computer processors can be configured to run a headset calibration module. The headset calibration module can comprise an interface. The headset calibration module, including its interface, can, for example, be configured for determining an interpupillary distance, a distance from the eye (e.g. pupil, iris, retina) to the display (e.g. a waveguide, mirror etc.), and/or for setting or adjusting an interpupillary distance in the headset, for setting or adjusting a field of view, for setting or adjusting a distance from the eye to the display for a given user, for setting or adjusting user display preferences (e.g. color, targeting tools, magnification, alphanumeric display, display window location, alphanumeric data location etc. The headset calibration module and/or an interface can be configured for communication with other operating modules, e.g. integrated with the first computing system or the second computing system.

An imaging and navigation module 1130. The one or more computer processors can be configured to run an imaging and navigation module. The imaging and navigation module can, for example, comprise a PACS interface, an interface to an imaging system, e.g. x-ray, C-arm, 3D C-arm, cone-beam CT, CT, MRI etc., a DICOM reader, an image processing and display unit, e.g. for multi-planar reconstruction and/or display, 3D reconstruction and/or display, a planning module, e.g. with an interface for a user, surgeon (e.g. for screw or implant selection and placement), a navigation module, e.g. with coordinate output from a planning module. The imaging and navigation module and/or an interface can be configured for communication with other operating modules, e.g. integrated with the first computing system or the second computing system.

An AR or VR wireless networking module 1140. In the AR or VR wireless networking module, one or more computer processors can be configured for packaging of data, e.g. data listed in Table 2. Packing of data can, optionally, comprise data compression.

Packaging of data can, optionally, comprise segmentation or separation into different time segments. Data packets for different time segments can, for example, be generated at a rate of 10 Hz, 15 Hz, 20 Hz, 25 Hz, 30 Hz, 35 Hz, 40 Hz, 45 Hz, 50 Hz, 55 Hz, 60 Hz, 65 Hz, 70 Hz, 80 Hz, 90 Hz, 100 Hz, or any other rate or frequency including higher rates or frequencies. One or more computer processors can be configured to transmit data packets using a wireless access point to a second, third, fourth or more computing system.

One or more computer processors can be configured to receive data packets using the wireless access point from a second, third, fourth or more computing system. In some embodiments, multiple wireless access points can be used. Any wireless communication protocol known in the art, e.g. Bluetooth, WiFi, LiFi, can be used.

An AR or VR visualization module 1150. One or more computer processors can be configured for generating display data for display by one or more HMDs or other augmented reality display systems. The display data can comprise targeting displays, e.g. target disk like, magnified displays, color labeled displays (e.g. red, yellow, green indicating position or alignment accuracy or thresholds), 3D models of the patient, image slices, 3D models or 3D or 2D graphical representations of tools or instruments (e.g. tracked physical tools or instruments) alphanumeric displays, and/or an AR or VR enabled graphical user interface (e.g. gesture recognition, using gesture recognition, virtual pointers, a virtual mouse, a virtual keyboard, virtual buttons, gaze recognition, gaze lock or a combination thereof). An AR or VR visualization module can comprise a display of a virtual user interface and/or a display of one or more virtual interactions, e.g. collisions, with a virtual user interface (e.g. with a tracked physical tool or instrument). The AR or VR visualization and/or display module and/or an interface can be configured for communication with other operating modules, e.g. integrated with the first computing system or the second computing system.

An AR or VR display module 1160. One or more computer processors can be configured for generating one or more 3D stereoscopic views, for example at a rate similar to the data transmission or reception and/or at a different rate. The 3D stereoscopic view can, for example, be adjusted for user specific characteristics (e.g. interpupillary distance, distance from pupil to mirror etc.). The 3D stereoscopic view can, for example, be adjusted for the distance from the pupil or the display to the patient, e.g. a surgical site, for example, in a spine, knee, hip, organ, vessel etc.; adjustments can comprise adjustments of focal plane or point, adjustments of scale or magnification of virtual displays and display items, adjustments of convergence. Adjustments can be in real-time or near real-time. Adjustments can be at less than real-time. An AR or VR display module can comprise a display of a virtual user interface and/or a display of one or more virtual interactions, e.g. collisions, with a virtual user interface (e.g. with a tracked physical tool or instrument).

The second computing system can be part of one or more mobile, wireless HMD or other augmented reality display system units. A second computing system can be part of a first mobile, wireless HMD or other augmented reality display system unit. A third computing system can be part of a second mobile wireless HMD or other augmented reality display system unit. A fourth computing system can be part of a third mobile wireless HMD or other augmented reality display system unit. A fifth computing system can be part of a third mobile wireless HMD or other augmented reality display system unit, etc. The first, second, third, fourth etc. mobile wireless HMD unit can be worn by a user, e.g. a physician, a surgeon, a dentist, a physician or dental assistant etc. The first, second, third, fourth etc. mobile wireless HMD unit can be a video see-through HMD. The first, second, third, fourth etc. mobile wireless HMD unit can be an optical see-through HMD.

One or more modules can be combined or integrated and can, for example, be operated by the same one or more computer processors or, optionally, by different one or more computer processors.

One or more of the computer processors operating a tracking engine or tracking module 1100, one or more computer processors operating an instrument calibration module 1110, one or more of the computer processors operating a headset calibration module 1120, one or more of the computer processors operating an imaging and navigation module 1130, one or more of the computer processors operating an AR wireless networking module 1140, one or more of the computer processors operating an AR visualization module 1150, and/or one or more of the computer processors operating an AR display module 1160 can be the same.

One or more of the computer processors operating a tracking engine or tracking module 1100, one or more computer processors operating an instrument calibration module 1110, one or more of the computer processors operating a headset calibration module 1120, one or more of the computer processors operating an imaging and navigation module 1130, one or more of the computer processors operating an AR wireless networking module 1140, one or more of the computer processors operating an AR visualization module 1150, and/or one or more of the computer processors operating an AR display module 1160 can be different.

One or more modules can be operated by a first computing system, while one or more different modules can be operated by a second, or third, or fourth, etc. computing system. One or more modules can be operated by a first computing system, while one or more different modules can be operated by a second, and third, and fourth, etc. computing system.

One or more modules can be operated by a first computing system, while one or more same modules can be operated by a second, or third, or fourth, etc. computing system. One or more modules can be operated by a first computing system, while one or more same modules can be operated by a second, and third, and fourth, etc. computing system.

In one example, a first computing system can comprise a tracking module or tracking engine 1100, an instrument calibration module 1110, a headset calibration module 1120, an imaging and navigation module 1130, a AR wireless networking module 1140, and an AR visualization module 1150; a second computing system can comprise an AR display module 1160.

In another example, a first computing system can comprise a tracking module or tracking engine 1100, an instrument calibration module 1110, a headset calibration module 1120, an imaging and navigation module 1130, and a AR wireless networking module 1140; a second computing system can comprise an AR visualization module 1150 and an AR display module 1160.

In another example, a first and a second computing system can comprise one or more of the same modules, for example dedicated to the same and/or different functions. For example, a first computing system can comprise an AR wireless networking module 1140, for example for data transmission; a second computing system can also comprise an AR wireless networking module 1140, for example for data reception.

In another example, a first computing system can comprise a tracking module or tracking engine 1100, an instrument calibration module 1110, an imaging and navigation module 1130, and an AR wireless networking module 1140; a second computing system can comprise a headset calibration module 1120, an AR wireless networking module 1140, an AR visualization module 1150 and an AR display module 1160.

Any combination of same and/or different modules, including duplication of modules on different (first, second, third, fourth, fifth) computing systems is possible and within the scope of this disclosure.

Using one or more computer processors, e.g. in a second computing system, the AR display 1160 module can generate the stereoscopic or non-stereoscopic view of a first person for the first person's respective view angle in relationship to one or more anatomic landmarks or anatomic structures of a patient. Using one or more computer processors, e.g. in a third computing system, the AR display 1160 module can generate the stereoscopic or non-stereoscopic view of a second person for the second person's respective view angle in relationship to one or more anatomic landmarks or anatomic structures of the patient. Using one or more computer processors, e.g. in a fourth computing system, the AR display 1160 module can generate the stereoscopic or non-stereoscopic view of a third person for the third person's respective view angle in relationship to one or more anatomic landmarks or anatomic structures of the patient. Using one or more computer processors, e.g. in a fifth computing system, the AR display 1160 module can generate the stereoscopic or non-stereoscopic view of a fourth person for the fourth's person's respective view angle in relationship to one or more anatomic landmarks or anatomic structures of the patient, etc.

The second, third, fourth, fifth or more computing systems can be the same. The second, third, fourth, fifth or more computing systems can be different, e.g. integrated or connected to different mobile units and/or different HMDs or other augmented reality display systems.

A first, second, third, fourth, fifth or more computing systems can be the same. A first, second, third, fourth, fifth or more computing systems can be different. A first, second, third, fourth, fifth or more computer processors can be the same. A first, second, third, fourth, fifth or more computer processors can be different.

A first, second, third, fourth, fifth or more computer processor can have the same processing speed. At least one of a first, second, third, fourth, fifth or more or more computer processor can have a different processing speed. For example, a computer processor can have a processing speed of 1 GHz, 1.5 GHz, 2.0 GHz, 2.1 GHz, 2.2 GHz, 2.3 GHz, 2.4 GHz, 2.5 GHz, 2.6 GHz, 2.7 GHz, 2.8 GHz, 2.9 Ghz, 3.0 GHz or greater. Any value is possible. Some applications of the disclosure can benefit from higher processing speeds, e.g. above 1.5 GHz or 2.0 GHz, for example when data intense, complex data packets are being acquired, generated, transmitted and/or received (see Table 2 also). A computer processor can, for example, be a Qualcomm Snapdragon 845 or later (Qualcomm, San Diego, CA 92121).

Unicast, Multicast, or Broadcast Transmission and/or Reception

Unicast

In some embodiments, data or data packets, e.g. as listed in Table 2, can be transmitted and/or received with unicast transmission and/or reception, for example between a first computing system or server and a second computing system or client; the second computing system can be configured to generate the stereoscopic or non-stereoscopic 2D or 3D display 1160 by the HMD or other augmented reality display system.

In some embodiments, a first unicast transmission can be transmitted from a first computing system and received by a second computing system, e.g. integrated into or connected to a first HMD or other augmented reality display system, with the first unicast transmission comprising the specific tracking information for the first HMD or other augmented reality display system and, optionally, instrument and/or surgical site tracking data. A second, third, fourth, fifth or more unicast transmission can be transmitted from a first computing system to a third, fourth, fifth, sixth or more computing system, e.g. integrated into or connected to a second, third, fourth, fifth or more HMD or other augmented reality display system, respectively. The second, third, fourth, fifth or more unicast transmission can be sequential, e.g. overlapping or non-overlapping.

A second unicast transmission can be transmitted from a first computing system and received by a third computing system, e.g. integrated into or connected to a second HMD or other augmented reality display system, with the second unicast transmission comprising the specific tracking information for the second HMD or other augmented reality display system and, optionally, instrument and/or surgical site tracking data.

A third unicast transmission can be transmitted from a first computing system and received by a fourth computing system, e.g. integrated into or connected to a third HMD or other augmented reality display system, with the third unicast transmission comprising the specific tracking information for the third HMD or other augmented reality display system and, optionally, instrument and/or surgical site tracking data.

A fourth unicast transmission can be transmitted from a first computing system and received by a fifth computing system, e.g. integrated into or connected to a fourth HMD or other augmented reality display system, with the fourth unicast transmission comprising the specific tracking information for the fourth HMD or other augmented reality display system and, optionally, instrument and/or surgical site tracking data.

A fifth unicast transmission can be transmitted from a first computing system and received by a sixth computing system, e.g. integrated into or connected to a fifth HMD or other augmented reality display system, with the fifth unicast transmission comprising the specific tracking information for the fifth HMD or other augmented reality display system and, optionally, instrument and/or surgical site tracking data.

Any number of unicast transmissions can be transmitted from a first computing system and received by a corresponding number of HMDs or other augmented reality display systems. If an overall transmission and reception rate of 30 Hz, 40 Hz, 50 Hz, 60 Hz, or 70 Hz is desired, the sequential unicast transmissions can be completed within 0.0333 sec, 0.025 sec, 0.02 sec, 0.0166 sec, 0.01428 sec, or any other value. The next round of sequential unicast transmissions and/or receptions can then start in order to achieve near real-time or real-time transmission and/or reception of specific tracking information for the different headsets, along with, optionally, instrument tracking and/or patient tracking data for stereoscopic and/or non-stereoscopic display of instrument and/or patient data by the one or more HMDs or other augmented reality display systems.

Multicast, Broadcast

In some embodiments, data or data packets, e.g. as listed in Table 2, can be transmitted and/or received with multicast transmission and/or reception, for example between a first computing system or server and multiple clients, e.g. a second computing system, third computing system, fourth computing system, fifth computing system, etc., optionally each with one or more computer processors; the second computing system, third computing system, fourth computing system, fifth computing system, etc. can be configured to generate the stereoscopic or non-stereoscopic 2D or 3D display 1160 by the corresponding first, second, third, and fourth etc. HMDs or other augmented reality display systems.

In some embodiments, data or data packets, e.g. as listed in Table 2, can be transmitted and/or received with broadcast transmission and/or reception, for example between a first computing system or server and multiple clients (for example all available clients), e.g. a second computing system, third computing system, fourth computing system, fifth computing system, etc., optionally each with one or more computer processors; the second computing system, third computing system, fourth computing system, fifth computing system, etc. can be configured to generate the stereoscopic or non-stereoscopic 2D or 3D display 1160 by the corresponding first, second, third, and fourth etc. HMDs or other augmented reality display systems.

With multicast or broadcast transmission and/or reception, the position, orientation, position and orientation, direction of movement and/or tracking data for each HMD or other augmented reality display system can be labelled for each HMD or other augmented reality display system, e.g. corresponding to the HMD or other augmented reality display system number, for example label "1" for the first HMD or other augmented reality display system, label "2" for the second HMD or other augmented reality display system, label "3" for the third HMD or other augmented reality display system, label "4" for the fourth HMD or other augmented reality display system, label "5" for the fifth HMD or other augmented reality display system, etc. The second computing system, third computing system, fourth computing system, fifth computing system, etc. can be configured to generate the stereoscopic or non-stereoscopic 2D or 3D display 1160 for the corresponding first, second, third, and fourth etc. HMDs or other augmented reality display systems based on the labels corresponding to each HMD or other augmented reality display system and tracking data for each respective HMD or other augmented reality display system. For example, the second computing system can identify the label for the first HMD or other augmented reality display system, e.g. "1", in the received data and generate the stereoscopic or non-stereoscopic 2D or 3D display for the first HMD or other augmented reality display system using the HMD or other augmented reality display system tracking data labeled for the first HMD or other augmented reality display system; the third computing system can identify the label for the second HMD or other augmented reality display system, e.g. "2", in the received data and generate the stereoscopic or non-stereoscopic 2D or 3D display for the second HMD or other augmented reality display system using the HMD or other augmented reality display system tracking data labeled for the second HMD or other augmented reality display system; the fourth computing system can identify the label for the third HMD or other augmented reality display system, e.g. "3", in the received data and generate the stereoscopic or non-stereoscopic 2D or 3D display for the third HMD or other augmented reality display system using the HMD or other augmented reality display system tracking data labeled for the third HMD or other augmented reality display system; the fifth computing system can identify the label for the fourth HMD or other augmented reality display system, e.g. "4", in the received data and generate the stereoscopic or non-stereoscopic 2D or 3D display for the fourth HMD or other augmented reality display system using the HMD or other augmented reality display system tracking data labeled for the fourth HMD or other augmented reality display system; and so forth for any number of HMDs or other augmented reality display systems used. In this manner, each client or second, third, fourth, fifth etc. computing system, optionally with one or more computer processors, can generate the stereoscopic or non-stereoscopic 2D or 3D display or augmented view for each HMD or other augmented reality display system with the correct view angle and viewing perspective for each specific HMD or other augmented reality display system, for example in relationship to one or more tracked anatomic structures of the patient and/or one or more tracked physical tools, instruments and/or implants and/or one or more markers attached to a patient, e.g. a fiducial array attached to a bone. For example, each client or second, third, fourth, fifth etc. computing system, optionally with one or more computer processors, can generate the stereoscopic or non-stereoscopic 2D or 3D display for each HMD or other augmented reality display system with the correct view angle and viewing perspective for each specific HMD or other augmented reality display system for a virtual display, e.g. a virtual user interface or display of one or more interactions of a tracked physical surgical tool or instrument with a virtual user interface, for example in relationship to one or more tracked anatomic structures of the patient and/or one or more tracked physical tools, instruments and/or implants and/or one or more markers attached to a patient, e.g. a fiducial array attached to a bone. In this manner, a display of a virtual user interface or of one or more interactions therewith can, for example, be displayed in the display plane of the physical HMD unit, e.g. a waveguide display or mirror based display. In this manner, for example, a display of a virtual user interface or of one or more interactions therewith can be displayed in a predetermined display plane for a first, second, third, fourth, fifth and/or sixth HMDs, for example a display plane substantially parallel to the user's retina or a display plane substantially perpendicular to one or more pupillary axes of the user's eyes. In other embodiments, a display of a virtual user interface or of one or more interactions therewith can be displayed in a predetermined position and/or orientation for a first, second, third, fourth, fifth and/or sixth HMDs, for example a display plane at a predetermined position and/or orientation in relationship to a patient, a surgical site, one or more markers attached to the patient, e.g. a fiducial array attached to a bone, one or more markers attached to a structure in an operating room, e.g. an OR table, OR light etc.

Network of HMD or Other Augmented Reality Display System Systems

In some embodiments, a network of HMDs or other augmented reality display systems can be used. One or more HMDs or other augmented reality display systems can comprise at least one camera, scanner, 3D scanner, LIDAR system, depth sensor, IMU or a combination thereof integrated into or attached to the HMD or other augmented reality display system. The at least one camera, scanner, 3D scanner, LIDAR system, depth sensor, IMU or a combination thereof integrated into or attached to the one or more HMDs or other augmented reality display systems can be used to generate coordinate and/or tracking information of one or more HMDs or other augmented reality display systems, a patient, an anatomic structure of a patient, one or more physical surgical tools, one or more physical surgical instruments, one or more robot (e.g. a robot with a robotic arm, a handheld robot, or a combination thereof) or a combination thereof.

Two or more of the HMDs or other augmented reality display systems can optionally interconnect and create a network, e.g. for a shared experience of the augmented views and/or for multi-directional generation of coordinate information and/or tracking information. The use of multi-directional generation of coordinate information and/or tracking information can be helpful to reduce or avoid line of sight issues. For example, when the line of sight is blocked for a first camera, scanner, 3D scanner, LIDAR system, depth sensor, IMU or a combination thereof integrated into or attached to a first HMD, the line of sight can be intact or maintained for a second, third, fourth, fifth, etc. or combination thereof camera, scanner, 3D scanner, LIDAR system, depth sensor, IMU or a combination thereof integrated into or attached to a first, second, third, fourth of fifth, etc. HMD.

The HMDs or other augmented reality display systems can be organized in a client-server network where multiple HMD clients can centralized around a single server, e.g. a first computing unit.

Thus, HMD devices can be relieved of computing power when outsourcing tasks which are computational intensive (image processing) to the server. Moreover, battery life of the HMD's can be significantly prolonged which can make the approach attractive even in case of a single HMD client. The server can be accessible in the OR.

In case of multiple clients, different data inputs from the various perspectives (e.g. from a first, second, third, fourth, fifth etc. HMD) can be used by the server to increase the accuracy of the calculations (e.g. by averaging out errors). In some embodiments, coordinate information and/or tracking information, e.g. from spatial maps from two or more HMD clients, can be obtained and processed by the server. For example, spatial maps can consist of triangular meshes built from each HMD's depth sensor information. Once spatial maps have been transferred from a first, second, third, fourth, fifth or combination there of HMD to the server, the different meshes can be combined into a combined, more accurate mesh using, for example, an averaging algorithm: For example, the data from a first HMD can be used as the baseline. From each face in the baseline mesh, a ray can be cast along the surface normal of the face. Intersection points between the ray and all other meshes can be calculated. A new vertex for the combined mesh can be derived as the average of all intersection points along the ray. The new vertices from adjacent triangles in the baseline mesh can be connected to form the faces in the combined mesh. The combined mesh can then be transferred back to the individual HMD's for refinement of the registration, coordinate or tracking information and/or for refinement of the real-time or near real-time updating of the stereoscopic or non-stereoscopic HMD display, e.g. superimposed and/or aligned with an anatomic structure or anatomic landmark of a patient.

In some embodiments, once coordinate information, registration information, tracking information, surface information, e.g. of one or more HMDs or other augmented reality display systems, a patient, an anatomic structure of a patient, one or more physical surgical tools, one or more physical surgical instruments, one or more robot or a combination thereof has been obtained using at least one camera, scanner, 3D scanner, LIDAR system, depth sensor, IMU or a combination thereof integrated into or attached to the HMDs or other augmented reality display systems and the information has been transferred from a first, second, third, fourth, fifth or combination there of HMD to the server, the data generated by the at least one camera, scanner, 3D scanner, LIDAR system, depth sensor, IMU or a combination thereof integrated into or attached to the two or more HMDs or other augmented reality display systems can be combined, e.g. into a combined, more accurate surface or surface mesh using, for example, an averaging algorithm. Optionally, a weighting can be applied to the data transferred by different HMDs or other augmented reality display systems, e.g. with a higher weight for HMDs or other augmented reality display systems located closer to the patient and/or closer to the at least one camera, scanner, 3D scanner, LIDAR system, depth sensor, IMU or a combination thereof.

Intrinsic and/or Extrinsic Tracking of Surgical Robots

In some embodiments, surgical robots can comprise a robotic arm, a handheld robot, handheld portions, or a combination thereof. In some embodiments, surgical robots can comprise one or more sensor, camera, video system, scanner, e.g. 3D scanner, LIDAR system, depth sensor, controller, electric controller, mechanical controller, drive, actuator, end effector, attachment mechanism, potentiometer, inertial measurement unit, accelerometer, magnetometer, gyroscope, force sensor, pressure sensor, position sensor, orientation sensor, motion sensor, wire, step motor, electric motors, hydraulic motor, electric and/or mechanical actuator, switch, display unit, computer processor, or a combination thereof.

In some embodiments, coordinate information, tracking data or a combination thereof of one or more end effectors, physical tools or instruments integrated or attached to a or part of a robot and/or of one or more physical implants, physical implant components, or physical trial implants attached to a robot can be generated with use of pose data, sensor data, camera data, 3D scanner data, controller data, drive data, actuator data, end effector data or a combination thereof of the robot or one or more robot components, for example obtained using intrinsic or internal data generated by or including intrinsic or internal, integrated or attached sensors, potentiometers, cameras, video systems, 3D scanners, LIDAR systems, depth sensors, inertial measurement units, accelerometers, magnetometers, gyroscopes, force sensors, pressure sensors, position sensors, orientation sensors, motion sensors, position and/or orientation feedback from robot step motors, position and/or orientation feedback from robot electric motors, position and/or orientation feedback from robot hydraulic motors, position and/or orientation feedback from robot electric and/or mechanical actuators, position and/or orientation feedback from robot drives, position and/or orientation feedback from robotic controllers, position and/or orientation feedback from one or more robotic computer processors, or a combination thereof. If one or more integrated or attached cameras, video systems, 3D scanners, LIDAR systems, depth sensors, or a combination thereof is used for generating intrinsic or internal robot data, the data can optionally be corrected for any distance and/or angular offset between the one or more integrated or attached cameras, video systems, 3D scanners, LIDAR systems, depth sensors, or a combination thereof and an end effector, a surgical tool or instrument attached to or integrated into or part of the robot, e.g. a cutting tool, tissue removal tool (e.g. a drill, saw, reamer, impactor), or an ablation tool. Alternatively and/or additionally, If one or more integrated or attached cameras, video systems, 3D scanners, LIDAR systems, depth sensors, or a combination thereof is used for generating intrinsic or internal robot data, the data can optionally be corrected for any distance and/or angular offset between the one or more integrated or attached cameras, video systems, 3D scanners, LIDAR systems, depth sensors, or a combination thereof and an anatomic structure, surface and/or landmark of a patient. Any combination of offset, e.g. distance and/or angle, correction is possible. In some embodiments, one or more cameras, video systems, 3D scanners, LIDAR systems, depth sensors external to a robot (e.g. on a stand, in an OR light and/or one or more HMDs or other augmented reality display systems) can be used for determining the distance and/or angle offset.

In some embodiments, coordinate information, tracking data or a combination thereof of one or more end effectors, physical tools or instruments integrated or attached to or part of a robot and/or of one or more physical implants, physical implant components, or physical trial implants attached to a robot can be obtained or generated with use of one or more cameras, video systems, 3D scanners, LIDAR systems, depth sensors, or combination thereof extrinsic or external to the robot and, for example, integrated or attached to one or more HMDs or other augmented reality display systems, separate from one or more HMDs or other augmented reality display systems (e.g. on a stand, tripod, attached to or integrated into OR lighting, OR fixtures, an imaging system (e.g. x-ray, cone beam CT, CT)), or a combination thereof. One or more computer processors can be configured, for example, using the one or more cameras, video systems, 3D scanners, LIDAR systems, depth sensors, or combination thereof extrinsic or external to the robot, to determine the position, orientation, direction of movement, one or more coordinates, or combination thereof of at least a portion of the one or more end effectors, physical surgical tools, at least a portion of the robot, or a combination thereof (e.g. using image processing and/or pattern recognition and/or an artificial neural network) or of one or more markers, e.g. active markers (e.g. RF markers), passive markers (e.g. infrared markers), optical markers (e.g. with geometric patterns, QR codes, bar codes, defined shapes, e.g. triangles, squares, rectangles etc.), LEDs or a combination thereof integrated or attached to the one or more end effectors, physical tools or instruments, integrated or attached to at least portions of the robot, or a combination thereof (extrinsic or external data).

In some embodiments, one or more displays by one or more computer monitors or by one or more HMDs or other augmented reality display systems can be generated, wherein the display can be non-stereoscopic (e.g. by the computer monitor, other augmented reality display device(s) and/or the HMD) or stereoscopic (e.g. by the HMD).

In some embodiments, one or more computer processors can generate a display, e.g. by a computer monitor and/or one or more HMDs or other augmented reality display systems, of virtual data, e.g. a virtual surgical plan, one or more virtual surgical guides (e.g. a virtual axis, virtual plane, virtual gut guide) and/or one or more patient surface(s) using intrinsic or internal robot data, e.g. registration data, coordinate data, and/or tracking data of one or more HMDs or other augmented reality display systems, a patient, an anatomic structure of a patient, one or more physical surgical tools, one or more physical surgical instruments, one or more robot, or a combination thereof.

In some embodiments, one or more computer processors can generate a display, e.g. by a computer monitor and/or one or more HMDs or other augmented reality display systems, of virtual data, e.g. a virtual surgical plan, one or more virtual surgical guides (e.g. a virtual axis, virtual plane, virtual gut guide) and/or one or more patient surface(s) using extrinsic or external robot data, e.g. registration data, coordinate data, and/or tracking data of end effectors, one or more physical surgical tools, one or more physical surgical instruments, one or more robot, or a combination thereof.

In some embodiments, one or more computer processors can generate a display, e.g. by a computer monitor and/or one or more HMDs or other augmented reality display systems, of virtual data, e.g. a virtual surgical plan, one or more virtual surgical guides (e.g. a virtual axis, virtual plane, virtual gut guide) and/or one or more patient surface(s) using intrinsic or internal and extrinsic or external robot data, e.g. registration data, coordinate data, and/or tracking data of one or more HMDs or other augmented reality display systems, a patient, an anatomic structure of a patient, one or more physical surgical tools, one or more physical surgical instruments, one or more robot, or a combination thereof. In this example, intrinsic and or internal robot data can, optionally, be displayed using a different color or display pattern than extrinsic or external robot data, thereby highlighting potential differences and/or deviations. In some embodiments, one or more computer processors can be used to compute any differences and/or deviations between intrinsic or internal and extrinsic or external robot data, e.g. a difference in a projected instrument or tool path, e.g. a drill path, a saw path, a difference in a planned or executed tissue resection. One or more computer processors can be configured to generate a difference display, for example by a computer monitor and/or one or more HMDs or other augmented reality display systems, e.g. using color coding, line or bar charts or any other chart known in the art, and/or alphanumeric display. The difference between intrinsic or internal and extrinsic or external robot data, e.g. registration data, coordinate data, and/or tracking data of one or more HMDs or other augmented reality display systems, a patient, an anatomic structure of a patient, one or more physical surgical tools, one or more physical surgical instruments, one or more robot, or a combination thereof can be used to highlight any potential deviation of a robot from a predetermined plan, e.g. a predetermined tissue resection (for example a predetermined tissue resection volume, tissue resection area, tissue resection surface, bone cut, drilling, reaming, milling, impacting).

Intrinsic and/or Extrinsic Tracking of Imaging Systems and Imaging System Components In some embodiments, an imaging system can comprise one or more imaging system components. In some embodiments, one or more imaging system components can comprise one or more sensor, camera, video system, scanner, e.g. 3D scanner, LIDAR system, depth sensor, controller, electric controller, mechanical controller, drive, actuator, end effector, attachment mechanism, potentiometer, inertial measurement unit, accelerometer, magnetometer, gyroscope, force sensor, pressure sensor, position sensor, orientation sensor, motion sensor, wire, step motor, electric motors, hydraulic motor, electric and/or mechanical actuator, switch, display unit, computer processor, or a combination thereof.

In some embodiments, coordinate information, tracking data or a combination thereof of one or more imaging system components can be generated with use of pose data, sensor data, camera data, 3D scanner data, controller data, drive data, actuator data, end effector data or a combination thereof of the one or more imaging system components, for example obtained using intrinsic or internal data generated by or including intrinsic or internal, integrated or attached sensors, potentiometers, cameras, video systems, 3D scanners, LIDAR systems, depth sensors, inertial measurement units, accelerometers, magnetometers, gyroscopes, force sensors, pressure sensors, position sensors, orientation sensors, motion sensors, position and/or orientation feedback from imaging system component step motors, position and/or orientation feedback from imaging system component electric motors, position and/or orientation feedback from imaging system component hydraulic motors, position and/or orientation feedback from system component electric and/or mechanical actuators, position and/or orientation feedback from imaging system component drives, position and/or orientation feedback from imaging system component controllers, position and/or orientation feedback from imaging system component computer processors, or a combination thereof. If one or more integrated or attached cameras, video systems, 3D scanners, LIDAR systems, depth sensors, or a combination thereof is used for generating intrinsic or internal imaging system component data, the data can optionally be corrected for any distance and/or angular offset between the one or more integrated or attached cameras, video systems, 3D scanners, LIDAR systems, depth sensors, or a combination thereof and one or more imaging system components. Alternatively and/or additionally, If one or more integrated or attached cameras, video systems, 3D scanners, LIDAR systems, depth sensors, or a combination thereof is used for generating intrinsic or internal imaging system component data, the data can optionally be corrected for any distance and/or angular offset between the one or more integrated or attached cameras, video systems, 3D scanners, LIDAR systems, depth sensors, or a combination thereof and an anatomic structure, surface and/or landmark of a patient. Any combination of offset, e.g. distance and/or angle, correction is possible. In some embodiments, one or more cameras, video systems, 3D scanners, LIDAR systems, depth sensors external to one or more imaging system components (e.g. on a stand, in an OR light and/or one or more HMDs or other augmented reality display systems) can be used for determining the distance and/or angle offset.

In some embodiments, coordinate information, tracking data or a combination thereof of one or more imaging system components can be obtained or generated with use of one or more cameras, video systems, 3D scanners, LIDAR systems, depth sensors, or combination thereof extrinsic or external to the imaging system components and, for example, integrated or attached to one or more HMDs or other augmented reality display systems, separate from one or more HMDs or other augmented reality display systems (e.g. on a stand, tripod, attached to or integrated into OR lighting, OR fixtures, an imaging system (e.g. x-ray, cone beam CT, CT)), or a combination thereof. One or more computer processors can be configured, for example, using the one or more cameras, video systems, 3D scanners, LIDAR systems, depth sensors, or combination thereof extrinsic or external to the one or more imaging system components, to determine the position, orientation, direction of movement, one or more coordinates, or combination thereof of at least a portion of the one or more imaging system components (e.g. using image processing and/or pattern recognition and/or an artificial neural network) or of one or more markers, e.g. active markers (e.g. RF markers), passive markers (e.g. infrared markers), optical markers (e.g. with geometric patterns, QR codes, bar codes, defined shapes, e.g. triangles, squares, rectangles etc.), LEDs or a combination thereof integrated or attached to the one or more imaging system components (extrinsic or external data).

In some embodiments, one or more displays by one or more computer monitors or by one or more HMDs or other augmented reality display systems can be generated, wherein the display can be non-stereoscopic (e.g. by the computer monitor, other augmented reality display device(s) and/or the HMD) or stereoscopic (e.g. by the HMD).

In some embodiments, one or more computer processors can generate a display, e.g. by a computer monitor and/or one or more HMDs or other augmented reality display systems, of virtual data, e.g. a virtual surgical plan, one or more virtual surgical guides (e.g. a virtual axis, virtual plane, virtual gut guide), one or more pre-operative or intra-operative imaging data and/or one or more patient surface(s) using intrinsic or internal imaging system data, e.g. registration data, coordinate data, and/or tracking data of one or more imaging system components.

In some embodiments, one or more computer processors can generate a display, e.g. by a computer monitor and/or one or more HMDs or other augmented reality display systems, of virtual data, e.g. a virtual surgical plan, one or more virtual surgical guides (e.g. a virtual axis, virtual plane, virtual gut guide) one or more pre-operative or intra-operative imaging data and/or one or more patient surface(s) using extrinsic or external tracking data, e.g. registration data, coordinate data, and/or tracking data of one or more HMDs or other augmented reality display systems, a patient, an anatomic structure of a patient, one or more physical surgical tools, one or more physical surgical instruments, one or more imaging system components, or a combination thereof.

In some embodiments, one or more computer processors can generate a display, e.g. by a computer monitor and/or one or more HMDs or other augmented reality display systems, of virtual data, e.g. a virtual surgical plan, one or more virtual surgical guides (e.g. a virtual axis, virtual plane, virtual gut guide) and/or one or more patient surface(s) using intrinsic or internal and extrinsic or external data, e.g. registration data, coordinate data, and/or tracking data of one or more HMDs or other augmented reality display systems, a patient, an anatomic structure of a patient, one or more physical surgical tools, one or more physical surgical instruments, one or more imaging system components, or a combination thereof. In this example, intrinsic and or internal imaging system data can, optionally, be displayed using a different color or display pattern than extrinsic or external imaging system data, thereby highlighting potential differences and/or deviations. In some embodiments, one or more computer processors can be used to compute any differences and/or deviations between intrinsic or internal and extrinsic or external imaging system data. One or more computer processors can be configured to generate a difference display, for example by a computer monitor and/or one or more HMDs or other augmented reality display systems, e.g. using color coding, line or bar charts or any other chart known in the art, and/or alphanumeric display.

Aspects of the disclosure relate to a system comprising at least one head mounted display or other augmented reality display device, at least one camera or scanning device, a first computing system comprising one or more computer processors and a second computing system comprising one or more computer processors,

- wherein the first computing system is configured to obtain real-time tracking information of the at least one head mounted display or other augmented reality display device, of at least one anatomic structure of a patient, and of at least one physical surgical tool or physical surgical instrument using the at least one camera or scanning device,
- wherein the first computing system is configured for wireless transmission of the real-time tracking information of the at least one head mounted display or other augmented reality display device, the at least one anatomic structure of the patient, and the at least one physical surgical tool or physical surgical instrument,
- wherein the second computing system is connected to or integrated into the at least one head mounted display or other augmented reality display device,
- wherein the second computing system is configured for wireless reception of the real-time tracking information of the at least one head mounted display or other augmented reality display device, the at least one anatomic structure of the patient, and the at least one physical surgical tool or physical surgical instrument, and
- wherein the second computing system is configured to generate a 3D stereoscopic view, wherein the stereoscopic view comprises a 3D representation of the at least one physical surgical tool or physical surgical instrument.

In some embodiments, the one or more computer processors of the second computing system generate the 3D stereoscopic view for the view angle of the head mounted display or other augmented reality display device relative to the at least one anatomic structure of the patient using the real-time tracking information of the at least one head mounted display or other augmented reality display device.

In some embodiments, the real-time tracking information comprises tracking information of two or more head mounted display or other augmented reality display devices.

In some embodiments, the real-time tracking information comprises a head mounted display or other augmented reality display device specific label for each head mounted display or other augmented reality display device. In some embodiments, the real-time tracking information is labeled for each tracked head mounted display or other augmented reality display device.

In some embodiments, the real-time tracking information comprises tracking information of two or more head mounted display or other augmented reality display devices. In some embodiments, the two or more head mounted display or other augmented reality display devices are located in different locations. In some embodiments, the real-time tracking information comprises a head mounted display or other augmented reality display device specific label for each head mounted display or other augmented reality display device. In some embodiments, the real-time tracking information is labeled for each tracked head mounted display or other augmented reality display device.

In some embodiments, the one or more computer processors of the second computing system generate the 3D stereoscopic view for an interpupillary distance adjusted for a person wearing the head mounted display or other augmented reality display device.

In some embodiments, the second computing system is integrated with the at least one head mounted display or other augmented reality display device.

In some embodiments, the second computing system is separate from the at least one head mounted display or other augmented reality display device and is connected to the display unit of the at least one head mounted display or other augmented reality display device using at least one cable.

In some embodiments, the wireless transmission or reception or transmission and reception comprises a WiFi signal, a LiFi signal, a Bluetooth signal or a combination thereof.

In some embodiments, the camera or scanning device is separate from the at least one head mounted display or other augmented reality display device.

In some embodiments, the camera or scanning device is integrated or attached to the at least one head mounted display or other augmented reality display device.

In some embodiments, the wireless transmission comprises sending data packets comprising the real-time tracking information of the at least one head mounted display or other augmented reality display device, the at least one anatomic structure of a patient, and the at least one physical surgical tool or physical surgical instrument, at a rate of 20 Hz or greater.

In some embodiments, the wireless reception comprises receiving data packets comprising the real-time tracking information of the at least one head mounted display or other augmented reality display device, the at least one anatomic structure of a patient, and the at least one physical surgical tool or physical surgical instrument, at a rate of 20 Hz or greater.

In some embodiments, the system comprising a third computing system, wherein the third computing system is configured for wireless reception of the real-time tracking information from the first computing system and wherein the third computing system is configured for wireless transmission of the real-time tracking information to the second computing system.

In some embodiments, the third computing system comprises a chain of computing systems configured for wireless reception and wireless transmission of the real-time tracking information.

In some embodiments, the system comprises a third computing system, wherein the third computing system is connected to or integrated into a second head mounted display or other augmented reality display device, wherein the third computing system is configured for wireless reception of the real-time tracking information of the second head mounted display or other augmented reality display device, the at least one anatomic structure of a patient, and the at least one physical surgical tool or physical surgical instrument, wherein the third computing system is configured to generate a 3D stereoscopic view by the second head mounted display or other augmented reality display device using the tracking information of the second head mounted display or other augmented reality display device.

In some embodiments, the tracking information of the second head mounted comprises a label specific to the second head mounted display or other augmented reality display device for identifying the tracking information of the second head mounted display or other augmented reality display device by the third computing system.

In some embodiments, the system comprising a fourth computing system, wherein the fourth computing system is connected to or integrated into a third head mounted display or other augmented reality display device, wherein the fourth computing system is configured for wireless reception of the real-time tracking information of the third head mounted display or other augmented reality display device, the at least one anatomic structure of a patient, and the at least one physical surgical tool or physical surgical instrument, and wherein the fourth computing system is configured to generate a 3D stereoscopic view by the third head mounted display or other augmented reality display device using the tracking information of the third head mounted display or other augmented reality display device.

In some embodiments, the tracking information of the third head mounted comprises a label specific to the third head mounted display or other augmented reality display device for identifying the tracking information of the third head mounted display or other augmented reality display device by the fourth computing system.

In some embodiments, the system comprises a fifth computing system, wherein the fifth computing system is connected to or integrated into a fourth head mounted display or other augmented reality display device, wherein the fifth computing system is configured for wireless reception of the real-time tracking information of the fourth head mounted display or other augmented reality display device, the at least one anatomic structure of a patient, and the at least one physical surgical tool or physical surgical instrument, and wherein the fifth computing system is configured to generate a 3D stereoscopic view by the fourth head mounted display or other augmented reality display device using the tracking information of the fourth head mounted display or other augmented reality display device.

In some embodiments, the tracking information of the fourth head mounted comprises a label specific to the fourth head mounted display or other augmented reality display device for identifying the tracking information of the fourth head mounted display or other augmented reality display device by the fifth computing system.

In some embodiments, the real-time tracking information comprises one or more coordinates.

In some embodiments, the one or more coordinates comprise coordinates of the at least one anatomic structure of the patient.

In some embodiments, the one or more coordinates comprise coordinates of the at least one physical surgical tool or physical surgical instrument.

In some embodiments, the one or more coordinates comprise coordinates of the at least one head mounted display or other augmented reality display device.

In some embodiments, the at least one head mounted display or other augmented reality display device comprises at least one optical see-through head mounted display or other augmented reality display device.

In some embodiments, the at least one head mounted display or other augmented reality display device comprises at least one video see-through head mounted display or other augmented reality display device.

In some embodiments, the at least one camera, the at least one scanning device or the at least one camera and the at least one scanning device comprises a laser scanner, a time-of-flight 3D laser scanner, a structured-light 3D scanner, a hand-held laser scanner, a LIDAR scanner, a time-of-flight camera, a depth camera, a video system, a stereoscopic camera system, a camera array, or a combination thereof.

In some embodiments, the system comprises at least one inertial measurement unit. In some embodiments, the at least one inertial measurement unit is integrated or attached to the at least one physical surgical tool or physical surgical instrument. In some embodiments, the at least one inertial measurement unit is integrated or attached to the at least one anatomic structure of the patient. In some embodiments, the at least one inertial measurement unit is integrated or attached to the at least one head mounted display or other augmented reality display device.

In some embodiments, the real-time tracking information of the at least one head mounted display or other augmented reality display device comprises information from the at least one inertial measurement unit.

Aspects of the disclosure relate to a system comprising two or more head mounted display or other augmented reality display devices, at least one camera or scanning device, a first computing system comprising one or more computer processors, wherein the first computing system is configured to obtain real-time tracking information of at least one anatomic structure of a patient, of at least one physical surgical tool or physical surgical instrument, and of the two or more head mounted display or other augmented reality display devices, using the at least one camera or scanning device, wherein the tracking information of the two or more head mounted display or other augmented reality display devices is labeled specific for each head mounted display or other augmented reality display device, wherein the first computing system is configured for wireless transmission of the real-time tracking information of the at least one anatomic structure of the patient, the tracking information of the at least one physical surgical tool or physical surgical instrument, and the labeled tracking information of the two or more head mounted display or other augmented reality display devices, a second computing system, wherein the second computing system is connected to or integrated into a first of the two or more head mounted display or other augmented reality display devices, wherein the second computing system is configured for wireless reception of the real-time tracking information of the at least one anatomic structure of the patient, the tracking information of the at least one physical surgical tool or physical surgical instrument, and the labeled tracking information of the first of the two or more head mounted display or other augmented reality display devices, wherein the second computing system is configured to generate a 3D stereoscopic display specific for the viewing perspective of the first head mounted display or other augmented reality display device using the labeled tracking information of the first head mounted display or other augmented reality display device, a third computing system, wherein the third computing system is connected to or integrated into a second of the two or more head mounted display or other augmented reality display devices, wherein the third computing system is configured for wireless reception of the real-time tracking information of the at least one anatomic structure of the patient, the tracking information of the at least one physical surgical tool or physical surgical instrument, and the labeled tracking information of the second of the two or more head mounted display or other augmented reality display devices, wherein the third computing system is configured to generate a 3D stereoscopic display specific for the viewing perspective of the second head mounted display or other augmented reality display device using the labeled tracking information of the second head mounted display or other augmented reality display device, wherein the stereoscopic view comprises a 3D representation of the at least one physical surgical tool or physical surgical instrument.

Virtual User Interface

In some embodiments, a physical tool or instrument (see Table 2), e.g. a tracked pointer, a tracked stylus, a tracked tool, a tracked instrument or a combination thereof, can be used for interacting with a virtual interface display by an HMD. Any tracking technique known in the art can be used, e.g. inside-out tracking, outside-in tracking or a combination thereof, as described, for example in PCT International Application Serial Nos. PCT/US2017/021859, PCT/US2018/013774, PCT/US2019/61698 and PCT/US2019/015522, which are hereby incorporated in their entirety.

A tracked pointer, a tracked stylus, or another tracked tool or tracked instrument or a combination thereof can comprise one or more markers. In some embodiments, the marker can be configured to reflect or emit light with a wavelength between 380 nm and 700 nm or any value or range or subrange therebetween. In some embodiments, the marker can be configured to reflect or emit light with a wavelength greater than 700 nm. For example, the marker can be configured to reflect or emit light with a wavelength between 700 nm and 1 mm or any value or range or subrange therebetween. In some embodiments, the marker can be configured to reflect or emit light with a wavelength less than 380 nm. For example, the marker can be configured to reflect or emit light with a wavelength between 50 nm and 380 nm or any value or range or subrange therebetween. In some embodiments, the marker can be a radiofrequency marker, e.g. an active marker, an infrared marker, e.g. a retroreflective or passive marker. The marker can be an optical marker, e.g. an optical marker that comprises a geometric pattern. One, two or more markers can be attached to or integrated into a tracked pointer, a tracked stylus, other tracked tool, other tracked instrument or a combination thereof. A tracked pointer, a tracked stylus, other tracked tool, other tracked instrument or a combination thereof can also comprise one or more integrated or attached IMUs.

In some embodiments, the system comprises at least one camera, scanner (e.g. 3D scanner, laser scanner), LIDAR system, depth sensor, IMU or a combination thereof integrated into or attached to the head mounted display or other augmented reality display device. In some embodiments, at least one camera, scanner (e.g. 3D scanner, laser scanner), LIDAR system, depth sensor, IMU or a combination thereof can be separate from the head mounted display or other augmented reality display device. The at least one camera, scanner (e.g. 3D scanner, laser scanner), LIDAR system, depth sensor, IMU or a combination thereof integrated or attached to the one or more HMDs or other augmented reality display systems and/or separate from the one or more HMDs or other augmented reality display systems can be configured to scan and/or detect a pointer, stylus, tool, instrument or a combination thereof; the pointer, stylus, tool, instrument or a combination thereof can be tracked in 3D space, e.g. as they are being moved by a user. The tracking can be direct, e.g. by directly recognizing the instrument, for example utilizing a stored shape, surface, and/or 2D or 3D outline data of the pointer, stylus, tool, instrument or combination thereof or a library of shapes, surfaces, and/or 2D or 3D outline data of one or more pointer, stylus, tool, instrument or combination thereof, using one or more computer processors.

Direct Tracking of Tool and/or Instrument for Interaction with Virtual Interface One or more computer processors can be configured to detect a physical tool or instrument, e.g. a tracked pointer, a tracked stylus, other tracked tool or tracked instrument, or a combination thereof, using a camera and/or scanner (e.g. a video camera, infrared camera, 3D scanner, laser scanner, LIDAR, imaging system etc.), e.g. in the image or scanner data, and, optionally, follow and/or track the pointer, stylus, tool, instrument, or combination thereof in real-time or near real-time, for example within the 3D space included in the image or scanner data. The one or more camera and/or scanner (e.g. a video camera, infrared camera, 3D scanner, laser scanner, LIDAR, imaging system etc.) can be integrated into or attached to one or more HMD units or can be separate from one or more HMD units or a combination thereof. Optionally, a pointer, stylus, tool, instrument, or combination thereof included in the image or scanner data can be compared against a database or library of stored shapes, surfaces, and/or 2D or 3D outline data of one or more (optionally different) pointer(s), stylus(s), other tool(s), other instrument(s) or combination thereof and can be identified using the database of stored shapes, surfaces, and/or 2D or 3D outline data of the one or more (optionally different) pointer(s), stylus(s), other tool(s), other instrument(s) or combination thereof. Identification of the pointer, stylus, tool, instrument, or combination thereof included in the image or scanner data can, optionally, facilitate tracking of the pointer, stylus, tool, instrument or combination thereof. The database can also comprise information about one or more optical markers, fiducials, fiducial arrays, and/or marker or array configurations.

In some embodiments, a pointer, a surgical tool or instrument can comprise a unique marker, fiducial array or marker/array configuration. In this manner, one or more computer processors can be configured to detect and/or identify the unique marker, fiducial array or marker/array configuration associated with that pointer, surgical tool or instrument. If a pointer, tool or instrument has been identified by at least one computer processor using any of the foregoing techniques, the at least one computer processor can associate and/or activate and/or display certain functions, e.g. display functions and/or system functions associated with that tool.

For example, if a pointer has been identified by the at least one computer processor, e.g. based on identification of its unique shape (e.g. relative to a database of tool shapes) or based on identification of a unique marker, fiducial array or marker/array configuration, the identification by the at least one computer processor can trigger or initiate a specific function. For example, during set-up of an augmented reality system for a surgical procedure, a calibration procedure can be activated. When a pointer (or other tool or instrument) is identified the system can, for example, automatically display, by an HMD or other augmented reality device, a virtual object, e.g. one associated with the calibration procedure. In this example of an AR display calibration, the virtual object can be moved by moving the tracked physical pointer. The movement of the virtual object can be corresponding to the movement of the tracked physical pointer, or it can be at a different movement ratio between movement of the virtual object and movement of the tracked physical pointer, e.g. 1:1, 1.5:1, 2.0:1, 0.5:1.0, or any other ratio, for example expressed in mm, cm, and/or angular degrees. By moving the tracked physical pointer so that the virtual object, e.g. a virtual marker ball, is superimposed and/or aligned with a corresponding physical object, e.g. a physical marker ball, the system can determine the coordinate difference and/or coordinate transfer and/or distance, angular movement required to superimpose the virtual object onto the physical object; the information can be used to move a virtual display, facilitated by at least one computer processor, as a means of optimizing the superimposition and/or alignment for a user between virtual display of any virtual objects (e.g. a virtual spine and/or virtual instrument and/or virtual implant) and the corresponding physical objects and/or structures (e.g. a corresponding physical spine and/or a corresponding physical instrument and/or a corresponding physical implant). The data/information related to the coordinate difference and/or coordinate transfer and/or distance and/or angular movement required to superimpose a virtual object onto a corresponding physical object can be used, by the at least one computer processor, as a means of AR system calibration to more closely match a virtual AR display, axis of an AR display, center of an AR display with the optical axis of the user's eye(s).

The data can optionally be wirelessly transmitted and/or received by a first computing system (e.g. communicably connected to a navigation system, a robot, and/or an imaging system) and a second (or more) computing system(s) (communicably connected to one or more HMDs or other augmented reality display devices).

In another example, a system can detect another unique marker, fiducial array or marker/array configuration associated, for example, with another instrument, e.g. an awl. The identification of the unique marker, fiducial array or marker/array configuration associated with the awl can trigger a display, by an HMD or other augmented reality display device, of a targeting tool for targeting the awl, e.g. superimposed onto a target anatomic structure of the patient.

One or more computer processors can be configured to detect and/or identify the tip and/or axis and/or direction of movement of a pointer, stylus, tool, instrument or combination thereof, for example by detecting a shape, contour and/or outline, optional identification of the stylus, tool, instrument or combination thereof used, and optional use of known shape data and/or dimensions of the stylus, tool, instrument or combination thereof.

The one or more computer processors configured to detect a pointer, stylus, other tool, other instrument, or combination thereof using a camera and/or scanner, e.g. in the image or scanner data, and, optionally, configured to follow and/or track the pointer, stylus, other tool, other instrument, or combination thereof in real-time or near real-time can be part of a first computing system, for example, a server or controller or computing unit as shown in FIG. 1, 1180. The one or more computer processors configured to detect a pointer, stylus, other tool, other instrument, or combination thereof using a camera and/or scanner, e.g. in the image or scanner data, and, optionally, configured to follow and/or track the pointer, stylus, other tool, other instrument, or combination thereof in real-time or near real-time can be part of a second computing system, e.g. a client or mobile unit integrated into, attached to or connected via cable to an HMD. Inside-out and/or outside-in tracking techniques can be used by one or more computer processors for tracking a pointer, stylus, other tool, other instrument, or combination thereof using a camera and/or scanner.

Tracking of Tool and/or Instrument Using Markers for Interaction with Virtual Interface One or more computer processors can be configured to detect one or more markers integrated or attached to one or more physical tool or instrument, e.g. a tracked pointer, a tracked stylus, other tracked tool or tracked instrument, or a combination thereof, using a camera and/or scanner, e.g. a video camera, infrared camera, 3D scanner, laser scanner, LIDAR, imaging system etc., and, optionally, follow and/or track the one or more pointer, stylus, tool, or instrument in real-time or near real-time, using the one or more markers. The one or more camera and/or scanner (e.g. a video camera, infrared camera, 3D scanner, laser scanner, LIDAR, imaging system etc.) can be integrated into or attached to one or more HMD units or can be separate from one or more HMD units or a combination thereof.

One or more computer processors can be configured to detect and/or identify the tip and/or axis and/or direction of movement of a pointer, stylus, other tool, other instrument or combination thereof, using one or more integrated or attached markers.

The one or more computer processors configured to detect and/or track one or more markers integrated or attached to one or more pointer, stylus, other tool, other instrument, or combination thereof, using a camera and/or scanner in real-time or near real-time can be part of a first computing system, for example, a server or controller or computing unit as shown in FIG. 1, 1180. The one or more computer processors configured to detect and/or track one or more markers integrated or attached to one or more pointer, stylus, other tool, other instrument, or combination thereof, using a camera and/or scanner in real-time or near real-time can be part of a second computing system, e.g. a client or mobile unit integrated into, attached to or connected via cable to an HMD. Inside-out and/or outside-in tracking techniques can be used by one or more computer processors for tracking one or more markers integrated into or attached to a pointer, stylus, tool, instrument, or combination thereof using a camera and/or scanner. The markers can be any of the markers described in the specification or known in the art, e.g. active markers, passive markers, infrared markers, retroreflective markers, radiofrequency markers, optical markers, e.g. with geometric patterns, bar codes, QR codes, Aruco codes etc.

Virtual Interface Display

One or more HMDs or other augmented reality display systems can optionally generate a 2D or 3D stereoscopic or non-stereoscopic virtual display or augmented view comprising a virtual interface, e.g. superimposed on a physical patient, physical anatomic structure, physical anatomic landmark and/or physical anatomic surface and/or near or adjacent to a physical patient, physical anatomic structure, physical anatomic landmark and/or physical anatomic surface. One or more computer processors, e.g. in a first (e.g. a server) or second (e.g. a client) computing system can be configured to generate a 2D or 3D stereoscopic or non-stereoscopic virtual display comprising a virtual interface at a predetermined location and/or orientation relative to one or more anatomic structures and/or the patient. One or more computer processors, e.g. in a first (e.g. a server) or second (e.g. a client) computing system can be configured to generate a 2D or 3D stereoscopic or non-stereoscopic virtual display comprising a virtual interface, for example at a predetermined location and/or orientation relative to one or more markers (e.g. infrared markers, radiofrequency markers, active markers, passive markers, optical markers [e.g. with geometric patterns, bar codes, QR codes etc.], LED's etc.) attached to one or more anatomic structures and/or the patient and/or a fixed structure in the operating room. The one or more markers can, for example, be a fiducial array attached to one or more bones. One or more computer processors, e.g. in a first (e.g. a server) or second (e.g. a client) computing system can be configured to generate a 2D or 3D stereoscopic or non-stereoscopic virtual display comprising a virtual interface at a predetermined location and/or orientation relative to one or more structures in the operating room, e.g. an OR table, an OR light, an external computer monitor etc. One or more computer processors, e.g. in a first (e.g. a server) or second (e.g. a client) computing system can be configured to generate a 2D or 3D stereoscopic or non-stereoscopic virtual display comprising a virtual interface at a predetermined location and/or orientation relative to the user's eyes and/or face and/or relative to the physical HMD or other augmented reality display unit, e.g. the housing of the HMD unit or the physical display (e.g. combiner, waveguide and/or mirror) of the HMD.

A 2D or 3D stereoscopic or non-stereoscopic virtual display comprising a virtual interface displayed by one or more HMDs or other augmented reality display systems can comprise, for example, one or more virtual button, virtual field, virtual cursor, virtual pointer, virtual slider, virtual trackball, virtual node, virtual numeric display, virtual touchpad, virtual keyboard, or a combination thereof. The one or more one or more virtual button, virtual field, virtual cursor, virtual pointer, virtual slider, virtual trackball, virtual node, virtual numeric display, virtual touchpad, virtual keyboard, or a combination thereof can be displayed, by the one or more HMDs or other augmented reality display systems, using one or more computer processors, in 2D, in 3D, or a combination thereof. For example, a virtual slider can be in 2D and/or in 3D. A 3D virtual slider can, for example, comprise an activation or sliding field oriented in x-direction, an activation or sliding field oriented in y-direction, and an activation or sliding field oriented in z-direction. The system can be configured for detecting various interactions by a user with the one or more virtual objects of a virtual interface, for example an interaction via gesture recognition, gaze recognition, gaze lock, eye tracking, hand tracking, pointer tracking, instrument tracking, tool tracking, or a combination thereof. For example, a tracked finger, tracked hand, tracked pointer, tracked instrument, tracked tool can interact with the virtual interface. The interaction can trigger an event message, optionally managed by an event handler, and/or a command. The interaction, event message, command or combination thereof can optionally be transmitted and/or received between a first and a second computing system, for example a first computing system (e.g. communicably connected to a navigation system, a robot, and/or an imaging system) and a second (or more) computing system(s) (communicably connected to one or more HMDs or other augmented reality display devices.

Collision Detection

In some embodiments, the system can comprise a collision detection module or other interaction module. The collision detection module or other interaction module can be a module separate from other modules, such as an AR visualization module 1150 or an AR display module 1160. The collision detection module or other interaction module can be part of another module, e.g. a submodule of another module, such as an AR visualization module 1150 or an AR display module 1160.

One or more of the computer processors operating a collision detection module or other interaction module, one or more computer processors operating a tracking engine or tracking module 1100, one or more computer processors operating an instrument calibration module 1110, one or more of the computer processors operating a headset calibration module 1120, one or more of the computer processors operating an imaging and navigation module 1130, one or more of the computer processors operating an AR wireless networking module 1140, one or more of the computer processors operating an AR visualization module 1150, and/or one or more of the computer processors operating an AR display module 1160 can be the same.

One or more of the computer processors operating a collision detection module or other interaction module, one or more computer processors operating a tracking engine or tracking module 1100, one or more computer processors operating an instrument calibration module 1110, one or more of the computer processors operating a headset calibration module 1120, one or more of the computer processors operating an imaging and navigation module 1130, one or more of the computer processors operating an AR wireless networking module 1140, one or more of the computer processors operating an AR visualization module 1150, and/or one or more of the computer processors operating an AR display module 1160 can be different.

In some embodiments, one or more HMDs or other augmented reality display systems and one or more physical tools or physical instruments, e.g. a pointer, a stylus, other tools, other instruments, can be tracked, e.g. using inside-out or outside-in tracking. The coordinates, position and/or orientation of a virtual display comprising a virtual interface displayed by one or more HMDs or other augmented reality display systems can also be tracked. One or more computer processors can be configured, using one or more collision detection modules, to detect collisions between a gaze (e.g. using gaze tracking, gaze lock), a finger (e.g. using finger/hand tracking), a hand (e.g. using hand tracking), an eye (e.g. using eye tracking), one or more tracked physical tools or physical instruments, e.g. a tracked pointer, a tracked stylus, other tracked physical tools, other tracked physical instruments, or a combination thereof and a virtual display comprising the virtual interface, e.g. one or more virtual objects such as virtual button, virtual field, virtual cursor, virtual pointer, virtual slider, virtual trackball, virtual node, virtual numeric display, virtual touchpad, virtual keyboard, or a combination thereof.

One or more computer processors can use polygon based collision detection or detection of other interactions. One or more computer processors can use volume based collision detection or detection of other interactions. One or more computer processors can be configured with a predetermined tolerance for a collision detection or detection of other interactions, e.g. <0.1, <0.5, <1.0, <1.5, <2.0, <3.0, <4.0, <5.0, <10.0 mm, or any other value, and/or <0.1, <0.5, <1.0, <1.5, <2.0, <3.0, <4.0, <5.0, <10.0, <15.0, <20.0 degrees, or any other value. In some embodiments, the tolerance for a collision detection or detection of other interactions can be selected and/or predetermined, for example, to enable a particular application, e.g. activating or executing a command, moving a virtual slider, selecting a virtual button, etc. The tolerance for a collision detection or detection of other interactions can be the same or different for different applications, e.g. an HMD calibration, an instrument calibration, an AR visualization module, e.g. comprising selection of a predetermined path for a physical tool or instrument.

Different collision detection modules or packages known in the art include, for example I-collide [Cohen et al. "I—COLLIDE: An Interactive and Exact Collision Detection System for Large-Scale Environments," in *The* 1995 *ACM International* 3*D Graphics Conference*], V-clip [Mirtich et al. "V-Clip: Fast and Robust Polyhedral Collision Detection," ACM Trans. Graphics, 17, 3, pp. 177-208], SWIFT [Ehrmann et al. "SWIFT: Accelerated Proximity Queries Between Convex Polyhedra by Multi-Level Voronoi Marching," Technical report, Computer Science Department, University of North Carolina at Chapel Hill], RAPID [Gottschalk et al. OBB-Tree: A Hierarchical Structure for Rapid Interference Detection," Computer Graphics SIGGRAPH '96 Proceedings 30, pp. 171-180], V-collide [Hudson et al. "V-COLLIDE: Accelerated Collision Detection for VRML", in *Proceedings of the Second Symposium on Virtual Reality Modeling Language*. California, United States, ACM Press], PQP [Larsen et al. "Fast Proximity Queries With Swept Sphere Volumes" Technical Report TR99-018, Department of Computer Science, University of North Carolina. SOLID [Bergen et al. "User's Guide to the SOLID Interference Detection Library"; SWIFT [Ehrmann et al. "Accurate and Fast Proximity Queries Between Polyhedra Using Surface Decomposition", Eurographics.

Computer Graphics Forum, 20, 3, or VPS [McNeely et al. "Six Degree-of-Freedom Haptic Rendering Using Voxel Sampling", SIGGRAPH 99 Conference Proceedings, Annual Conference Series, pp. 401-408].

In some embodiments, a collision detection module, e.g. I-collide, can utilize convex polyhedra for multi-body collision detection. In some embodiments, a collision detection module such as RAPID can utilize non-convex models, detecting, for example, detects pair-wise collisions. Some collision detection modules, e.g. V-collide, can be configured to detect multiple body collisions.

Some collision detection modules, e.g. PQP, can support non-convex modes and/or can optionally perform distance computation and/or tolerance verification queries. Some collision detection modules, e.g. SWIFT, can comprise intersection detection, tolerance verification, exact and approximate distance computation, contact determination, or a combination thereof. Some collision detection methods, e.g. I-collide, RAPID, PQP and/or SWIFT, can be based on polygon intersection. Some collision detection packages, e.g. VPS, can utilize voxels and can, for example, detect collisions, perform tolerance verification, approximate distances, and determine contact normal, center of mass, or a combination thereof.

One or more computer processors can be configured to utilize sweep-based continuous collision detection. Sweep-based continuous collision detection can use a Time Of Impact (TOI) algorithm to compute potential collisions, e.g. for a gaze (e.g. using gaze tracking, gaze lock), a finger (e.g. using finger/hand tracking), a hand (e.g. using hand tracking), an eye (e.g. using eye tracking), for one or more tracked physical pointer, tracked physical tool, tracked physical instrument, or a combination thereof by sweeping its forward trajectory using its current velocity based on the tracking data. If there are contacts with the virtual display, comprising, for example a virtual interface, e.g. along the moving direction of the one or more tracked physical pointer, tracked physical tool, tracked physical instrument, or a combination thereof, one or more computer processors can be configured to detect the collision. In some embodiments, one or more computer processors can be configured to compute a time of impact, e.g. for a given moving direction and/or speed of a tracked physical pointer, physical tool, tracked physical instrument, or combination thereof. The one or more computer processors can perform sub steps from that time onwards, computing the velocity after TOI then re-sweep.

One or more computer processors can be configured to utilize speculative continuous collision detection. Speculative continuous collision detection can operate by increasing a broad-phase axis-aligned minimum bounding box of a tracked physical surgical tool, tracked physical instrument or combination thereof, based on the linear and angular motion of the tracked physical surgical tool, tracked physical instrument or combination thereof. The algorithm can be speculative since it can pick all potential contacts during the next physical step. The contacts can then be fed into a solving program operated by one or more computer processors, which can ensure that applicable or predetermined contact constraints can be satisfied. One or more computer processors, e.g. on a first computing unit (e.g. a server) and/or a second computing unit (e.g. a client integrated or connected to an HMD or other augmented reality display device) can operate commercially available software with one or more integrated collision detection modules or programs, e.g. Unity software (Unity Software, Inc.).

Commands and/or Executable Actions Triggered Using Virtual Interface

In some embodiments, a first computing unit, e.g. a server or controller, can comprise a collision detection module or a module for detection of other interactions (e.g. software program). In some embodiments, a second computing unit, e.g. a mobile client (for example communicably connected to or part of one or more HMD or other augmented reality display units) can comprise a collision detection module or a module for detection of other interactions, program or software. In some embodiments, for example when a system comprises multiple HMDs or other augmented reality display systems, a second, third, fourth, fifth, sixth, etc. computing unit, e.g. a second, third, fourth, fifth, sixth, etc. wireless, mobile client, can comprise a collision detection module or a module for detection of other interactions, program or software, for example a collision detection module or a module for detection of other interactions, program or software for each HMD unit and associated computing unit. In some embodiments, one or more computer processors of a first computing unit and a second, and/or third, and/or fourth, and/or fifth, and/or sixth, etc. computing unit can operate the same collision detection module or module for detection of other interactions. In some embodiments, one or more computer processors of a first computing unit and a second, and/or third, and/or fourth, and/or fifth, and/or sixth, etc. computing unit can operate different collision detection modules or modules for detection of other interactions.

In some embodiments, one or more computer processors of a first computing unit and a second, and/or third, and/or fourth, and/or fifth, and/or sixth, etc. computing unit can operate the same collision detection module or module for detection of other interactions, which can be used for the same functions and/or interactions and/or commands of/with a virtual object displayed as part of a virtual interface. In some embodiments, one or more computer processors of a first computing unit and a second, and/or third, and/or fourth, and/or fifth, and/or sixth, etc. computing unit can operate the same collision detection module or module for detection of other interactions, which can be used for the different functions and/or interactions and/or commands of/with a virtual interface.

In some embodiments, one or more data packets, for example as described in Table 2, e.g. tracking data of one or more HMDs or other augmented reality display systems, one or more virtual displays, one or more physical pointers, physical tools, or physical instruments, one or more physical implants, one or more robots or robotic arms, can be transmitted from a first computing system wirelessly to a second, and/or third, and/or fourth, and/or fifth, and/or sixth, etc. computing system, e.g. a second, and/or third, and/or fourth, and/or fifth, and/or sixth, etc. wireless, mobile client integrated into or connected to a first, and/or second, and/or third, and/or fourth, and/or fifth, etc. HMD or other augmented reality display unit. One or more computer processors of the second, and/or third, and/or fourth, and/or fifth, and/or sixth, etc. wireless, mobile client can operate one or more collision detection modules, e.g. using Unity software (Unity Software, Inc., 30 3rd Street, San Francisco, CA 94103), to detect collisions of one or more tracked physical tools or instruments, e.g. a physical pointer or a physical stylus or other physical tool or instrument, with a virtual interface displayed by the one or more HMDs or other augmented reality display systems; the collision(s) of the tracked physical tool or instrument, or a gaze (e.g. using gaze tracking, gaze lock), a finger (e.g. using finger/hand tracking), a hand (e.g. using hand tracking), an eye (e.g. using eye tracking) with different portions, aspects, fields or displays of the virtual interface, e.g. a virtual button, virtual field, virtual cursor, virtual pointer, virtual slider, virtual trackball, virtual node, virtual numeric display, virtual touchpad, virtual keyboard, or a combination thereof, can be used to trigger one or more actions and/or one or more commands, which can, optionally be transmitted from the second, and/or third, and/or fourth, and/or fifth, and/or sixth, etc. wireless, mobile client and be received by the first computing unit for further processing, e.g. execution of commands by one or more computer processors.

In some embodiments, coordinate and/or tracking data of one or more HMDs or other augmented reality display systems and/or one or more virtual displays by one or more HMDs or other augmented reality display systems (see Table 2) can be received by a first computing unit, along with tracking data of one or more physical tools or physical instruments, one or more physical implants, one or more robots or robotic arms. The first computing unit or system can operate one or more collision detection modules to detect collisions of one or more tracked physical tools or instruments, e.g. a physical pointer or a physical stylus or other physical tool or instrument, with the virtual display, e.g. a virtual interface, displayed by the one or more HMDs or other augmented reality display systems. The collision(s) of the tracked physical tool or instrument with different portions, aspects, fields or displays of the virtual interface, e.g. a virtual object such as a virtual button, virtual field, virtual cursor, virtual pointer, virtual slider, virtual trackball, virtual node, virtual numeric display, virtual touchpad, virtual keyboard, or a combination thereof, can be used to trigger one or more actions and/or one or more commands, which can be processed by one or more computer processors of the first computing system and which can, optionally be transmitted to a second, and/or third, and/or fourth, and/or fifth, and/or sixth, etc. wireless, mobile client connected to or integrated into a first, second, third, fourth, and/or fifth etc. HMD or other augmented reality display device, optionally triggering commands and/or actions by one or more computer processors of the second, and/or third, and/or fourth, and/or fifth, and/or sixth, etc. wireless, mobile client(s) and one or more connected HMDs or other augmented reality display systems.

In some embodiments, a physical tool or instrument (see Table 2), e.g. a tracked pointer, a tracked stylus, a tracked tool, a tracked instrument or a combination thereof, can be used for interacting with a virtual interface display by an HMD or other augmented reality display device. In some embodiments, a gaze (e.g. using gaze tracking, gaze lock), a finger (e.g. using finger/hand tracking), a hand (e.g. using hand tracking), an eye (e.g. using eye tracking) or a combination thereof can be used for interacting with a virtual interface display by an HMD or other augmented reality display device. In some embodiments, a collision or other interaction, e.g. of a tracked physical tool or instrument, with a virtual display, e.g. a virtual object in a virtual user interface, displayed by a first HMD can be detected by one or more computer processors in a first computing system, e.g. a server, and/or a second computing system, e.g. a client integrated, attached to or connected to the first HMD (and/or optionally a second, third, fourth, fifth, sixth or more HMD). The collision and/or other interaction can optionally be used to execute a function and/or to change the appearance of the virtual display, e.g. virtual interface, e.g. with a color change, display of different buttons and/or functions, etc.

Data and/or execution functions related to or triggered by a collision and/or other interaction of a tracked physical tool or instrument with a virtual display, e.g. a virtual interface, and/or changes in a virtual display, e.g. a virtual interface, triggered by the collision or other interaction with the tracked physical tool or instrument for display by one or more HMDs or other augmented reality display systems can be generated by one or more computer processors in a first computing unit, e.g. a server, and can be transmitted to one or more additional computing units, for example a second, third, fourth, fifth or more computing unit, e.g. a client integrated, attached to or connected to one or more HMDs or other augmented reality display systems.

Data and/or execution functions related to or triggered by a collision and/or other interaction of a tracked physical tool or instrument with a virtual display, e.g. a virtual interface, and/or changes in a virtual display, e.g. a virtual interface, triggered by the collision or other interaction with the tracked physical tool or instrument for display by one or more HMDs or other augmented reality display systems can be generated by one or more computer processors in a second (or first) computing unit, e.g. a client integrated, attached to or connected to a first HMD, and can be transmitted to a first (or second) computing unit, e.g. a server (e.g. separate from the one or more HMDs or other augmented reality display systems). One or more computer processors in the second (or first) computing unit, e.g. the server, can be configured to process and/or transmit the data and/or execution functions related to or triggered by the collision and/or other interaction of the tracked physical tool or instrument with the virtual display, e.g. a virtual interface, and/or changes in the virtual display, e.g. a virtual interface, triggered by the collision or other interaction with the tracked physical tool or instrument to one or more additional computing units, for example a second, third, fourth, fifth or more computing unit, e.g. one or more clients integrated, attached to or connected to one or more additional HMDs or other augmented reality display systems for display by the one or more additional HMDs or other augmented reality display systems.

Figure 3:
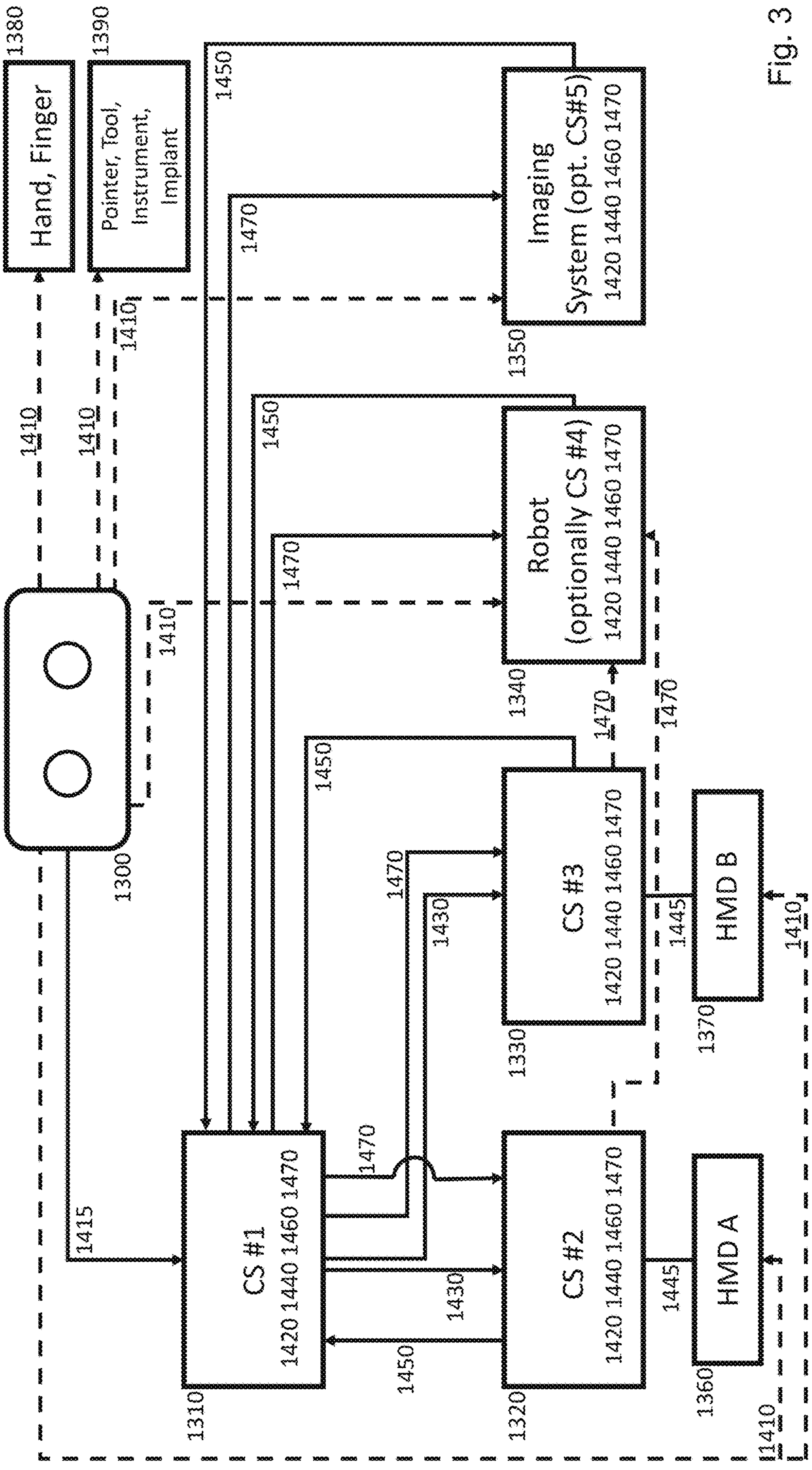
FIG. 3 shows a non-limiting example of a tracking system, one or more computer systems, one or more robots, one or more imaging systems, and/or one or more head mounted displays, wherein, for example, a computer system can be configured to generate a command, e.g. by interaction of a user with a virtual object displayed by a virtual user interface, for activating, de-activating, operating, moving one or more systems, components, displays etc. of a navigation system, the one or more head mounted displays, the robot and/or the imaging system.

FIG. 3 is a representative, non-limiting example of a tracking system 1300, e.g. one or more cameras, including cameras using visible and/or infrared light, stereoscopic cameras, a Lidar system and/or camera(s), a scanner, for example a 3D scanner, one or more computer systems (CS) CS #1 1310, CS #2 1320, CS #3 1330, each with one or more computer processors, one or more robots 1340, e.g. handheld, attached to an OR table, and/or comprising a robotic arm, one or more imaging systems 1350, e.g. a C-arm, 3D C-arm, cone beam CT, spiral CT, MRI, and/or one or more head mounted displays HMD A 1360 HMD B 1370, e.g. a stereoscopic optical see-through head mounted display and/or a stereoscopic video see-through head mounted display. The one or more robots 1340 and/or one or more imaging systems 1350 can also comprise one or more computer systems (e.g. CS #4, CS #5), for example each with one or more computer processors.

A first computer system CS #1 1310 can, for example, reside in a server or computer, for example located in the operating room. The one or more first computer systems CS #1 1310 can also be located in a remote location, e.g. outside the operating room, and/or can comprise a cloud computing system and/or communicate through a cloud computing system, e.g. through a wired or a wireless connection. One or more second CS #2 1320, third CS #3 1330, or more computer systems can be integrated into, connected to or attached to one or more head mounted displays HMD A 1360 and/or HMD B 1370 or other augmented reality display devices. The tracking system 1300 can be separate from the one or more head mounted displays HMD A 1360 and/or HMD B 1370 or other augmented reality display devices. In some embodiments, the tracking system 1300 can be integrated or attached to the one or more head mounted displays HMD A 1360 and/or HMD B 1370 or other augmented reality display devices.

The tracking system 1300 can be configured to track 1410 optionally a hand and/or finger 1380, a pointer, tool, instrument and/or implant 1390, optionally a first 1360, second 1370, third, fourth, fifth etc. head mounted display, a patient (not shown), and/or a robot 1340 and/or an imaging system 1350 or a combination thereof, for example with use of the first computer system CS #1 1310 and/or optionally with use of a second computer system CS #2 1320, a third computer CS #3 1330, and/or additional computer systems.

The tracking system 1300 can be configured to track 1410 optionally a hand and/or finger 1380, a pointer, tool, instrument and/or implant 1390, optionally a first 1360, second 1370, third, fourth, fifth etc. head mounted display, a patient (not shown), and/or a robot 1340 and/or an imaging system 1350 or a combination thereof, and to transmit the tracking information 1415 to a first computer system CS #1 1310 and/or optionally a second computer system CS #2 1320, a third computer CS #3 1330, and/or additional computer systems.

The second CS #2 1320, third CS #3 1330, and/or additional computer systems can be integrated into, connected to or attached to one or more HMDs 1360 1370 or other augmented reality display systems. The one or more additional computer systems can be attached to, connected to or located inside a robotic system 1340 and/or an imaging system 1350. The tracking 1410 can comprise recording one or more coordinates of and/or tracking a hand and/or finger 1380, a pointer, tool, instrument, and/or implant 1390, and/or a first 1360, second 1370, third, fourth, fifth etc. head mounted display or other augmented reality display device, and/or a patient (not shown) by the first computer system CS #1 1310 and/or the second computer system CS #2 1320, and/or the third computer CS #3 1330, and/or additional computer systems, e.g. in a robot 1340 or imaging system 1350, for example using the camera or scanner 1300. The tracking 1410 can comprise recording one or more coordinates of a hand and/or finger 1380, a pointer, tool, instrument, and/or implant 1390, and/or a first 1360, second 1370, third, fourth, fifth etc. head mounted display, and/or the patient (not shown) by the first computer system CS #1 1310 and/or the second computer system CS #2 1320, and/or the third computer CS #3 1330, and/or additional computer systems, e.g. in a robot 1340 or imaging system 1350, for example using the camera or scanner 1300. The system can track a hand and/or finger 1380, a pointer, tool, instrument, and/or implant 1390, and/or a first 1360, second 1370, third, fourth, fifth etc. head mounted display, and/or the patient (not shown) by the first computer system CS #1 1310 and/or the second computer system CS #2 1320, and/or the third computer CS #3 1330, and/or additional computer systems, e.g. in a robot 1340 or imaging system 1350, for example using the camera or scanner 1300.

One or more computer processors of the one or more first 1310, second 1320, third 1330 etc. computer systems, can be configured to perform one or more coordinate transformations 1420 and/or to determine a pose 1420 of the hand or finger 1380, the one or more pointer, tool, instrument, and/or implant 1390, the first 1360, second 1370, third, fourth, fifth etc. head mounted display, and/or the patient (not shown).

The one or more computer processors of the one or more first 1310, second 1320, third 1330 etc. or additional computer systems, e.g. also in a robot 1340 and/or an imaging system 1350, can be configured to transmit and/or receive 1430 information about the finger or hand 1380, or the one or more pointer, tool, instrument, and/or implant 1390, e.g. their pose, information about or for the first 1360, second 1370, third, fourth, fifth etc. head mounted display or other augmented reality display devices, e.g. the pose of the head mounted display(s) or other augmented reality display devices or display data for the head mounted display(s) 1360 1370 or other augmented reality display devices, and/or the patient (not shown), for example using Bluetooth or a WiFi or LiFi wireless access point, e.g. including a transmitter and/or receiver, or a wired connection. The transmission and/or reception 1430 can comprise data about gaze direction of the wearer of a headset, e.g. a first 1360, second 1370, third, fourth, fifth etc. head mounted display. The transmission and/or reception 1430 can be wireless, e.g. using a broadcast or multiple unicast transmissions to and/or from the first 1360, second 1370, third, fourth, fifth etc. head mounted display, as described in the specification. The transmission can comprise positional data, display data and/or other data. The transmission 1430 can be to or from a first computer system 1310 to or from a second computer system 1320, to or from a third computer system 1330, to or from a fourth, fifth or more computer system. The transmission can be to or from a second computer system 1320 to or from a first computer system 1310, to or from a third computer system 1330, to or from a fourth, fifth or more computer system. The transmission can be to or from a third computer system 1330 to or from a first computer system 1310, to or from a second computer system 1320, to or from a fourth, fifth or more computer system, and so forth.

In any of the embodiments throughout the specification, the transmission 1430 can be unidirectional and/or bi-directional, simultaneous uni-directional and/or bi-directional, and/or non-simultaneous, e.g. sequential uni-directional and/or bi-directional, or a combination thereof between the one or more first 1310, second 1320, third 1330 etc. or additional computer systems, e.g. also integrated into or attached to a robot and/or an imaging system.

In any of the embodiments throughout the specification, a second 1320, third 1330 etc. or additional computer systems, can be integrated into, connected to, and/or attached to and/or separate from one or more HMDs 1360, 1370 or other augmented reality display systems, one or more robotic systems 1340, and/or one or more imaging systems 1350. One or more computer systems 1310 can be separate from, e.g. standalone, from one or more HMDs 1360, 1370 or other augmented reality display systems, one or more robotic systems 1340, and/or one or more imaging systems 1350.

One or more computer processors of one or more first 1310, second 1320, third 1330 etc. or additional computer systems, e.g. also in a robot 1340 and/or an imaging system 1350, can be configured to generate one or more user interface controls 1440. The one or more user interface controls 1440 can, for example, be virtual interface controls. The one or more user interface controls 1440 can comprise, for example, one or more virtual button, virtual field, virtual cursor, virtual pointer, virtual slider, virtual trackball, virtual node, virtual numeric display, virtual touchpad, virtual keyboard, or a combination thereof.

One or more computer processors of the one or more first 1310, second 1320, third 1330 etc. or additional computer systems, e.g. also in a robot 1340 and/or an imaging system 1350, can be configured to perform one or more collision detections 1445, for example between a hand or finger 1380 and a virtual interface displayed by one or more head mounted displays 1360 1370 or other augmented reality display devices, or a tracked physical pointer, physical tool, physical instrument, physical implant component 1390 or a combination thereof and a virtual interface displayed by one or more head mounted displays 1360 1370 or other augmented reality display devices; the collision detection can be performed, for example, using the tracking system 1300 (or a camera or scanner integrated or attached to an HMD or other augmented reality display devices). One or more computer processors of the one or more first 1310, second 1320, third 1330 etc. or additional computer systems, e.g. also in a robot 1340 and/or an imaging system 1350, can be configured to perform a gesture recognition, for example between a hand or finger 1380 and a virtual interface using one or more cameras, optionally integrated or attached to one or more head mounted displays 1360 1370. The first computer system 1310 can, for example, be a standalone computer system or a cloud computing system. The second 1320, third 1330 etc. or additional computer systems, can be, for example, integrated into, connected to, and/or attached to and/or separate from one or more HMDs 1360, 1370 or other augmented reality display systems, one or more robotic systems 1340, and/or one or more imaging systems 1350.

One or more computer systems, e.g. a first 1310, second 1320, third 1330 etc. or additional computer systems, e.g. also in a robot 1340 and/or an imaging system 1350, can be configured to generate and/or transmit, optionally wirelessly, one or more event message 1450. The one or more event message can, for example, be an event message relative to a collision detection 1445 between a hand or finger 1380, a tracked physical pointer, physical tool, physical instrument, physical implant component 1390 or a combination thereof and a virtual interface, e.g. using the tracking system 1300. The one or more event message 1450 can optionally comprise an event message related to a robot 1340 control, interface, force, and/or position and/or orientation and/or an imaging system 1350 control, interface, force, and/or position and/or orientation.

One or more computer systems, e.g. a first 1310, second 1320, third 1330, fourth, fifth etc. or additional computer systems, e.g. also in a robot 1340 and/or an imaging system 1350, can comprise an optional event handler 1460 configured to handle, manage and/or process one or more optional event message 1450.

One or more computer systems, e.g. a first 1310, second 1320, third 1330 etc. or additional computer systems, e.g. also in a robot 1340 and/or an imaging system 1350, can be configured to initiate and/or process an optional event action 1470, e.g. executing a command, e.g. based on the event message 1450 and, optionally, information or data received from the event handler 1460. The command can be transmitted through a wireless or a wired connection, e.g. to a robot 1340 or an imaging system 1350.

In some embodiments, the one or more computer systems configured to generate an event message 1450 can be the same or different computer system comprising the event handler 1460 and/or can be the same or different computer system initiating and/or processing the event action 1470, e.g. executing a command. In some embodiments, one or more computer processors configured to generate an event message 1450 can be the same or different computer processors comprising the event handler 1460 and/or can be the same or different computer processors initiating and/or processing the event action 1470, e.g. executing a command. In some embodiments, a first, second, third, fourth, fifth, sixth or more computer system can be the same for managing different tasks, or can be different for managing different tasks.

Figure 4:
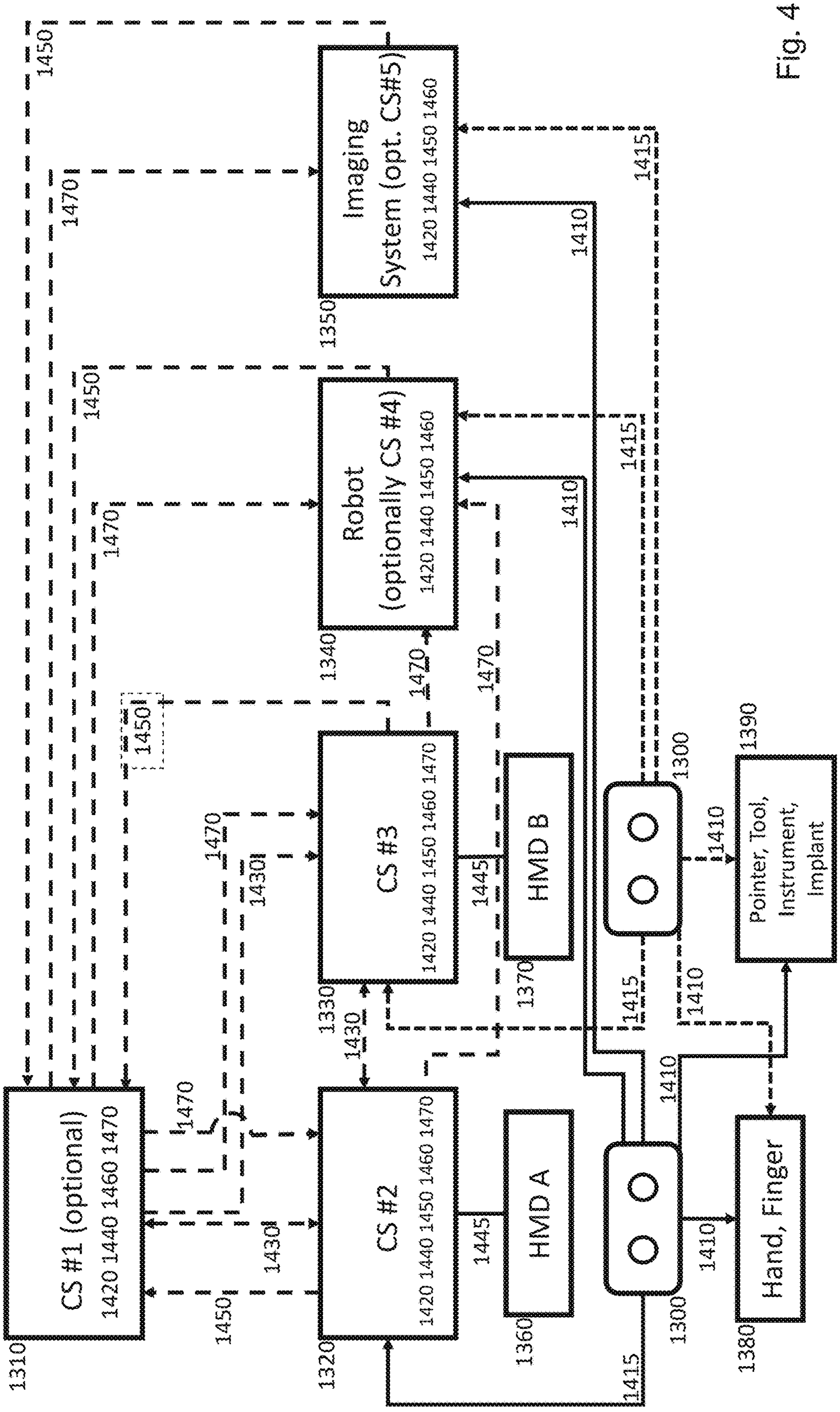
FIG. 4 shows a non-limiting example of one or more tracking systems, in this example integrated or attached to one or more head mounted displays, one or more computer systems, one or more computer processors, one or more robots, one or more imaging systems, and/or one or more head mounted displays, for example configured for activating, de-activating, operating, moving one or more systems, components, displays etc. of a navigation system, the one or more head mounted displays, the robot and/or the imaging system.

FIG. 4 is a representative, non-limiting example of one or more tracking systems 1300, e.g. one or more cameras, including cameras using visible and/or infrared light, stereoscopic cameras, a Lidar system and/or camera(s), a scanner, for example a 3D scanner, in this example integrated or attached to one or more head mounted displays 1360 1370 or other augmented reality display devices, one or more computer systems (CS) CS #1 1310, CS #2 1320 (e.g. integrated, connected, or attached to a head mounted display 1360 or other augmented reality display device), CS #3 1330 (e.g. integrated, connected, or attached to a head mounted display 1370 or other augmented reality display device), each with one or more computer processors, one or more robots 1340, e.g. handheld, attached to an OR table, and/or comprising a robotic arm, one or more imaging systems 1350, e.g. a C-arm, 3D C-arm, cone beam CT, spiral CT, MRI, and/or one or more head mounted displays HMD A 1360 HMD B 1370, e.g. a stereoscopic optical see-through head mounted display and/or a stereoscopic video see-through head mounted display, or other augmented reality display devices. The one or more robots 1340 and/or one or more imaging systems 1350 can also comprise one or more computer systems (e.g. CS #4, CS #5), for example each with one or more computer processors.

A first, optional computer system CS #1 1310 can, for example, reside in a server or computer, for example located in the operating room. The one or more optional first computer systems CS #1 1310 can also be located in a remote location, e.g. outside the operating room, and/or can comprise a cloud computing system and/or communicate through a cloud computing system, e.g. through a wired or a wireless connection. One or more second CS #2 1320, third CS #3 1330, or more computer systems can be integrated into, connected to or attached to one or more head mounted displays HMD A 1360 and/or HMD B 1370 or other augmented reality display devices.

The one or more tracking system(s) 1300 can be integrated or attached to the one or more head mounted displays HMD A 1360 and/or HMD B 1370 or other augmented reality display devices.

The one or more tracking systems 1300 can be configured to track 1410 optionally a hand and/or finger 1380, e.g. of a user, a pointer, tool, instrument and/or implant 1390, a patient (not shown), and/or a robot 1340 and/or an imaging system 1350 or a combination thereof, for example with use of a second computer system CS #2 1320, a third computer CS #3 1330, and/or additional computer systems. An optional first computer system CS #1 1310 can also be used for tracking, including for processing tracking information.

The tracking system 1300 can be configured to track 1410 optionally a hand and/or finger 1380, a pointer, tool, instrument and/or implant 1390, a patient (not shown), and/or a robot 1340 and/or an imaging system 1350 or a combination thereof, and to transmit the tracking information 1415 to a second computer system CS #2 1320, a third computer CS #3 1330, and/or additional computer systems; the transmission can be wired or wireless. The one or more tracking systems 1300 can be integrated into or attached to one or more head mounted displays 1360 1370 or other augmented reality display devices. The one or more computer systems 1320 1330, including one or more computer processors, can be integrated into or connected to the one or more head mounted displays 1360 1370 or other augmented reality display devices. The second CS #2 1320, third CS #3 1330, and/or additional computer systems can be integrated into, connected to or attached to one or more HMDs 1360 1370 or other augmented reality display systems. The one or more additional computer systems can be attached to, connected to or located inside a robotic system 1340 and/or an imaging system 1350.

The tracking 1410 can comprise recording one or more coordinates of and/or tracking a hand and/or finger 1380, a pointer, tool, instrument, and/or implant 1390, and/or a patient (not shown) by a second computer system CS #2 1320, and/or a third computer CS #3 1330, and/or additional computer systems, e.g. in a robot 1340 or imaging system 1350, for example using the camera(s) or scanner(s) 1300. The tracking 1410 can comprise recording one or more coordinates of a hand and/or finger 1380, a pointer, tool, instrument, and/or implant 1390, and/or the patient (not shown) by the second computer system CS #2 1320, and/or the third computer CS #3 1330, and/or additional computer systems, e.g. in a robot 1340 or imaging system 1350, for example using the camera or scanner 1300. The system can track a hand and/or finger 1380, a pointer, tool, instrument, and/or implant 1390, and/or the patient (not shown) by the second computer system CS #2 1320, and/or the third computer CS #3 1330, and/or additional computer systems, e.g. in a robot 1340 or imaging system 1350, for example using tracking system, for example with a camera or scanner 1300.

One or more computer processors of the one or more first 1310, second 1320, third 1330 etc. computer systems, can be configured to perform one or more coordinate transformations and/or to determine a pose 1420 of the hand or finger 1380, the one or more pointer, tool, instrument, and/or implant 1390, and/or optionally the first 1360, second 1370, third, fourth, fifth etc. head mounted display or other augmented reality display device (e.g. in relationship to a marker attached to a patient), and/or the patient (not shown).

The one or more computer processors of the one or more first, optional, 1310, second 1320, third 1330 etc. or additional computer systems, e.g. also in a robot 1340 and/or an imaging system 1350, can be configured to transmit and/or receive 1430 information about the finger or hand 1380, or the one or more pointer, tool, instrument, and/or implant 1390, e.g. their pose, and/or optionally information about or for the first 1360, second 1370, third, fourth, fifth etc. head mounted display, e.g. the pose of the head mounted display(s) (or other augmented reality display device) (e.g. relative to a marker on a patient) or display data for the head mounted display(s) 1360 1370 or other augmented reality display devices, and/or the patient (not shown), for example using a wireless connection, e.g. Bluetooth or a wireless WiFi or LiFi access point, optionally including a transmitter and/or receiver, or using a wired connection. The transmission and/or reception 1430 can comprise data about gaze direction of the wearer of a headset (for example for use with a gaze cursor) (or data about gaze direction of the user of another augmented reality display devices), e.g. a first 1360, second 1370, third, fourth, fifth etc. head mounted display. The transmission and/or reception 1430 can be wired or wireless, e.g. using a broadcast or multiple unicast transmissions to and/or from the first 1360, second 1370, third, fourth, fifth etc. head mounted display, as described in the specification. The transmission can comprise positional data, display data and/or other data. The transmission 1430 can be to or from an optional first computer system 1310 to or from a second computer system 1320, to or from a third computer system 1330, to or from a fourth, fifth or more computer system. The transmission can be to or from a second computer system 1320 to or from an optional first computer system 1310, to or from a third computer system 1330, to or from a fourth, fifth or more computer system. The transmission can be to or from a third computer system 1330 to or from an optional first computer system 1310, to or from a second computer system 1320, to or from a fourth, fifth or more computer system, and so forth.

In any of the embodiments throughout the specification, the transmission 1430 can be unidirectional and/or bi-directional, simultaneous uni-directional and/or bi-directional, and/or non-simultaneous, e.g. sequential uni-directional and/or bi-directional, or a combination thereof between the one or more first (optional) 1310, second 1320, third 1330 etc. or additional computer systems, e.g. also integrated into or attached to a robot and/or an imaging system.

In any of the embodiments throughout the specification, a second 1320, third 1330 etc. or additional computer systems, can be integrated into, connected to, and/or attached to and/or separate from one or more HMDs 1360, 1370 or other augmented reality display systems, one or more robotic systems 1340, and/or one or more imaging systems 1350. One or more computer systems 1310 can be separate from, e.g. standalone, from one or more HMDs 1360, 1370 or other augmented reality display systems, one or more robotic systems 1340, and/or one or more imaging systems 1350.

One or more computer processors of one or more first 1310, second 1320, third 1330 etc. or additional computer systems, e.g. also in a robot 1340 and/or an imaging system 1350, can be configured to generate one or more user interface controls 1440. The one or more user interface controls 1440 can, for example, be virtual interface controls. The one or more user interface controls 1440 can comprise, for example, one or more virtual button, virtual field, virtual cursor, virtual pointer, virtual slider, virtual trackball, virtual node, virtual numeric display, virtual touchpad, virtual keyboard, or a combination thereof.

One or more computer processors of the one or more first (optional) 1310, second 1320, third 1330 etc. or additional computer systems, e.g. also in a robot 1340 and/or an imaging system 1350, can be configured to perform one or more collision detections 1445, for example between a hand or finger 1380 and a virtual interface displayed by one or more head mounted displays 1360 1370 or other augmented reality display devices, or a tracked physical pointer, physical tool, physical instrument, physical implant component 1390 or a combination thereof and a virtual interface displayed by one or more head mounted displays 1360 1370 or other augmented reality display devices; the collision detection can be performed, for example, using the tracking system 1300. One or more computer processors of the one or more first 1310, second 1320, third 1330 etc. or additional computer systems, e.g. also in a robot 1340 and/or an imaging system 1350, can be configured to perform a gesture recognition, for example between a hand or finger 1380 and a virtual interface, displayed by one or more head mounted displays 1360 1370, using one or more cameras, optionally integrated or attached to one or more head mounted displays 1360 1370. The one or more cameras can be part of the one or more tracking systems 1300. The optional first computer system 1310 can, for example, be a standalone computer system or a cloud computing system. The second 1320, third 1330 etc. or additional computer systems, can be, for example, integrated into, connected to, and/or attached to and/or separate from one or more HMDs 1360, 1370 or other augmented reality display systems, one or more robotic systems 1340, and/or one or more imaging systems 1350.

One or more computer systems, e.g. a first 1310, second 1320, third 1330 etc. or additional computer systems, e.g. also in a robot 1340 and/or an imaging system 1350, can be configured to generate and/or transmit, optionally wirelessly, one or more event message 1450. The one or more event message can, for example, be an event message relative to a collision detection 1445 between a hand or finger 1380, a tracked physical pointer, physical tool, physical instrument, physical implant component 1390 or a combination thereof and a virtual interface, e.g. detected using the tracking system 1300. The one or more event message 1450 can optionally comprise an event message related to a robot 1340 control, interface, force, and/or position and/or orientation and/or an imaging system 1350 control, interface, force, and/or position and/or orientation.

One or more computer systems, e.g. a first 1310, second 1320, third 1330, fourth, fifth etc. or additional computer systems, e.g. also in a robot 1340 and/or an imaging system 1350, can comprise an optional event handler 1460 configured to handle, manage and/or process one or more optional event message 1450.

One or more computer systems, e.g. a first 1310, second 1320, third 1330 etc. or additional computer systems, e.g. also in a robot 1340 and/or an imaging system 1350, can be configured to initiate and/or process an optional event action 1470, e.g. executing a command, e.g. based on the event message 1450 and, optionally, information or data received from the event handler 1460. The command can be transmitted through a wireless or a wired connection, e.g. to a robot 1340 or an imaging system 1350.

In some embodiments, the one or more computer systems configured to generate an event message 1450 can be the same or different computer system comprising the event handler 1460 and/or can be the same or different computer system initiating and/or processing the event action 1470, e.g. executing a command. In some embodiments, one or more computer processors configured to generate an event message 1450 can be the same or different computer processors comprising the event handler 1460 and/or can be the same or different computer processors initiating and/or processing the event action 1470, e.g. executing a command. In some embodiments, a first, second, third, fourth, fifth, sixth or more computer system can be the same for managing different tasks, or can be different for managing different tasks.

Figure 5:
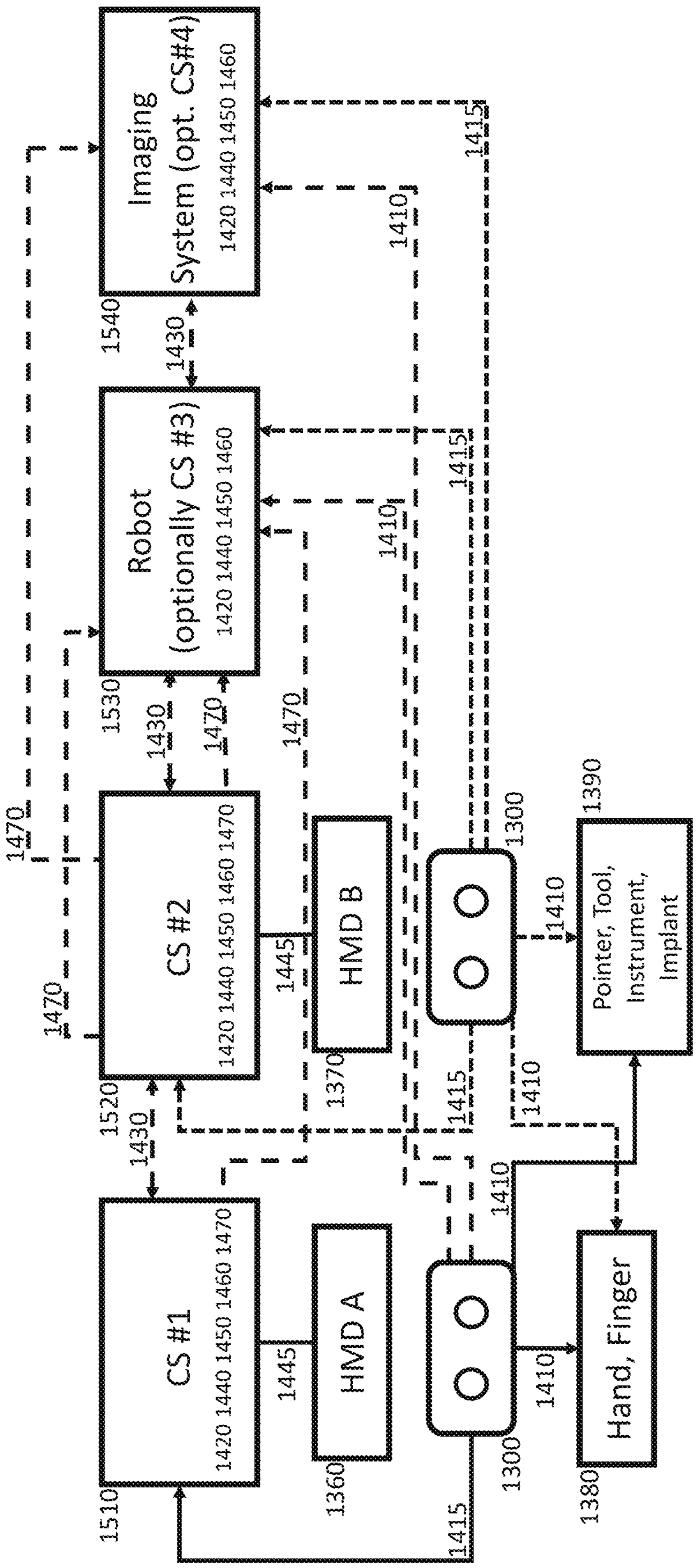
FIG. 5 shows a non-limiting example of one or more tracking systems, in this example integrated or attached to one or more head mounted displays, one or more computer systems, e.g. integrated, connected, or attached to a head mounted display, each with one or more computer processors, one or more robots, one or more imaging systems, and/or one or more head mounted displays, for example configured for activating, de-activating, operating, moving one or more systems, components, displays etc. of a navigation system, the one or more head mounted displays, the robot and/or the imaging system.

FIG. 5 is a representative, non-limiting example of one or more tracking systems 1300, e.g. one or more cameras, including cameras using visible and/or infrared light, stereoscopic cameras, a Lidar system and/or camera(s), a scanner, for example a 3D scanner, in this example integrated or attached to one or more head mounted displays 1360 1370 or other augmented reality display devices, one or more computer systems (CS) CS #1 1510 (e.g. integrated, connected, or attached to a head mounted display 1360), CS #2 1520 (e.g. integrated, connected, or attached to a head mounted display 1360), each with one or more computer processors, one or more robots 1530, e.g. handheld, attached to an OR table, and/or comprising a robotic arm, one or more imaging systems 1540, e.g. a C-arm, 3D C-arm, cone beam CT, spiral CT, MRI, and/or one or more head mounted displays HMD A 1360 HMD B 1370, e.g. a stereoscopic optical see-through head mounted display and/or a stereoscopic video see-through head mounted display, or other augmented reality display devices. The one or more robots 1530 and/or one or more imaging systems 1540 can also comprise one or more computer systems (e.g. CS #3, CS #4), for example each with one or more computer processors.

One or more first CS #1 1510, second CS #2 1520, or more computer systems can be integrated into, connected to or attached to one or more head mounted displays HMD A 1360 and/or HMD B 1370. The one or more tracking system(s) 1300 can be integrated or attached to the one or more head mounted displays HMD A 1360 and/or HMD B 1370 or other augmented reality display devices.

The one or more tracking systems 1300 can be configured to track 1410 optionally a hand and/or finger 1380, e.g. of a user a pointer, tool, instrument and/or implant 1390, a patient (not shown), and/or a robot 1530 and/or an imaging system 1540 or a combination thereof, for example with use of a first computer system 1510, a second computer 1520, and/or additional computer systems.

The tracking system 1300 can be configured to track 1410 optionally a hand and/or finger (e.g. of a user) 1380, a pointer, tool, instrument and/or implant 1390, a patient (not shown), and/or a robot 1530 and/or an imaging system 1540 or a combination thereof, and to transmit the tracking information 1415 to a first computer system CS #1 1510, a second computer CS #2 1520, and/or additional computer systems; the transmission can be wired or wireless. The one or more tracking systems 1300 can be integrated into or attached to one or more head mounted displays 1360 1370 or other augmented reality display devices. The one or more computer systems 1510 1520, including one or more computer processors, can be integrated into or connected to the one or more head mounted displays 1360 1370 or other augmented reality display devices. The first CS #1 1510, second CS #2 1520, and/or additional computer systems can be integrated into, connected to or attached to one or more HMDs 1360 1370 or other augmented reality display systems. The one or more additional computer systems can be attached to, connected to or located inside a robotic system 1530 and/or an imaging system 1540.

The tracking 1410 can comprise recording one or more coordinates of and/or tracking a hand and/or finger 1380, a pointer, tool, instrument, and/or implant 1390, and/or a patient (not shown) by a first computer system CS #1 1510, and/or a second computer CS #2 1520, and/or additional computer systems, e.g. in a robot 1530 or imaging system 1540, for example using the camera(s) or scanner(s) 1300. The tracking 1410 can comprise recording one or more coordinates of a hand and/or finger 1380, e.g. of a user, a pointer, tool, instrument, and/or implant 1390, and/or the patient (not shown) by the first computer system CS #1 1510, and/or the second computer CS #2 1520, and/or additional computer systems, e.g. in a robot 1530 or imaging system 1540, for example using the camera or scanner 1300. The system can track a hand and/or finger 1380, a pointer, tool, instrument, and/or implant 1390, and/or the patient (not shown) by the first computer system CS #1 1510, and/or the second computer CS #2 1520, and/or additional computer systems, e.g. in a robot 1530 or imaging system 1540, for example using the tracking system with, for example, a camera or scanner 1300.

One or more computer processors of the one or more first 1510, second 1520, etc. computer systems, can be configured to perform one or more coordinate transformations 1420 and/or to determine a pose 1420 of the hand or finger 1380, the one or more pointer, tool, instrument, and/or implant 1390, and/or optionally the first 1360, second 1370, third, fourth, fifth etc. head mounted display (e.g. in relationship to a marker attached to a patient), and/or the patient (not shown).

The one or more computer processors of the one or more first 1510, second 1520, and/or additional computer systems, e.g. also in a robot 1530 and/or an imaging system 1540, can be configured to transmit and/or receive 1430 information about the finger or hand 1380, e.g. of a user, or the one or more pointer, tool, instrument, and/or implant 1390, e.g. their pose, and/or optionally information about or for the first 1360, second 1370, third, fourth, fifth etc. head mounted display, e.g. the pose of the head mounted display(s) (e.g. relative to a marker on a patient) or display data for the head mounted display(s) 1360 1370 or other augmented reality display devices, and/or the patient (not shown), for example using a wireless connection, e.g.

Bluetooth or a wireless WiFi or LiFi access point, optionally including a transmitter and/or receiver, or using a wired connection. The transmission and/or reception 1430 can comprise data about gaze direction of the wearer of a headset (for example for use with a gaze cursor), e.g. a first 1360, second 1370, third, fourth, fifth etc. head mounted display or other augmented reality display devices. The transmission and/or reception 1430 can be wired or wireless, e.g. using a broadcast or multiple unicast transmissions to and/or from the first 1360, second 1370, third, fourth, fifth etc. head mounted display or other augmented reality display devices, as described in the specification. The transmission can comprise positional data, display data and/or other data. The transmission 1430 can be to or from a first computer system 1510 to or from a second computer system 1520, to or from a third computer system, e.g. part of or coupled to a robot 1530, to or from a fourth, fifth or more computer system. The transmission can be to or from a second computer system 1520 to or from a first computer system 1510, to or from a third computer system 1530, to or from a fourth, fifth or more computer system. The transmission can be to or from a third computer system 1530 to or from a first computer system 1510, to or from a second computer system 1520, to or from a fourth, fifth or more computer system, and so forth.

In any of the embodiments throughout the specification, the transmission (and/or reception) 1430 can be unidirectional and/or bi-directional, simultaneous uni-directional and/or bi-directional, and/or non-simultaneous, e.g. sequential uni-directional and/or bi-directional, or a combination thereof between the one or more first 1510, second 1320, third 1330 etc. or additional computer systems, e.g. also integrated into or attached to a robot and/or an imaging system.

In any of the embodiments throughout the specification, a first 1510, second 1520 etc. or additional computer systems, can be integrated into, connected to, and/or attached to and/or separate from one or more HMDs 1360, 1370 or other augmented reality display systems, one or more robotic systems 1530, and/or one or more imaging systems 1540. One or more computer systems can be separate from, e.g. standalone, from one or more HMDs 1360, 1370 or other augmented reality display systems, one or more robotic systems 1530, and/or one or more imaging systems 1540.

One or more computer processors of one or more first 1510, second 1520, or additional computer systems, e.g. also in a robot 1530 and/or an imaging system 1540, can be configured to generate one or more user interface controls 1440. The one or more user interface controls 1440 can, for example, be virtual interface controls. The one or more user interface controls 1440 can comprise, for example, one or more virtual button, virtual field, virtual cursor, virtual pointer, virtual slider, virtual trackball, virtual node, virtual numeric display, virtual touchpad, virtual keyboard, or a combination thereof.

One or more computer processors of the one or more first 1510, second 1520, or additional computer systems, e.g. also in a robot 1530 and/or an imaging system 1540, can be configured to perform one or more collision detections 1445, for example between a hand or finger 1380 and a virtual interface displayed by one or more head mounted displays 1360 1370 or other augmented reality display devices, or a tracked physical pointer, physical tool, physical instrument, physical implant component 1390 or a combination thereof and a virtual interface displayed by one or more head mounted displays 1360 1370; the collision detection can be performed, for example, using the tracking system 1300. One or more computer processors of the one or more first 1510, second 1520, or additional computer systems, e.g. also in a robot 1530 and/or an imaging system 1540, can be configured to perform a gesture recognition, for example between a hand or finger 1380 and a virtual interface, displayed by one or more head mounted displays 1360 1370, using one or more cameras, optionally integrated or attached to one or more head mounted displays 1360 1370. The one or more cameras can be part of the one or more tracking systems 1300. The first 1510, second 1520 or additional computer systems, can be, for example, integrated into, connected to, and/or attached to and/or separate from one or more HMDs 1360, 1370 or other augmented reality display systems, one or more robotic systems 1530, and/or one or more imaging systems 1540.

One or more computer systems, e.g. a first 1510, second 1520, or additional computer systems, e.g. also in a robot 1530 and/or an imaging system 1540, can be configured to generate and/or transmit, optionally wirelessly, one or more event message 1450. The one or more event message can, for example, be an event message relative to a collision detection 1445 between a hand or finger 1380, a tracked physical pointer, physical tool, physical instrument, physical implant component 1390 or a combination thereof and a virtual interface, e.g. detected using the tracking system 1300. The one or more event message 1450 can optionally comprise an event message related to a robot 1530 control, interface, force, and/or position and/or orientation and/or an imaging system 1540 control, interface, force, and/or position and/or orientation.

One or more computer systems, e.g. a first 1510, second 1520, third, fourth, fifth etc. or additional computer systems, e.g. also in a robot 1530 and/or an imaging system 1540, can comprise an optional event handler 1460 configured to handle, manage and/or process one or more optional event message 1450.

One or more computer systems, e.g. a first 1510, second 1520, third or additional computer systems, e.g. also in a robot 1530 and/or an imaging system 1540, can be configured to initiate and/or process an optional event action 1470, e.g. executing a command, e.g. based on the event message 1450 and, optionally, information or data received from the event handler 1460. The command can be transmitted through a wireless or a wired connection, e.g. to a robot 1530 or an imaging system 1540.

In some embodiments, the one or more computer systems configured to generate an event message 1450 can be the same or different computer system comprising the event handler 1460 and/or can be the same or different computer system initiating and/or processing the event action 1470, e.g. executing a command. In some embodiments, one or more computer processors configured to generate an event message 1450 can be the same or different computer processors comprising the event handler 1460 and/or can be the same or different computer processors initiating and/or processing the event action 1470, e.g. executing a command. In some embodiments, a first, second, third, fourth, fifth, sixth or more computer system can be the same for managing different tasks, or can be different for managing different tasks.

AR System Architecture for Use with Multiple Devices Including One or More HMD

In some embodiments, a system can comprise at least one head mounted display or augmented reality display device, at least one camera or scanning device, wherein the at least one camera or scanning device can be configured to track real-time information of the at least one head mounted display or augmented reality display device, of at least one anatomic structure of a patient, and of at least one physical surgical tool or physical surgical instrument, a first computing system comprising one or more computer processors, wherein the first computing system can be configured to obtain the real-time tracking information of the at least one head mounted display or augmented reality display device, the at least one anatomic structure of a patient, and the at least one physical surgical tool or physical surgical instrument, wherein the first computing system can be configured for wireless transmission of the real-time tracking information of the at least one head mounted display, the at least one anatomic structure of the patient, and the at least one physical surgical tool or physical surgical instrument, a second computing system comprising one or more computer processors, wherein the second computing system can be configured for wireless reception of the real-time tracking information of the at least one head mounted display or augmented reality display device, the at least one anatomic structure of the patient, and the at least one physical surgical tool or physical surgical instrument, wherein the second computing system can be configured to generate an augmented or 3D stereoscopic view, wherein the augmented or stereoscopic view can comprise a 3D representation of the at least one tracked physical surgical tool or physical surgical instrument, and wherein the at least one head mounted display or augmented reality display device can be configured to display the 3D stereoscopic view or augmented view. In some embodiments, the one or more computer processors of the second computing system can generate the 3D stereoscopic view for a view angle of the head mounted display relative to the at least one anatomic structure of the patient using the real-time tracking information of the at least one head mounted display. In some embodiments, the real-time tracking information can comprise tracking information of multiple head mounted displays. In some embodiments, the real-time tracking information can comprise a head mounted display or augmented reality display device specific label or tag for each head mounted display, or the real-time tracking information can be labeled for each tracked head mounted display or augmented reality display device. In some embodiments, the wireless transmission can be a multicast or broadcast transmission to the multiple head mounted displays.

In some embodiments, the real-time tracking information can comprise tracking information of two or more head mounted displays or augmented reality display devices. In some embodiments, the two or more head mounted displays or augmented reality display devices are located in different locations. In some embodiments, the real-time tracking information can comprise a head mounted display or augmented reality display device label for each head mounted display or augmented reality display device, wherein each head mounted display or augmented reality display device has a different label. In some embodiments, the real-time tracking information can be labeled for each tracked head mounted display or augmented reality display device. In some embodiments, one or more computer processors of a second computing system can generate a 3D stereoscopic view for an interpupillary distance adjusted for a user wearing the head mounted display. In some embodiments, the second computing system can be integrated with the at least one head mounted display. In some embodiments, the second computing system can be separate from the at least one head mounted display and is connected to a display unit of the at least one head mounted display using at least one cable. In some embodiments, the wireless transmission, the wireless reception, or both comprise a WiFi signal, a LiFi signal, a Bluetooth signal, a radiofrequency signal or a combination thereof. In some embodiments, a camera or scanning device is separate from at least one head mounted display. In some embodiments, a camera or scanning device can be integrated or attached to at least one head mounted display. In some embodiments, the wireless transmission can comprise sending data packets comprising the real-time tracking information of at least one head mounted display, at least one augmented reality display device, at least one anatomic structure of a patient, and at least one physical surgical tool or physical surgical instrument, at a rate of 20 Hz or greater. In some embodiments, a wireless reception can comprise receiving data packets comprising the real-time tracking information of the at least one head mounted display, the at least one augmented reality display device, the at least one anatomic structure of a patient, and the at least one physical surgical tool or physical surgical instrument, at a rate of 20 Hz or greater. In some embodiments, the real-time tracking information comprises one or more coordinates, e.g. for wireless transmission and/or reception, e.g. to and from a first and second computing system. In some embodiments, the one or more coordinates can comprise coordinates of the at least one anatomic structure of the patient. In some embodiments, the one or more coordinates can comprise coordinates of the at least one physical surgical tool or physical surgical instrument. In some embodiments, the one or more coordinates can comprise coordinates of the at least one head mounted display or augmented reality display device. In some embodiments, at least one head mounted display can comprise at least one optical see-through head mounted display. In some embodiments, at least one head mounted display can comprise at least one video see-through head mounted display. In some embodiments, at least one camera or scanning device can comprise a laser scanner, a time-of-flight 3D laser scanner, a structured-light 3D scanner, a hand-held laser scanner, a LIDAR scanner, a time-of-flight camera, a depth camera, a video system, a stereoscopic camera system, a camera array, or a combination thereof. In some embodiments, a system can comprise at least one inertial measurement unit. In some embodiments, the at least one inertial measurement unit can be integrated or attached to the at least one physical surgical tool or physical surgical instrument.

In some embodiments, the at least one inertial measurement unit can be integrated or attached to the at least one anatomic structure of the patient. In some embodiments, the at least one inertial measurement unit can be integrated or attached to the at least one head mounted display or augmented reality display device. In some embodiments, the real-time tracking information of the at least one head mounted display or augmented reality display device can comprises information from the at least one inertial measurement unit. In some embodiments, a second computing system is communicatively coupled to the at least one head mounted display.

In some embodiments, a system can comprise two or more head mounted displays or augmented reality display devices, at least one camera or scanning device, wherein the at least one camera or scanning device can be configured to track real-time information of the at least two or more head mounted displays or augmented reality display devices, of at least one anatomic structure of a patient, and of at least one physical surgical tool or physical surgical instrument, a first computing system comprising one or more computer processors, wherein the first computing system can be configured to obtain real-time tracking information of at least one anatomic structure of a patient, of at least one physical surgical tool or physical surgical instrument, and of the two or more head mounted displays or augmented reality devices, wherein the tracking information of the two or more head mounted displays or augmented reality display devices can be labeled for each of the two or more head mounted displays or augmented reality display devices, wherein the first computing system can be configured for wireless transmission of the real-time tracking information of the at least one anatomic structure of the patient, the tracking information of the at least one physical surgical tool or physical surgical instrument, and the labeled tracking information of the two or more head mounted displays or augmented reality display devices, a second computing system, wherein the second computing system can be configured for wireless reception of the real-time tracking information of the at least one anatomic structure of the patient, the tracking information of the at least one physical surgical tool or physical surgical instrument, and the labeled tracking information of the first of the two or more head mounted displays or augmented reality display devices, wherein the second computing system can be configured to generate a first 3D stereoscopic display specific for a first viewing perspective of the first head mounted display or augmented reality display device using the labeled tracking information of the first head mounted display or augmented reality display device, wherein the first head mounted display or augmented reality display device can be configured to display the 3D stereoscopic display or augmented view, a third computing system, wherein the third computing system can be configured for wireless reception of the real-time tracking information of the at least one anatomic structure of the patient, the tracking information of the at least one physical surgical tool or physical surgical instrument, and the labeled tracking information of the second of the two or more head mounted displays or augmented reality display devices, wherein the third computing system can be configured to generate a second 3D stereoscopic display or augmented view specific for a second viewing perspective of the second head mounted display or augmented reality display device using the labeled tracking information of the second head mounted display or augmented reality display devices, and wherein the first and second stereoscopic displays or augmented reality display devices can comprise a 3D representation of the at least one physical surgical tool or physical surgical instrument.

AR Guidance of Surgical Robots

In some embodiments of the disclosure, a system can comprise at least one head mounted display, a robot, wherein the robot can comprise an end effector, a first computing system comprising one or more computer processors, wherein the first computing system can be in communication with the robot, a second computing system comprising one or more computer processors, wherein the second computing system can be in communication with the at least one head mounted display, wherein the second computing system can configured to display, by the at least one head mounted display, a virtual user interface comprising at least one virtual object, wherein the second computing system can be configured to generate a command based at least in part on at least one interaction with the at least one virtual object displayed in the virtual user interface, wherein the second computing system can be configured to transmit the command to the first computing system using wireless transmission, wherein the command can be configured to cause the first computing system to control the robot for movement, activation, operation, de-activation, or any combination thereof, of a robot component, a robot motor, a robot actuator, a robot drive, a robot controller, a robot hydraulic system, a robot piezoelectric system, a robot switch, the end effector, or any combination thereof. In some embodiments, the command can be configured to control the end effector within a predetermined operating boundary, a predetermined operating range, a predetermined operating zone, or a predetermined operating volume. In some embodiments, the first computing system can be connected to the robot by wire, or the first computing system can be connected to the robot by wireless connection. In some embodiments, the second computing system can be connected to the at least one head mounted display by wire, or the second computing system can be connected to the at least one head mounted display by wireless connection. In some embodiments, the second computing system can be configured to display, by the at least one head mounted display, a representation of a predetermined operating boundary, a predetermined operating range, a predetermined operating zone, or a predetermined operating volume of the end effector or an expected outcome following the movement, activation, operation, de-activation or a combination thereof of the robot component, robot motor, robot actuator, robot drive, robot controller, robot hydraulic system, robot piezoelectric system, robot switch, the end effector, or any combination thereof. In some embodiments, the end effector can comprise a physical surgical tool or a physical surgical instrument.

In some embodiments, a first computing system can be configured to obtain real-time tracking information of a component of the robot, an end effector, a target object, a target anatomic structure of a patient, at least one head mounted display, a physical tool, a physical instrument, a physical implant, a physical object, or any combination thereof. In some embodiments, a second computing system can be configured to obtain real-time tracking information of a component of a robot, an end effector, a target object, a target anatomic structure of a patient, at least one head mounted display, a physical tool, a physical instrument, a physical implant, a physical object, or any combination thereof. In some embodiments, the first computing system can be configured to obtain real-time tracking information of a physical tool, a physical instrument, or any combination thereof coupled to the robot. In some embodiments, the second computing system can be configured to obtain real-time tracking information of a physical tool, a physical instrument, or any combination thereof coupled to the robot. In some embodiments, the first computing system can be configured to wirelessly transmit the real-time tracking information of the component of the robot, the end effector, a target object, a target anatomic structure of a patient, the at least one head mounted display, a physical tool, a physical instrument, a physical implant, a physical object, or any combination thereof. In some embodiments, the second computing system can be configured to wirelessly transmit the real-time tracking information of the component of the robot, the end effector, a target object, a target anatomic structure of a patient, the at least one head mounted display, a physical tool, a physical instrument, a physical implant, a physical object, or any combination thereof.

In some embodiments, a second computing system can be configured for displaying, by the at least one head mounted display, a 3D stereoscopic view. In some embodiments, the 3D stereoscopic view can be superimposed onto an anatomic structure of a patient. In some embodiments, the 3D stereoscopic view can comprise a predetermined trajectory of the end effector, a representation of a predetermined operating boundary of the end effector, a representation of a predetermined operating range of the end effector, a representation of a predetermined operating zone of the end effector, a representation of a predetermined operating volume of the end effector, or a combination thereof. In some embodiments, the 3D stereoscopic view can comprise a predetermined trajectory of the end effector, a representation of a predetermined operating boundary of the end effector, a representation of a predetermined operating range of the end effector, a representation of a predetermined operating zone of the end effector, a representation of a predetermined operating volume of the end effector or a combination thereof following the movement, activation, operation, de-activation or combination thereof of the robot component, robot motor, robot actuator, robot drive, robot controller, robot hydraulic system, robot piezoelectric system, robot switch, the end effector or any combination thereof.

In some embodiments, a first computing system, a second computing system, or both can be configured to turn on or turn off the display of the virtual user interface. In some embodiments, a wireless transmission can comprise a Bluetooth signal, WiFi signal, LiFi signal, a radiofrequency signal, a microwave signal, an ultrasound signal, an infrared signal, an electromagnetic wave or any combination thereof.

In some embodiments, a 3D stereoscopic view can comprise a predetermined trajectory of an end effector, a representation of a predetermined operating boundary of the end effector, a representation of a predetermined operating range of the end effector, a representation of a predetermined operating zone of the end effector, a representation of a predetermined operating volume of the end effector or a combination thereof prior to executing a command.

In some embodiments, a the system can comprise two or more head mounted displays, wherein the wireless transmission can be a multicast, broadcast transmission or any combination thereof.

In some embodiments, a virtual object displayed by the HMD can comprise one or more virtual button, virtual field, virtual cursor, virtual pointer, virtual slider, virtual trackball, virtual node, virtual numeric display, virtual touchpad, virtual keyboard, or a combination thereof. In some embodiments, an interaction with a virtual interface can comprise a collision detection between a physical object and the at least one virtual object. In some embodiments, an interaction can be a collision detection between a user's finger and at least one virtual object displayed by an HMD.

In some embodiments, an interaction can comprise a collision detection between a tracked pointer, tracked tool, tracked instrument, or a combination thereof and at least one virtual object displayed by the HMD. In some embodiments, an interaction with a virtual object displayed by the HMD can comprise a gesture recognition, gaze recognition, gaze lock, hand tracking, eye tracking or a combination thereof. In some embodiments, hand tracking, eye tracking and voice control can be used, e.g. also without interaction with a virtual object displayed by the HMD.

In some embodiments, an end effector can comprise a scalpel, a saw, a cutting tool, a wire, a needle, a pin, a drill, a burr, a mill, a reamer, an impactor, a broach, a laser, a radiofrequency device, a thermocoagulation device, a cryoablation device, a radioactive probe, a radioactivity emitting device, a pulsed energy emitting device, an ultrasonic energy emitting device, a microwave energy emitting device or a combination thereof. In some embodiments, a command can comprise a subcommand, wherein the subcommand is configured to execute an accept or cancel function of the command.

In some embodiments, a system can comprise at least one head mounted display, a robot, wherein the robot can comprise an end effector, a first computing system comprising one or more computer processors, wherein the first computing system can be in communication with the robot, a second computing system comprising one or more computer processors, wherein the second computing system can be in communication with the at least one head mounted display, wherein the second computing system can be configured to display, by the at least one head mounted display, a virtual user interface comprising at least one virtual object, wherein the second computing system can be configured to generate an event message based at least in part on at least one interaction with the at least one virtual object displayed in the virtual user interface, wherein the second computing system can be configured to transmit the event message to the first computing system using wireless transmission, wherein the second computing system can be configured to generate a command based on the event message, wherein the command can be configured to cause the first computing system to control the robot for movement, activation, operation, de-activation, or any combination thereof, of a robot component, a robot motor, a robot actuator, a robot drive, a robot controller, a robot hydraulic system, a robot piezoelectric system, a robot switch, the end effector, or a combination thereof.

AR Guidance of Imaging Systems and/or Image Acquisitions

In some embodiments, preparing an image acquisition by an imaging system in a patient (prior to the actual image acquisition) can comprise tracking, by at least one computer processor, one or more components of the imaging system in real time, optionally obtaining, by the at least one computer processor, information about a geometry of one or more components of the imaging system, information about a position, orientation and/or geometry of the image acquisition, information about one or more image acquisition parameters, or a combination thereof, generating, by the at least one computer processor, a 3D representation of a surface, a volume or combination thereof, wherein the 3D representation of the surface, the volume or combination thereof can be at least in part derived from or based on the information about the geometry of the one or more components of the imaging system, information about the position, orientation and/or geometry of the image acquisition, information about the one or more image acquisition parameters, or a combination thereof, generating, by the at least one computer processor, a 3D stereoscopic view or an augmented view, wherein the 3D stereoscopic view or augmented view can comprise the 3D representation of the surface, volume or combination thereof, optionally displaying, by an augmented reality display device, e.g. a head mounted display, a tablet, an iPad, an iPhone or other AR display device, the 3D stereoscopic view or augmented view at a position defined relative to the one or more components of the imaging system or at a position defined relative to the patient, wherein the position and orientation of the 3D stereoscopic view or augmented view can be determined based on the real time tracking information of the imaging system, and then acquiring, by the imaging system, 2D, 3D, or 2D and 3D imaging data of the patient within the 3D representation of the surface, volume or combination thereof or at the location of the 3D representation of the surface, volume or combination thereof.

In some embodiments, the 3D representation of the surface, volume or combination thereof does not contain imaging data from the patient. In some embodiments, the 3D representation of the surface, volume or combination thereof can comprise imaging data from the patient from a prior image acquisition, preceding the current, planned, intended image acquisition. In some embodiments, the 3D representation of the surface, volume or combination thereof can comprise model data, e.g. a generic 3D model of patient anatomy, an avatar of patient anatomy, etc. In some embodiments, the 3D representation can comprise a 2D outline, 3D outline, a mesh, a group of surface points, or a combination thereof at least in part derived from or based on the information about the geometry of the one or more components of the imaging system, information about the position, orientation and/or geometry of the image acquisition, information about the one or more image acquisition parameters, or a combination thereof.

The shape of the 3D representation of the surface, volume or combination thereof, optionally displayed, by a head mounted display or another augmented reality display device can change responsive to changes in a geometry of one or more components of the imaging system (e.g. a collimator), changes in a position, orientation and/or geometry of the image acquisition (e.g. a change in tube location, detector location, image intensifier location, field of view, collimation), and/or changes in one or more image acquisition parameters.

In some embodiments, the imaging system or one or more of its components can be moved, e.g. by a user, optionally assisted by one or more motors, controllers, drives, hydraulic and/or electric system, and/or robotic components and/or arms, and the augmented view or 3D stereoscopic view, in some embodiments optionally superimposed onto the patient, can be configured by the system and/or one or more computer processor to move in relation with the tracked one or more components of the imaging system. When the imaging system or one or more of its components are moved or when one or more parameters determining the location and/or orientation of the image acquisition are changed, the system can be configured to adjusting the position, orientation, position and orientation of the augmented view or 3D stereoscopic view in response to the movement of the tracked imaging system, the movement of the one or more of its components and/or the changes in the one or more parameters determining the location and/or orientation of the image acquisition. In some embodiments, the adjusting or adjustment is configured to maintain the augmented view at the defined position and orientation relative to the one or more components of the imaging system. In some embodiments, the augmented view at the defined position relative to the one or more components of the imaging system moves in relation with the tracked one or more components of the imaging system, wherein the moving facilitates superimposing or aligning the 3D representation with a target anatomic structure of the patient. In some embodiments, the imaging system can be configured to acquire 2D, 3D, or 2D and 3D imaging data of a patient, and wherein the 2D, 3D, or 2D and 3D imaging data of the patient are acquired within the 3D representation of the surface, volume or combination thereof.

In some embodiments, the step of generating the augmented view is before the step of acquiring 2D, 3D, or 2D and 3D imaging data of the patient, or wherein the step of displaying the augmented view is before the step of acquiring 2D, 3D, or 2D and 3D imaging data of the patient.

In some embodiments, at least one computer processor can be configured to generate a 3D representation of a surface, a volume or combination thereof for display by an HMD or an augmented reality device, wherein the 3D representation of the surface, volume or combination thereof can comprise information about a geometry of the one or more components of the imaging system, information about a position, orientation and/or geometry of the image acquisition, information about one or more image acquisition parameters, or a combination thereof, wherein the 3D representation of the surface, volume or combination thereof can, for example, not contain imaging data from a patient. A user can move the 3D representation of the surface or volume superimposed onto the patient, for example by interaction with a virtual user interface displayed by the HMD or an augmented reality or mixed reality display device. The movement of the 3D representation can, for example, be intended to move the 3D representation into a desired anatomic area or volume (e.g. of a target anatomic area) to be included and/or for inclusion in an imaging data acquisition. The system can then optionally be configured to move the imaging system, one or more components of the imaging system, a patient table used in conjunction with the imaging system, or any combination thereof, for example using one or more motors, controllers, drives, hydraulic and/or electric system, and/or robotic components and/or arms, responsive to the movement of the 3D representation. In this fashion, a subsequent imaging data acquisition can be obtained in the desired area or volume of the subsequent imaging data acquisition.

In some embodiments, the step of acquiring the 2D or 3D or 2D and 3D images can be after the step of generating the augmented view or 3D stereoscopic view. In some embodiments, the step of acquiring the 2D or 3D or 2D and 3D images can be after the step of displaying the augmented view or 3D stereoscopic view.

In some embodiments, at least one computer processor can be configured to generate a 3D representation of the surface, volume or combination thereof before acquisition of 2D, 3D, or 2D and 3D imaging data of the patient, or at least one computer processor can be configured to display the 3D representation of the surface, volume or combination thereof before acquisition of 2D, 3D, or 2D and 3D imaging data of the patient.

In some embodiments, a system of preparing an imaging data acquisition associated with a patient can comprise at least one computer processor, a head mounted display, e.g. a video see-through head mounted display or an optical see-through head mounted display, an augmented reality display device, e.g. a tablet or smart phone, an imaging system, wherein the at least one computer processor can be configured to obtain real-time tracking information of one or more components of the imaging system (and optionally a patient table, the HMD, the augmented reality display device, an anatomic structure of a patient, a robot), wherein the at least one computer processor can be configured to generate a 3D representation of a surface, a volume or combination thereof, wherein the 3D representation of the surface, volume or combination thereof can comprise information about a geometry of the one or more components of the imaging system, information about a position, orientation and/or geometry of the image acquisition, information about one or more image acquisition parameters, or a combination thereof, wherein the 3D representation of the surface, volume or combination thereof can, for example, not contain imaging data from a patient, or can contain imaging data from a prior imaging data acquisition but not the current, planned, intended image acquisition, of the patient, wherein the at least one computer processor can be configured to generate an augmented view or 3D stereoscopic view, the augmented view or 3D stereoscopic view comprising the 3D representation of the surface, volume or combination thereof, wherein the at least one computer processor can be configured to display, by the head mounted display or augmented reality device, the augmented view or 3D stereoscopic view, e.g. superimposed onto the patient or combined with a video feed of the patient or the imaging system (if an augmented reality display device such as a table or smart phone is used), wherein the position and/or orientation of the augmented view or 3D stereoscopic view (including, optionally, an intended position and/or orientation) can be determined based on the real time tracking information of the one or more components of the imaging system, and wherein the imaging system can be configured to acquire 2D, 3D, or 2D and 3D imaging data of the patient within the or at the location of the 3D representation of the surface, volume or combination thereof. In some embodiments, the imaging system can also acquire imaging studies with more than 3 dimensions, four example when sequential scanning is performed with time being the $4^{th}$ dimension. Representative examples comprise, for example, ultrasound flow studies, Doppler ultrasound, angiography including vascular run-offs, spiral CT imaging after contrast bolus for vascular imaging (e.g. through or during a cardiac cycle) or MR angiography studies or imaging combination studies, e.g. SPECT-CT or PET-MRI.

In some embodiments, the at least one computer processor can be configured to generate the 3D representation of the surface, volume or combination thereof before acquisition of the 2D, 3D, or 2D and 3D imaging data of the patient and/or in some embodiments, the at least one computer processor can be configured to display the 3D representation of the surface, volume or combination thereof before acquisition of the 2D, 3D, or 2D and 3D imaging data of the patient.

In some embodiments, at least one computer processor can be configured to generate a 3D representation of a surface, volume or combination thereof, which can comprise information about a limit, an edge, a margin, a boundary, a circumference, a perimeter, or a combination thereof of a planned or intended or upcoming imaging data acquisition, e.g. a 2D, 3D, 4D, 5D or combination thereof imaging acquisition. The limit, edge, margin, boundary, circumference, perimeter, or a combination thereof of a planned or intended or upcoming imaging data acquisition can not contain or comprise any imaging data of the patient or can comprise imaging data of the patient from a prior imaging data acquisition, but not from the planned or intended or upcoming imaging data acquisition. The limit, edge, margin, boundary, circumference, perimeter, or a combination thereof of a planned or intended or upcoming imaging data acquisition can comprise information about a geometry of the one or more components of the imaging system, information about a position, orientation and/or geometry of the image acquisition, information about one or more image acquisition parameters, or a combination thereof. The limit, edge, margin, boundary, circumference, perimeter, or a combination thereof of a planned or intended or upcoming imaging data acquisition can be based on or can be derived from information about a geometry of the one or more components of the imaging system, information about a position, orientation and/or geometry of the image acquisition, information about one or more image acquisition parameters, or a combination thereof.

The location, position, and/or orientation of the limit, edge, margin, boundary, circumference, perimeter, or a combination thereof, the location, position, and/or orientation of the surface or volume of the 3D representation of a planned or intended or upcoming imaging data acquisition can be based on the tracked location, position, orientation, and/or coordinates of the imaging system, and/or the tracked location, position, orientation, and/or coordinates of one or more components of the imaging system.

In some embodiments, the at least one computer processor can be configured to generate the surface, volume or combination thereof at least in part from information about a geometry of the imaging system, information about a position, orientation and/or geometry of one or more components of the imaging system, information about a geometry of the image acquisition, information about one or more image acquisition parameters, or a combination thereof. In some embodiments, the at least one computer processor can be configured to determine a desired location and orientation of the augmented view or 3D stereoscopic view associated with the imaging system, wherein the at least one computer processor can be configured to generate the 3D representation of the surface, volume or combination thereof before acquisition of the 2D, 3D, or 2D and 3D imaging data of the patient, or wherein the at least one computer processor can be configured to display the 3D representation of the surface, volume or combination thereof before acquisition of the 2D, 3D, or 2D and 3D imaging data of the patient.

In some embodiments, the system can be configured to acquire the 2D, 3D, or 2D and 3D imaging data from the patient by the imaging system at the location and orientation of the 3D representation of the surface, volume or combination thereof and/or at the location and orientation of the stereoscopic view or augmented view, displayed by an HMD or an augmented reality display device such as a tablet or smart phone, of the 3D representation of the surface, volume or combination thereof.

In some embodiments, the at least one computer processor can be configured to project the augmented view or 3D stereoscopic view of the 3D representation of the surface, volume or combination thereof (based at least in part on information about a geometry of the imaging system, information about a position, orientation and/or a geometry of one or more components of the imaging system, information about a geometry of the image acquisition, information about one or more image acquisition parameters, or a combination thereof) at the coordinates of the planned imaging data acquisition of the patient, which can be a 2D, 3D, 4D, 5D or more imaging data acquisition (accounting, for example, also for temporal elements, subtraction imaging etc.).

In some embodiments, the location of the imaging data acquisition, e.g. a 2D, 3D, 4D or combination thereof imaging data acquisition, can comprise one or more anatomic structures of the patient. The anatomic structures can optionally be tracked using any of the techniques described in the specification or known in the art.

In some embodiments, the system can be configured to facilitate determining a desired position and orientation of the augmented view, wherein the desired position and orientation comprises a target anatomic structure of the patient. In some embodiments, the at least one computer processor can be configured to adjust the position, orientation, or position and orientation of the augmented view or 3D stereoscopic view in response to movement of one or more tracked components of the imaging system and/or movement of the patient table. The adjustment can be configured to maintain the augmented view at the defined position and orientation relative to the one or more components of the imaging system.

In some embodiments, the information (for example used for generating the representation of the surface or volume of the planned imaging data acquisition) about the geometry of the imaging system, information about the position, orientation and/or geometry of one or more imaging system components, information about the geometry of the image acquisition, information about one or more image acquisition parameter, or a combination thereof can comprise information about one or more imaging system components, a geometric relationship between one or more imaging system components, a collimator, a grid, an image intensifier, a detector resolution, an x-ray source, an x-ray tube setting, a kVp setting, an mA setting, an mAs setting, a collimation, a tube—detector distance, a tube—patient distance, patient—detector distance, a patient—image intensifier distance, a table height relative to a tube, a detector, a table position relative to a tube, a detector, or combination thereof, a patient position, a C-arm position, orientation, or combination thereof, a gantry position, orientation or combination thereof, a grid height, a grid width, a grid ratio, a field of view, a center of a field of view, a margin or periphery of a field of view, a matrix, a pixel size, a voxel size, an image size, an image volume, an imaging plane, an image dimension in x, y, z and/or oblique direction, an image location, an image volume location, a scan coverage, a pitch, an in-plane resolution, a slice thickness, an increment, a detector configuration, a detector resolution, a detector density, a tube current, a tube potential, a reconstruction algorithm, a scan range, a scan boundary, a scan limit, a rotational center of a scan acquisition, a rotational axis of a scan acquisition, a reconstructed slice thickness, a segmentation algorithm, a window, a level, a brightness, a contrast, a display resolution, or any other setting parameter tabulated in Table 1, or any combination thereof.

The geometric relationship between one or more imaging system components can, for example, comprise a tube—detector distance, a tube—image intensifier distance, a rotational axis (e.g. in a spiral CT or cone beam CT or 3D C-arm), a center of rotation, an MRI coil dimension, a sensitivity profile (e.g. for an MRI profile) in relationship to one or more dimensions/geometries etc. The information about a collimator can comprise, for example, a grid spacing, a grid depth, a collimator dimension and any changes thereto, e.g. induced by movement of one or more motors, controllers and or drives.

In some embodiments, an imaging system can comprise an x-ray system, a fluoroscopy system, a C-arm, a 3D C-arm, a digital tomosynthesis imaging system, an angiography system, a bi-planar angiography system, a 3D angiography system, a CT scanner, an MRI scanner, a PET scanner, a SPECT scanner, a nuclear scintigraphy system, a 2D ultrasound imaging system, a 3D ultrasound imaging system, or a combination thereof.

In some embodiments, at least one computer processor can be configured to obtain real-time tracking information of a head mounted display, an augmented reality display device, an anatomic structure of the patient, a patient table used with the imaging system, an imaging system, one or more components of the imaging system, a surgical instrument, a surgical tool, an implant, a surgical robot, a robot integrated with or part of the imaging system, or any combination thereof. Any of the tracking techniques described in the specification using extrinsic and intrinsic tracking can be used. For example, a surgical navigation system, camera, 3D scanner can be used. Inside out or outside in tracking can be used. Intrinsic information can be used for tracking as described throughout the specification.

In some embodiments, the system can comprise a camera or scanner configured to acquire the real-time tracking information of the head mounted display, the anatomic structure of the patient, the patient table used with the imaging system, the imaging system, the one or more components of the imaging system, a surgical instrument, a surgical tool, an implant or a combination thereof. In some embodiments, a camera or scanner comprise at least one of a navigation system, a 3D scanner, a LIDAR system, a depth sensor, an IMU or a combination thereof. In some embodiments, tracking information can comprise coordinate information of a head mounted display, an augmented or mixed reality display device, an anatomic structure of the patient, a patient table used with the imaging system, an imaging system, one or more components of the imaging system, or a combination thereof. In some embodiments, tracking information can comprise location information of a head mounted display, an augmented or mixed reality display device, an anatomic structure of the patient, a patient table used with the imaging system, an imaging system, one or more components of the imaging system components, or a combination thereof. In some embodiments, a camera or scanner can comprise a laser scanner, time-of-flight 3D scanner, structured-light 3D scanner, hand-held laser scanner, a time-of-flight camera or a combination thereof.

In some embodiments, a system can be configured to obtain real time tracking information of an imaging system using intrinsic information from the imaging system. Intrinsic information can comprise pose data, sensor data, camera data, 3D scanner data, controller data, drive data, actuator data, end effector data, data from one or more potentiometers, data from one or more video systems, data from one or more LIDAR systems, data from one or more depth sensors, data from one or more inertial measurement units, data from one or more accelerometers, data from one or more magnetometers, data from one or more gyroscopes, data from one or more force sensors, data from one or more pressure sensors, data from one or more position sensors, data from one or more orientation sensors, data from one or more motion sensors, position and/or orientation data from step motors, position and/or orientation data from electric motors, position and/or orientation data from hydraulic motors, position and/or orientation data from electric and/or mechanical actuators, position and/or orientation data from drives, position and/or orientation data from robotic controllers, position and/or orientation data from one or more robotic computer processors, or a combination thereof.

In some embodiments, an imaging system, e.g. an x-ray system, fluoroscopy system, C-arm, 3D C-arm, cone beam CT, CT scanner, SPECT CT scanner, PET CT scanner can be configured to generate an x-ray beam. In some embodiments, an x-ray beam of an imaging system can be cone shaped or cylindrical, pencil shaped, or fan shaped. In some embodiments, an x-ray beam of an imaging system can originate from one or more point sources. In some embodiments, an x-ray beam of can imaging system can be collimated. The collimation can be adjustable. The adjustment of the collimation can be performed using a graphical user interface, e.g. a virtual user interface displayed by an HMD. The collimation can determine the shape, limit, margin, perimeter of a 3D representation of a surface or volume of an image acquisition. The 3D representation can be displayed in stereoscopic form by an HMD, superimposed onto a patient lying on a patient table in the imaging system.

In some embodiments, the system can comprise a user interface. In some embodiments, a user interface can comprise a virtual user interface, wherein the virtual interface can comprise at least one virtual object. In some embodiments, a virtual object, e.g. displayed as part of a virtual interface by an HMD or other augmented reality display device, can comprise one or more virtual button, virtual field, virtual cursor, virtual pointer, virtual slider, virtual trackball, virtual node, virtual numeric display, virtual touchpad, virtual keyboard, or a combination thereof. In some embodiments, a virtual user interface can comprise a gesture recognition, gaze recognition, gaze lock or a combination thereof. Other interfaces can comprise a voice recognition, eye tracking, hand tracking, pointer tracking, instrument tracking, tool tracking, or a combination thereof, which can optionally also be used to "touch" and/or activate one or more virtual objects displayed by an virtual interface. In some embodiments, at least one computer processor can be configured to generate a command based at least in part on at least one interaction of a user with at least one virtual object displayed by an HMD or other augmented reality display device in a virtual user interface. In some embodiments, a command can be configured to move, tilt, or rotate one or more components of an imaging system, one or more components of a patient table or a combination thereof. In some embodiments, a command can be configured to activate, operate, de-activate or a combination thereof a motor, an actuator, a drive, a controller, a hydraulic system, a switch, an x-ray tube, an image intensifier, or an imaging system or an ultrasound transducer, an ultrasound receiver, a robot (e.g. a surgical robot) or a combination thereof.

In some embodiments, a command, e.g. from a virtual interface, can be configured to move one or more components of a robot and/or one or more end effectors, to move or modify a geometry of am imaging system, a patient table, a geometric relationship between one or more imaging system components, a collimator, a grid, an image intensifier, a detector resolution, a setting of the imaging system, a parameter of the imaging system, a parameter of the imaging data acquisition, a display parameter, an x-ray source setting, an x-ray tube setting, a kVp setting, an mA setting, an mAs setting, a collimation, a tube—detector distance, a tube—patient distance, patient—detector distance, a patient—image intensifier distance, a center of rotation, e.g. of an image acquisition, a center of rotation of a rotational movement of a tube and/or detector system, a center of rotation of a rotational movement of a C-arm, a center of rotation of a rotational movement of a cone beam CT scanner, a center of a spiral acquisition of a spiral CT scanner, a table height relative to a tube, a detector, a table position relative to a tube, a detector, a patient position, a C-arm position, orientation, or combination thereof, a gantry position, orientation or combination thereof, a grid height, a grid width, a grid ratio, a field of view, a matrix, a pixel size, a voxel size, an image size, an image volume, an imaging plane, an image dimension in x, y, z and/or oblique direction, an image location, an image volume location, a scan coverage, a pitch, an in-plane resolution, a slice thickness, an increment, a detector configuration, a detector resolution, a detector density, a tube current, a tube potential, a reconstruction algorithm, a scan range, a scan boundary, a scan limit, a reconstructed slice thickness, a segmentation algorithm, a window, a level, a brightness, a contrast, a display resolution, or a combination thereof.

In some embodiments, a command can be configured to set and/or modify one or more image acquisition parameters of an imaging system, e.g. an x-ray system, C-arm, 3D C-arm, cone beam CT system, CT scanner, spiral CT scanner, MRI scanner, ultrasound system, radionuclide imaging device, SPECT scanner, PET system, cardiac imaging system, angiography system, or any combination thereof.

In some embodiments, a command can be configured to set, move, and/or modify a position, orientation, size, area, volume, or combination thereof of am imaging data acquisition, e.g. a 2D, 3D, 4D, 5D imaging data acquisition or any combination thereof. In some embodiments, a command can be configured to set, move, and/or modify one or more coordinates of the 3D representation, e.g. of a surface or volume representing the limit, perimeter, outer margin of an upcoming, planned, intended image acquisition, e.g. for stereoscopic display by an HMD or augmented display, e.g. of a video feed from an imaging system, a patient etc., by another augmented reality display device. In some embodiments, a command can be configured to set, move, and/or modify one or more coordinates of an upcoming, planned, intended imaging data acquisition, e.g. a 2D, 3D, 4D, 5D imaging data acquisition or any combination thereof.

In some embodiments, a command can be configured to set, move and/or modify a dimension, a size, an area, a volume or a combination thereof of a 3D representation, e.g. of a surface or volume representing the limit, perimeter, outer margin of an upcoming, planned, intended image acquisition, e.g. for stereoscopic display by an HMD.

In some embodiments, a command can be configured to set, move and/or modify a dimension, a size, an area, a volume or a combination thereof of an upcoming, planned, intended imaging data acquisition, e.g. a 2D, 3D, 4D, 5D imaging data acquisition or any combination thereof.

In any embodiments throughout the specification, a command can be configured to activate, operate, de-activate or a combination thereof a sensor, a camera, a video system, a 3D scanner, a Lidar system, a navigation system, a potentiometer, an electronic circuit, a computer chip, a piezoelectric system, a piezoelectric mechanism, a piezoelectric lock or release system, a controller, a drive, a motor, a hydraulic system, an actuator, a functional unit or a combination thereof of an imaging system, an imaging system component, a patient table or a combination thereof.

In any embodiments throughout the specification, a command can be configured to activate, operate, de-activate or a combination thereof a sensor, a camera, a video system, a 3D scanner, a Lidar system, a navigation system, a potentiometer, an electronic circuit, a computer chip a piezoelectric system, a piezoelectric mechanism, a piezoelectric lock or release system, a controller, a drive, a motor, a hydraulic system, an actuator, or a combination thereof of a surgical robot, a component of a surgical robot, a functional unit of a surgical robot, a patient table used in conjunction with a surgical robot or a combination thereof.

In any embodiments throughout the specification, a sensor can comprise a depth sensor, inertial measurement unit, accelerometer, magnetometer, gyroscope, force sensor, pressure sensor, position sensor, orientation sensor, motion sensor, or a combination thereof.

In some embodiments, one or more components of an imaging system can be attached to, integrated with, or part a robot. A robot can be configured to move one or more components of the imaging system.

In some embodiments, a virtual user interface can be configured to generate an event message triggered by a user interaction, e.g. a collision detection. The system can comprise an event handler configured to process the event message. An event handler can be configured to generate a command. In some embodiments, a computing system can be configured to generate a command, wherein the command can be triggered by a virtual user interface.

In some embodiments, a system can be configured to determine/identify a desired location/orientation of an augmented view or 3D stereoscopic view, optionally associated with the imaging system, to acquire imaging data, e.g. 2D, 3D, 4D or any combination thereof, at a desired location/orientation.

In some embodiments, a system can be configured to determine a desired location of an augmented view associated with the imaging system to acquire 2D, 3D, or 2D and 3D imaging data at the desired location. In some embodiments, an augmented reality display device can be a head mounted display, and wherein the augmented view can comprise a 2D, 3D and/or a 3D stereoscopic view. In some embodiments, at least one computer processor can be configured to project the 3D stereoscopic view at the coordinates of intended 2D, 3D or 2D and 3D imaging data acquisition of the patient. In some embodiments, the location of the 2D, 3D, or 2D and 3D imaging data acquisition comprises one or more target anatomic structures of the patient.

Figure 6A:
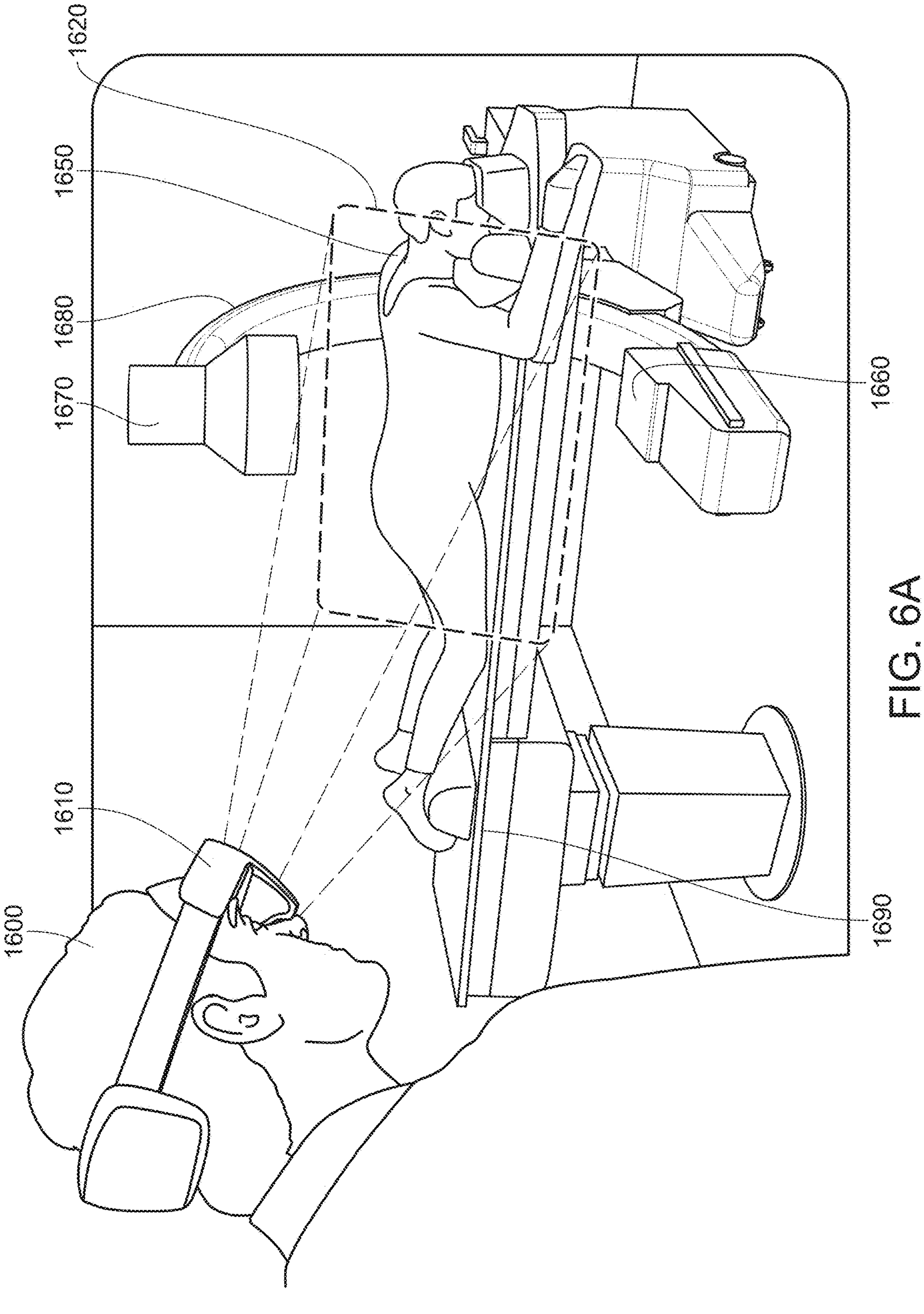
FIG. 6A shows a non-limiting example of a C-arm system, e.g. a 2D or 3D C-arm, and applications of a virtual display by a head mounted display (HMD) or other augmented reality device.
Figure 6B:
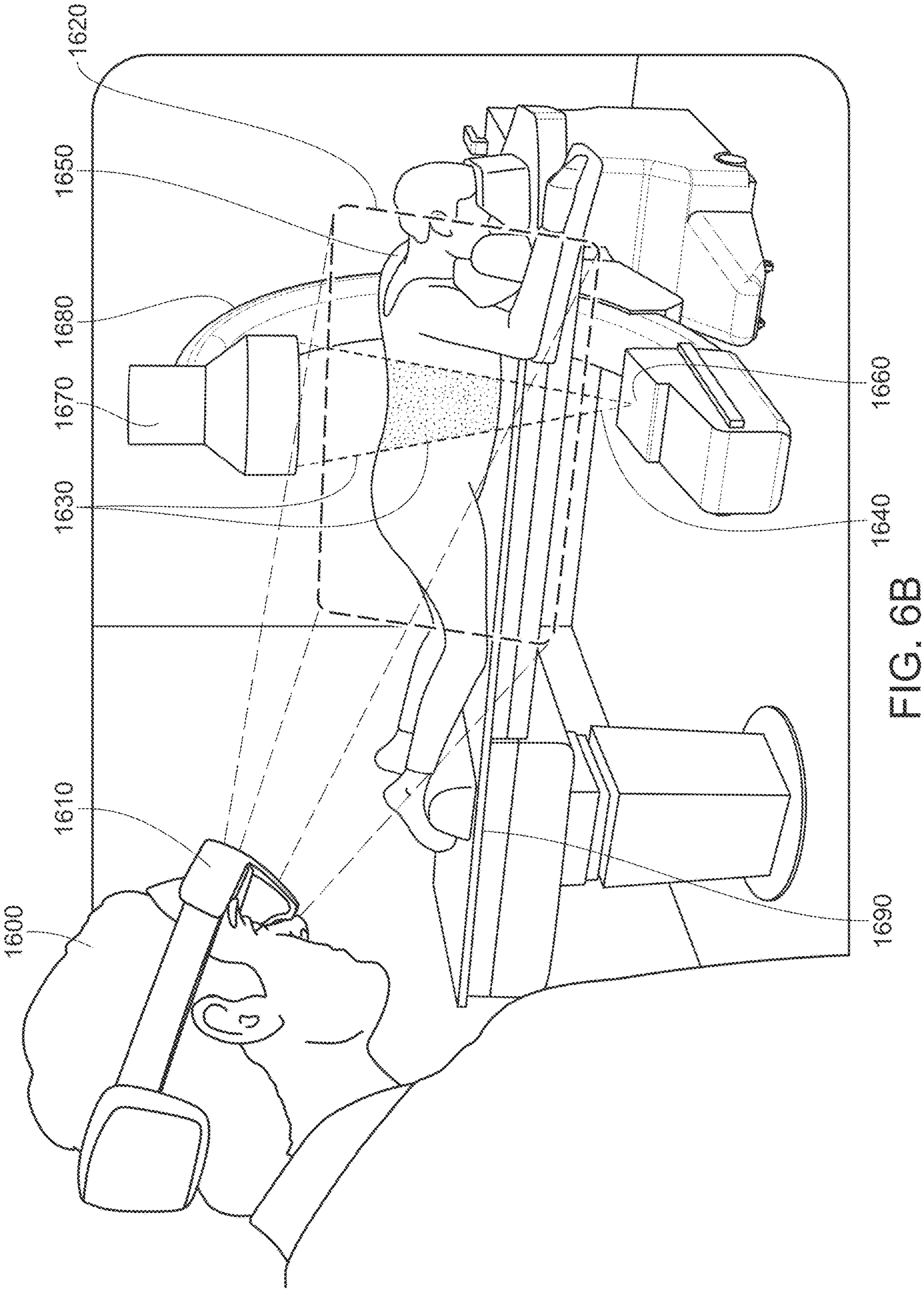
FIG. 6B shows a non-limiting example of a C-arm system, e.g. a 2D or 3D C-arm, and applications of a virtual display by a head mounted display (HMD) or other augmented reality device, e.g. with display of an outer envelope or perimeter of an x-ray beam prior to turning on the x-ray beam.

FIGS. 6A-6B show non-limiting examples of a C-arm system, e.g. a 2D or 3D C-arm, and applications of a virtual display by a head mounted display (HMD) or other augmented reality display device, e.g. a tablet, iPad, smart phone, iPhone etc. One or more users 1600 can wear a head mounted display (HMD) 1610. The head mounted display or other augmented reality display device can generate a virtual display of one or more virtual objects within a field of view 1620 of the HMD 1610 or other augmented reality display device. A virtual display can comprise a 3D representation 1630 of a surface or volume of an energy beam, e.g. an x-ray beam 1640.

The surface of volume can describe an outer envelope, margin, perimeter, of the energy beam 1640. The 3D representation and the stereoscopic display by the HMD or other augmented reality display device can be generated prior to activating/turning on the energy beam. The 3D representation 1630 of the surface or volume can be based on/derived from a geometry of the one or more components of the imaging system, information about a geometry of the image acquisition, information about one or more image acquisition parameters, or a combination thereof. The 3D representation 1630 of the surface, volume or combination thereof can, for example, not contain imaging data from a patient 1650, or can contain imaging data from a prior imaging data acquisition but not the current, planned, intended, desired image acquisition, of the patient 1650. Also shown are an x-ray tube 1660 and an image intensifier 1670 of a C-arm system. The position, orientation, position and orientation of the 3D representation 1630 can be defined in relationship to one or more components of the imaging system, the patient table, or a combination thereof. The position, orientation, position and orientation of the 3D representation 1630 can be fixed in relationship to one or more components of the imaging system; the system can be configured that the 3D representation moves with movement of the one or more components of the imaging system, and/or any changes in the position, orientation, and/or geometry of the imaging system, any changes in the position, orientation, and/or geometry of one or more imaging system components (including, for example, also a collimator), any changes in the position, orientation, and/or geometry of the image acquisition, any changes in one or more image acquisition parameters or a combination thereof.

Figure 6C:
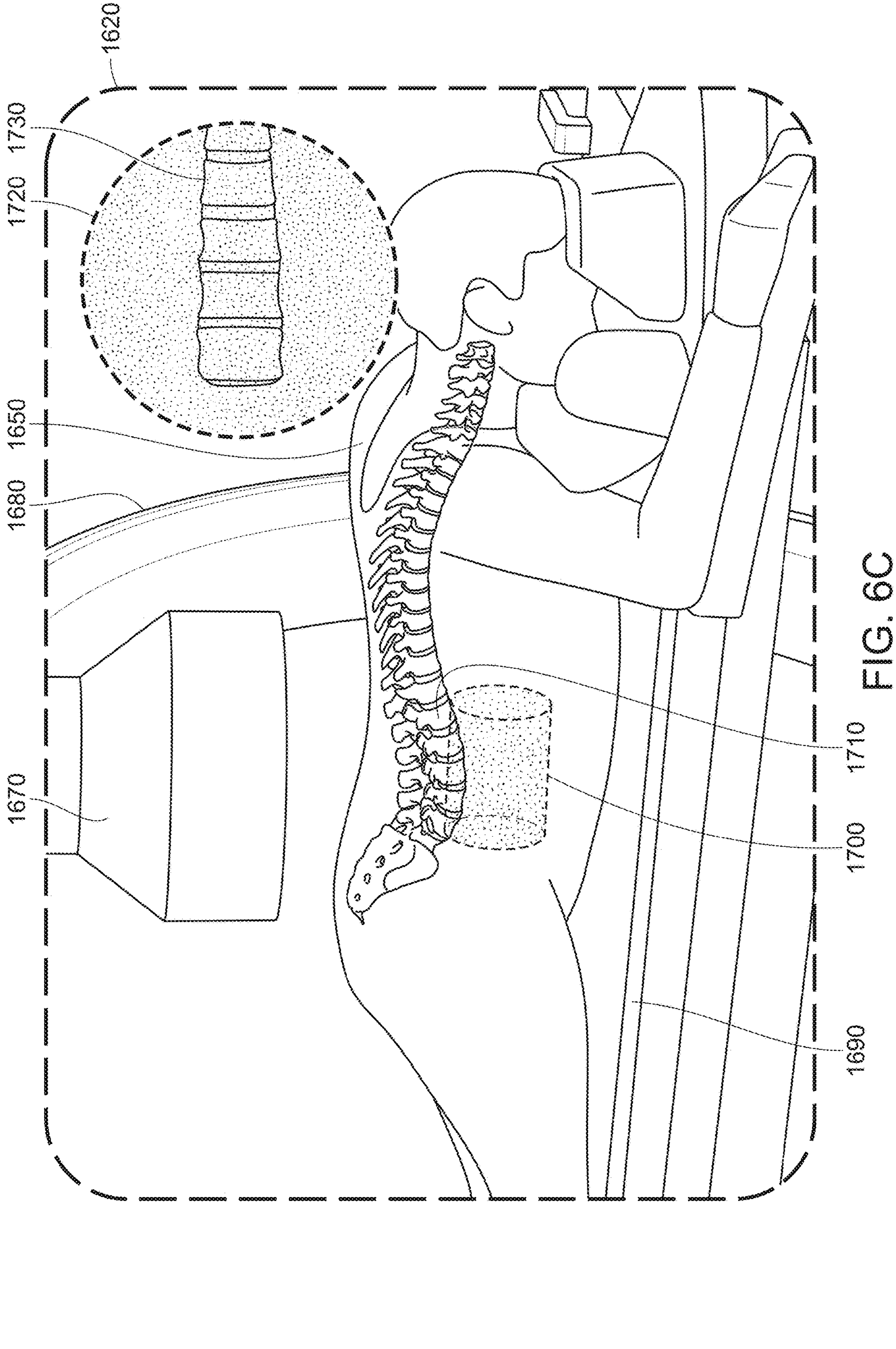
FIG. 6C-6E show non-limiting examples of a 3D C-arm system and applications of a virtual display by a head mounted display (HMD) or other augmented reality device, e.g. with display of an outer envelope or perimeter or limit of an intended 3D imaging data acquisition.
Figure 6D:
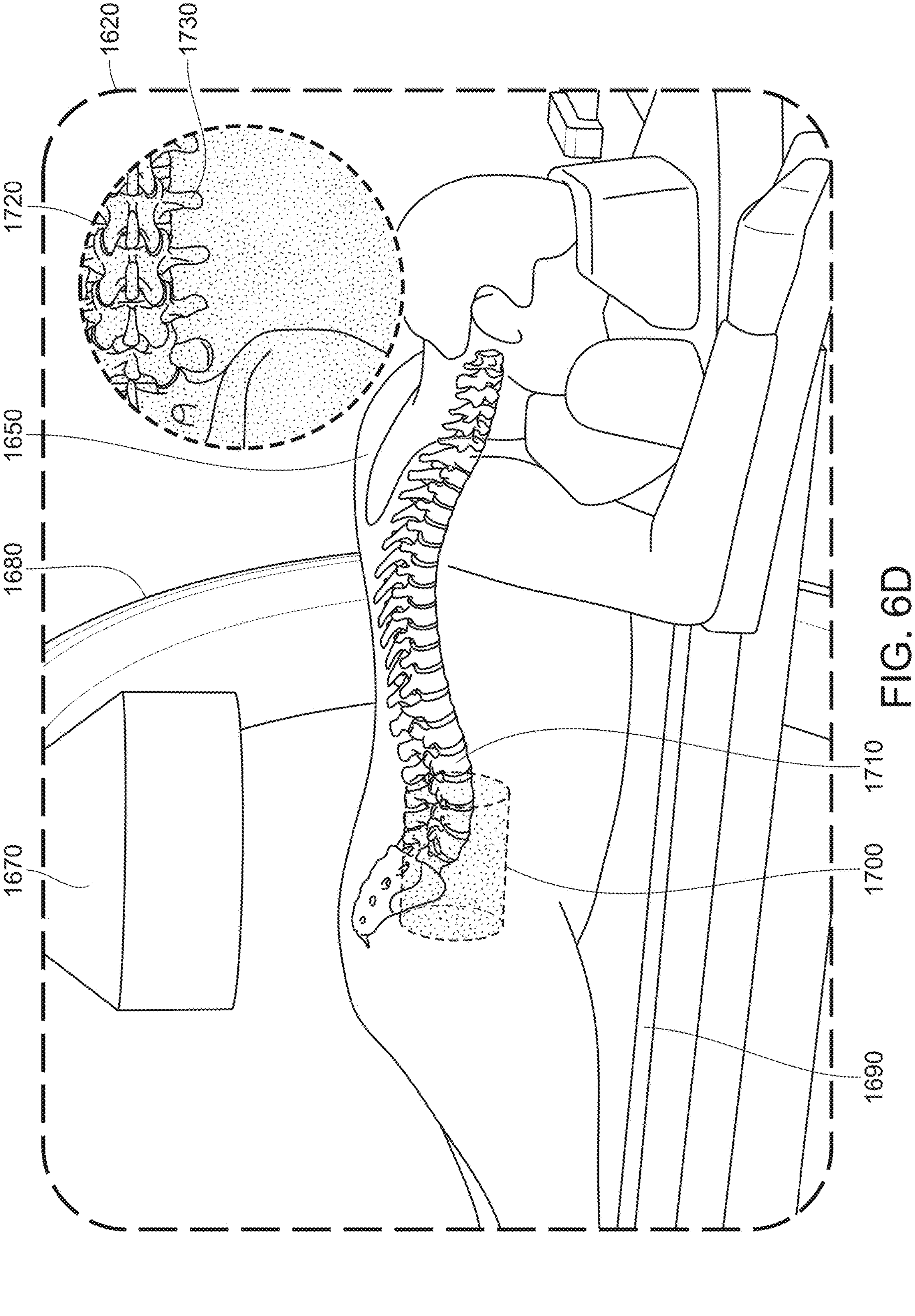
Figure 6E:
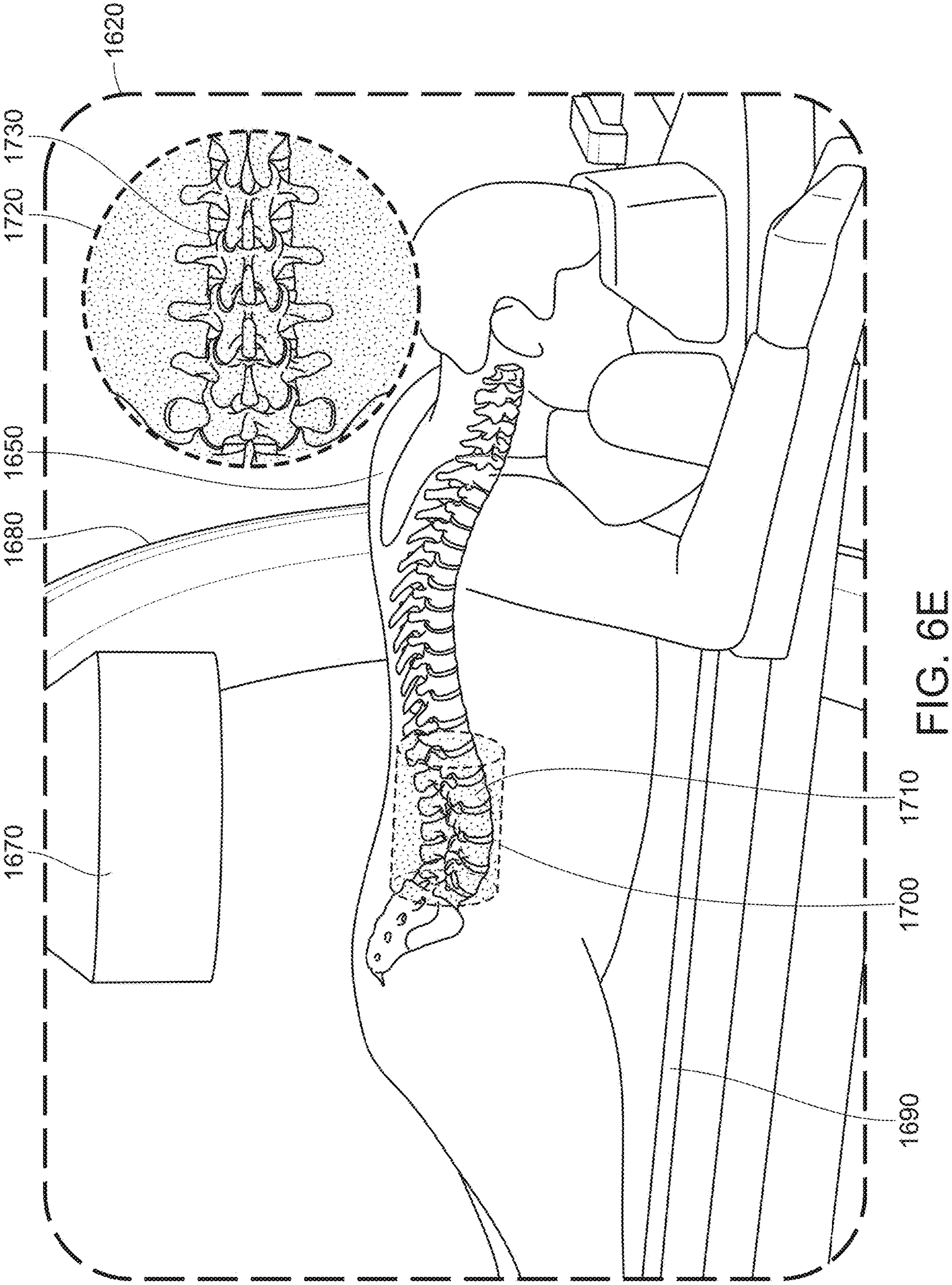

FIG. 6C-6E show non-limiting examples of a 3D C-arm system and applications of a virtual display by a head mounted display (HMD) or other augmented reality display device, e.g. with augmented reality or stereoscopic display of a 3D representation 1700 of a surface or volume representing, for example, an outer envelope or perimeter or limit of an intended or planned 3D imaging data acquisition, prior to the actual 3D imaging data acquisition. The view 1620 through an HMD or other augmented reality device shows a virtual display, by the HMD or other augmented reality display device, of a 3D representation 1700 of a surface or volume of a 3D imaging data volume acquisition intended for a patient 1650, displayed by the HMD or other augmented reality display device prior to the actual 3D imaging data volume acquisition. The imaging data volume acquisition with the 3D C-arm 1680, in this non-limiting example, (or with any 3D or 4D imaging system) intended in this patient 1650 can be a volumetric, cylinder shaped acquisition, in this example. Any other 3D shapes of image acquisitions are possible, depending on the imaging system used, its components and its unique geometries. The 3D representation 1700 of the surface or volume of the 3D imaging data acquisition can be based on/derived from a position, orientation and/or geometry of the one or more components of the imaging system, information about a position, orientation and/or geometry of the image acquisition, information about one or more image acquisition parameters, or a combination thereof. The 3D representation 1700 of the surface or volume of the intended 3D imaging data acquisition can be displayed, for example in an overlay fashion, superimposed onto the patient 1650 and/or a target organ or target anatomic structure, such as a portion of a spine 1710 in this non-limiting example.

The imaging system, in this non-limiting example a 3D C-arm 1680, and/or one or more of its components, and/or the patient table 1690 can be moved, e.g. by a user, optionally assisted by one or more motors, controllers, drives, hydraulic and/or electric system, and/or robotic components and/or arms. Optionally, the imaging system, in this non-limiting example a 3D C-arm 1680, and/or one or more of its components, and/or the patient table 1690 can be tracked, e.g. using any of the techniques described throughout the specification. In addition, the patient 1650 and/or the target organ or target anatomic structure, such as a portion of a spine 1710 can also optionally be tracked, e.g. using any of the techniques described throughout the specification. The system, including one or more of its computing systems and/or computer processors, can be configured so that the 3D stereoscopic view or augmented view of the 3D representation 1700 of the surface or volume of the envelope, perimeter, limits, margin, or combination thereof of the intended or desired imaging data acquisition, for example, superimposed, by the HMD or other augmented reality display device, onto the patient (prior to the actual imaging data acquisition) can move in relation with the tracked imaging system 1680, tracked one or more components of the imaging system 1660 1670, tracked patient table 1690, and/or, optionally, the tracked anatomic target structure, such as a spine 1710 (e.g. optionally with one or more attached markers or fiducials or fiducial arrays, not shown). When the imaging system 1680 or one or more of its components 1660 1670 are moved, or when the patient table 1690 is moved, or when one or more parameters determining and/or influencing the location and/or orientation of the image acquisition are changed, or any combination thereof, the system can be configured to adjusting the position, orientation, position and orientation of the 3D stereoscopic view or augmented view of the 3D representation 1700 in response to the movement of the tracked imaging system 1680, the movement of the one or more of its components 1660 1670, the movement of the tracked patient table 1690, and/or the changes in the one or more parameters determining and/or influencing the location and/or orientation of the image acquisition.

FIGS. 6C-6E show how the 3D representation 1700 of the surface or volume of the envelope, perimeter, limits, margin, or combination thereof of the intended or desired imaging data acquisition displayed by the HMD or other augmented reality display device at a defined position and orientation relative to the one or more components of the imaging system (optionally superimposed onto the patient) prior to the actual imaging data acquisition moves in relationship to a target anatomic structure, such as a spine 1710 with the movement of the tracked imaging system 1680, the movement of the one or more of its components 1660 1670, optionally the movement of the tracked patient table 1690, and/or the changes in the one or more parameters determining and/or influencing the location and/or orientation of the image acquisition.

In FIG. 6C, the 3D representation 1700 of the surface or volume of the envelope, perimeter, limits, margin, or combination thereof of the intended or desired imaging data acquisition superimposed, by the HMD or other augmented reality device, in this example onto the patient 1650 prior to the actual imaging data acquisition is too far anterior relative to a target anatomic structure, such as a spine 1710. This can occur, for example, when the imaging system 1680 or one or more of its components are too low in position relative to the patient 1650 or the target anatomic structure, such as a spine 1710, or when the patient table 1690 is too high relative to the imaging system 1680. An exploded view 1720, shows what the images will look like after the image data acquisition. Only a small anterior portion of the spine 1730 will be included in the actual image data volume acquisition and the resultant images.

In FIG. 6D, the 3D representation 1700 of the surface or volume of the envelope, perimeter, limits, margin, or combination thereof of the intended or desired imaging data acquisition in this example superimposed by the HMD or other augmented reality device onto the patient 1650 prior to the actual imaging data acquisition is too far lateral, off to the side, relative to a target anatomic structure, such as a spine 1710. This can occur, for example, when the imaging system 1680 or one or more of its components are too far lateral or mal-aligned in position relative to the patient 1650 or the target anatomic structure, such as a spine 1710, or when the patient table 1690 is too far lateral, off to the side relative to the imaging system 1680, e.g. the center of the imaging system, the center of a rotation of a C-arm, the center of a spin of a cone beam CT, and/or the center of a spiral, e.g. with a CT scan, or when the patient 1650 is not correctly positioned on the patient table 1690, e.g. not in the center of the patient table, off to the side.

An exploded view 1720, shows what the images will look like after the actual image data acquisition. Only a small lateral portion of the spine 1730 will be included in the image data volume acquisition and the resultant images.

In FIG. 6E, the 3D representation 1700 of the surface or volume of the envelope, perimeter, limits, margin, or combination thereof of the intended or desired imaging data acquisition superimposed in this example by the HMD or other augmented reality display device onto the patient 1650 prior to the actual imaging data acquisition is correctly positioned relative to a target anatomic structure, such as a spine 1710. This can occur, for example, when the imaging system 1680 or one or more of its components are correctly positioned, e.g. centered relative to the patient 1650 or the target anatomic structure, such as a spine 1710, and/or when the patient table 1690 is correctly positioned relative to the imaging system 1680, and/or when the patient 1650 is correctly positioned on the patient table 1690, e.g. in the center of the patient table, not off to the side. An exploded view 1720, shows what the images will look like after actual the image data acquisition. The entire target portion of the spine 1730 will be included in the image data volume acquisition and the resultant images.

Figure 7A:
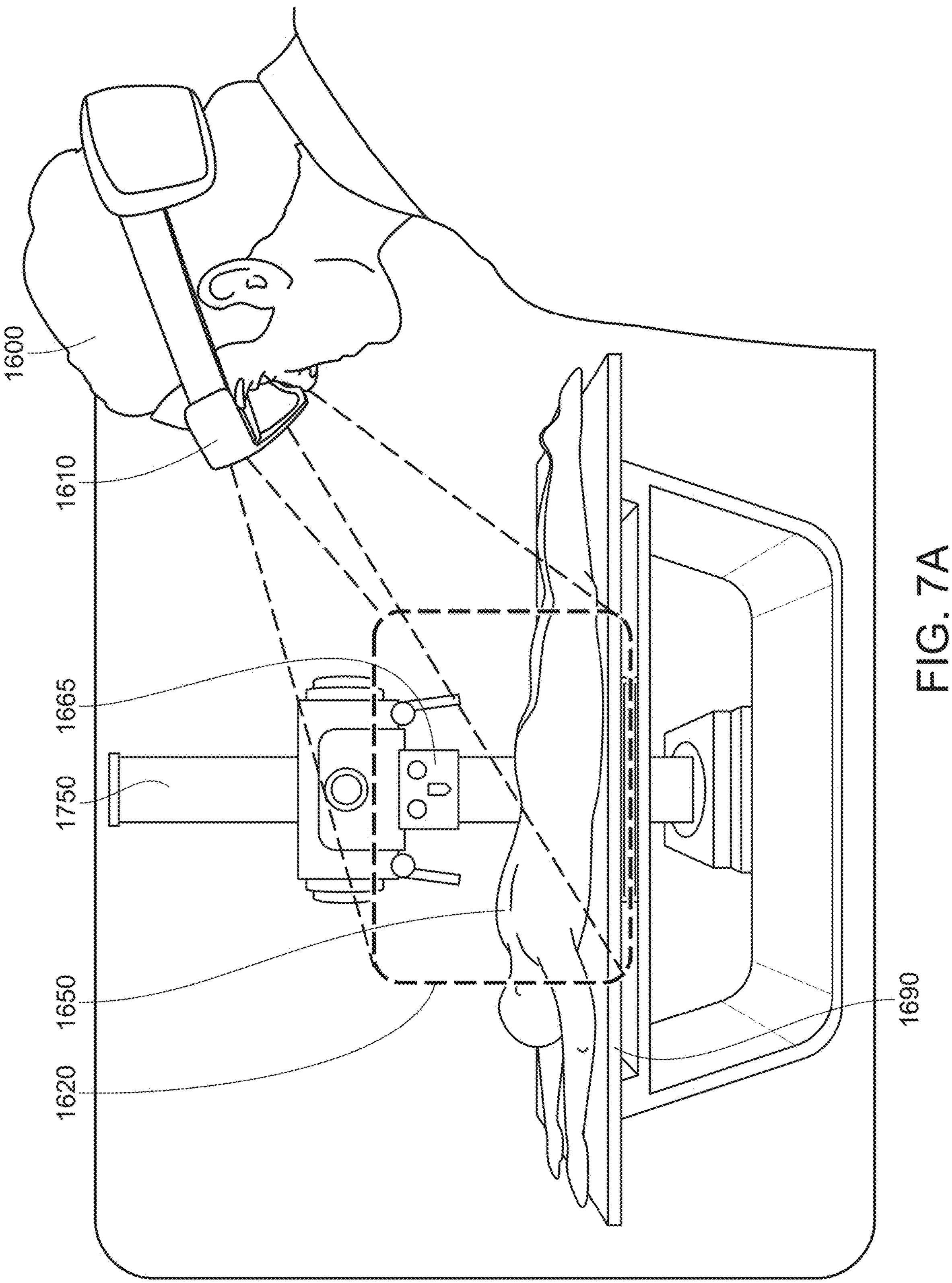
FIG. 7A shows a non-limiting example of a radiography (e.g. 2D, 3D), angiography (e.g. 2D, 3D, 4D) or other x-ray based imaging system, and applications of a virtual display by a head mounted display (HMD) or other augmented reality device.
Figure 7B:
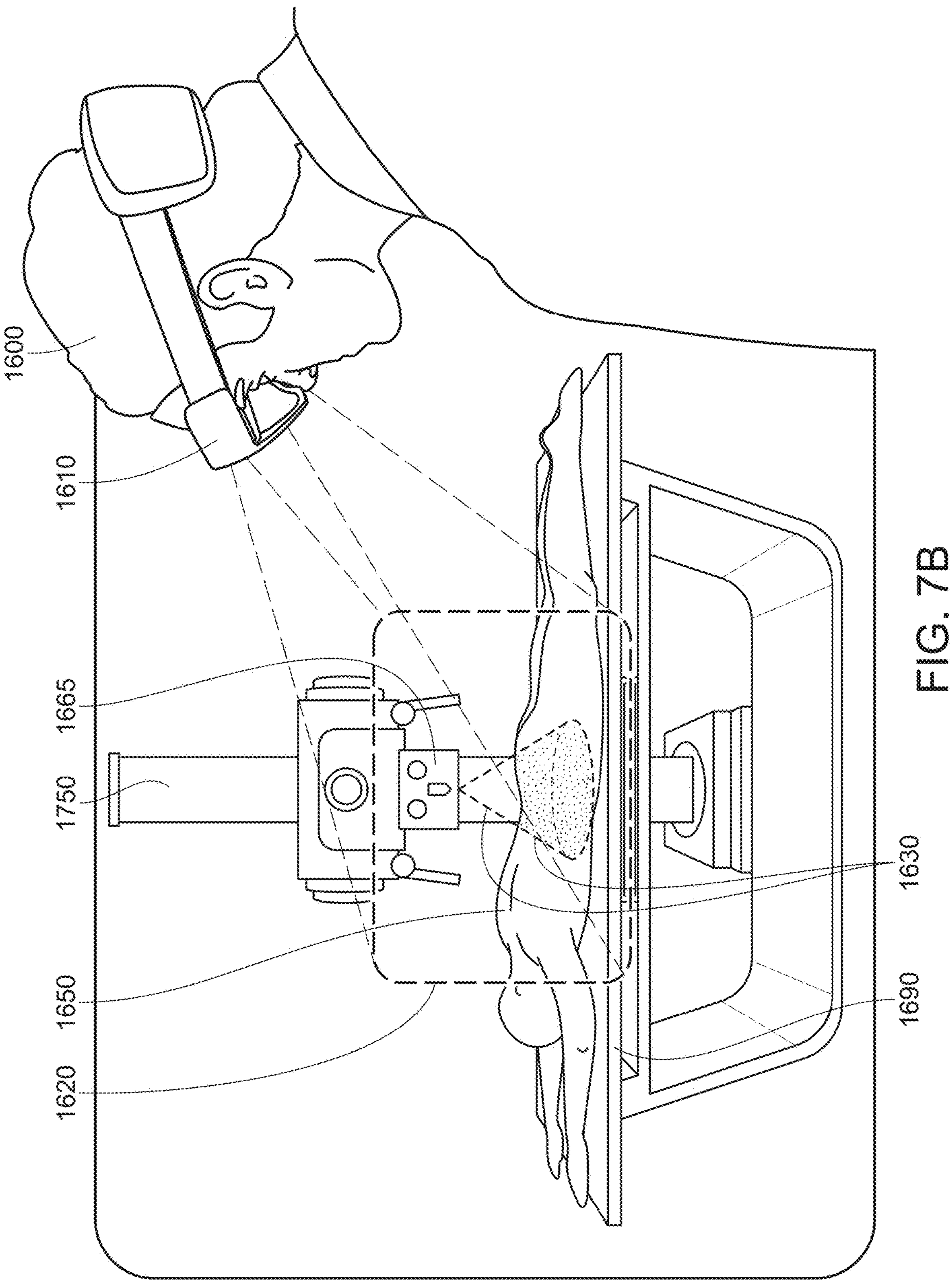
FIGS. 7B-7C show a non-limiting example of a radiography (e.g. 2D, 3D), angiography (e.g. 2D, 3D, 4D) or other x-ray based imaging system, and applications of a virtual display by a head mounted display (HMD) or other augmented reality device, e.g. with display of a 3D representation of an outer envelope or perimeter of an x-ray beam prior to turning on the x-ray beam.
Figure 7C:
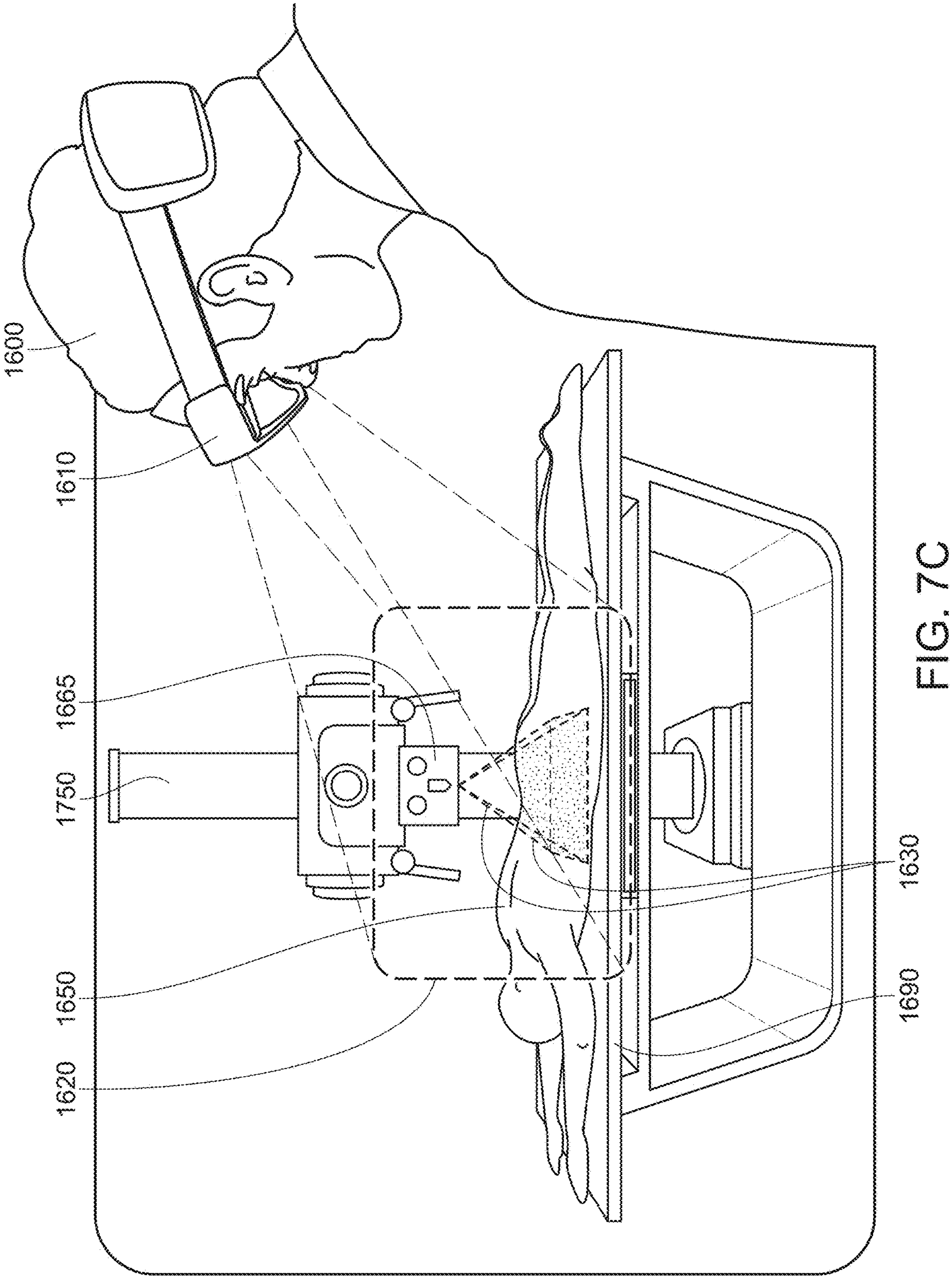

FIGS. 7A-7C show non-limiting examples of a radiography (e.g. 2D, 3D) 1750, angiography (e.g. 2D, 3D, 4D) 1750 or other x-ray based imaging system 1750, and applications of a virtual display by a head mounted display (HMD) or other augmented reality display device. One or more users 1600 can wear a head mounted display (HMD) 1610 or use another type of augmented reality display device. The head mounted display or other augmented reality display device can generate a virtual display of one or more virtual objects within a field of view 1620 of the HMD 1610 or other augmented reality display device. A virtual display can comprise a 3D representation 1630 of a surface or volume of an energy beam, e.g. an x-ray beam. The surface of volume can describe an outer envelope, margin, perimeter, of the energy beam. The 3D representation and the stereoscopic display by the HMD or other augmented reality display device can be generated prior to activating/turning on the energy beam, e.g. x-ray beam. The 3D representation 1630 of the surface or volume can be based on/derived from a position, orientation, and/or geometry of the one or more components of the imaging system, information about a position, orientation and/or geometry of the image acquisition, information about one or more image acquisition parameters, or a combination thereof. The 3D representation 1630 of the surface, volume or combination thereof can, for example, not contain imaging data from a patient 1650, or can contain imaging data from a prior imaging data acquisition but not the current, planned, intended, desired image acquisition, of the patient 1650. Also shown is an x-ray tube housing 1665. In FIG. 7B, the x-ray beam and corresponding 3D representation 1630 are cone shaped with a round base. In FIG. 7C, the x-ray beam and corresponding 3D representation 1630 have a rectangular or quadratic perimeter with a rectangular or quadratic base.

Figure 7D:
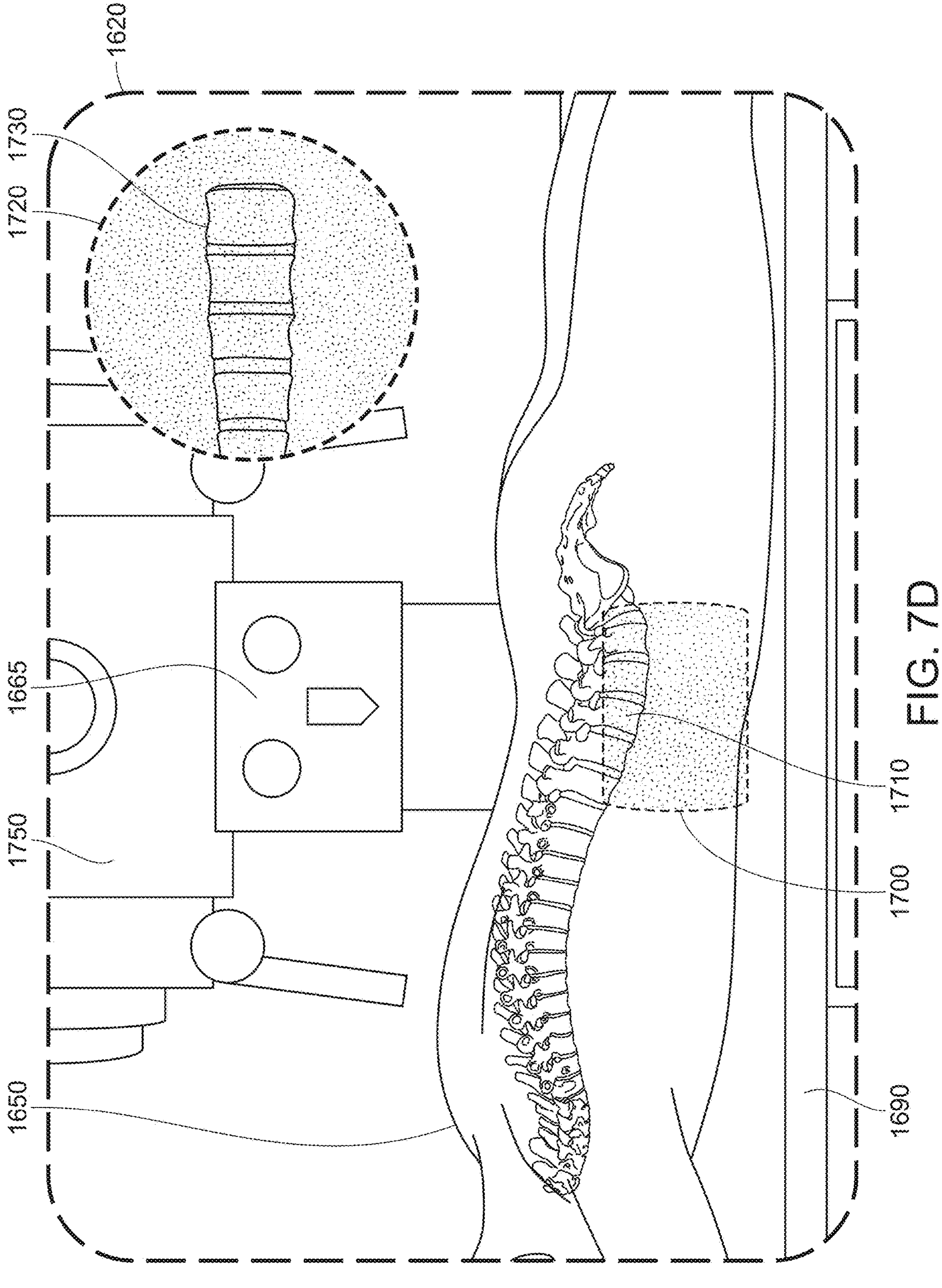
FIGS. 7D-7E show non-limiting examples of a radiography (e.g. 2D, 3D), angiography (e.g. 2D, 3D, 4D) or other x-ray based imaging system and applications of a virtual display by a head mounted display (HMD) or other augmented reality device, e.g. with display of a 3D representation of an outer envelope or perimeter or limit of a 3D imaging data acquisition prior to the actual imaging data acquisition.
Figure 7E:
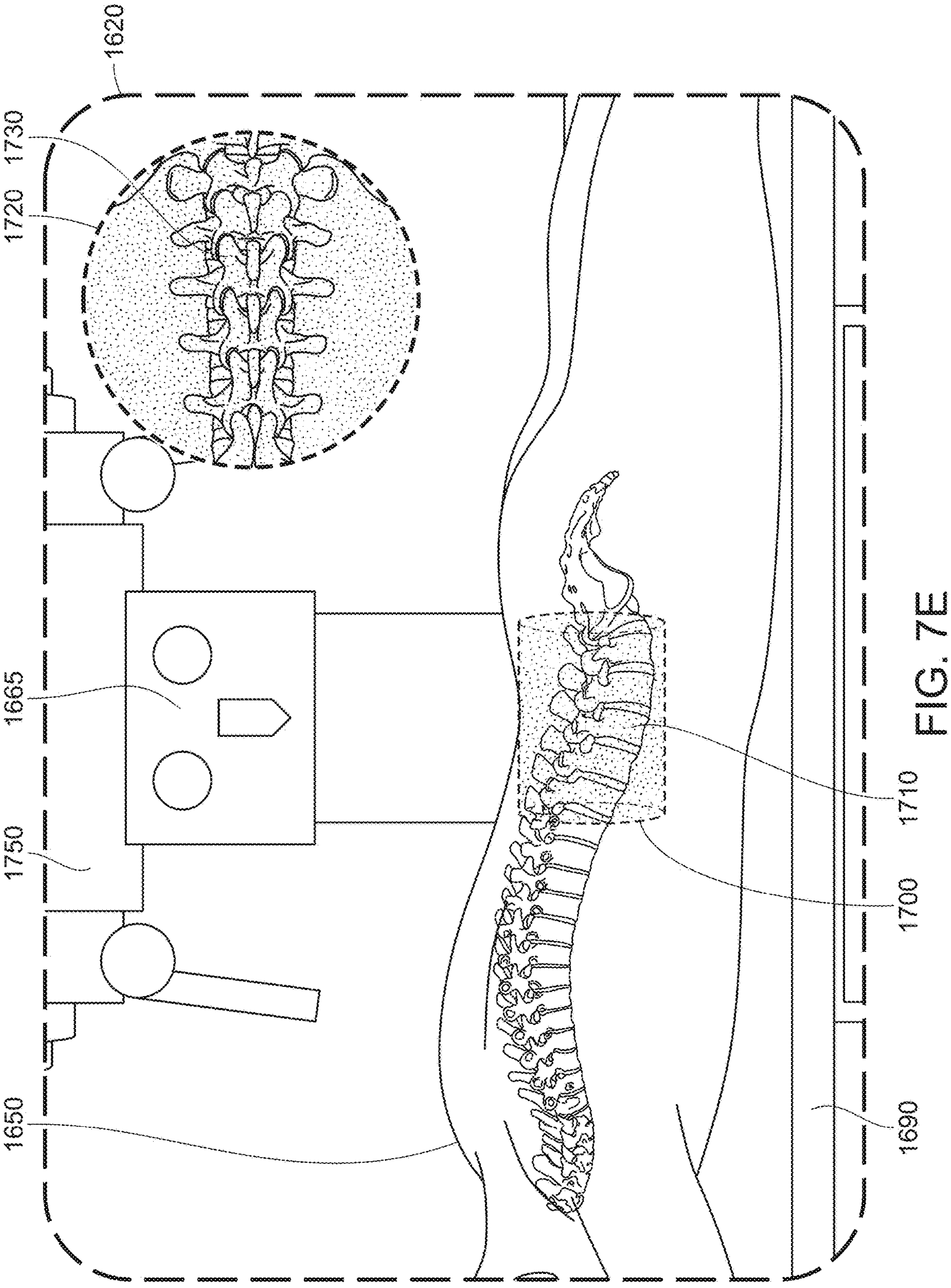

FIG. 7D-7E show non-limiting examples of a radiography (e.g. 3D) 1750, angiography (e.g. 3D, 4D) 1750 or other x-ray based imaging system 1750, and applications of a virtual display by a head mounted display (HMD), e.g. with stereoscopic display of a 3D representation 1700 of a surface or volume representing, for example, an outer envelope or perimeter or limit of an intended or planned 3D (or, optionally 4D) imaging data acquisition, prior to the actual 3D (or, optionally 4D) imaging data acquisition. The view 1620 through the HMD or other augmented reality device shows a virtual display, by the HMD, of a 3D representation 1700 of a surface or volume of a 3D imaging data volume acquisition intended for a patient 1650, displayed by the HMD or other augmented reality device prior to the actual 3D imaging data volume acquisition. The imaging data volume acquisition with the radiography (e.g. 3D) 1750, angiography (e.g. 3D, 4D) 1750 or other x-ray based imaging system 1750, in this non-limiting example, (or with any 3D or 4D imaging system) intended in this patient 1650 can be a volumetric, cylinder shaped acquisition, in this example. Any other 3D shapes of image acquisitions are possible, depending on the imaging system used, its components and/or its unique geometries. The 3D representation 1700 of the surface or volume of the 3D imaging data (or, optionally, 4D) acquisition can be based on/derived from a position, orientation and/or geometry of the one or more components of the imaging system, information about a position, orientation and/or geometry of the image acquisition, information about one or more image acquisition parameters, or a combination thereof. The 3D representation 1700 of the surface or volume of the intended 3D imaging data acquisition can be displayed, for example in an overlay fashion, superimposed onto the patient 1650 and/or a target organ or target anatomic structure, such as a portion of a spine 1710 by an HMD or other augmented reality device, e.g. a table, iPad, smart phone etc., in this non-limiting example.

The imaging system, in this non-limiting example a radiography (e.g. 3D) 1750, angiography (e.g. 3D, 4D) 1750 or other x-ray based imaging system 1750, and/or one or more of its components, and/or the patient table 1690 can be moved, e.g. by a user, optionally assisted by one or more motors, controllers, drives, hydraulic and/or electric system, and/or robotic components and/or arms. Optionally, the imaging system, in this non-limiting example a radiography (e.g. 3D) 1750, angiography (e.g. 3D, 4D) 1750 or other x-ray based imaging system 1750, and/or optionally one or more of its components, and/or optionally the patient table 1690 can be tracked, e.g. using any of the techniques described throughout the specification. In addition, the patient 1650 and/or the target organ or target anatomic structure, such as a portion of a spine 1710, can optionally also be tracked, e.g. using any of the techniques described throughout the specification. The system, including one or more of its computing systems and/or computer processors, can be configured so that the 3D stereoscopic view of the 3D representation 1700 of the surface or volume of the envelope, perimeter, limits, margin, or combination thereof of the intended or desired imaging data acquisition displayed by the HMD or other augmented reality device at a defined position, orientation, coordinates or combination thereof in relationship to the one or more components of the imaging system (and, as in this example, onto the patient) prior to the actual imaging data acquisition can move in relation with the tracked imaging system 1750, tracked one or more components of the imaging system, optionally tracked patient table 1690, and/or the (optionally tracked) anatomic target structure, such as a spine 1710 (e.g optionally with one or more attached markers or fiducials or fiducial arrays, not shown). When the imaging system 1750 or one or more of its components are moved, or, optionally, when the patient table 1690 is moved, or when one or more parameters determining and/or influencing the location and/or orientation of the image acquisition are changed, or any combination thereof, the system can be configured to adjusting the position, orientation, position and orientation of the 3D stereoscopic view or augmented view of the 3D representation 1700 in response to the movement of the tracked imaging system 1750, the movement of the one or more of its components, the movement of the tracked patient table 1690, and/or the changes in the one or more parameters determining and/or influencing the location and/or orientation of the image acquisition.

FIGS. 7D-7E show how the 3D representation 1700 of the surface or volume of the envelope, perimeter, limits, margin, or combination thereof of the intended or desired imaging data acquisition displayed, by the HMD or other augmented reality device, in a defined position, orientation and/or coordinates relative to the one or more components of the imaging moves in relationship to a target anatomic structure, such as a spine 1710, with the movement of the tracked imaging system 1750, the movement of the one or more of its components, the movement of the tracked patient table 1690, and/or the changes in the one or more parameters determining and/or influencing the location and/or orientation of the image acquisition.

In FIG. 7D, the 3D representation 1700 of the surface or volume of the envelope, perimeter, limits, margin, or combination thereof of the intended or desired imaging data acquisition superimposed, by the HMD or other augmented reality device, onto the patient 1650 prior to the actual imaging data acquisition is too far anterior relative to a target anatomic structure, such as a spine 1710. This can occur, for example, when the imaging system 1750 or one or more of its components are too low in position relative to the patient 1650 or the target anatomic structure, such as a spine 1710, or when the patient table 1690 is too high relative to the imaging system 1750. An exploded view 1720, shows what the images will look like after the image data acquisition. Only a small anterior portion of the spine 1730 will be included in the actual image data volume acquisition and the resultant images.

In FIG. 7E, the 3D representation 1700 of the surface or volume of the envelope, perimeter, limits, margin, or combination thereof of the intended or desired imaging data acquisition superimposed, by the HMD or other augmented reality device, onto the patient 1650 prior to the actual imaging data acquisition is correctly positioned relative to a target anatomic structure, such as a spine 1710. This can occur, for example, when the imaging system 1750 or one or more of its components are correctly positioned, e.g. centered relative to the patient 1650 or the target anatomic structure, such as a spine 1710, and/or when the patient table 1690 is correctly positioned relative to the imaging system 1750, and/or when the patient 1650 is correctly positioned on the patient table 1690, e.g. in the center of the patient table, not off to the side.

An exploded view 1720, shows what the images will look like after actual the image data acquisition. The entire target portion of the spine 1730 will be included in the image data volume acquisition and the resultant images.

Thus, by moving one or more of the tracked imaging system 1750, tracked one or more components of the imaging system, optionally tracked patient table 1690, and/or the patient 1650, and/or the anatomic target structure, such as a spine 1710 prior to the actual image data acquisition and by optimizing the position, orientation, or position and orientation and/or coordinates of the 3D representation 1700, displayed by the HMD or other augmented reality display device, of a surface or volume of the envelope, margin, perimeter and/or limits of the 3D imaging data volume acquisition intended for a patient 1650, and/or the target anatomic target structure, such as a spine 1710, the actual image data acquisition can be optimized with regard to the coverage and/or inclusion of the target anatomic target structure, such as a spine 1710.

This approach can obviate the need for repeat scout images and/or x-ray images (e.g. AP, lateral) prior to the actual 3D volume acquisition.

Figure 8A:
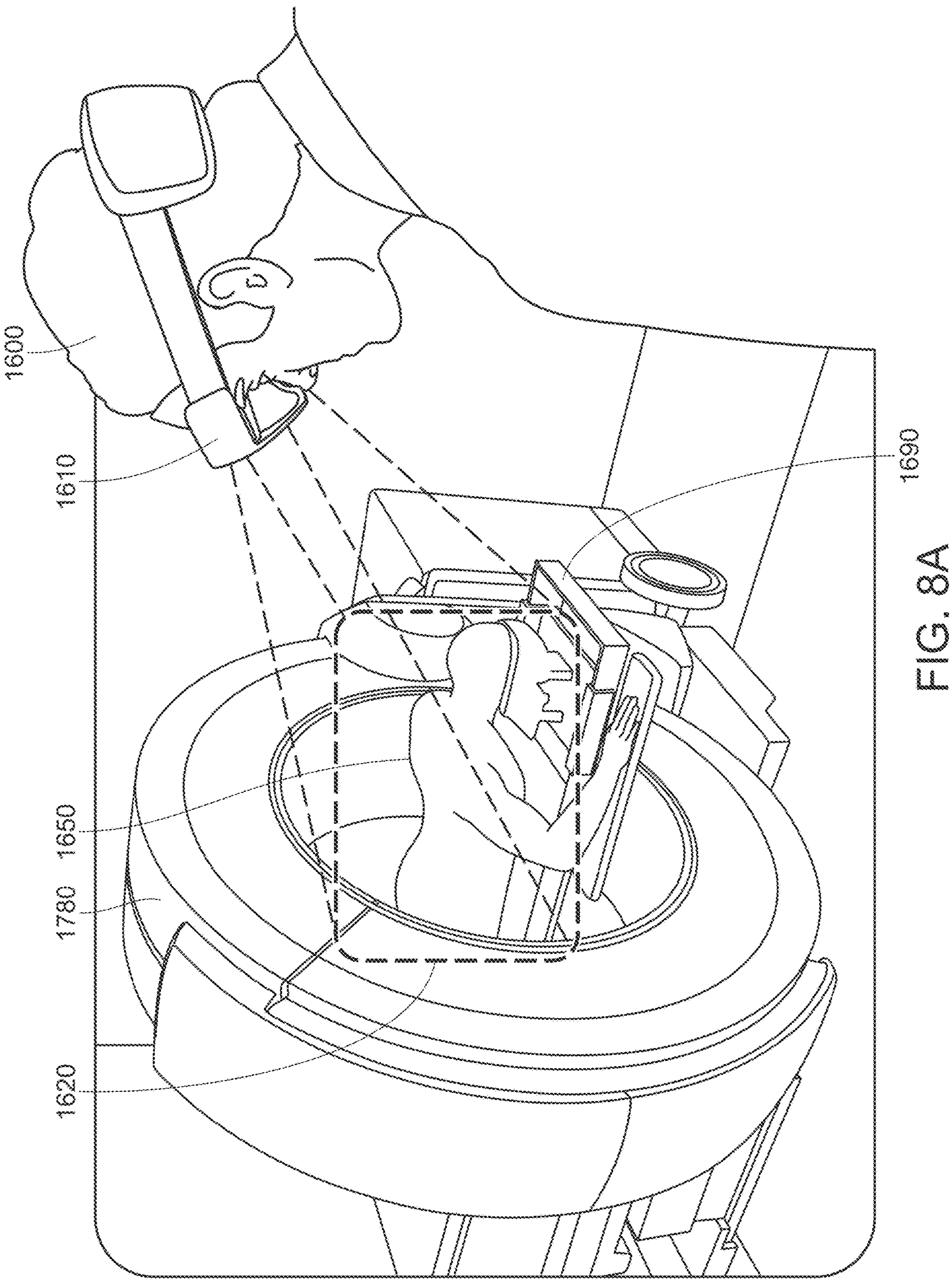
FIG. 8A shows a non-limiting example of a CT, cone beam CT, spiral CT, MRI system, SPECT system, PET system, or a combination thereof, and applications of a virtual display by a head mounted display (HMD) or other augmented reality device.
Figure 8B:
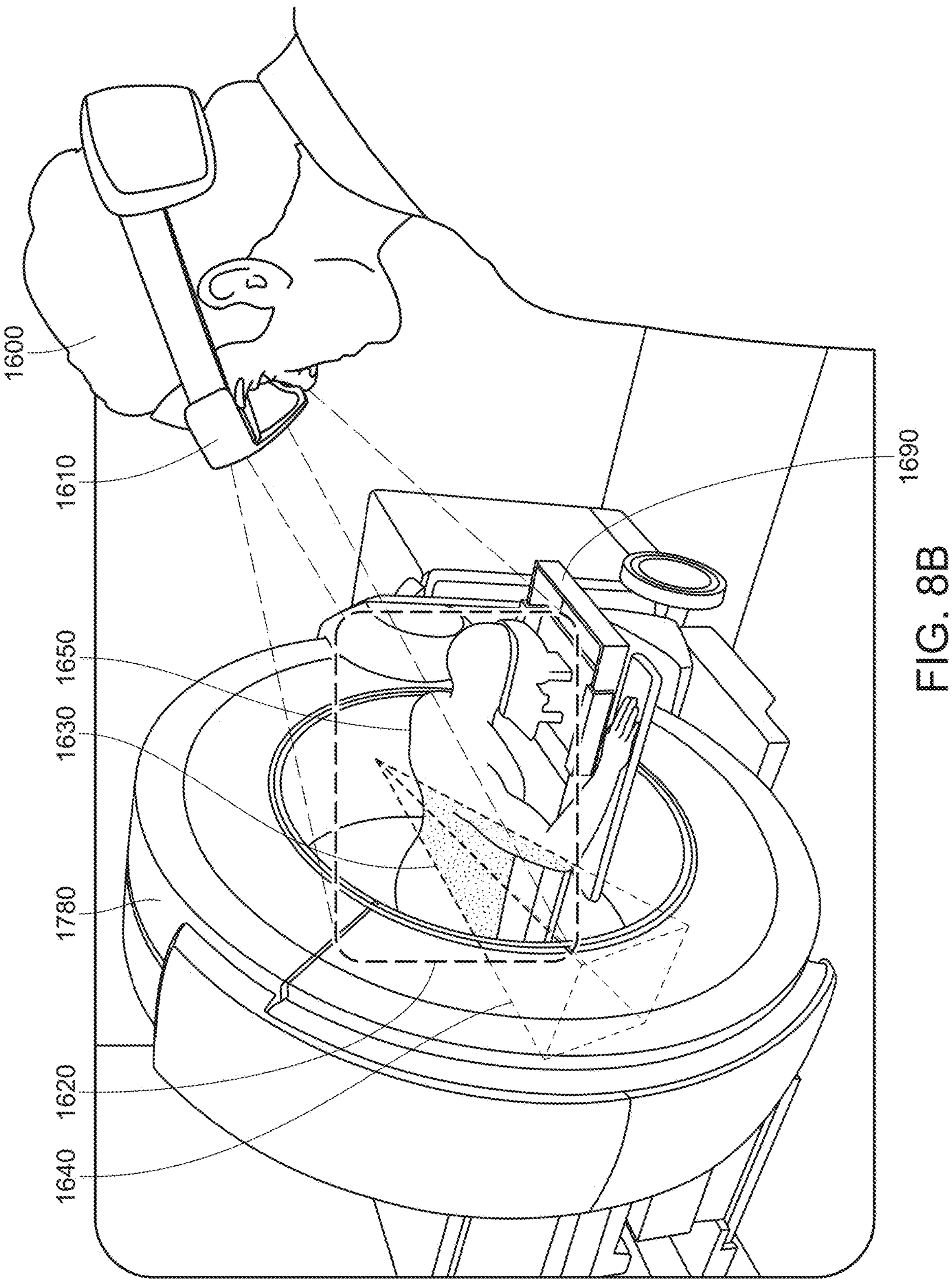
FIG. 8B shows a non-limiting example of a CT, cone beam CT, spiral CT, SPECT system, PET system, or a combination thereof, and applications of a virtual display by a head mounted display (HMD) or other augmented reality device, e.g. with display of an outer envelope or perimeter of an x-ray or energy beam prior to turning on the x-ray or energy beam.

FIGS. 8A-8B show non-limiting examples of a CT, cone beam CT, spiral CT, MRI system, SPECT system, PET system 1780 or a combination thereof, and applications of a virtual display by a head mounted display (HMD) or other augmented reality device. One or more users 1600 can wear a head mounted display (HMD) 1610 or carry another augmented reality device. The head mounted display or other augmented reality device can generate a virtual display of one or more virtual objects within a field of view 1620 of the HMD 1610 or other augmented reality device. A virtual display can comprise a 3D representation 1630 of a surface or volume of an energy beam 1640, e.g. an x-ray beam. The surface of volume can describe an outer envelope, margin, perimeter, of the energy beam 1640. The 3D representation and the stereoscopic display or augmented view by the HMD or other augmented reality device can be generated prior to activating/turning on the energy beam 1640, e.g. x-ray beam. The 3D representation 1630 of the surface or volume can be based on/derived from a position, orientation and/or geometry of the one or more components of the imaging system (e.g. an imaging transmit and/or receiver coil with an MRI system, one or more gradients, gradient coils, etc.), information about a position, orientation, and/or geometry of the image acquisition, information about one or more image acquisition parameters, or a combination thereof. The 3D representation 1630 of the surface, volume or combination thereof can, for example, not contain imaging data from a patient 1650, or can contain imaging data from a prior imaging data acquisition but not the current, planned, intended, desired image acquisition, of the patient 1650.

Figure 8C:
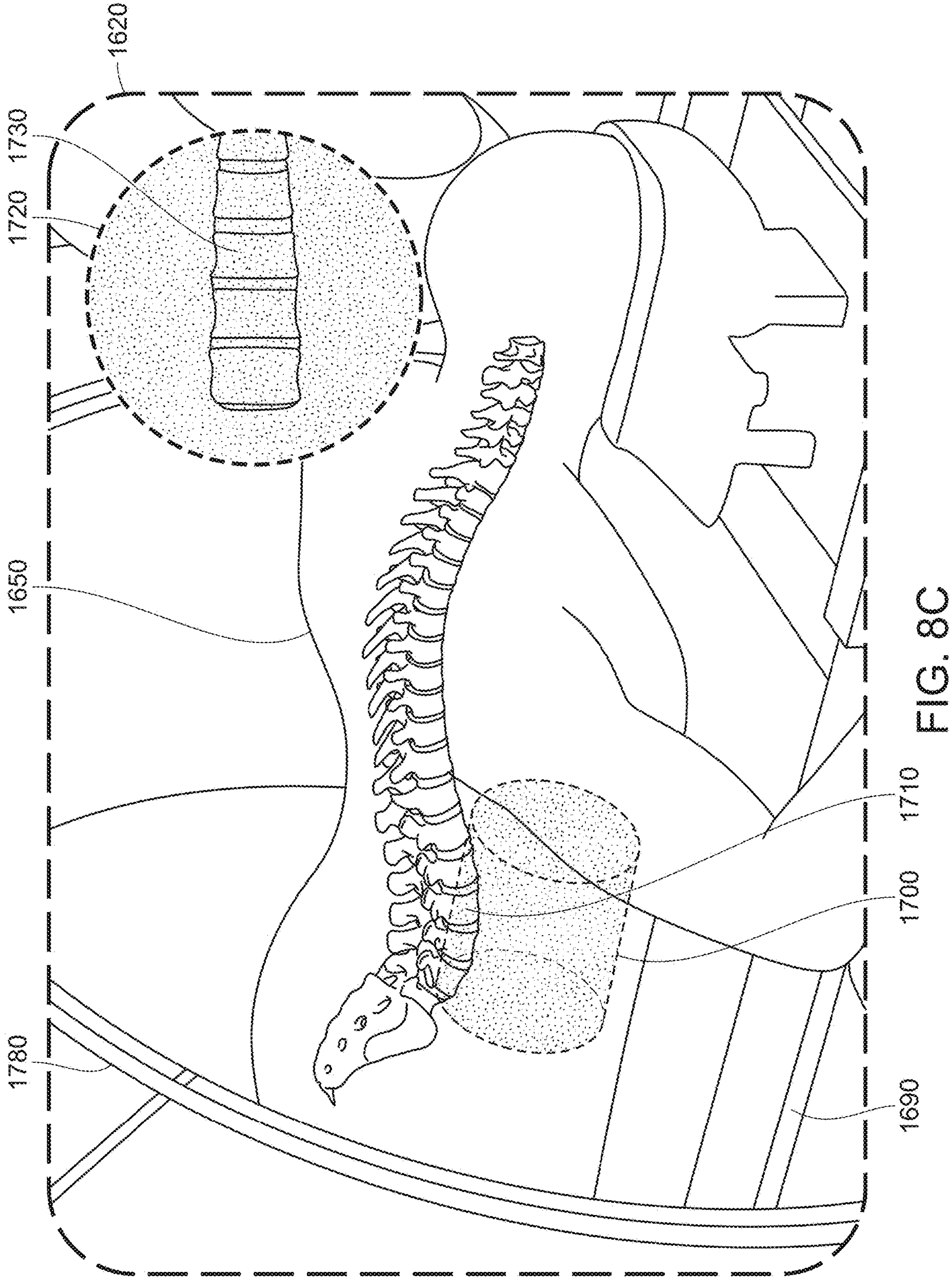
FIG. 8C-8E show non-limiting examples of a CT, cone beam CT, spiral CT, MRI system, SPECT system, PET system, or a combination thereof and applications of a virtual display by a head mounted display (HMD) or other augmented reality device, e.g. with display of an outer envelope or perimeter or limit of a 3D imaging data acquisition prior to the actual imaging data acquisition.
Figure 8D:
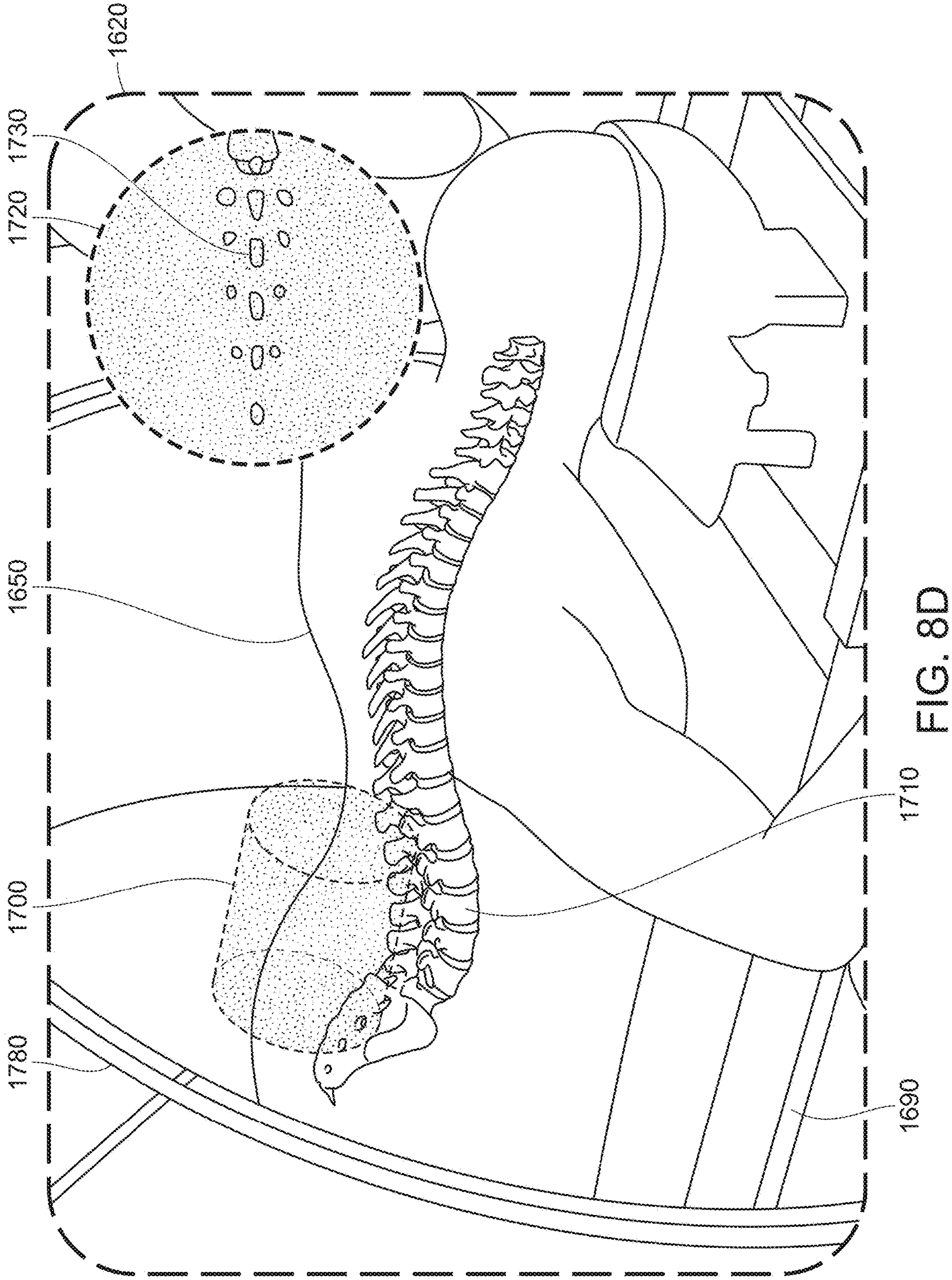
Figure 8E:
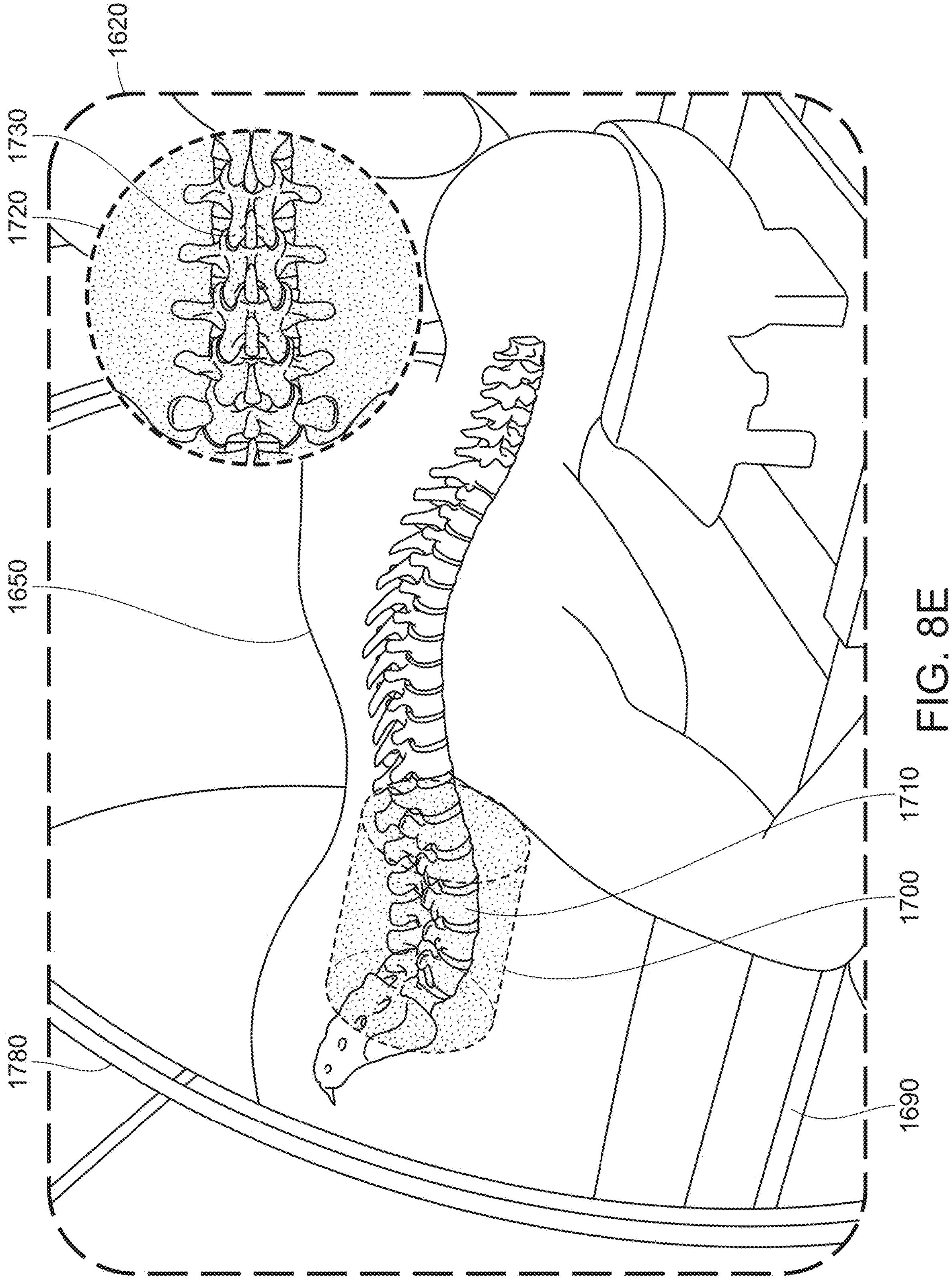

FIG. 8C-8E show non-limiting examples of a CT, cone beam CT, spiral CT, MRI system, SPECT system, PET system 1780 or a combination thereof, and applications of a virtual display by a head mounted display (HMD) or other augmented reality device, e.g. with stereoscopic and/or augmented display of a 3D representation 1700 of a surface or volume representing, for example, an outer envelope or perimeter or limit of an intended or planned 3D (or, optionally 4D [e.g. vascular flow or angiographic, for example with spiral CT angiography or MRI angiography]) imaging data acquisition, prior to the actual 3D (or, optionally 4D) imaging data acquisition. The view 1620 through the HMD or other augmented reality device shows a virtual and/or augmented display, by the HMD or other augmented reality device, of a 3D representation 1700 of a surface or volume of a 3D imaging data volume acquisition intended for a patient 1650, displayed by the HMD prior to the actual 3D imaging data volume acquisition. The imaging data volume acquisition with the CT, cone beam CT, spiral CT, MRI system, SPECT system, PET system 1780 or a combination thereof, in this non-limiting example, (or with any 3D or 4D imaging system) intended in this patient 1650 can be a volumetric, cylinder shaped acquisition, in this example. Any other 3D shapes of image acquisitions are possible, depending on the imaging system used, its components and its unique geometries. The 3D representation 1700 of the surface or volume of the 3D imaging data (or, optionally, 4D) acquisition can be based on/derived from a position, orientation and/or geometry of the one or more components of the imaging system, information about a position, orientation and/or geometry of the image acquisition, information about one or more image acquisition parameters, or a combination thereof. The 3D representation 1700 of the surface or volume of the intended 3D imaging data acquisition can be displayed by the HMD or other augmented reality device in a defined position, orientation and/or at defined coordinates relative to one or more components of the imaging system, for example in an overlay fashion superimposed onto a patient 1650 and/or a target organ or target anatomic structure, such as a portion of a spine 1710 in this non-limiting example.

The imaging system, in this non-limiting example a CT, cone beam CT, spiral CT, MRI system, SPECT system, PET system 1780 or a combination thereof, and/or one or more of its components, and/or the patient table 1690 can be moved, e.g. by a user, optionally assisted by one or more motors, controllers, drives, hydraulic and/or electric system, and/or robotic components and/or arms. Optionally, the imaging system, in this non-limiting example a CT, cone beam CT, spiral CT, MRI system, SPECT system, PET system 1780 or a combination thereof, and/or one or more of its components, and/or optionally the patient table 1690 can be tracked, e.g. using any of the techniques described throughout the specification. In addition, the patient 1650 and/or the target organ or target anatomic structure, such as a portion of a spine 1710, can also optionally be tracked, e.g. using any of the techniques described throughout the specification. The system, including one or more of its computing systems and/or computer processors, can be configured so that the 3D stereoscopic view or augmented view of the 3D representation 1700 of the surface or volume of the envelope, perimeter, limits, margin, or combination thereof of the intended or desired imaging data acquisition displayed by the HMD or other augmented reality device at a defined position/orientation relative to one or more components of the imaging system, optionally superimposed onto the patient, prior to the actual imaging data acquisition can move in relation with the tracked imaging system 1780, tracked one or more components of the imaging system, (optionally tracked) patient table 1690, and/or the anatomic target structure, such as a spine 1710 (optionally also tracked, e.g. with one or more attached markers or fiducials or fiducial arrays, not shown). When the imaging system 1780 or one or more of its components are moved, or when the patient table 1690 is moved, or when one or more parameters determining and/or influencing the location and/or orientation of the image acquisition are changed, or any combination thereof, the system can be configured to adjusting the position, orientation, position and orientation of the 3D stereoscopic view or augmented view of the 3D representation 1700 in response to the movement of the tracked imaging system 1750, the movement of the one or more of its components, the movement of the optionally tracked patient table 1690, and/or the changes in the one or more parameters determining and/or influencing the location and/or orientation of the image acquisition.

FIGS. 8C-8E show how the 3D representation 1700 of the surface or volume of the envelope, perimeter, limits, margin, or combination thereof of the intended or desired imaging data acquisition displayed by the HMD or other augmented reality device in a defined position, orientation or combination thereof relative to the one or more components of the imaging system prior to the actual imaging data acquisition, optionally superimposed onto the patient, moves in relationship to a target anatomic structure, such as a spine 1710 with the movement of the tracked imaging system 1780, the movement of the one or more of its components, the movement of the optionally tracked patient table 1690, and/or the changes in the one or more parameters determining and/or influencing the location and/or orientation of the image acquisition.

In FIG. 8C, the 3D representation 1700 of the surface or volume of the envelope, perimeter, limits, margin, or combination thereof of the intended or desired imaging data acquisition superimposed, by the HMD or other augmented reality display device, onto the patient 1650 prior to the actual imaging data acquisition is too far anterior relative to a target anatomic structure, such as a spine 1710. This can occur, for example, when the imaging system 1780 or one or more of its components are too low in position relative to the patient 1650 or the target anatomic structure, such as a spine 1710, or when the patient table 1690 is too high relative to the imaging system 1780. An exploded view 1720, shows what the images will look like after the image data acquisition. Only a small anterior portion of the spine 1730 will be included in the actual image data volume acquisition and the resultant images.

In FIG. 8D, the 3D representation 1700 of the surface or volume of the envelope, perimeter, limits, margin, or combination thereof of the intended or desired imaging data acquisition superimposed, by the HMD or other augmented reality display device, onto the patient 1650 prior to the actual imaging data acquisition is too far posterior relative to a target anatomic structure, such as a spine 1710. The 3D representation 1700 is partially floating above the patient 1650. This can occur, for example, when the imaging system 1780 or one or more of its components are too high or mal-aligned in position relative to the patient 1650 or the target anatomic structure, such as a spine 1710, or when the patient table 1690 is too low relative to the imaging system 1780, e.g. the center of the imaging system, the center of a rotation of a C-arm, the center of a spin of a cone beam CT, and/or the center of a spiral, e.g. with a CT scan. An exploded view 1720, shows what the images will look like after the actual image data acquisition.

Only a small posterior portion of the spine 1730 will be included in the image data volume acquisition and the resultant images.

In FIG. 8E, the 3D representation 1700 of the surface or volume of the envelope, perimeter, limits, margin, or combination thereof of the intended or desired imaging data acquisition superimposed, by the HMD or other augmented reality display device, onto the patient 1650 prior to the actual imaging data acquisition is correctly positioned relative to a target anatomic structure, such as a spine 1710. This can occur, for example, when the imaging system 1780 or one or more of its components are correctly positioned, e.g. centered relative to the patient 1650 or the target anatomic structure, such as a spine 1710, and/or when the patient table 1690 is correctly positioned relative to the imaging system 1780, and/or when the patient 1650 is correctly positioned on the patient table 1690, e.g. in the center of the patient table, not off to the side. An exploded view 1720, shows what the images will look like after actual the image data acquisition. The entire target portion of the spine 1730 will be included in the image data volume acquisition and the resultant images.

Thus, by moving one or more of the tracked imaging system 1780, tracked one or more components of the imaging system, (optionally tracked) patient table 1690, and/or the patient 1650, and/or the (optionally tracked) anatomic target structure, such as a spine 1710 prior to the actual image data acquisition and by optimizing the position, orientation, or position and orientation and/or coordinates of the 3D representation 1700 of a surface or volume of the envelope, margin, perimeter and/or limits of the 3D imaging data volume acquisition intended or desired for a patient 1650, and/or the target anatomic target structure, such as a spine 1710, displayed by the HMD or other augmented reality device prior to the actual image data acquisition, the actual image data acquisition can be optimized with regard to the coverage and/or inclusion of the target anatomic target structure, such as a spine 1710. This approach can obviate the need for repeat scout images, e.g. MRI scout images, CT scout images, and/or x-ray images (e.g. AP, lateral) prior to the actual 3D volume acquisition.

Calibration Phantoms for Determining the Location of a 3D Representation of a Surface, Volume, Envelope or Perimeter of an Intended Image Acquisition in Relationship to One or More Components of an Imaging System for Various Imaging System Settings In some embodiments, an imaging calibration phantom can be used for determining the location of a 3D representation of a surface or volume containing information about an envelope, limit, perimeter, and/or boundary of an intended imaging acquisition in relationship to one or more components of an imaging system. The imaging calibration phantom can, for example, comprise one or more image visible markers, e.g. spheres, components, or compartments, containing various type of materials depending on the imaging modality used. For example, for imaging systems using x-rays or x-ray beams, the materials can comprise a metal, e.g. aluminum, titanium, steel, lead or any other metal. For imaging systems utilizing radionuclides, the phantom can comprise image visible markers, e.g. spheres, compartments or containers holding, containing one or more radioisotopes or radionuclides. The phantom can comprise spheres, compartments or containers holding, containing contrast media suitable for a particular imaging modality or imaging system. For example, for MRI, the phantom can comprise spheres, compartments or containers containing gadolinium-DTPA-doped water; alternatively, oil based fluids can also be used.

The phantom can comprise defined geometric patterns or arrangements of image visible markers within a single plane or within multiple planes. For example, for imaging modality using x-rays, one or more metal spheres or beads, i.e. image visible markers, can be arranged in a 3D layout, with multiple different spheres or beads located in different locations, each with different x, y, and z-coordinates, for example in multiple layers.

The phantom and the image visible markers, e.g. spheres, beads etc. contained therein can be smaller, similar in size, or larger than the surface, volume, envelope, limit, perimeter of an intended imaging acquisition. For example, the phantom can be larger than the maximum envelope, limit, perimeter and/or boundary of the imaging acquisition. The image visible markers can be closely spaced in 3 dimensions, e.g. at 20 mm, 15 mm, 10 mm, 5 mm, 3 mm, 2 mm, 1 mm intervals or any other interval. The phantom can be tracked using any of the tracking or registration techniques known in the art or described in the specification. For example, the phantom can comprise one or more fiducial markers, optical markers, fiducial arrays etc.

In some embodiments, the phantom can be placed on a table associated with the imaging system, e.g. a patient table, located in the general area and/or opening of the imaging system or imaging system components, e.g. a C-arm or O-arm, CT scanner, cone beam CT or other imaging system.

The system can be configured to track a head mounted display, an augmented or mixed reality display device, a patient table used with the imaging system, an imaging system, one or more components of the imaging system components, or a combination thereof and the phantom.

The geometry of the image visible markers within the phantom or integrated or attached to the phantom can be known based on the manufacturing specification and/or an optional post-manufacturing imaging test.

A computer processor can be configured to detect the image visible markers of the phantom automatically, for example using automated image segmentation software. The phantom with the image visible markers can be placed on the patient table of the imaging system. The location, position, and/or orientation of the phantom can be determined using the tracking system in relationship to the tracked imaging system or tracked one or more components of the imaging system. An image acquisition can be performed; the computer processor can detect the image visible markers included in the image acquisition. Thus, the computer processor can determine which image visible markers were included in the image acquisition and which of the image visible markers of the phantom were not included; the boundary of the image visible markers included in the image(s)/image volume and the image visible markers not included in the image(s)/image volume can be used by the computer processor to determine the boundary, limit, perimeter, envelope, surface or volume of the image acquisition, e.g. in relationship to the tracked phantom and, with that, in relationship to the tracked one or more components of the imaging system. The one or more components of the imaging system can be tracked using extrinsic or intrinsic tracking information and/or techniques, as described throughout the specification. Someone skilled in the art can recognize that the definition of the boundary, limit, perimeter, envelope of the image acquisition, used for the generation of the 3D representation of the surface or volume of the image acquisition, can be improved the more closely the image visible markers are spaced together within the phantom. In some embodiments, the phantom can be larger than the largest image acquisition volume provided by the imaging system.

With the location, position, and/or orientation of the tracked phantom in relationship to the tracked imaging system or tracked one or more components of the imaging system known based on the tracking information, and the geometry of the image visible markers of the phantom known, and/or the image visible markers detected in the image acquisition data/volume known, a computer processor can generate an estimate of a surface or volume of the boundary, limit, perimeter, and/or envelope of the image acquisition.

In some embodiments, the image acquisition can be repeated for different geometries of the imaging system (e.g. different tube detector distances), different patient table heights, different positions, orientations and/or geometries of one or more components of the imaging system (e.g. a collimator), different geometries of the image acquisition, and/or different image acquisition parameters. Using the foregoing techniques for determining the surface or volume of the boundary, limit, perimeter, and/or envelope of the image acquisition, the data and corresponding 3D representations of the surface or volume of the boundary, limit, perimeter, and/or envelope of the image acquisitions can be stored for a given imaging system and different geometries, positions, orientations, and/or image acquisition parameters.

When a patient is subsequently placed on the imaging system table, a 3D representation of the surface or volume of the boundary, limit, perimeter, and/or envelope of the image acquisition can be generated and/or displayed corresponding to or reflecting a set of geometries, positions, orientations, and/or image acquisition parameters selected for that patient and the intended scan. The system can then display, by an HMD or other augmented reality display device, the 3D representation in relationship to the one or more imaging components; the imaging system can be moved to the target anatomic area of the patient, while maintaining the display of the 3D representation in relationship to the one or more imaging components. The imaging system can be moved to an optimized position for a subsequent image acquisition relative to the target anatomic area, as seen in the stereoscopic view or augmented view by the position of the 3D representation in relationship to the target anatomic area.

Someone skilled in the art can recognize that data or information related to the surface or volume of the boundary, limit, perimeter, and/or envelope of am image acquisition can also be retrieved from an imaging system profile or database provided by an imaging system manufacturer; the surface or volume of the boundary, limit, perimeter, and/or envelope of am image acquisition and the 3D representations and can be automatically updated and/or adjusted based on intrinsic imaging system information, e.g. different geometric settings of the imaging system (e.g. different tube detector distances), different positions, orientations and/or geometric settings of one or more components of the imaging system (e.g. a collimator), different geometric settings of the image acquisition, and/or different image acquisition parameters.

EXAMPLES

Example 1—Use of Multiple Head Mounted Displays

Figure 9:
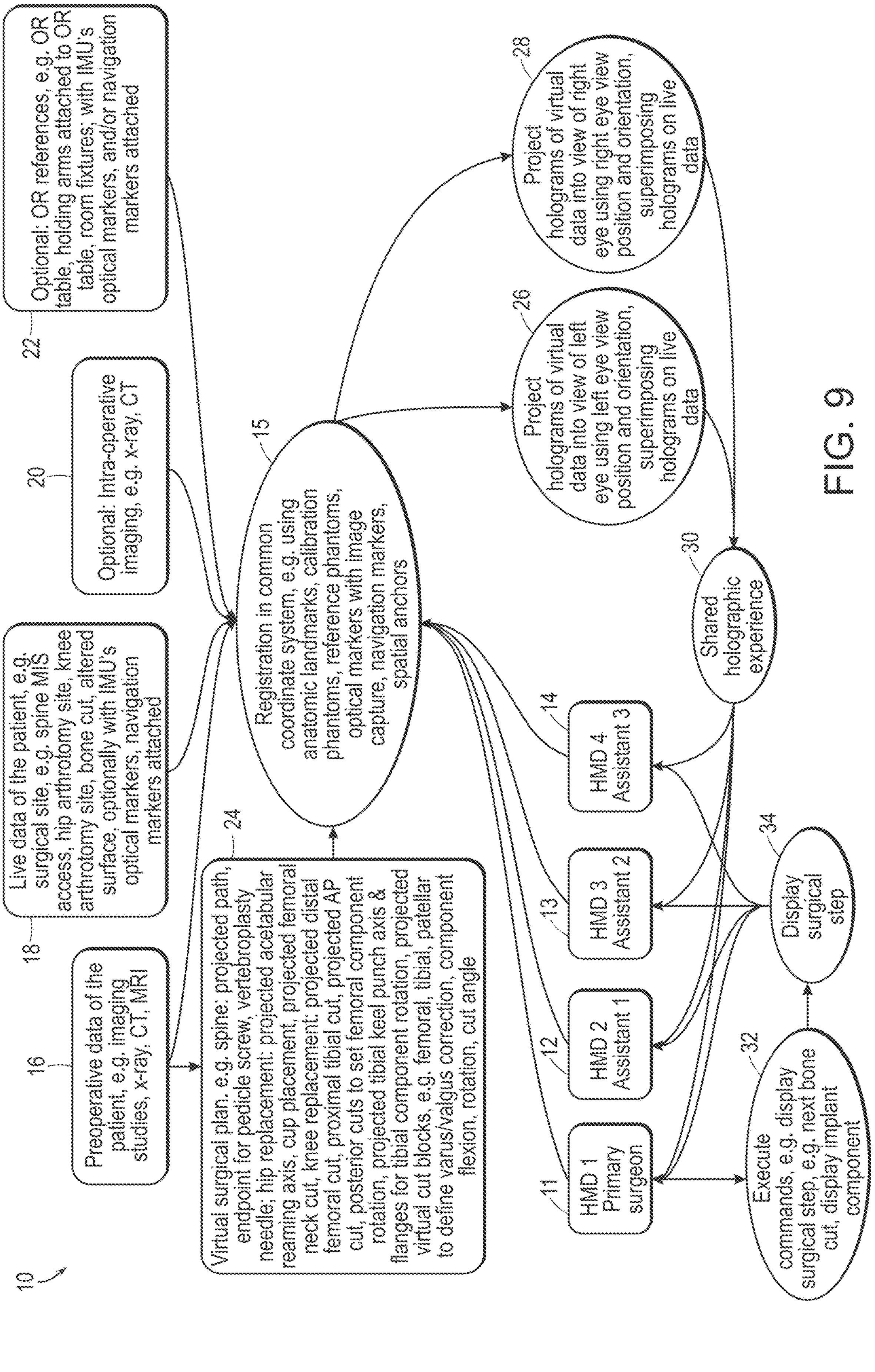
FIG. 9 shows a non-limiting example of the use of multiple HMDs or other augmented reality display systems for multiple viewer's, e.g. a primary surgeon, second surgeon, surgical assistant(s) and/or nurses(s) according to some embodiments of the present disclosure.

In some embodiments, multiple head mounted displays can be used. Head mounted displays (HMD) can be video see-through head mounted displays or optical see-through head mounted displays. Referring to FIG. 9, a system 10 for using multiple HMDs 11, 12, 13, 14 or other augmented reality display systems for multiple viewer's, e.g. a primary surgeon, second surgeon, surgical assistant(s) and/or nurses(s) is shown; video see-through head mounted displays could also be used in any of the embodiments. The multiple HMDs or other augmented reality display systems can be registered in a common coordinate system 15 using anatomic structures, anatomic landmarks, calibration phantoms, reference phantoms, optical markers, navigation markers, and/or spatial anchors, for example like the spatial anchors used by the Microsoft Hololens. Pre-operative data 16 of the patient can also be registered in the common coordinate system 15. Live data 18 of the patient, for example from the surgical site, e.g. a spine, optionally with minimally invasive access, a hip arthrotomy site, a knee arthrotomy site, a bone cut, an altered surface can be measured, for example using one or more IMU's, optical markers, navigation markers, image or video capture systems and/or spatial anchors. The live data 18 of the patient can be registered in the common coordinate system 15. Intra-operative imaging studies 20 can be registered in the common coordinate system 15. OR references, e.g. an OR table or room fixtures can be registered in the common coordinate system 15 using, for example, optical markers IMU's, navigation markers or spatial mapping 22. The pre-operative data 16 or live data 18 including intra-operative measurements or combinations thereof can be used to develop, generate or modify a virtual surgical plan 24. The virtual surgical plan 24 can be registered in the common coordinate system 15. The HMDs 11, 12, 13, 14 or other augmented reality display systems can project digital holograms of the virtual data or virtual data into the view of the left eye using the view position and orientation of the left eye 26 and can project digital holograms of the virtual data or virtual data into the view of the right eye using the view position and orientation of the right eye 28 of each user, resulting in a shared digital holographic experience 30. Using a virtual or other interface, the surgeon wearing HMD 1 11 can execute commands 32, e.g. to display the next predetermined bone cut, e.g. from a virtual surgical plan or an imaging study or intra-operative measurements, which can trigger the HMDs 11, 12, 13, 14 to project digital holograms of the next surgical step 34 superimposed onto and aligned with the surgical site in a predetermined position and/or orientation.

Virtual data of the patient can be projected superimposed onto live data of the patient for each individual viewer by each individual HMD for their respective view angle or perspective by registering live data of the patient, e.g. the surgical field, and virtual data of the patient as well as each HMD in a common, shared coordinate system. Thus, virtual data of the patient including aspects of a virtual surgical plan can remain superimposed and/or aligned with live data of the patient irrespective of the view angle or perspective of the viewer and alignment and/or superimposition can be maintained as the viewer moves his or her head or body.

Example 2—Optional Imaging Data or Other Data Segmentation

Figure 10:
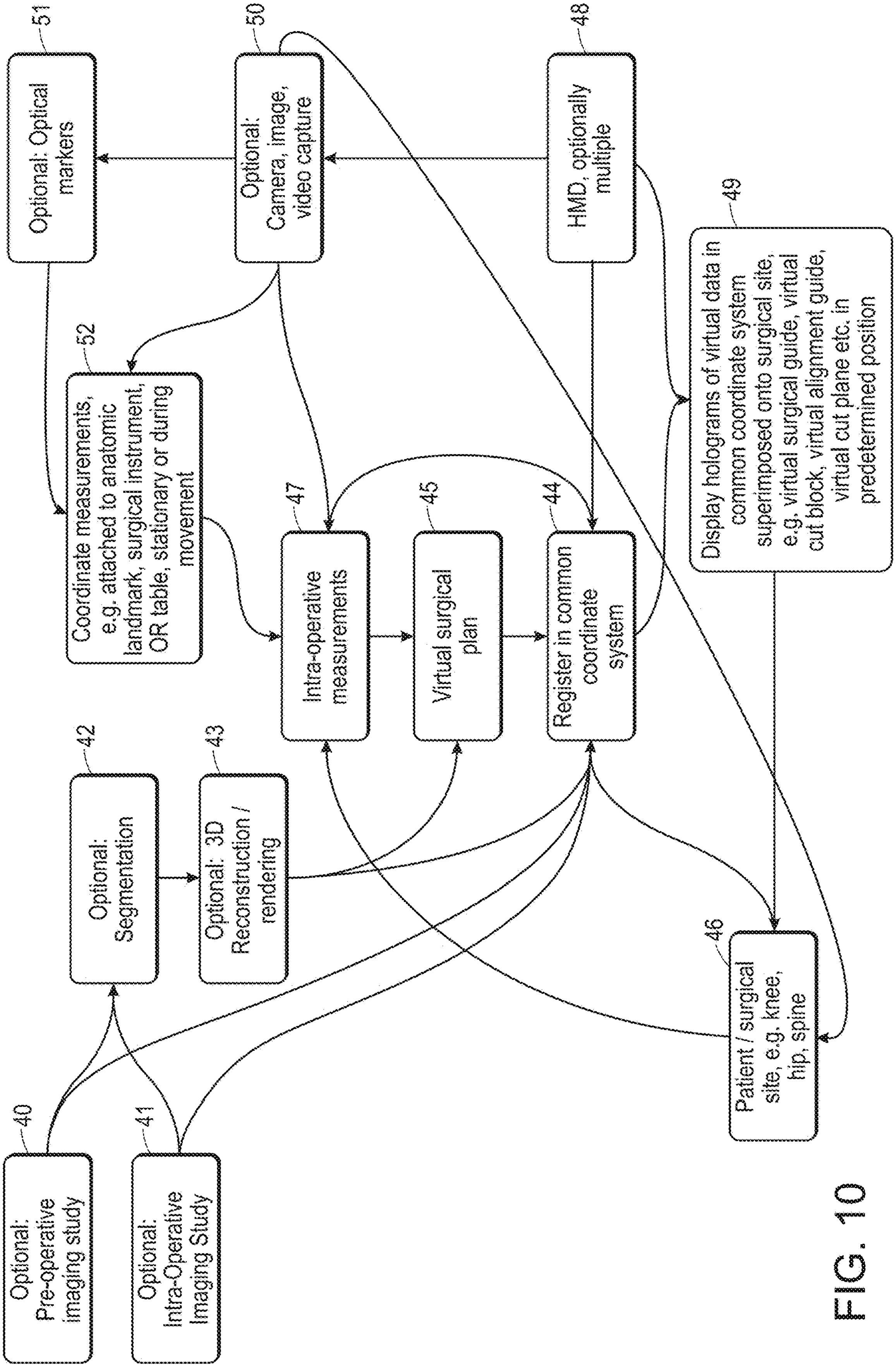
FIG. 10 shows a non-limiting example of a workflow for segmentation and select subsequent steps according to some embodiments of the present disclosure.

When images of the patient are superimposed onto live data seen through the optical head mounted display, in many embodiments image segmentation can be desirable. Any known algorithm in the art can be used for this purpose, for example thresholding, seed point techniques, live wire, deformable models, statistical models, active shape models, level set methods, marching cubes algorithms, artificial neural networks, deep learning techniques, or combinations thereof and the like. Many of these algorithms are available is part of open-source or commercial libraries, for instance the Insight Segmentation and Registration Toolkit (ITK), the Open Source Computer Vision Library OpenCV, G'MIC (GREYC's Magic for Image Computing), Caffe, or MATLAB (MathWorks, Natick, Mass.). A representative workflow for segmentation and subsequent is provided in FIG. 10. An optional pre-operative imaging study 40 can be obtained.

An optional intra-operative imaging study 41 can be obtained. The pre-operative 40 or intra-operative 41 imaging study can be segmented 42, extracting, for example, surfaces, volumes or key features. An optional 3D reconstruction or 3D rendering 43 can be generated. The pre-operative 40 or intra-operative 41 imaging study and any 3D reconstruction or 3D rendering 43 can be registered in a common coordinate system 44. The pre-operative 40 or intra-operative 41 imaging study and any 3D reconstruction or 3D rendering 43 can be used for generating a virtual surgical plan 45. The virtual surgical plan 45 can be registered in the common coordinate system 44. The surgical site 46 can be registered in the common coordinate system 44. Intra-operative measurements 47 can be obtained and can be used for generating a virtual surgical plan 45. A head mounted display 48 can project or display stereoscopic images of virtual data or virtual data 49 superimposed onto and aligned with the surgical site. The HMD 48 can be configured to use a built-in camera or image capture or video capture system 50 to optionally detect and/or measure the position and/or orientation and/or alignment of one or more optical markers 51, which can be used for the coordinate measurements 52, which can be part of the intra-operative measurements 47.

Example 3—Registration and Optional Re-Registration of Stereoscopic Displays

Figure 11:
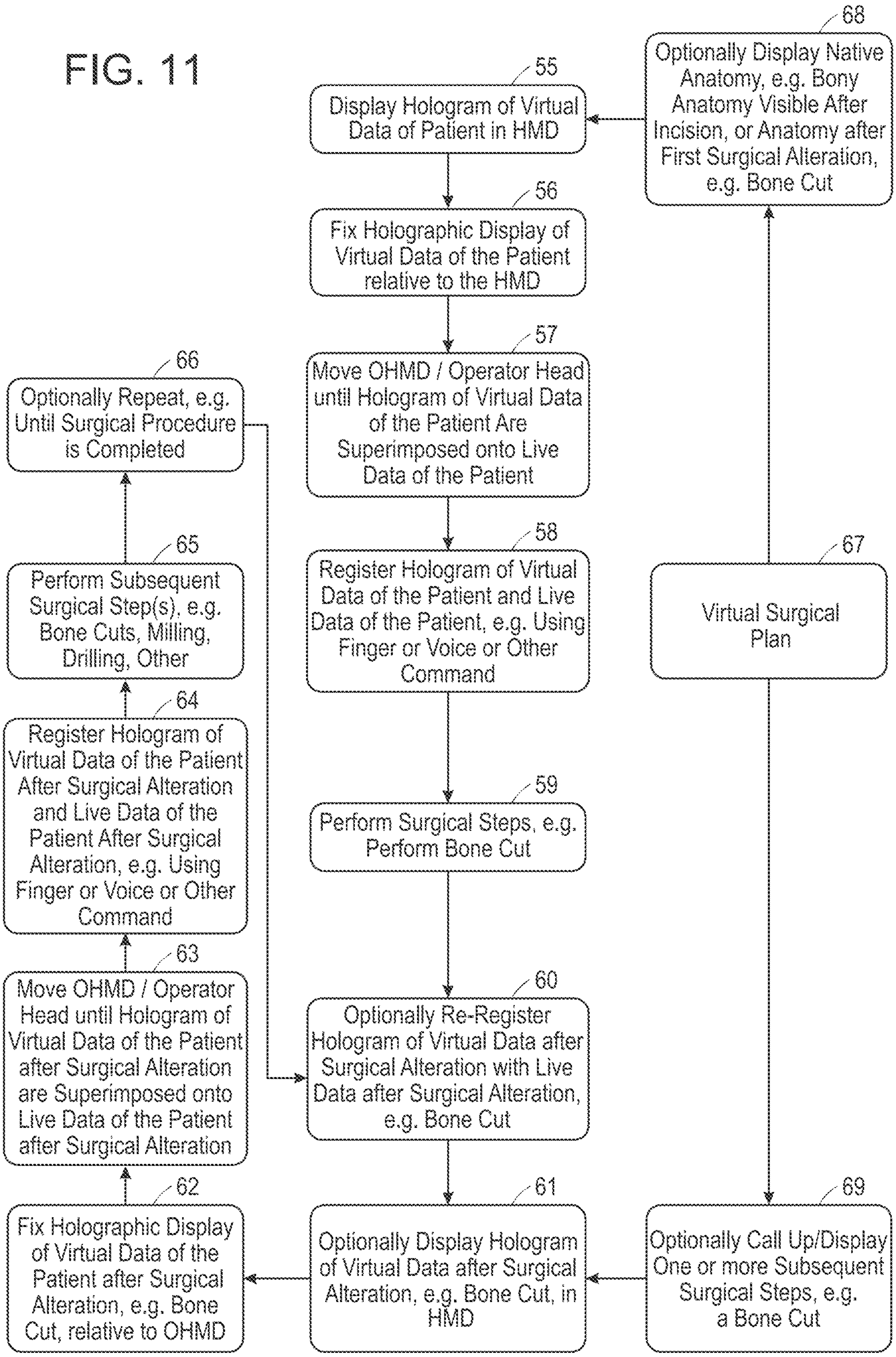
FIG. 11 illustrates a non-limiting example of registering a digital hologram for an initial surgical step, performing the surgical step and re-registering one or more digital holograms for subsequent surgical steps according to some embodiments of the present disclosure.

FIG. 11 illustrates an example of registering a stereoscopic display (e.g. digital hologram) or virtual data for an initial surgical step, performing the surgical step and re-registering one or more holograms for subsequent surgical steps. An optical head mounted display can project or display a digital hologram of virtual data or virtual data of the patient 55. The stereoscopic display/digital hologram can optionally be fixed to the HMD so that it will move with the movement of the HMD 56. The operator can move the HMD until digital hologram of the virtual data or virtual data of the patient is superimposed and aligned with the live data of the patient, e.g. the surgical site 57. The digital hologram of the virtual data or virtual data can then be registered using the same or similar coordinates as those of the live data with which the digital hologram is superimposed 58. The surgeon can then perform one or more predetermined surgical steps, e.g. bone cuts 59. A digital hologram of the virtual data or virtual data can optionally be registered or re-registered after the surgical alteration with the live data 60. The digital hologram of the virtual data or virtual data after the surgical alteration can optionally be displayed by the HMD 61. The digital hologram of the virtual data or virtual data after the surgical alteration can optionally be fixed relative to the HMD so that it will move with the movement of the HMD 62. The operator can move the HMD until digital hologram of the virtual data or virtual data of the patient after the surgical alteration is superimposed and aligned with the live data of the patient after the surgical alteration 63. The digital hologram of the virtual data or virtual data can then be registered using the same or similar coordinates as those of the live data after the surgical alteration with which the digital hologram is superimposed 64. The surgeon can then perform one or more predetermined subsequent surgical steps, e.g. bone cuts, milling or drilling 65. The preceding steps can optionally be repeated until the surgical procedures are completed 66. A virtual surgical plan 67 can be utilized. Optionally, the native anatomy of the patient including after a first surgical alteration can be displayed by the HMD 68. The HMD can optionally display stereoscopic displays/digital holograms of subsequent surgical steps 69.

Example 4—Display of Virtual Objects, Exemplary Applications for Virtual Interfaces, e.g. for Operating Robots and/or Imaging Systems In some embodiments, the HMD can display a virtual object, e.g. an arbitrary virtual plane over the surgical field. The virtual object/arbitrary virtual plane can be moveable using a virtual or other interface. For example, the virtual object/arbitrary virtual plane can include a "touch area", wherein gesture recognition software, for example the one provided by Microsoft with the Microsoft Hololens including, for example, the integrated virtual "drag function" for holograms can be used to move the arbitrary virtual plane. For example, one or more cameras integrated or attached to the HMD can capture the movement of the surgeon's finger(s) in relationship to the touch area; using gesture tracking software, the virtual object/virtual plane can then be moved by advancing the finger towards the touch area in a desired direction. The movement of the virtual object/virtual plane via the user interaction, e.g. with gesture recognition, gaze tracking, pointer tracking etc., can be used to generate a command by a computer processor. The command can trigger a corresponding movement of one or more components of a surgical robot and/or an imaging system.

The HMD can display the virtual object/arbitrary virtual plane in any location initially, e.g. projected onto or outside the surgical field, e.g. a hip joint, knee joint, shoulder joint, ankle joint, or a spine. The HMD can optionally display the virtual object/arbitrary virtual plane at a defined angle, e.g. orthogonal or parallel, relative to a fixed structure in the operating room, which can, for example, be recognized using one or more cameras, image capture or video capture systems and/or a 3D scanner integrated into the HMD and spatial recognition software such as the one provided by Microsoft with the Microsoft Hololens or which can be recognized using one or more attached optical markers or navigation markers including infrared or RF markers. For example, one or more optical markers can be attached to an extension of the operating table. The HMD can detect these one or more optical markers and determine their coordinates and, with that, the horizontal plane of the operating room table. The virtual object/arbitrary virtual plane can then be displayed perpendicular or at another angle relative to the operating room table.

For example, in a hip replacement, the HMD can display a virtual arbitrary plane over the surgical site. The virtual arbitrary plane can be perpendicular to the operating table or at another predefined or predetermined angle relative to the OR table. Using a virtual interface, e.g. a touch area on the virtual surgical plane and gesture tracking, the HMD can detect how the surgeon is moving the virtual arbitrary plane. Optionally, the virtual arbitrary plane can maintain its perpendicular (or of desired other angle) orientation relative to the OR table while the surgeon is moving and/or re-orienting the plane; a perpendicular orientation can be desirable when the surgeon intends to make a perpendicular femoral neck cut. A different angle can be desirable, when the surgeon intends to make the femoral neck cut with another orientation. The position and/or orientation of the virtual object can be transmitted from a second computing system in communication with the HMD to a first computing system, e.g. in communication with a surgical robot and/or an imaging system. The position and/or orientation of the virtual object can be used to set coordinates for an image acquisition, e.g. in an area or volume defined in relationship to the virtual object. The position and/or orientation of the virtual object can be used to set coordinates for a bone resection by a surgical robot, e.g. with an end effector, wherein the end effector can comprise a pin, drill, mill, saw, saw blade, reamer, impactor or a combination thereof.

Using the touch area or other virtual interface, the surgeon can move the virtual object, e.g. arbitrary virtual plane, into a desired position, orientation and/or alignment. The moving of the arbitrary virtual plane can include translation and rotation or combinations thereof in any desired direction using any desired angle or vector, which can be transmitted wirelessly from the second to the first computing system and which can be used to generate one or more commands, for example for moving, aligning, positioning and/or orienting an end effector, a surgical robot, an imaging system or a combination thereof. The surgeon can move the virtual object, e.g. arbitrary virtual plane to intersect with select anatomic landmarks or to intersect with select anatomic or biomechanical axes. The surgeon can move the virtual object, e.g. arbitrary virtual plane to be tangent with select anatomic landmarks or select anatomic or biomechanical axes.

Figure 12A:
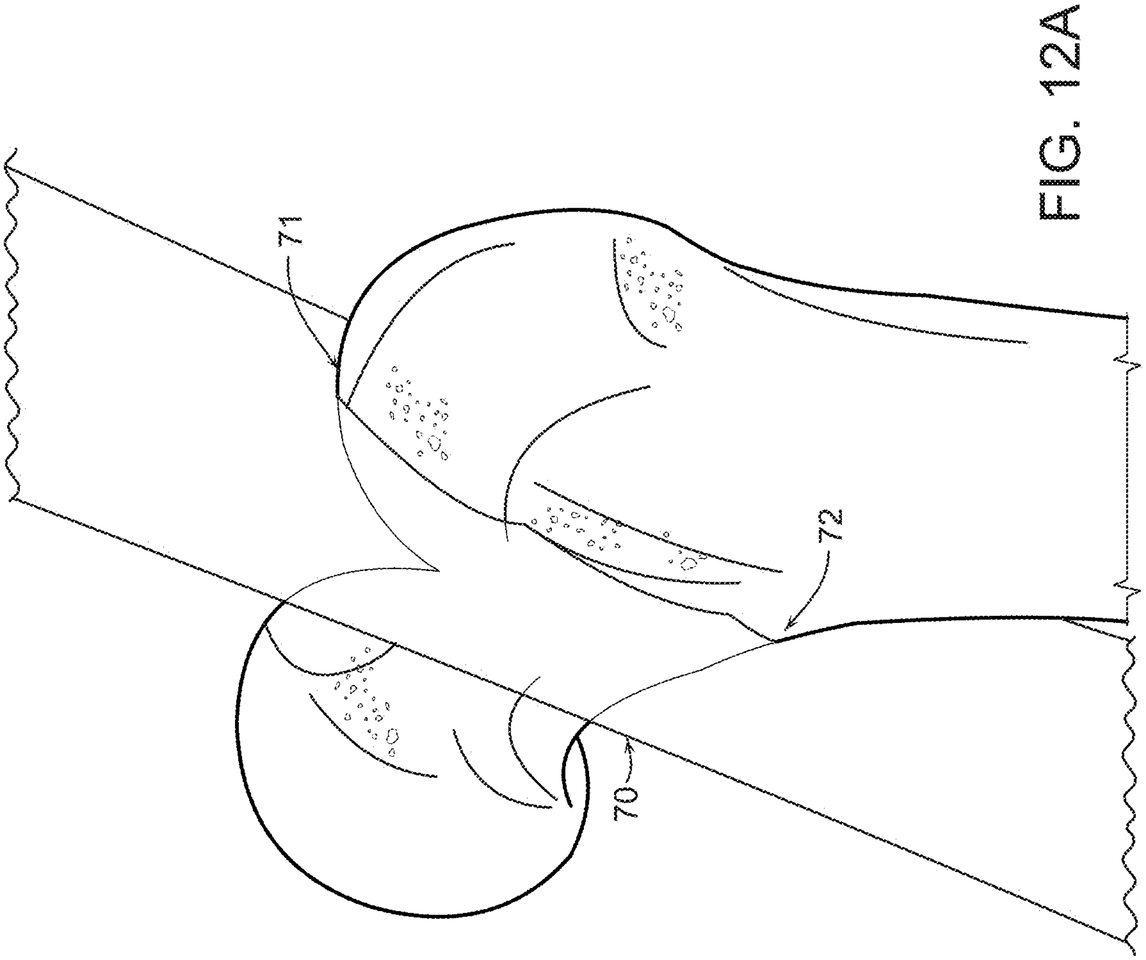
FIGS. 12A-12C are illustrative, non-limiting examples of virtual objects, e.g. arbitrary virtual planes, in a hip and a virtual femoral neck cut plane according to some embodiments of the present disclosure, e.g. for use in moving, directing, operating a surgical robot and/or an imaging system.
Figure 12B:
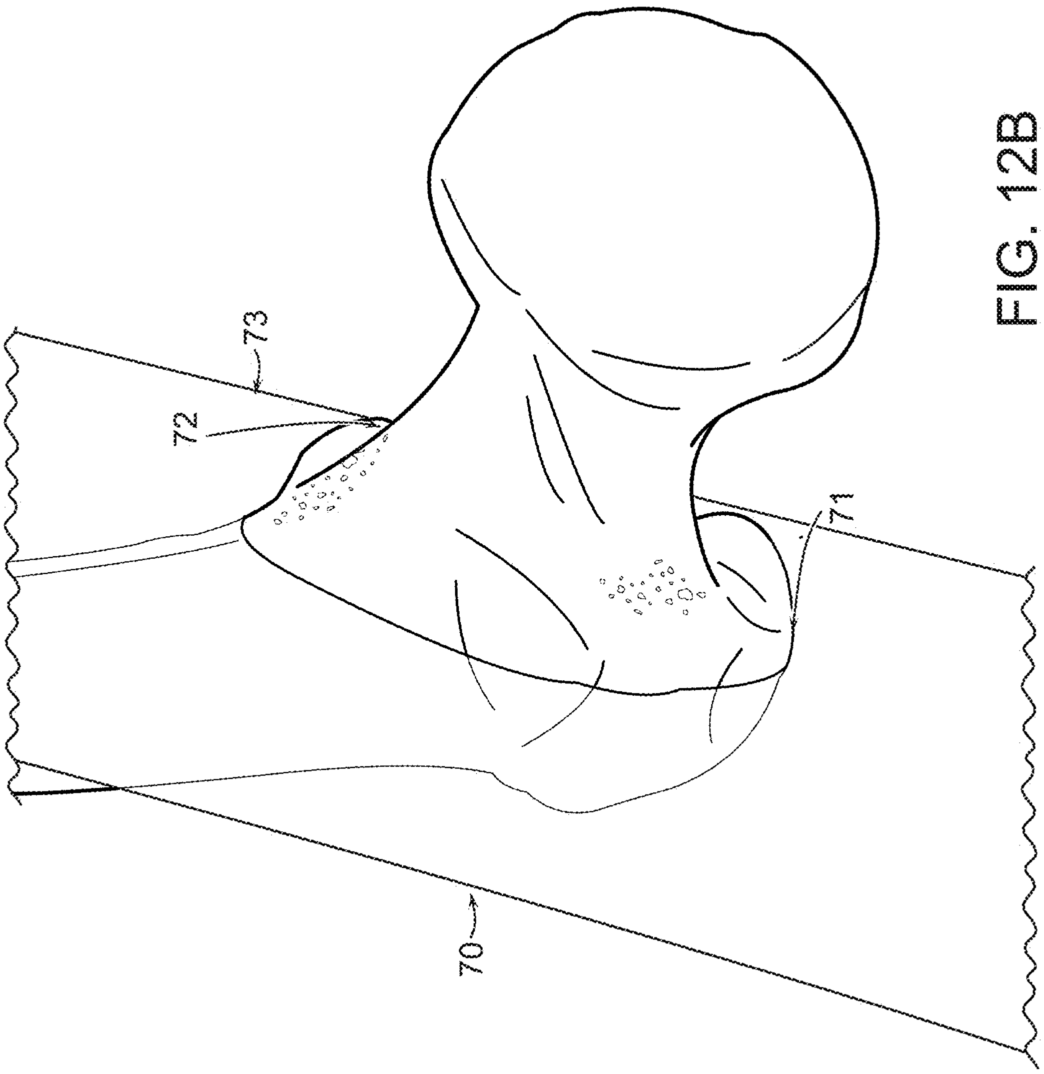

For example, in a hip replacement, the surgeon can move the arbitrary virtual plane to be tangent with the most superior aspect of the greater trochanter and the most superior aspect of the lesser trochanter. FIG. 12A shows an illustrative example of a virtual plane 70 that a primary surgeon has moved and aligned to be tangent with the most superior aspect of the greater trochanter 71 and the most superior aspect of the lesser trochanter 72. FIG. 12B shows an illustrative example of the same virtual plane 70 that the primary surgeon has moved and aligned to be tangent with the most superior aspect of the greater trochanter 71 and the most superior aspect of the lesser trochanter 72, now with the view from the optical head mounted display of a second surgeon or surgical assistant, e.g. on the other side of the OR table.

Figure 12C:
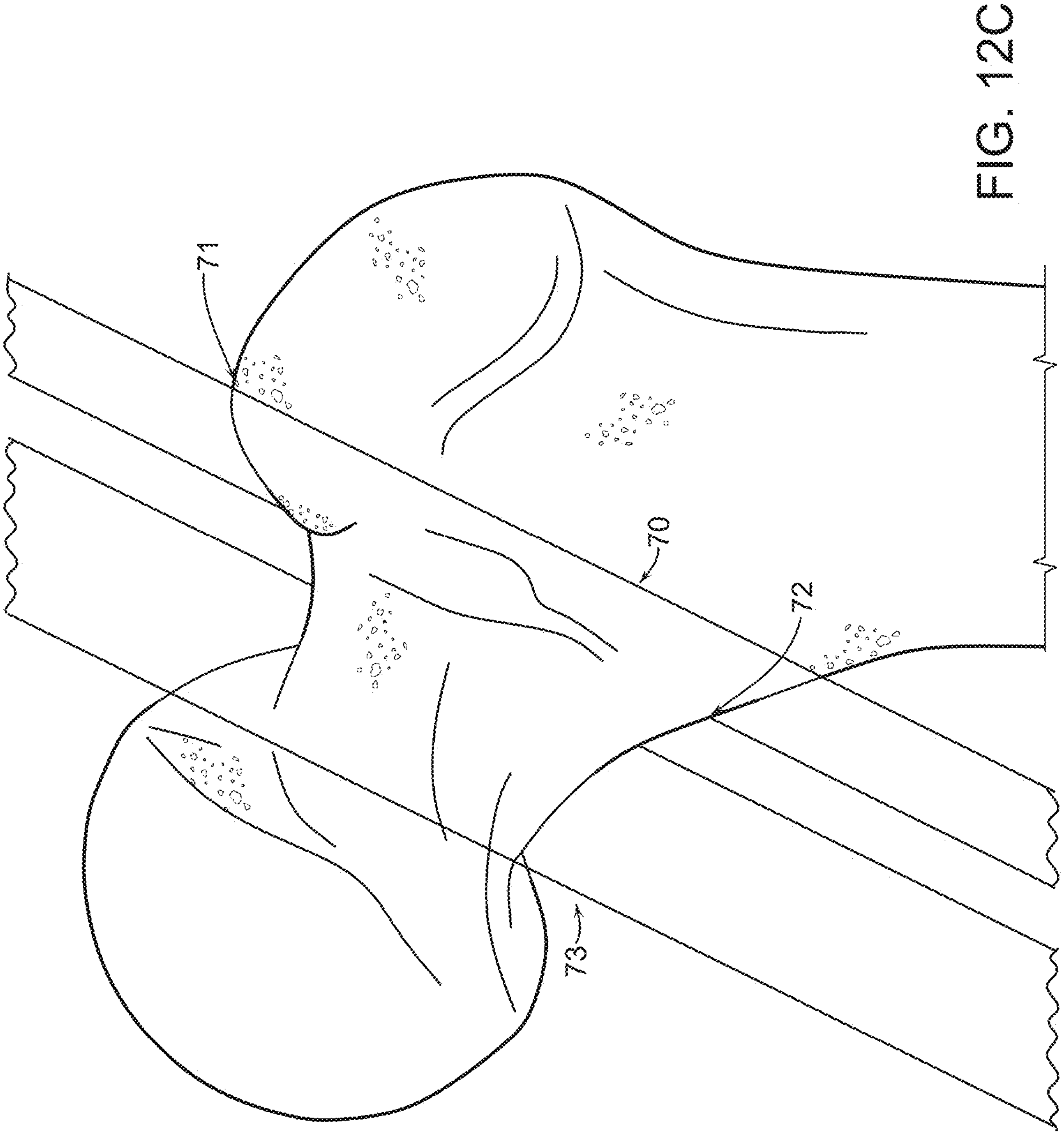

Optionally, for example with a pointer with an attached optical marker or an attached navigation marker, or with his finger detected using an image or video capture system integrated into the HMD and gesture recognition software such as the one provided by Microsoft with the Hololens, or with his finger with an attached optical marker or navigation marker, the surgeon can point at and identify the sulcus point, e.g. the lowest point between the greater trochanter and the femoral neck, which can be an additional reference. The line connecting the most superior aspect of the greater trochanter and the most superior aspect of the lesser trochanter can then be determined on a pre-operative or intra-operative AP radiograph of the hip; optionally, the sulcus point can also be detected on the AP radiograph. The AP radiograph can include a template used by the surgeon for selecting and sizing, for example, the femoral and acetabular component, as well as the liner and/or femoral heads. The radiographic template can include an indication for the femoral neck cut. The angle between the line connecting the most superior aspect of the greater trochanter and the most superior aspect of the lesser trochanter and the indication for the femoral neck cut can be determined. FIG. 12C is an illustrative example that shows that a second virtual plane 73, the virtual femoral neck cut plane 73, can then be projected or displayed by the HMD, also perpendicular to the OR table like the arbitrary virtual plane 70, the latter tangent with the most superior aspect of the greater trochanter 71 and the most superior aspect of the lesser trochanter 72, and the femoral neck cut plane 73 at the same angle and/or distance to the arbitrary virtual plane as the angle and distance between the line connecting the most superior aspect of the greater trochanter and the most superior aspect of the lesser trochanter and the indication for the femoral neck cut on the radiograph. In this manner, the femoral neck cut plane can be defined using a second virtual plane prescribed or predetermined based on the intra-operatively placed arbitrary virtual plane, moved by the operator to be tangent with the most superior aspect of the greater trochanter and the most superior aspect of the lesser trochanter. The second virtual plane, in this example, can be the femoral neck cut plane which can be transmitted wirelessly from a second computing system in communication with an HMD to a first computing system in communication with a surgical robot; a computer processor can be configured to generate one or more commands to move and/or adjust the end effector of the surgical robot to align with the virtual femoral neck cut plane and to subsequently execute the femoral cut, superimposed and aligned with the virtual femoral neck cut plane.

The virtual femoral neck cut plane prescribed and projected or displayed in this manner can also be a virtual guide, e.g. a virtual cut block that projects, for example, a virtual slot for guiding a physical saw. The virtual guide or virtual cut block can have one or more dimensions identical to a physical guide or cut block, so that the physical guide or cut block can be aligned with the virtual guide or cut block. The virtual guide or cut block can be an outline, 2D or 3D, partial or complete, of the physical guide or cut block, with one or more identical dimensions, so that the surgeon can align the physical guide or cut block with the virtual guide or cut block. The virtual guide or cut block can include placement indicia for the physical guide or cut block.

Figure 13:
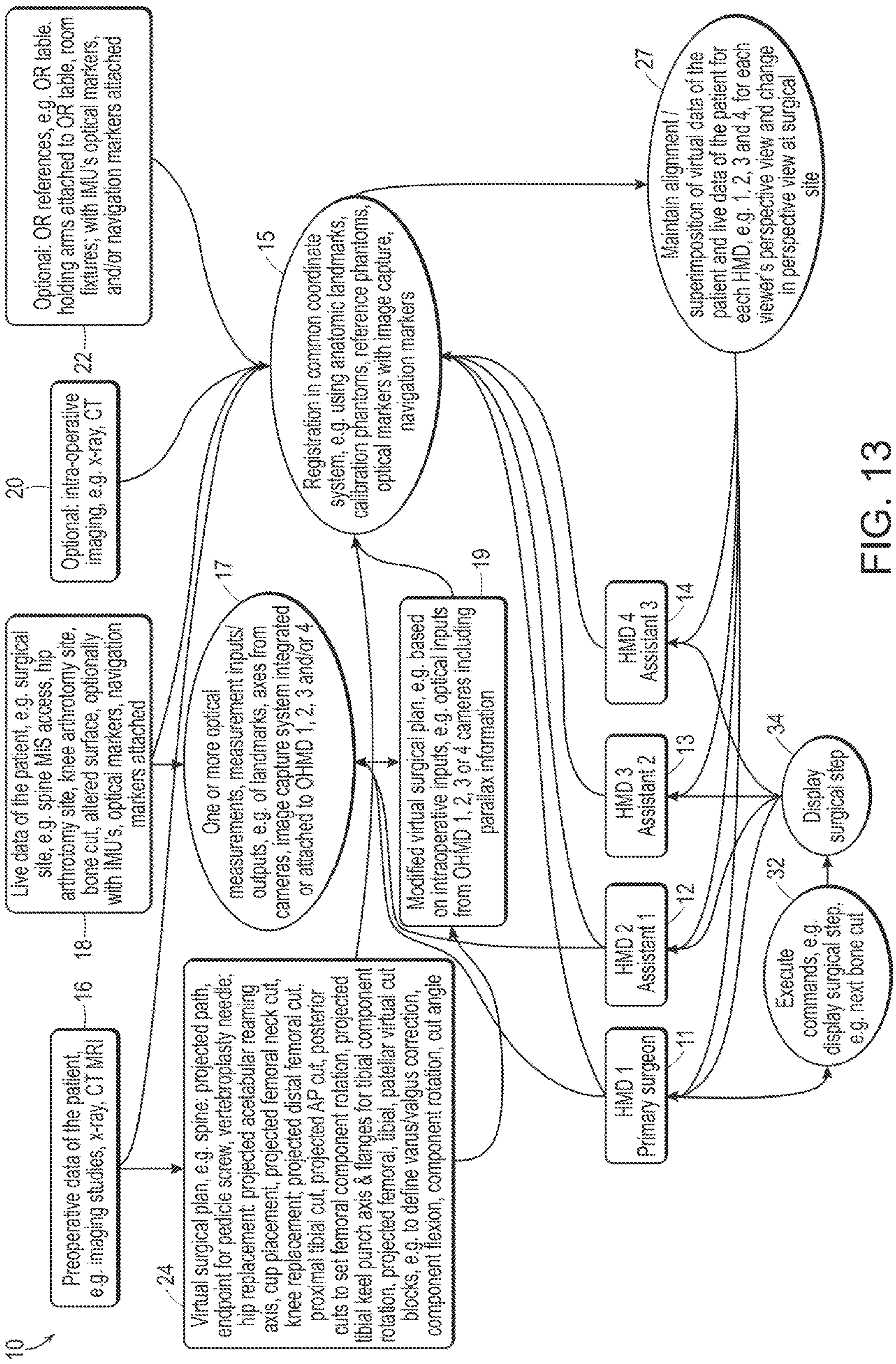
FIG. 13 shows an illustrative, non-limiting example how multiple HMDs or other augmented reality display systems can be used during a surgery, for example by a first surgeon, a second surgeon, a surgical assistant and/or one or more nurses and how a surgical plan can be modified and displayed during the procedure by multiple HMDs or other augmented reality display systems while preserving the correct perspective view of virtual data and corresponding live data for each individual operator according to some embodiments of the present disclosure.

Example 5—Use of One or More/Multiple HMDs or Other Augmented Reality Display Systems for Modifying Virtual Surgical Plans and/or for Operating a Surgical Robot or an Imaging System FIG. 13 shows an illustrative example how multiple HMDs or other augmented reality display systems can be used during a surgery, for example by a first surgeon, a second surgeon, a surgical assistant and/or one or more nurses and how a surgical plan, e.g. for use with a surgical robot, can be modified and displayed during the procedure by multiple HMDs or other augmented reality display systems while preserving the correct perspective view of virtual data and corresponding live data for each individual operator. A system 10 for using multiple HMDs 11, 12, 13, 14 or other augmented reality display systems for multiple viewer's, e.g. a primary surgeon, second surgeon, surgical assistant(s) and/or nurses(s) is shown. The multiple HMDs or other augmented reality display systems can be registered in a common coordinate system 15 using anatomic structures, anatomic landmarks, calibration phantoms, reference phantoms, optical markers, navigation markers, scanners, cameras, 3D scanners, and/or spatial anchors, for example like the spatial anchors used by the Microsoft Hololens. Pre-operative data 16 of the patient can also be registered in the common coordinate system 15. Live data 18 of the patient, for example from the surgical site, e.g. a spine, optionally with minimally invasive access, a hip arthrotomy site, a knee arthrotomy site, a bone cut, an altered surface can be measured, for example using one or more IMU's, optical markers, navigation markers, image or video capture systems and/or 3D scanner and/or spatial anchors. The live data 18 of the patient can be registered in the common coordinate system 15. Intra-operative imaging studies 20 can be registered in the common coordinate system 15. OR references, e.g. an OR table or room fixtures can be registered in the common coordinate system 15 using, for example, optical markers IMU's, navigation markers or spatial mapping 22. The pre-operative data 16 or live data 18 including intra-operative measurements or combinations thereof can be used to develop, generate or modify a virtual surgical plan 24. The virtual surgical plan 24 can be registered in the common coordinate system 15. The HMDs 11, 12, 13, 14 or other augmented reality display systems can maintain alignment and superimposition of virtual data of the patient and live data of the patient for each HMD 11, 12, 13, 14 for each viewer's perspective view and position and head position and orientation 27. Using a virtual or other interface, the surgeon wearing HMD 1 11 can interact with one or more virtual objects displayed by the HMDs or other augmented reality display systems to generate/execute commands 32, e.g. to display the next predetermined bone cut, e.g. from a virtual surgical plan or an imaging study or intra-operative measurements, which can trigger the HMDs 11, 12, 13, 14 or other augmented reality display systems to project virtual data of the next surgical step 34 superimposed onto and aligned with the surgical site in a predetermined position and/or orientation. One or more computing systems/computer processors in communication with the HMDs or other augmented reality display systems can generate the commands triggered by the user interaction with the virtual object(s) displayed by the HMD. The one or more computing systems/computer processors can optionally transmit the commands wirelessly to one or more different computing systems/computer processors, e.g. in communication with a robot and/or an imaging system. The one or more different computing systems/computer processors, e.g. in communication with a robot and/or an imaging system can, for example, process the command(s) to initiate, start, stop, activate, de-activate, move, adjust the position/orientation of one or more components, controllers, drivers, motors, sensors, relays, processors or combination thereof of a surgical robot and/or an imaging system. Any of the HMDs 11, 12, 13, 14 or other augmented reality display systems can acquire one or more optical or other measurements or measurement inputs, e.g. of anatomic landmarks, axes from cameras, anatomic axes, biomechanical axes, a mechanical axis of a leg 17, using for example an integrated or attached camera, image capture or video system or scanner, e.g. 3D scanner. By using multiple HMDs 11, 12, 13, 14 or other augmented reality display systems from different view angles with multiple cameras, image capture or video systems, scanners, 3D scanners the accuracy of the measurements can optionally be improved. Optionally, parallax/stereoscopic measurements can be performed using the multiple HMDs 11, 12, 13, 14 or other augmented reality display systems from different view angles with multiple cameras, image capture or video systems. The one or more optical measurements can be used to modify the virtual surgical plan 19, optionally using the information from multiple HMDs 11, 12, 13, 14 or other augmented reality display systems. Someone skilled in the art can recognize that multiple coordinate systems can be used instead of a common coordinate system. In this case, coordinate transfers can be applied from one coordinate system to another coordinate system, for example for registering the HMD, live data of the patient including the surgical site, virtual instruments and/or virtual implants and physical instruments and physical implants.

Example 6—HMD Display of Virtual Surgical Guides, e.g. Virtual Axes, for Example for Operating Surgical Robots and/or Imaging Systems In a spine, a joint, e.g. a hip joint, one or more HMDs or other augmented reality display systems, one or more virtual data sets or virtual data can be registered in a common coordinate system.

In a joint, e.g. a hip joint, two opposing articular surfaces, e.g. with opposing cartilage surfaces and underlying subchondral bone, can be registered separately and/or optionally jointly in a coordinate system, e.g. a common coordinate system. A first articular surface can be located on the pelvic side, i.e. on the acetabulum, a second articular surface can be located on the proximal femur. Registering the first articular surface and/or or associated bones and/or structures and the second articular surface and/or or associated bones and/or structures separately in a common coordinate system can have the benefit of allowing movement, e.g. flexion and/or extension and/or rotation and/or abduction, and/or adduction, and/or elevation and/or other movements, e.g. translation, of the first articular surface and/or or associated bones and/or structures, e.g. on the acetabular side, in relationship to the second articular surface and/or or associated bones and/or structures, e.g. on the proximal femoral side, while maintaining registration of the first articular surface and/or associated bones and/or structures, e.g. on the acetabular side, and/or the second articular surface and/or or associated bones and/or structures, e.g. on the proximal femoral side, e.g. in a common coordinate system or a sub-coordinate system, for example optionally along with one or more HMDs or other augmented reality display systems and/or optionally fixed structures in the operating room, e.g. the OR table, and/or other structures or anatomic landmarks of the patient, e.g. irrespective movement of the individual portions of the joint; the foregoing applies to any joint in the human body, e.g. a shoulder, elbow, wrist, finger, knee, ankle, foot or toe joint or a temporomandibular joint. In this manner, the hip joint or any other joint can be placed in different positions, e.g. flexion, extension, rotation, abduction, adduction, e.g. a degree of hip abduction, e.g. 20, 30, 40 or other degrees, e.g. during placement of a femoral component, and a degree of hip abduction, e.g. 30, 40, or 50 or other degrees, during placement of the acetabular component, or any other degrees for either component placement depending on surgical technique and surgeon preference, while the registration of the acetabular and/or the registration of the proximal femoral side and the display of any virtual data, e.g. a virtual surgical guide, a virtual cut plane, a virtual implant component on the acetabular side and/or the proximal femoral side can be maintained and superimposed onto the corresponding anatomic area, e.g. the area intended for implant component placement, irrespective of the movement of individual portions of the joint, thereby allowing the one or more HMDs or other augmented reality display systems to maintain anatomically registered displays of virtual data superimposed onto the corresponding portions of the physical joint anatomy, e.g. an articular surface, including a normal, damaged and/or diseased cartilage and/or subchondral bone and/or cortical bone, e.g. in a tangent, intersecting and/or offset manner, e.g. external and/or internal to the normal, damaged and/or diseased cartilage and/or subchondral bone and/or cortical bone.

Figure 14A:
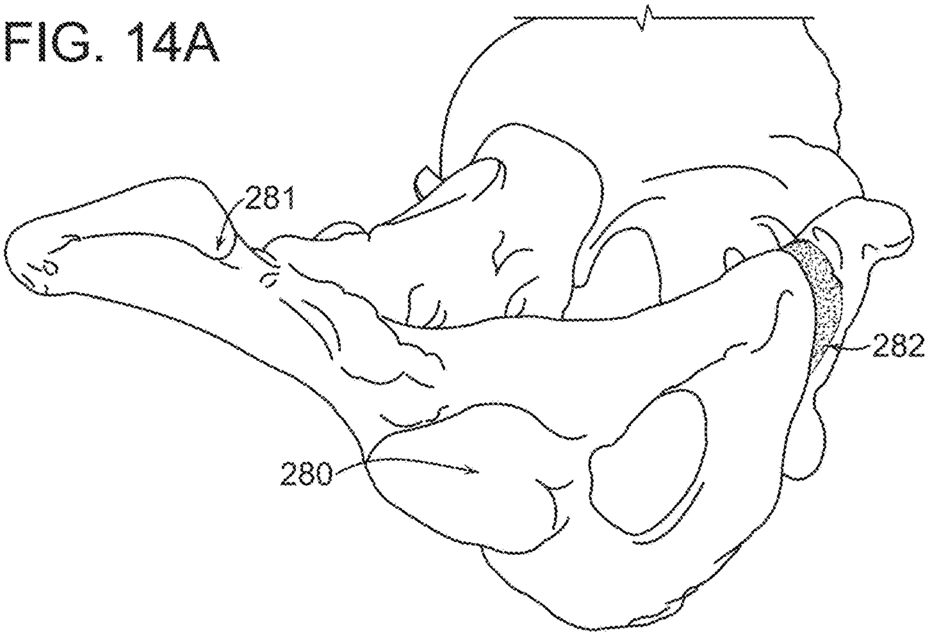
FIGS. 14A-14F are illustrative, non-limiting examples of displaying virtual surgical guides, e.g. a virtual acetabular reaming axis, using one or more HMDs or other augmented reality display systems and aligning a physical acetabular reamer (e.g. attached to or part of a surgical robot) with the virtual reaming axis for placing an acetabular cup with a predetermined cup angle, offset, medial or lateral position and/or anteversion according to some embodiments of the present disclosure.
Figure 14B:
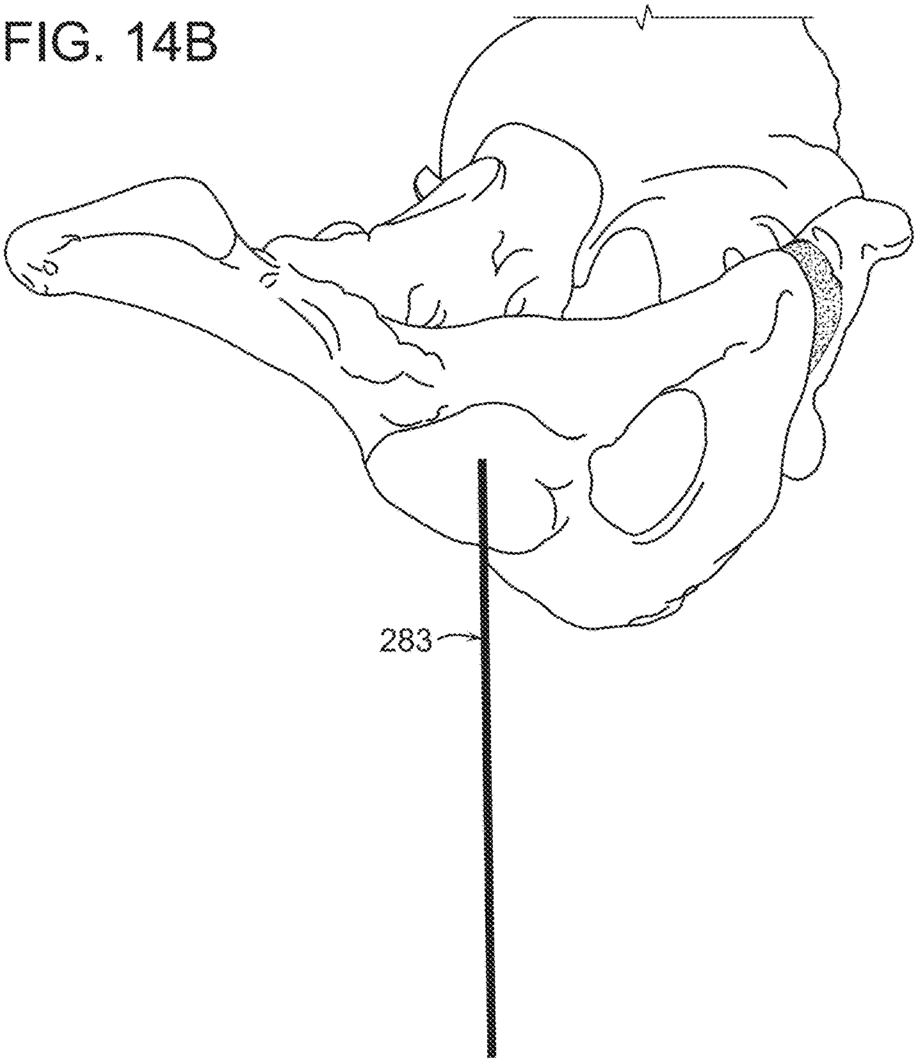
Figure 14C:
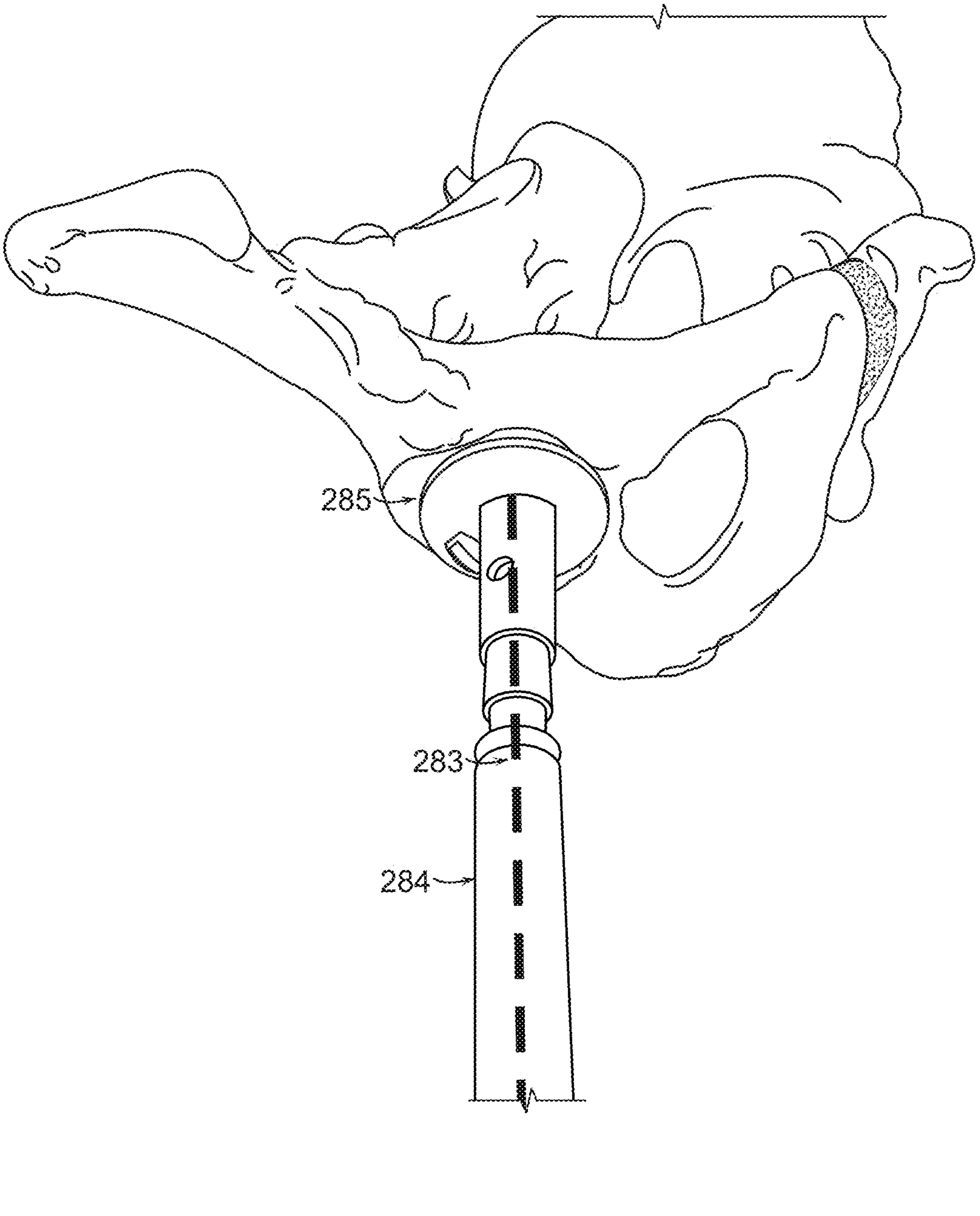

FIGS. 14A-14F are illustrative examples of displaying a virtual surgical guide, e.g. a virtual acetabular reaming axis, using one or more HMDs or other augmented reality display systems and aligning a physical acetabular reamer, e.g. attached to or part of a surgical robot, with the virtual reaming axis for placing an acetabular cup with a predetermined cup angle, offset, medial or lateral position and/or anteversion and/or inclination. FIG. 14A shows a first surgeon's view, e.g. through an HMD, onto the patient's exposed acetabulum 280. Note also the anterior superior iliac spine 281 and the symphysis pubis 282, which can optionally be used for registration purposes, for example using attached optical markers or navigation markers. In FIG. 14B, the first surgeon can see a virtual acetabular reaming axis 283 through the HMD, which can be oriented in a predetermined manner to achieve a predetermined acetabular cup angle, offset, medial or lateral position and/or anteversion and/or inclination, e.g. from a virtual surgical plan for the patient. In FIG. 14C, the first surgeon aligns the physical acetabular reamer shaft 284 so that its central axis is aligned or superimposed with the virtual acetabular reaming axis thereby placing the reamer head 285 in the acetabulum in a predetermined position and orientation for a predetermined acetabular cup angle, offset, medial or lateral position and/or anteversion and/or inclination.

Figure 14D:
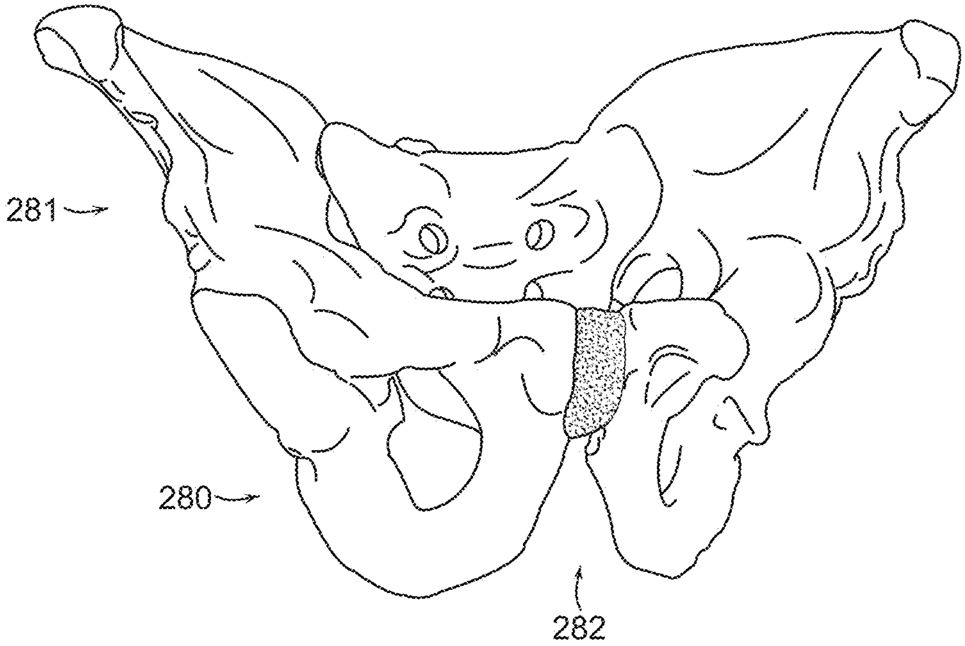
Figure 14E:
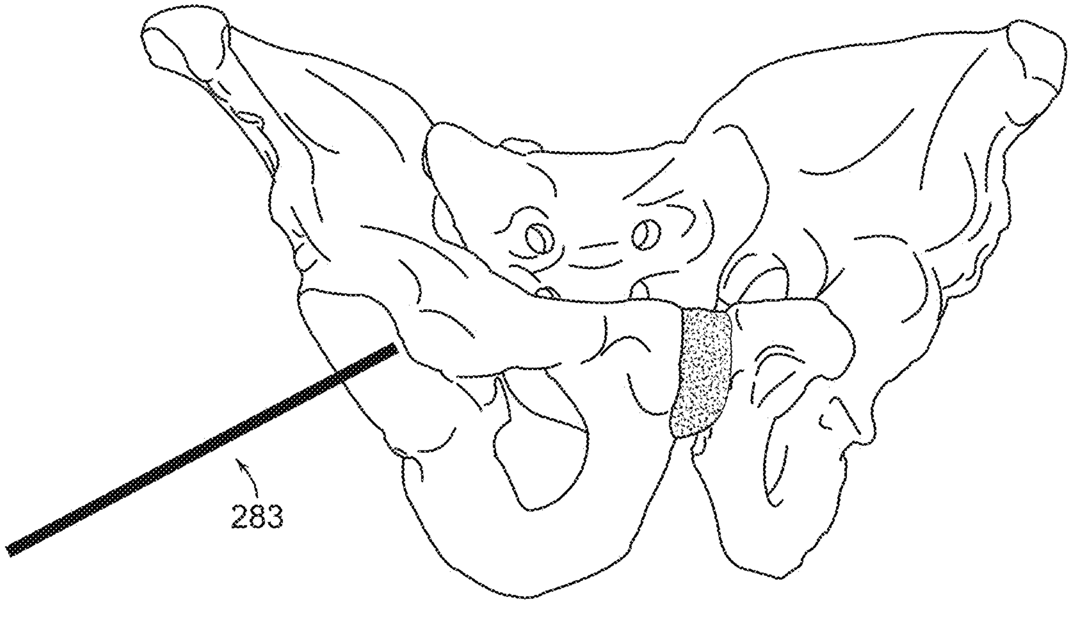
Figure 14F:
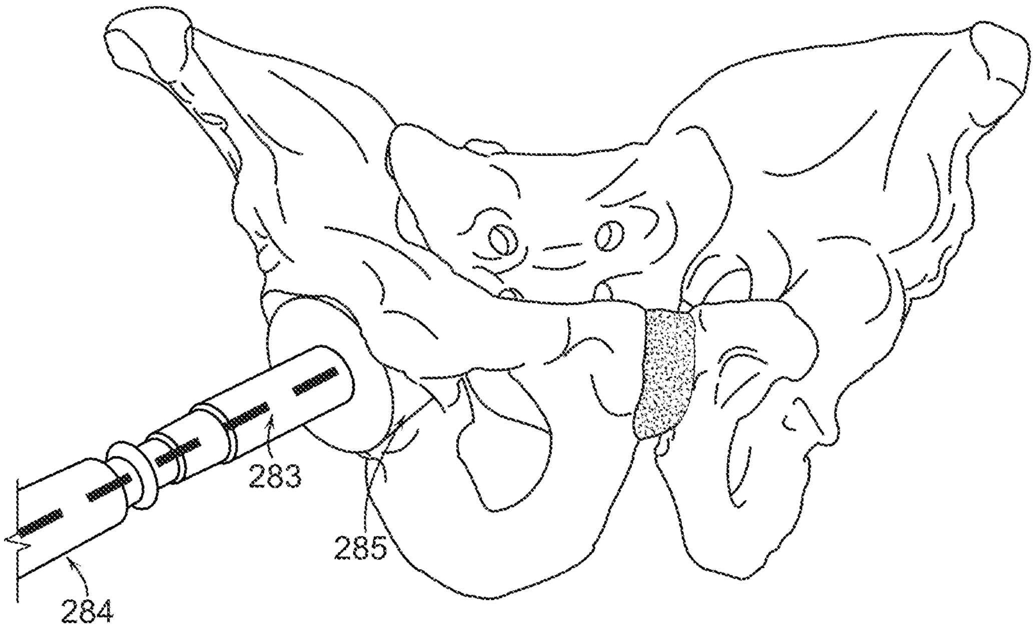

FIG. 14D shows a second surgeon's view with his or her respective view perspective of live data and virtual data through the HMD onto the patient's exposed acetabulum 280. Note also the anterior superior iliac spine 281 and the symphysis pubis 282, which can optionally be used for registration purposes, for example using attached optical markers or navigation markers. In FIG. 14E, the second surgeon can see the virtual acetabular reaming axis 283 through the HMD, which can be oriented in a predetermined manner to achieve a predetermined acetabular cup angle, offset, medial or lateral position and/or anteversion and/or inclination, e.g. from a virtual surgical plan for the patient. The virtual acetabular reaming axis is projected with a view angle or view perspective matching the view angle or view perspective of the live data of the patient seen by the second surgeon. In FIG. 14F, the second surgeon can see how the physical acetabular reamer shaft 284 is aligned by the first surgeon so that its central axis is aligned or superimposed with the virtual acetabular reaming axis thereby placing the reamer head 285 in the acetabulum in a predetermined position and orientation for a predetermined acetabular cup angle, offset, medial or lateral position and/or anteversion and/or inclination. Optionally, a virtual interface, e.g. with one or more virtual objects, can be displayed by the HMD(s), for interaction by the surgeon(s).

The interaction can be used to generate, by a computer processor, a command which can be configured, for example, to initiate, start, stop, activate, de-activate, move, adjust the position/orientation of one or more components, controllers, drivers, motors, sensors, relays, processors or combination thereof of a surgical robot and/or an imaging system.

Figure 15B:
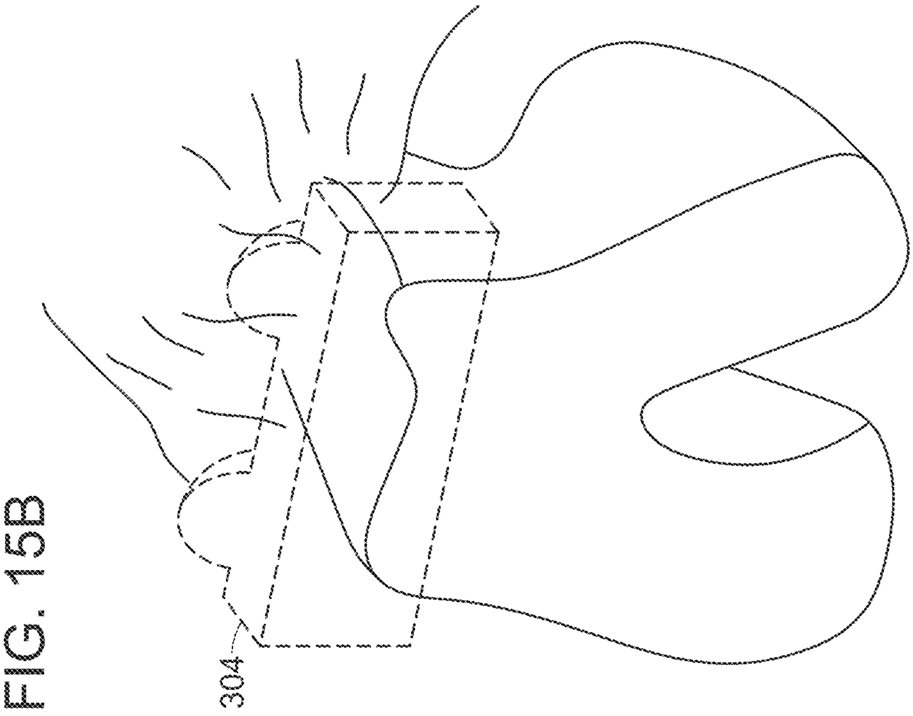
FIGS. 15A-15D provide illustrative, non-limiting examples of the use of virtual surgical guides such as a virtual distal femoral cut block displayed by an HMD and physical surgical guides such as physical distal femoral cut blocks (e.g. attached to or part of a surgical robot) for knee replacement according to some embodiments of the present disclosure.
Figure 15A:
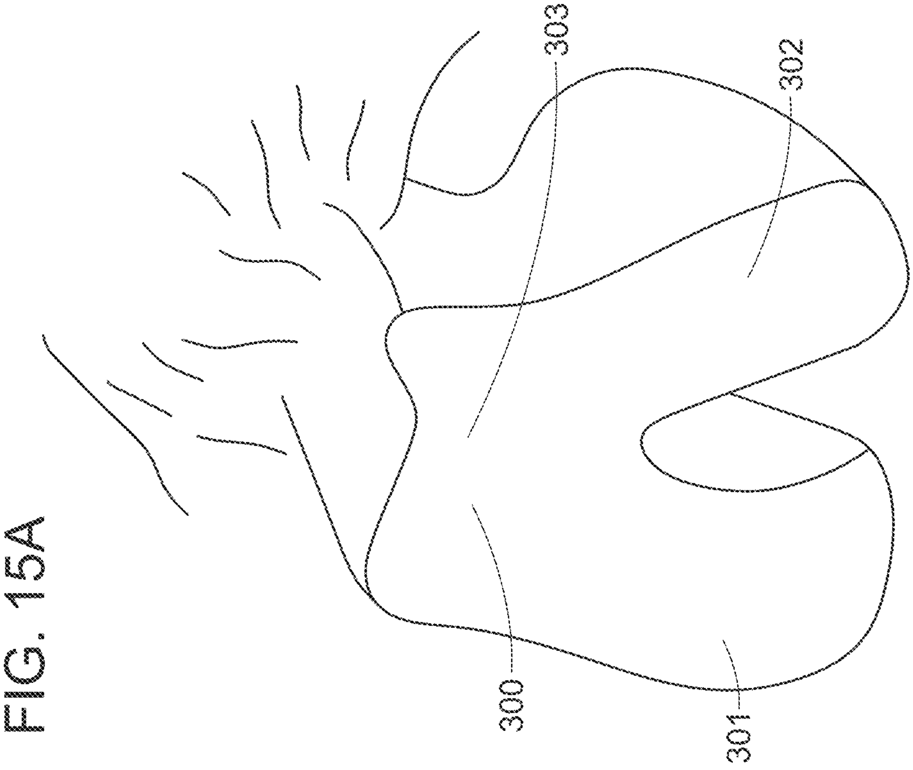
Figure 15D:
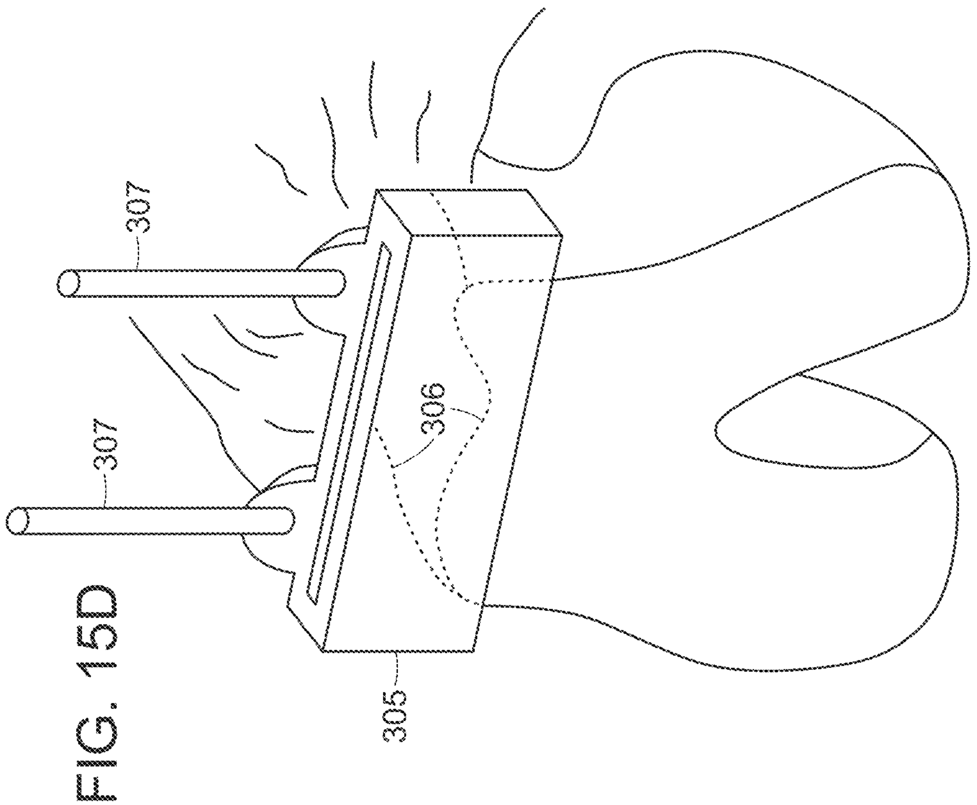
Figure 15C:
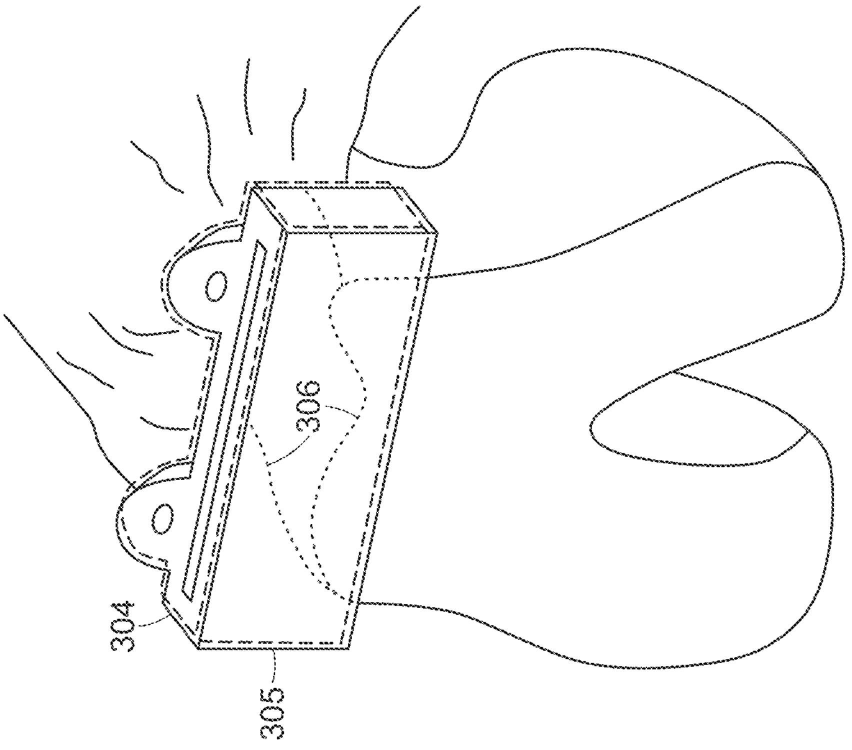

FIGS. 15A-15D provide an illustrative, non-limiting example of the use of virtual surgical guides such as a distal femoral cut block displayed by an HMD and physical surgical guides such as physical distal femoral cut blocks. FIG. 15A shows live data of a patient with a distal femur 300 exposed during knee replacement surgery, a medial condyle 301, a lateral condyle 302 and a trochlea 303. In FIG. 15B, one or more HMDs or other augmented reality display systems can display a virtual distal femoral cut block, e.g. in a stereoscopic manner for the left eye and the right eye of the surgeon(s) creating a form of electronic hologram of the virtual surgical guide, i.e. the virtual distal cut block. The virtual distal femoral cut block 304 in this example is an outline of the physical distal femoral cut block with substantially similar dimensions as those of the physical distal femoral cut block. The virtual distal femoral cut block 304 is aligned based at least in part on coordinates of a predetermined position for guiding the distal femoral cut, for example for achieving a predetermined varus or valgus correction and/or a predetermined femoral component flexion relative to the distal femur and, for example, its anatomic or biomechanical axes. In FIG. 15C, the physical surgical guide 305, i.e. the physical distal femoral cut block 305 (solid line) in this example (which can be optionally attached to or part of a surgical robot), can be moved and aligned (e.g. by the surgical robot) to be substantially superimposed with or aligned with the virtual surgical guide 304, i.e. the virtual distal femoral cut block 304 (broken line) in this example. The hidden areas of the knee joint 306, obscured or hidden by the physical distal femoral cut block 305, can optionally also be displayed by the HMD. In FIG. 15D, the physical distal femoral cut block 305 (which can be optionally attached to or part of a surgical robot) can be attached to the distal femoral bone using two pins 307. These pins 307 can be used for subsequent surgical steps, for example for referencing a flexion gap or an extension gap or for ligament balancing. The HMD can stop display the virtual surgical guide, i.e. the virtual distal femoral cut block in this example, but can optionally continue display the hidden anatomy, e.g. hidden areas of the knee joint 306. Optionally, a virtual interface, e.g. with one or more virtual objects, can be displayed by the HMD(s), for interaction by the surgeon(s). The interaction can be used to generate, by a computer processor, a command which can be configured, for example, to initiate, start, stop, activate, de-activate, move, adjust the position/orientation of one or more components, controllers, drivers, motors, sensors, relays, processors or combination thereof of a surgical robot and/or an imaging system. The command can, optionally, be transmitted from a computing system/computer processor in communication with the one or more HMDs or other augmented reality display systems to a computing system/computer processor in communication with a robot and/or an imaging system.

Figure 16B:
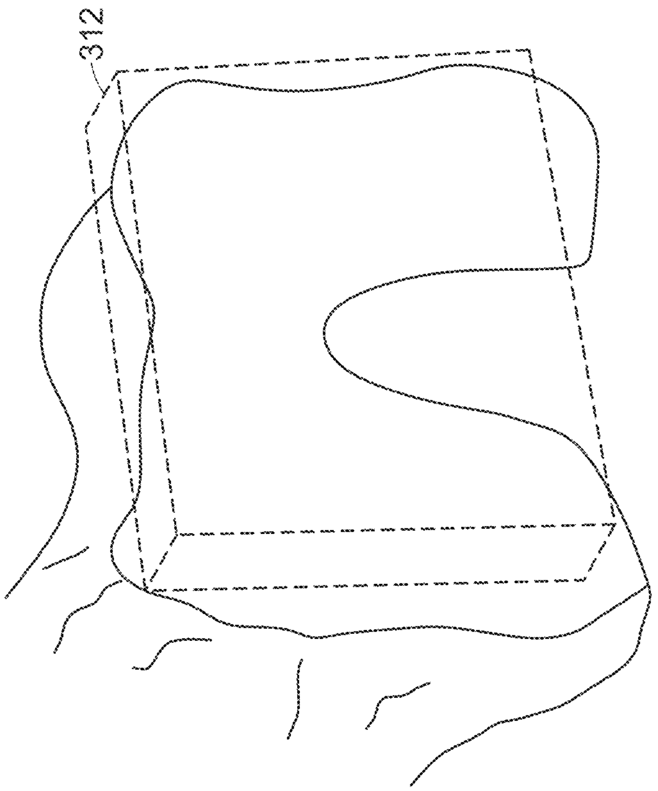
FIGS. 16A-16C provide an illustrative, non-limiting example of the use of virtual surgical guides such as an AP femoral cut block displayed by an HMD and physical surgical guides such as physical AP cut blocks (e.g. attached to or part of a surgical robot) for knee replacement according to some embodiments of the present disclosure.
Figure 16A:
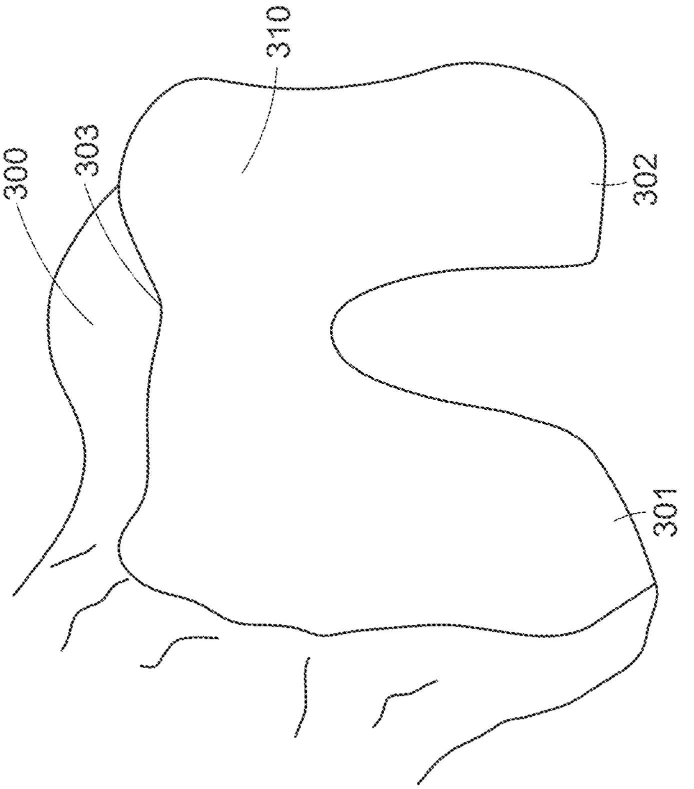
Figure 16C:
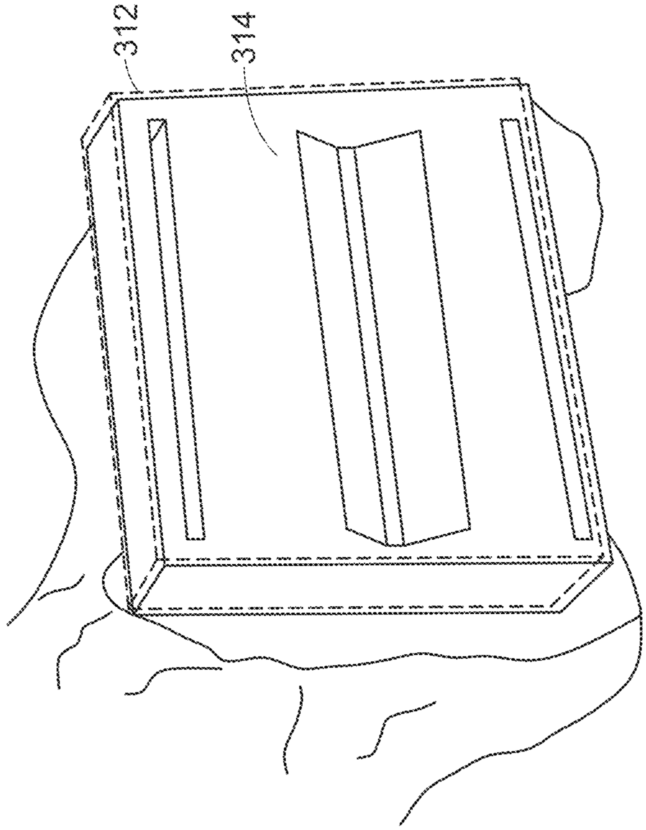

FIGS. 16A-16C provide an illustrative, non-limiting example of the use of virtual surgical guides such as an AP femoral cut block displayed by an HMD and physical surgical guides such as physical AP cut blocks for knee replacement. FIG. 16A shows live data of a patient with a distal femur 300 exposed during knee replacement surgery after a distal femoral cut creating a planar distal surface 310, a medial condyle 301, a lateral condyle 302 and a trochlea 303. In FIG. 16B, one or more HMDs or other augmented reality display systems can display a virtual femoral AP cut block 312, e.g. in a stereoscopic manner for the left eye and the right eye of the surgeon(s) creating a form of electronic or digital hologram of the virtual surgical guide, i.e. the virtual femoral AP cut block 312. The virtual femoral AP cut block 312 in this example is an outline of the physical femoral AP cut block with similar dimensions, edges, or planes as those of the physical femoral AP cut block. The virtual femoral AP cut block 312 is aligned based at least in part on coordinates of a predetermined position for guiding the different bone cuts, e.g. an anterior cut, posterior cut and/or chamfer cuts depending on the configuration of the physical femoral AP cut block, for example for achieving a predetermined femoral component rotation. In FIG. 16C, the physical surgical guide 314, i.e. the physical femoral AP cut block 314 (solid line) in this example (e.g. attached to or part of a surgical robot), can be moved and aligned to be substantially superimposed with or aligned with the virtual surgical guide 312, i.e. the virtual femoral AP cut block 312 (broken line) in this example. The physical femoral AP cut block (optionally attached to or part of a surgical robot) can be attached to the distal femoral bone using pins (not shown) and the cuts can be performed. Subsequent surgical steps can optionally be referenced based on one or more of the cuts executed using the physical femoral AP cut block.

The surgeon can align or substantially superimpose the physical femoral AP cut block with the digital hologram of the virtual femoral AP cut block or its 2D or 3D outline or one or more placement indicators projected by the HMD. Once adequate alignment or superimposition of the physical AP cut block with the virtual AP cut block or its 2D or 3D outline or one or more placement indicators displayed by the HMD has been achieved, the surgeon can pin the physical AP cut block and perform the cuts. By utilizing preoperative 3D data information or intra-operative information, e.g. from optical marker and image or video capture or scanner measurements (including stereoscopic imaging), for the position, alignment and rotation of the physical femoral AP cut block with the assistance of the HMD, the surgeon can perform the anterior and posterior femoral cuts in a highly accurate manner, thereby achieving accurate rotational alignment of the femoral component. The same approaches and display options, e.g. virtual cut blocks, 2D or 3D outline or one or more placement indicators, can be applied to all subsequent femoral preparation steps including chamfer cuts and chamfer cut blocks.

Optionally, a virtual interface, e.g. with one or more virtual objects, can be displayed by the HMD(s), for interaction by the surgeon(s). For example, the virtual object can be a virtual surgical guide, e.g. the virtual AP cut block. The interaction can comprise moving the virtual object, e.g. the virtual surgical guide, for example using a tracked pointer, a gesture recognition, a finger tracking, an object tracking, etc. The interaction can be used to generate, by a computer processor, a command which can be configured, for example, to initiate, start, stop, activate, de-activate, move, adjust the position/orientation of the virtual object, e.g. virtual surgical guide, and, optionally correspondingly, one or more components, controllers, drivers, motors, sensors, relays, processors or combination thereof of a surgical robot and/or an imaging system. The command can, optionally, be transmitted from a computing system/computer processor in communication with the one or more HMDs or other augmented reality display systems to a computing system/computer processor in communication with a robot and/or an imaging system.

Of note, similar steps and HMD guided femoral procedures are also possible using the HMD with any of the other registration and cross-referencing techniques described in the present disclosure or known in the art, for example intraoperative image guidance.

Figure 17A:
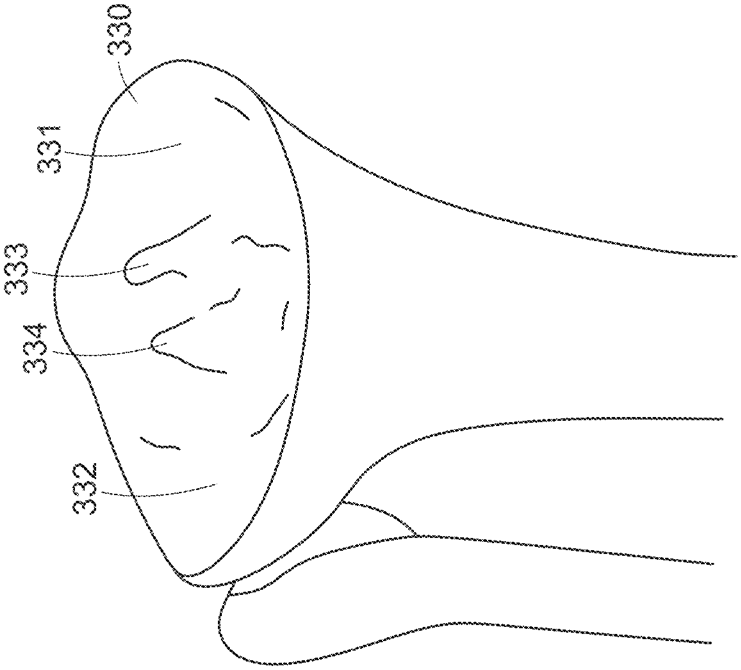
FIGS. 17A-17F provide a illustrative, non-limiting examples of the use of virtual surgical guides such as a virtual proximal tibial cut guide displayed by an HMD and physical surgical guides such as physical proximal tibial cut guide (e.g. attached to or part of a surgical robot) according to some embodiments of the present disclosure.
Figure 17C:
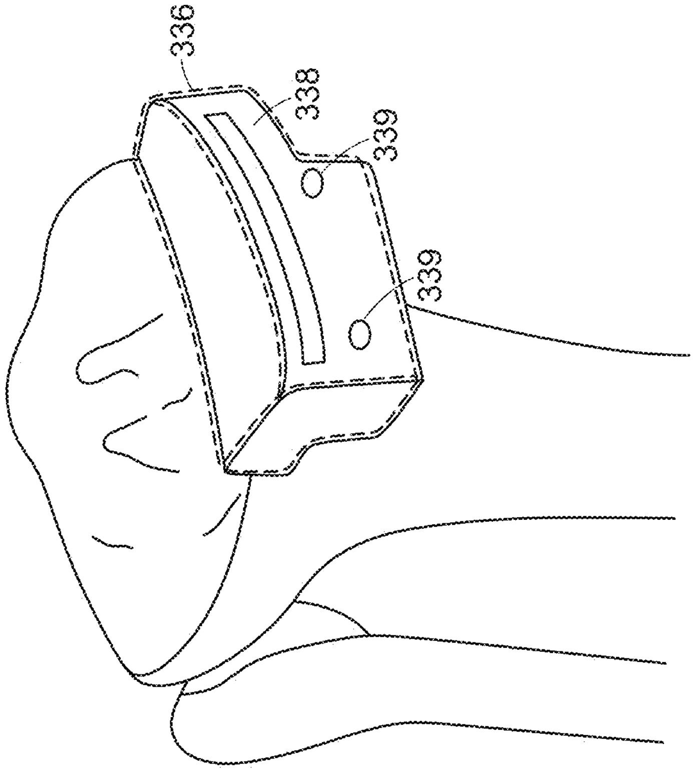
Figure 17B:
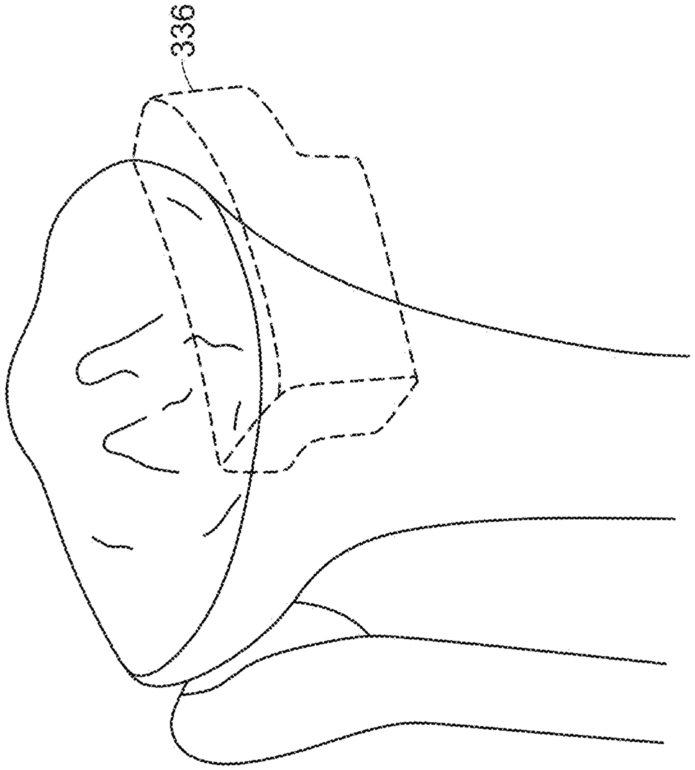

FIGS. 17A-17F provide an illustrative, non-limiting example of the use of virtual surgical guides such as a virtual proximal tibial cut guide displayed by an HMD and physical surgical guides such as physical proximal tibial cut guide. FIG. 17A shows live data of a patient with a proximal tibia 330 exposed during knee replacement surgery, a medial tibial plateau 331, a lateral tibial plateau 332 and a medial tibial spine 333 and a lateral tibial spine 334. In FIG. 17B, one or more HMDs or other augmented reality display systems can display a virtual proximal tibial cut guide, e.g. in a stereoscopic manner for the left eye and the right eye of the surgeon(s), creating a form of electronic hologram of the virtual surgical guide, i.e. the virtual proximal tibial cut guide. The virtual proximal tibial cut guide 336 in this example can be an outline of the physical proximal tibial cut guide with substantially similar dimensions as those of the physical proximal tibial cut guide. The virtual proximal tibial cut guide 336 is aligned based at least in part on coordinates of a predetermined position for guiding the proximal tibial cut, for example for achieving a predetermined varus or valgus correction and/or a predetermined slope relative to the proximal tibia and, for example, its anatomic or biomechanical axes. In FIG. 17C, the physical surgical guide (e.g. integrated, attached to, or part of a surgical robot) 338, i.e. the physical proximal tibial cut guide 338 (solid line) in this example, can be moved and aligned to be substantially superimposed with or aligned with the virtual surgical guide 336, i.e. the virtual proximal tibial cut guide 336 (broken line) in this example. Note two pin holes 339 in the physical proximal tibial cut guide 338.

Figure 17E:
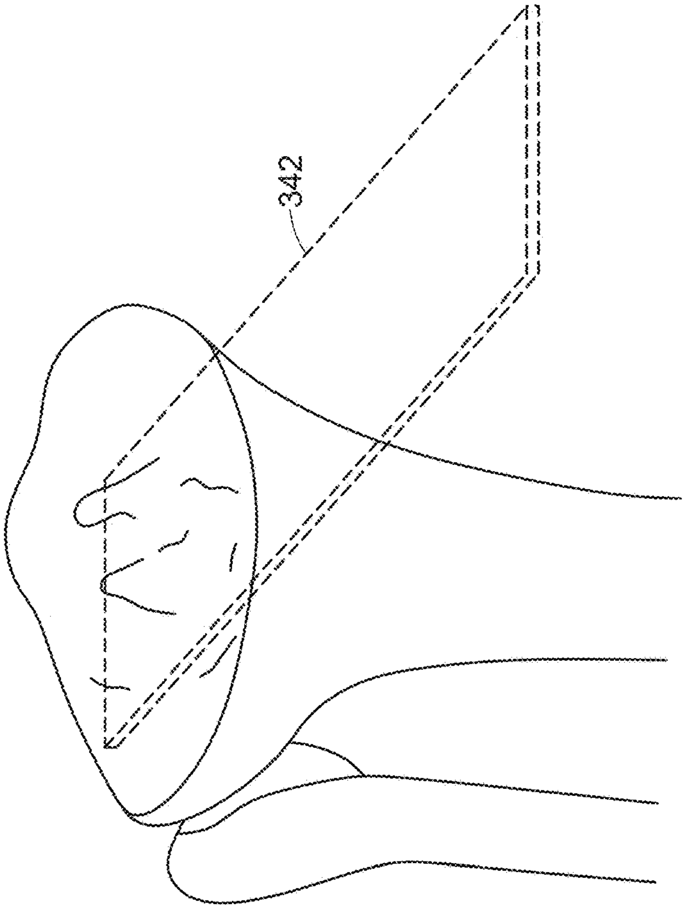
Figure 17D:
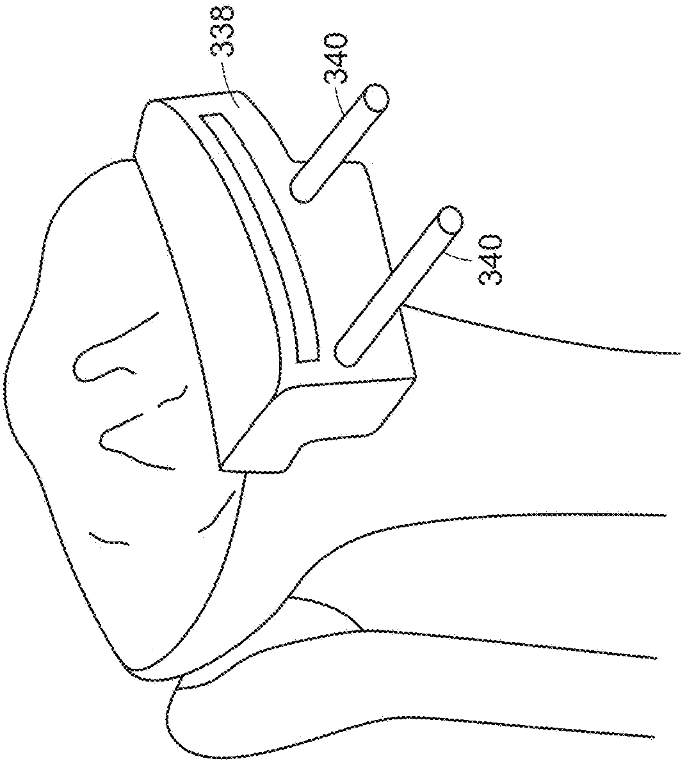
Figure 17F:
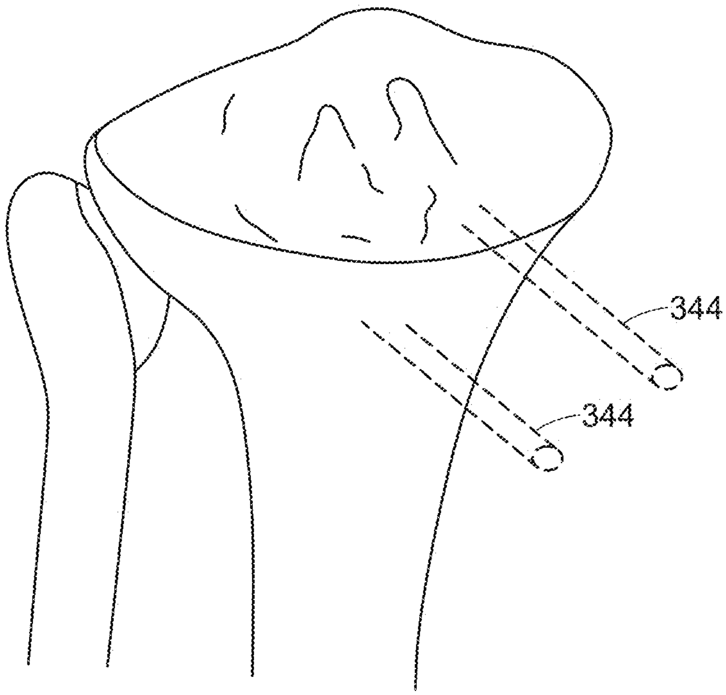

In FIG. 17D, the physical proximal tibial cut guide 338 can be attached to the proximal tibia bone using two pins 340. These pins 307 can be used for subsequent surgical steps, for example for referencing a flexion gap or an extension gap or for ligament balancing. In FIG. 17E, an alternative embodiment is shown to FIG. 17B. One or more HMDs or other augmented reality display systems can display a virtual proximal tibial cut plane 342, e.g. in a stereoscopic manner for the left eye and the right eye of the surgeon(s), creating a form of electronic hologram of the virtual tibial cut plane. The virtual proximal tibial cut plane 342 in this example is parallel with and substantially aligned and superimposed with the predetermined cut plane for the physical proximal tibial cut guide. The virtual proximal tibial cut plane 342 is aligned based at least in part on coordinates of a predetermined position for guiding the proximal tibial cut, for example for achieving a predetermined varus or valgus correction and/or a predetermined slope relative to the proximal tibia and, for example, its anatomic or biomechanical axes. A physical saw blade or a slot for aligning the physical saw blade (e.g. as an end effector of a surgical robot with an integrated or attached saw) in a physical proximal tibial cut guide or an open guide area for accommodating the saw blade in a physical proximal tibial cut guide can then be aligned and at least partially superimposed with the virtual proximal tibial cut plane 342. In FIG. 17F, an alternative embodiment is shown to FIG. 17B. One or more HMDs or other augmented reality display systems can display two or more virtual drills or pins 344 for placement in the proximal tibia, e.g. in a stereoscopic manner for the left eye and the right eye of the surgeon(s), creating a form of electronic hologram of the virtual tibial pins or drills. The virtual drills or pins 344 in this example can be an outline or a projected path of the physical pins or drills that can be used to fixate a physical proximal tibial cut guide to the proximal tibia. The virtual drills or pins 344 are aligned based at least in part on coordinates of a predetermined position foreguiding the proximal tibial cut, for example for achieving a predetermined varus or valgus correction and/or a predetermined slope relative to the proximal tibia and, for example, its anatomic or biomechanical axes. The physical drills or pins (not shown) can then be aligned and superimposed with the virtual drills or pins 344 and placed in the proximal tibia. A physical proximal tibial cut guide can then be attached to the physical pins and the proximal tibial cut can be executed.

Optionally, a virtual interface, e.g. with one or more virtual objects, can be displayed by the HMD(s), for interaction by the surgeon(s). For example, the virtual object can be a virtual surgical guide, e.g. a virtual cut plane, a virtual pin, a virtual drill, a virtual axis, a virtual tool, a virtual instrument, a virtual implant. The interaction can comprise moving the virtual object, e.g. the virtual surgical guide, for example using a tracked pointer, a gesture recognition, a finger tracking, an object tracking, etc. The interaction can be used to generate, by a computer processor, a command which can be configured, for example, to initiate, start, stop, activate, de-activate, move, adjust the position/orientation of the virtual object, e.g. virtual surgical guide, e.g. the virtual cut plane, virtual pin, virtual drill, virtual axis, virtual tool, virtual instrument, virtual implant and, optionally correspondingly, one or more components, controllers, drivers, motors, sensors, relays, processors or combination thereof of a surgical robot and/or an imaging system.

The command can, optionally, be transmitted from a computing system/computer processor in communication with the one or more HMDs or other augmented reality display systems to a computing system/computer processor in communication with a robot and/or an imaging system.

Example 7—Use of Markers, e.g. Optical Markers

In some embodiments, data can be obtained using an HMD, for example one manufactured by Microsoft, the Microsoft Hololens or Hololens 2 (Microsoft, Redmond, WI). The Hololens can use, for example, Windows holographic APIs including Unity (Unity Technologies, San Francisco, CA) and Vuforia 6.2 (PTC, Inc., Needham, MA).

Registration of Optical Markers Using Microsoft Hololens and Vuforia 6.2

Figure 18:
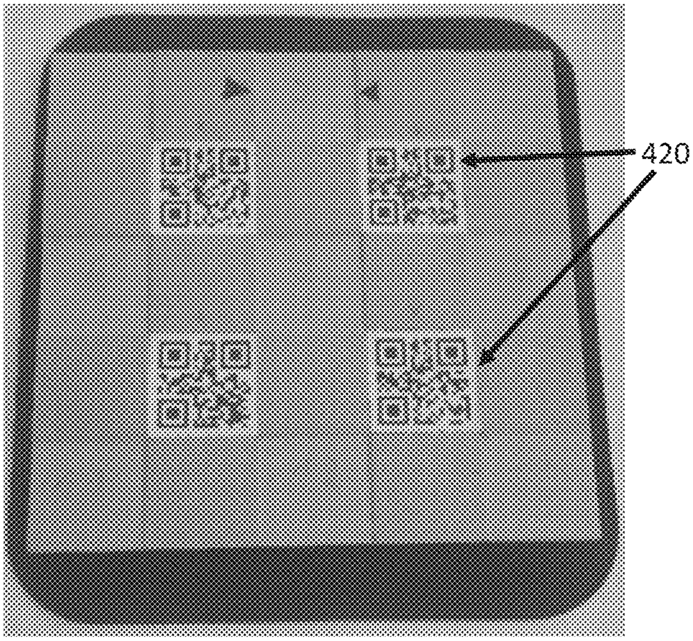
FIG. 18 shows a wooden board with 25 squares and four 4.0×4.0 cm optical markers.
Figure 19:
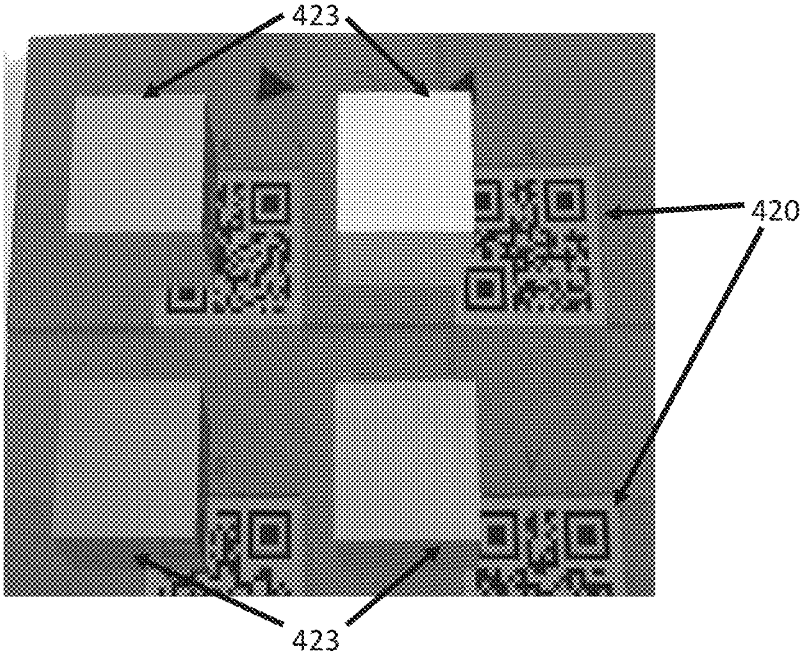
FIG. 19 shows an illustrative, non-limiting example of registration of four cubes in relationship to four optical markers using the image capture system of an HMD.
Figure 20:
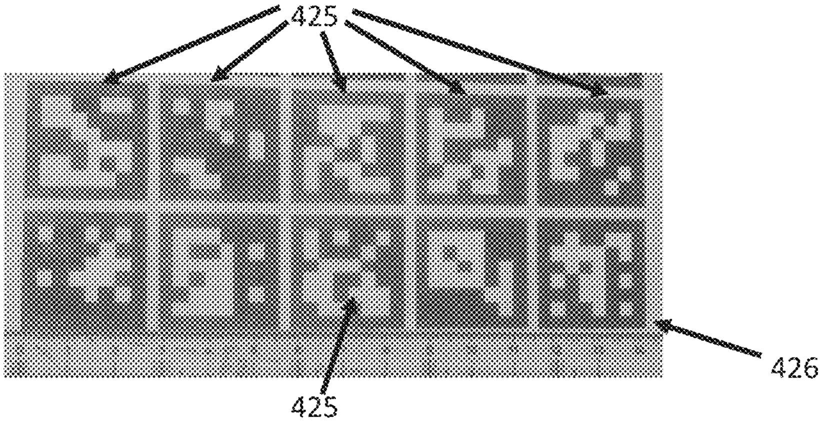
FIG. 20 shows an illustrative, non-limiting example of optical markers.
Figure 21:
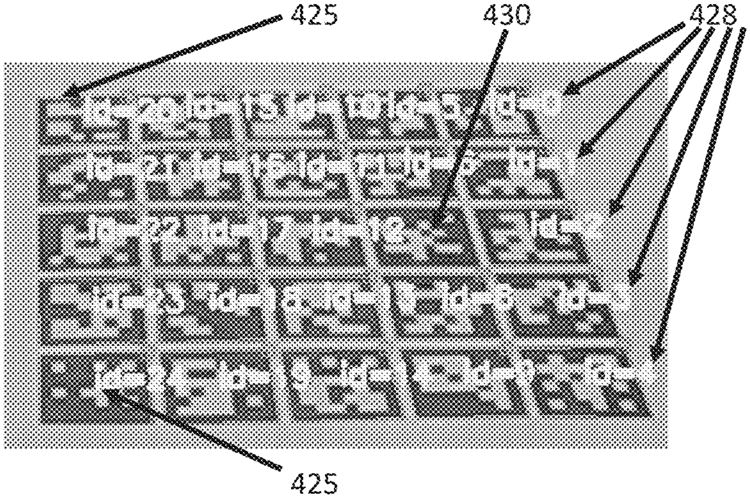
FIG. 21 shows an illustrative, non-limiting example of detection of optical markers using the image capture system of an HMD.

FIG. 18 shows a wooden board with 25 squares which was prepared and four 4.0×4.0 cm optical markers 420 with four distinct QR codes were applied in equidistant locations, 4.0 cm apart. As seen in FIG. 19, a software routine was implemented to project four cubes 423 with dimensions of 4.0×4.0×4.0 cm superimposed onto the squares and to maintain registration over the squares irrespective of head movement. The results are shown in FIG. 19. The Microsoft Hololens was not able to maintain registration of the four cubes over the designated optical markers; the cubes were at times displaced by as much as 3-4 cm and were also tilted. For example, registration of optical Markers using Hololens and OpenCV 2.4 can be implemented. OpenCV 2.4, an open source computer vision framework (Intel Inc., Santa Clara, CA), can be implemented on the Hololens system using OpenCVForUnity. As seen in FIG. 20, ArUco markers 425 available with OpenCV with a size of 2.8×2.8 cm can be arranged at a distance of 3.0×3.0 cm. A cm scale 426 is shown at the bottom of FIG. 20. Using this approach shown with the results shown in FIG. 21, acquisition of the 25 markers 425 using the internal Hololens camera required 1 second, corresponding to approximately 40 ms per marker. Markers were consistently recognized as indicated by the displayed green marker ID number 428, with only few occasional drop outs with no green marker ID number displayed 430 as seen in FIG. 21.

Markers can be mounted on a wooden board with a size of 2.8×2.8 cm and arranged at a distance of 3.0×3.0 cm and static measurements of displacement of optically detected marker positions vs. actual marker positions can be obtained at an angle of approximately 40 degrees between the Hololens and the board at a distance of approximately 32.5 cm to the center of the board.

Figure 22:
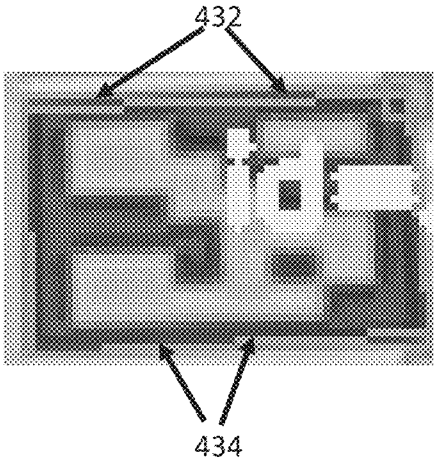
FIG. 22 shows an illustrative, non-limiting example of the accuracy of detecting an optical marker using a video camera integrated into an HMD.

FIG. 22 shows an example comparing the actual marker dimensions (2.8×2.8 cm) and position in black 432 with the optically detected marker using the Hololens camera seen as red outline 434.

The marker is not square in the image due to the angulation. The pixel size is approximately 0.5 mm in horizontal direction and 0.75 mm in vertical direction in this test. The data indicates sub-pixel accuracy which is why the following analysis of the data can be implemented: Pixels at the superior, inferior, left and right border are considered incorrectly detected if more than half have a grey value lower than the average grey value (i.e. the grey value between black and the grey background). For example, the horizontal red line at the superior border in FIG. 22 would need to be exactly 1 pixel higher in order to be counted as correctly detected. Conversely, the inferior second and third horizontal red line from the left are counted as accurately detected.

The percentage of each edge (superior, inferior, left, right) that is correctly detected can then determined, e.g. 100% for the superior edge and 50% for the inferior edge in FIG. 22. The analysis over the 25 markers shows that the maximum deviation between the optically detected marker position and the actual marker is 0.75 mm, i.e. one pixel size in vertical direction, with an average deviation between the optically detected marker position and the actual marker of 0.349 pixel=0.26 mm.

Example 8—Applications of Virtual User Interfaces

Figure 23A:
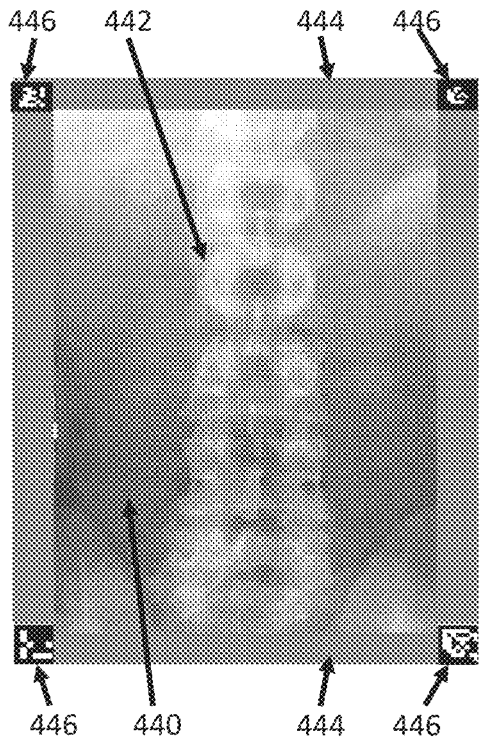
FIGS. 23A-23E show an illustrative, non-limiting example for placing an intended path of a pedicle screw using a virtual interface. The placement can be executed via free hand technique or, for example, using a surgical robot, e.g. with a robotic tool or instrument sleeve or drill guide.
Figure 23B:
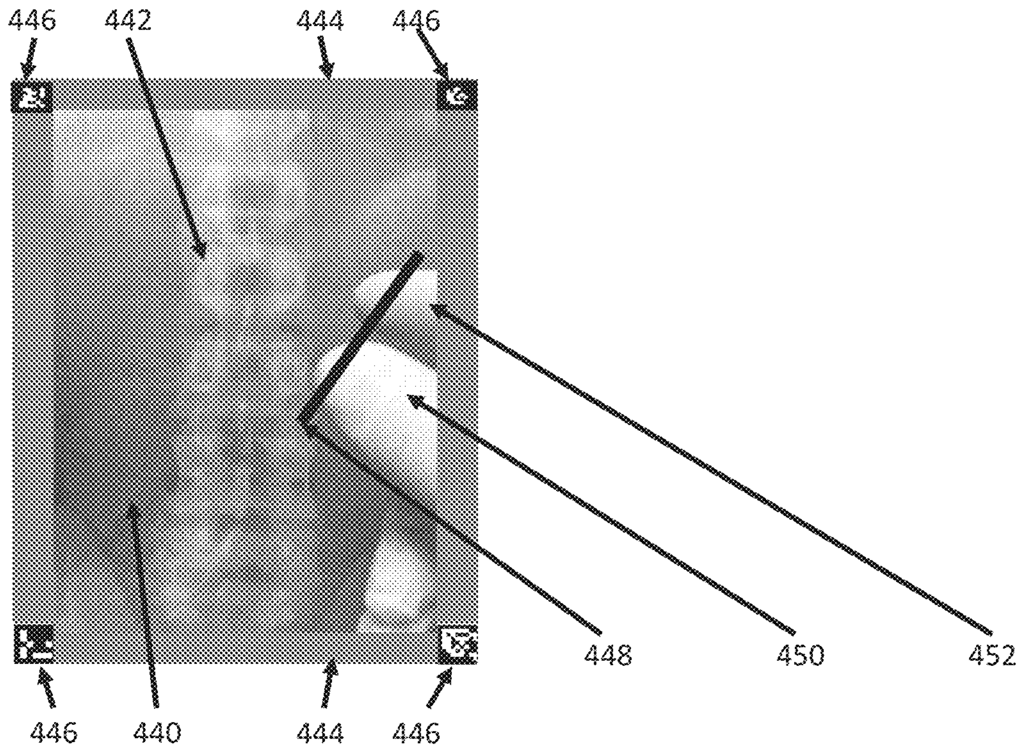
Figure 23C:
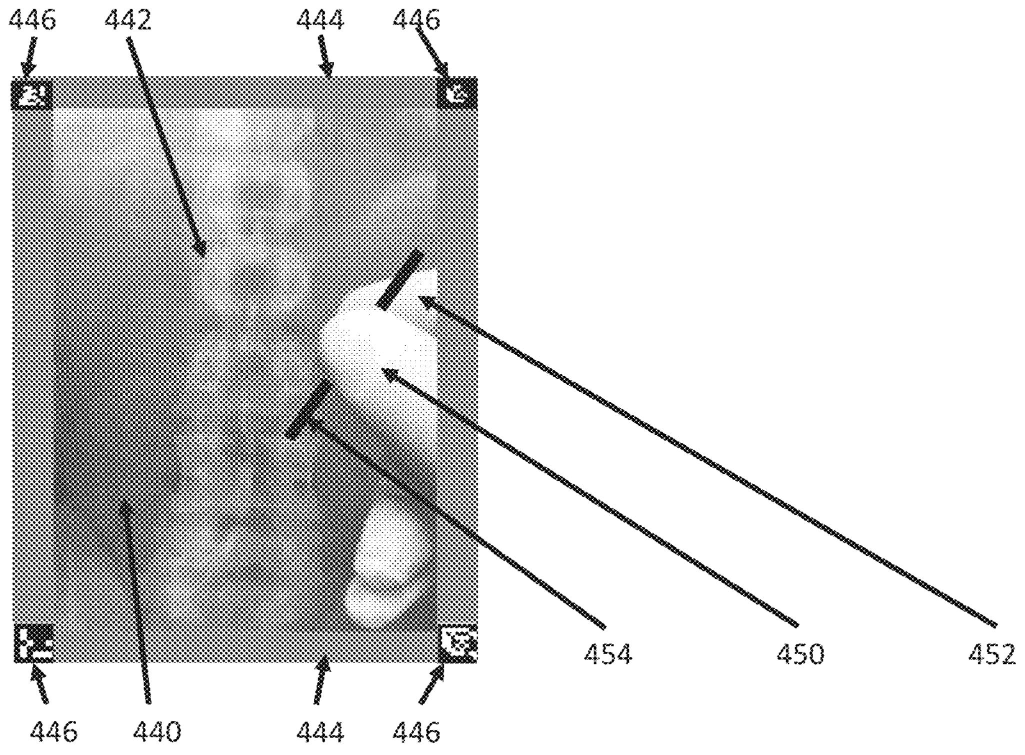
Figure 23D:
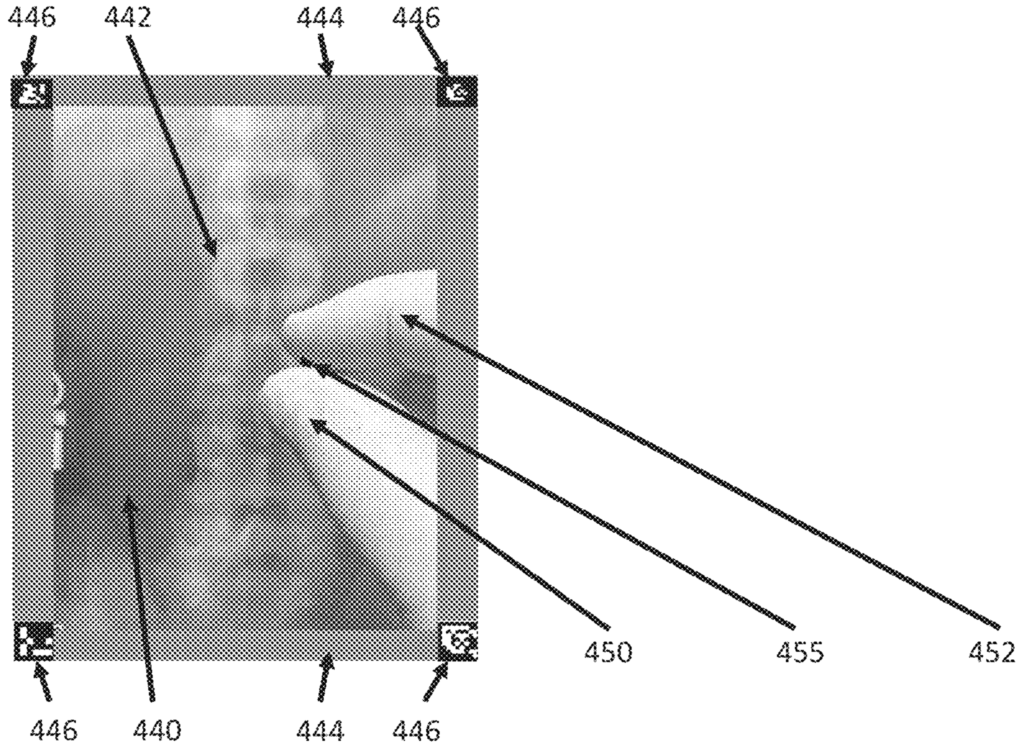
Figure 23E:
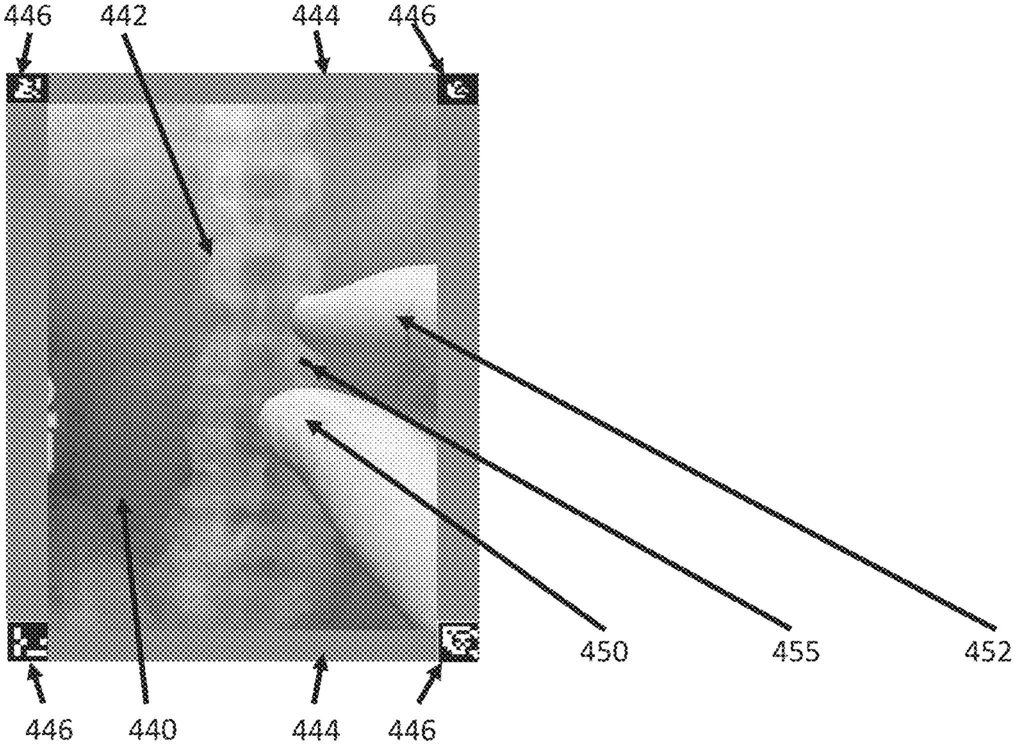

A virtual interface for the path of a pedicle screw, an interbody device, or other types of implant, e.g. for joint replacement, can use, for example, the Unity for HoloLens engine (Unity Technologies, San Francisco, CA). Unity's GestureRecognizer interface allows for recognition of different hold, navigation and manipulation functions. Additionally, the Gaze functionality can be available for implementation of a cursor controlled by the user's view direction. Thus, in select applications, the user's gaze can control the cursor including cursor movement. Closure of the eye lid can, for example, also be used to generate a command to execute a function. With the virtual interface, the planning can be performed, for example, on fluoroscopic images displayed by an HMD using gesture commands which are mapped to entry points and vectors. A vector corresponding to the intended path of the surgical instrument(s), e.g. an awl or the pedicle screw, can be placed by the surgeon using gesture commands, e.g. a closed position of the thumb and index finger or an open position of a thumb and index finger as shown in FIGS. 23A-23E. FIGS. 23A-23E show an illustrative example for placing an intended path of a pedicle screw. In FIGS. 23A-E, a fluoroscopic image 440 of a lumbar spine 442 showing lumbar levels L1-L5 is displayed by an HMD, registered with anatomic landmarks using reference frame 444 with optical markers 446 attached to patient's back. Each marker has its own unique QR or other code, thereby optionally identifying the patient's left and right side, superior and inferior. Other markers, e.g. retroreflective marker balls or disks, can be used. In FIG. 23B, the HMD displays a preliminary path 448 in arbitrary location; thumb 450 and index finger 452 are also seen. The surgeon can move the fingers towards the arbitrary path with fingers open. In FIG. 23C, the surgeon closes thumb 450 and index fingers 452 over the intended path 454, triggering a command via gesture recognition to move the intended path following the finger movement. In FIG. 23D, the surgeon moves the intended path 455 into desired orientation over the pedicle by moving the thumb 450 and index finger 452. In FIG. 23E, the surgeon opens the thumb 450 and index finger 452 triggering a command via gesture recognition to fixate the vector of the intended path 455 in the coordinate system. An open position indicates in this non-limiting example that the vector is anchored and the intended path is fixated relative to the global coordinate system and the anatomic landmarks. A closed position indicates in this non-limiting example that the vector can be moved with six degrees of freedom following the movement of the fingers. Any other finger symbols and movements can be used.

The user interaction, e.g. via gesture recognition or a virtual user interface, for example displaying virtual objects such as virtual buttons, sliders, keyboards, etc., can be used to generate, by a computer processor, a command which can be configured, for example, to initiate, start, stop, activate, de-activate, move, adjust the position/orientation of the virtual object, e.g. virtual surgical guide, e.g. the virtual cut plane, virtual trajectory, virtual pin, virtual drill, virtual axis, virtual tool, virtual instrument, virtual implant and, optionally correspondingly, one or more components, controllers, drivers, motors, sensors, relays, processors or combination thereof of a surgical robot and/or an imaging system. The command can, optionally, be transmitted from a computing system/computer processor in communication with the one or more HMDs or other augmented reality display systems to a computing system/computer processor in communication with a robot and/or an imaging system, which can then effect or cause the initiating, starting, stopping, activating, de-activating, moving, adjusting of the one or more components, controllers, drivers, motors, sensors, relays, processors or combination thereof of a surgical robot and/or an imaging system. For example, the command can cause the computing system/computer processor in communication with a robot to move a robotic arm and end effector and/or a drill guide to align with a trajectory defined by the surgeon using the virtual user interface and/or gesture recognition.

Figure 24A:
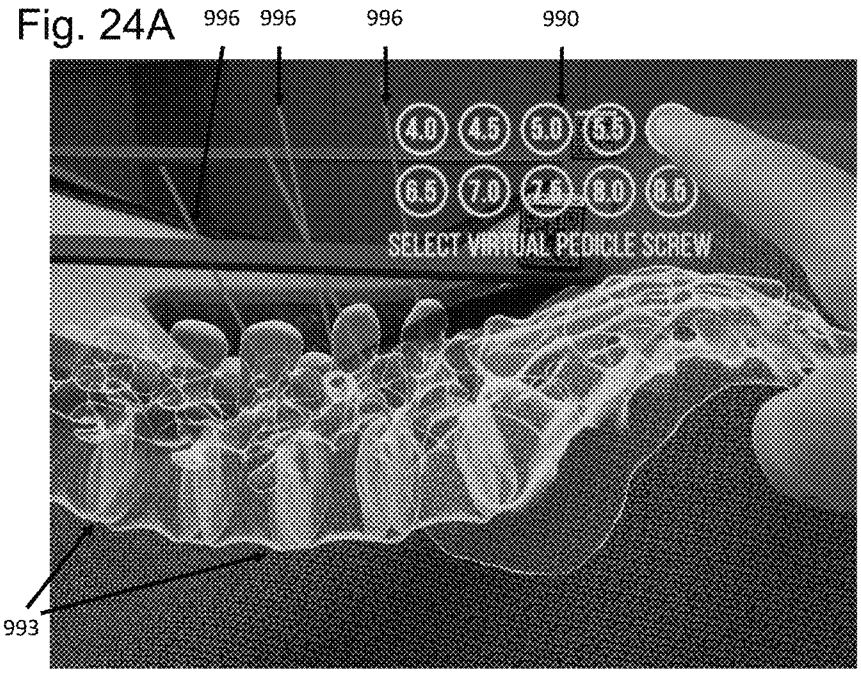
FIGS. 24A-24B provide illustrative, non-limiting examples of one or more augmented reality HMD displays including a virtual user interface for virtual placing, sizing, fitting, selecting and aligning of virtual pedicle screws and including OHMD displays for guidance of spinal instruments and implants.
Figure 24B:
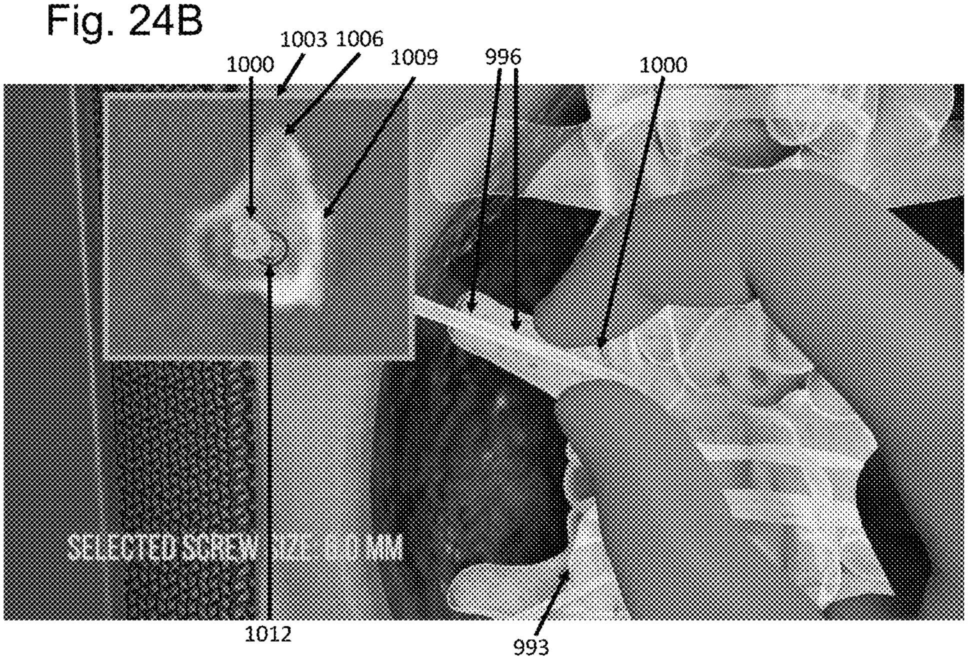

FIGS. 24A-24B provide illustrative, non-limiting examples of one or more augmented reality HMD displays including a virtual user interface 990, for example displaying one or more virtual button, virtual field, virtual cursor, virtual pointer, virtual slider, virtual trackball, virtual node, virtual numeric display, virtual touchpad, virtual keyboard, or a combination thereof, for virtual placing, sizing, fitting, selecting and aligning of virtual pedicle screws and including HMD displays for guidance of spinal instruments and implants. A virtual user interface 990 can be configured for selecting different sizes of virtual pedicle screws, e.g. in mm of diameter. A computer processor can be configured to allowing placing and moving of the virtual pedicle screws onto the virtually displayed spine 993 of the patient, e.g. using a 3D model generated based on a pre-operative CT scan or an intra-operative O-arm or 3D C-arm scan. The computer processor can be configured for selecting different sizes of implants (e.g. in mm), using, for example, voice commands or gesture commands, e.g. a size 6.0 mm. A virtual path 996 can be displayed for guiding the placement of the one or more physical pedicle screws. A computer processor can be configured to move, place, size, and align virtual pedicle screws 1000 using, for example, gesture recognition or voice commands, and, optionally to display magnified views 1003, e.g. from a CT scan, demonstrating the pedicle 1006 including the medial wall of the pedicle 1009. A target placement location 1012 for the virtual pedicle screw 1000 can also be shown. The virtual screw can be adjusted to be placed in the center of the pedicle. The physical screw and/or awl or screw driver can be tracked, e.g. using a navigation system or video system (for example with navigation markers or optical markers or direct optical tracking). When the screw path, awl path or screw driver path extends beyond the medial wall of the pedicle, a computer processor can generate an alarm, e.g. via color coding or acoustic signals. Physical instruments, e.g. a physical awl 1015, can be aligned with and superimposed onto the virtual path 996 projected by an HMD.

The user interaction, e.g. via gesture recognition or a virtual user interface, for example displaying virtual objects such as for example one or more virtual button, virtual field, virtual cursor, virtual pointer, virtual slider, virtual trackball, virtual node, virtual numeric display, virtual touchpad, virtual keyboard, or a combination thereof, can be used to generate, by a computer processor, a command which can be configured, for example, to initiate, start, stop, activate, de-activate, move, adjust the position/orientation of the virtual object, e.g. virtual surgical guide, e.g. the virtual cut plane, virtual trajectory, virtual pin, virtual drill, virtual axis, virtual tool, virtual instrument, virtual implant (e.g. a virtual screw or virtual cage or other interbody device) and, optionally correspondingly, one or more components, controllers, drivers, motors, sensors, relays, processors or combination thereof of a surgical robot and/or an imaging system. The command can, optionally, be transmitted from a computing system/computer processor in communication with the one or more HMDs or other augmented reality display systems to a computing system/computer processor in communication with a robot and/or an imaging system, which can then effect or cause the initiating, starting, stopping, activating, de-activating, moving, adjusting of the one or more components, controllers, drivers, motors, sensors, relays, processors or combination thereof of a surgical robot and/or an imaging system. For example, the command can cause the computing system/computer processor in communication with a robot to move a robotic arm and end effector and/or a drill guide to align with a trajectory defined by the surgeon using the virtual user interface and/or gesture recognition.

Figure 25A:
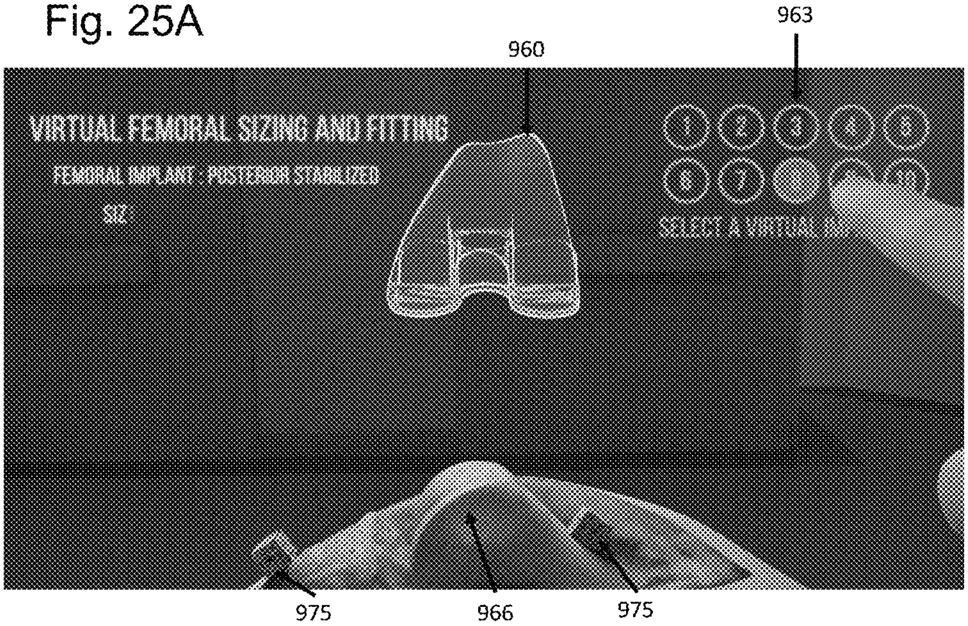
FIGS. 25A-25B provide illustrative, non-limiting examples of one or more augmented reality OHMD displays for virtual placing, sizing, fitting, selecting and aligning of implant components for free hand or robotic surgery.
Figure 25B:
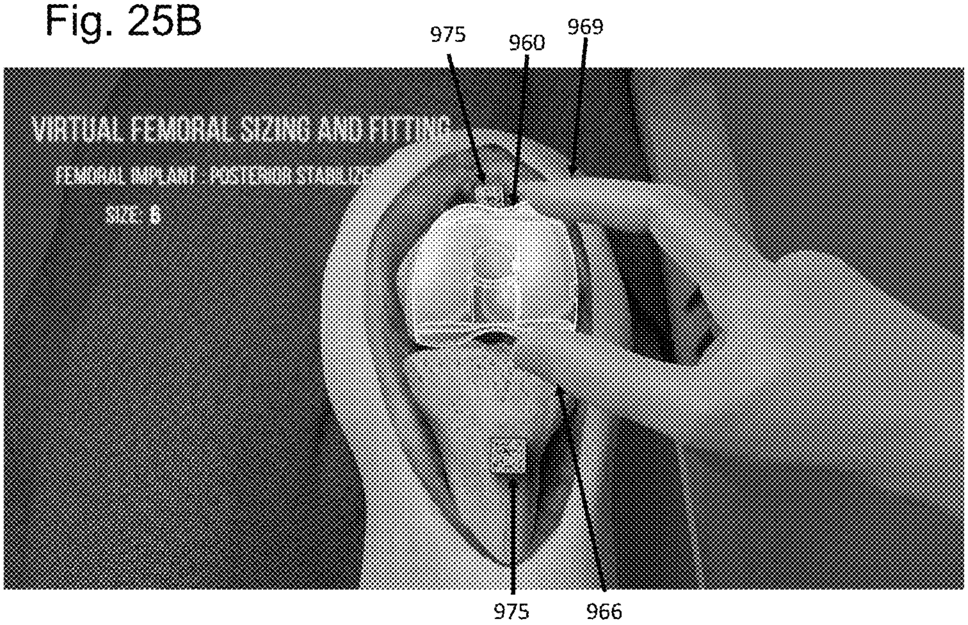

FIGS. 25A-25B provide illustrative, non-limiting examples of one or more augmented reality HMD displays for virtual placing, sizing, fitting, selecting and aligning of implant components. A virtual femoral component 960 can be displayed by one or more HMD displays. A virtual user interface 963, for example displaying one or more virtual button, virtual field, virtual cursor, virtual pointer, virtual slider, virtual trackball, virtual node, virtual numeric display, virtual touchpad, virtual keyboard, or a combination thereof, can be configured for selecting different sizes of virtual femoral components. A computer processor can be configured to allowing placing and moving of the virtual femoral component onto the physical distal femur 966 of the patient. The computer processor can be configured for selecting different sizes of implants, using, for example, voice commands, e.g. a size 6, and for aligning the virtual femoral component 960 with the physical distal femur of the live patient using gesture recognition configured to recognize an index finger 969 and thumb 972, in the example in FIG. 25B. The virtual implant can be registered and/or displayed in relationship to a coordinate system. One or more markers 975, e.g. with QR codes or a retroreflective or other markers, can be registered in the same coordinate system. The coordinates of the final position and/or orientation of the virtual implant, following adjustment via user interaction with the virtual user interface, can be transmitted, for example wirelessly, from a computing system/computer processor in communication with an HMD to a computing system/computer processor in communication with a surgical robot and/or imaging system. A command can be generated by one or more computer processors triggered by user interaction with the virtual user interface and can be transmitted, for example wirelessly, from a computing system/computer processor in communication with an HMD to a computing system/computer processor in communication with a surgical robot and/or imaging system. The command can cause the computing system/computer processor in communication with an imaging system to position and/or align the imaging system over the area, e.g. centered over the area, of the virtual implant. The command can cause the computing system/computer processor in communication with a surgical robot to position and/or align the surgical robot and/or its end effector over the area, e.g. centered over the area, of the virtual implant and to execute or facilitate execution of bone resections for the placement of the implant, e.g. a drilling, burring, cutting, milling, reaming and/or impacting with one or more end effectors.

All publications, patents mentioned herein are hereby incorporated by reference in their entirety as if each individual publication or patent was specifically and individually indicated to be incorporated by reference.

The invention claimed is:

1. A system, comprising:
- at least one head mounted display,
- at least one camera or scanning device, wherein the at least one camera or scanning device is configured to track real-time information of the at least one head mounted display, of a patient table used with an imaging system, and of the imaging system,
- inertial measurement units (IMU), wherein at least a first IMU is integrated or attached to the at least one head mounted display, wherein at least a second IMU is integrated or attached to the patient table, wherein at least a third IMU is integrated or attached to the imaging system,
  - wherein the at least first IMU is configured for real time tracking of the at least one head mounted display, wherein the at least second IMU is configured for real time tracking of the patient table, wherein the at least third IMU is configured for real time tracking of the imaging system,
- a first computing system comprising one or more computer processors,
  - wherein the first computing system is configured to obtain the real-time tracking information from the at least one camera or scanning device and the at least first, the at least second, and the at least third IMU,
  - wherein the first computing system is configured for wireless transmission of the real-time tracking information of the at least one head mounted display, the patient table, and the imaging system,
- a second computing system comprising one or more computer processors,
- wherein the second computing system is configured for wireless reception of the real-time tracking information of the at least one head mounted display, the patient table, and the imaging system,
- wherein the second computing system is configured to generate a 3D stereoscopic view comprising a 3D representation of one or more components of the imaging system, wherein the 3D representation is fixed or anchored in relationship to the one or more components of the imaging system,
- wherein the at least one head mounted display is configured to display the 3D stereoscopic view, and
- wherein the 3D stereoscopic view is updated in real-time for movement of the at least one head mounted display, the patient table, the imaging system or a combination thereof.

2. The system of claim 1, wherein the second computing system is integrated with the at least one head mounted display, or wherein the second computing system is separate from the at least one head mounted display and is connected to a display unit of the at least one head mounted display using at least one cable.

3. The system of claim 1, wherein the wireless transmission, the wireless reception, or both comprise a WiFi signal, a LiFi signal, a Bluetooth signal or a combination thereof.

4. The system of claim 1, wherein the camera or scanning device is separate from the at least one head mounted display or wherein the camera or scanning device is integrated or attached to the at least one head mounted display.

5. The system of claim 1, wherein the wireless transmission comprises sending data packets comprising the real-time tracking information of the at least one head mounted display, the patient table, and the imaging system, at a rate of 20 Hz or greater.

6. The system of claim 1, wherein the wireless reception comprises receiving data packets comprising the real-time tracking information of the at least one head mounted display, the patient table, and the imaging system, at a rate of 20 Hz or greater.

7. The system of claim 1, wherein the real-time tracking information comprises one or more coordinates, and wherein the one or more coordinates comprise coordinates of the patient table, the imaging system, and the at least one head mounted display.

8. The system of claim 1, wherein the imaging system comprises an x-ray system, a fluoroscopy system, a C-arm, a 3D C-arm, a digital tomosynthesis imaging system, an angiography system, a bi-planar angiography system, a 3D angiography system, a CT scanner, a PET scanner, a SPECT scanner, a nuclear scintigraphy system, or a combination thereof.

9. The system of claim 1, wherein the stereoscopic view comprises a 3D representation of at least a portion of the patient table.

10. The system of claim 1, wherein the at least one camera or scanning device is configured to track at least a portion of the patient and wherein the 3D stereoscopic view comprises a 3D representation of at least a portion of the patient.

11. The system of claim 1, comprising at least a fourth IMU is applied to the patient, wherein the at least fourth IMU is configured for tracking the patient, and wherein the 3D stereoscopic view comprises a 3D representation of at least a portion of the patient.

12. The system of claim 1, wherein the real-time tracking information from the at least one camera or scanning device and the IMUs is transmitted and received simultaneously.

13. The system of claim 1, wherein the real-time tracking information from the at least one camera or scanning device and the IMUs is transmitted and received separately.

14. The system of claim 1, wherein the first computing system, the second computing system, or the first and the second computing system comprise a collision detection module.

15. The system of claim 14, wherein the collision detection module is configured for detecting multi-body collision.

16. The system of claim 15, wherein the collision detection module is configured to detect a collision and change the stereoscopic view responsive to the collision.

17. The system of claim 16, wherein the change of the stereoscopic view comprises a color change.

18. The system of claim 14, wherein the collision detection module is configured to utilize the real-time tracking information.

19. The system of claim 18, wherein the first computing system, the second computing system, or the first and the second computing system comprising the collision detection module are configured to generate one or more event messages.

20. The system of claim 19, wherein the one or more event messages comprise information about a position, orientation or combination thereof of the imaging system.

* * * * *